(12) United States Patent
Wheelhouse et al.

(10) Patent No.: US 8,008,303 B2
(45) Date of Patent: Aug. 30, 2011

(54) BIPHENYL DERIVATIVES AND THEIR USE IN TREATING HEPATITIS C

(75) Inventors: Christopher James Wheelhouse, London (GB); Alexander James Floyd Thomas, London (GB); David John Bushnell, London (GB); James Lumley, London (GB); James Iain Salter, London (GB); Malcolm Clive Carter, London (GB); Neil Mathews, London (GB); Christopher John Pilkington, London (GB); Richard Martyn Angell, London (GB)

(73) Assignee: AstraZeneca AB, Sodertalje (SE)

( * ) Notice: Subject to any disclaimer, the term of this patent is extended or adjusted under 35 U.S.C. 154(b) by 317 days.

(21) Appl. No.: 12/066,983

(22) PCT Filed: Sep. 18, 2006

(86) PCT No.: PCT/GB2006/003469
§ 371 (c)(1),
(2), (4) Date: Mar. 14, 2008

(87) PCT Pub. No.: WO2007/031791
PCT Pub. Date: Mar. 22, 2007

(65) Prior Publication Data
US 2008/0255105 A1    Oct. 16, 2008

(30) Foreign Application Priority Data

Sep. 16, 2005 (GB) .................................. 0518971.7
May 30, 2006 (GB) .................................. 0610663.7
May 30, 2006 (GB) .................................. 0610664.5

(51) Int. Cl.
*C07D 295/02* (2006.01)
*A61K 31/495* (2006.01)

(52) U.S. Cl. ................... 514/252.13; 544/359; 544/383; 514/252.12

(58) Field of Classification Search ........... 544/359, 544/383; 514/252.13, 252.12
See application file for complete search history.

(56) References Cited

U.S. PATENT DOCUMENTS

| 5,356,893 | A | 10/1994 | Bradshaw et al. |
| 6,433,236 | B1 | 8/2002 | Schiraldi et al. |
| 2005/0020590 | A1 | 1/2005 | Lang et al. |
| 2006/0004010 | A1 | 1/2006 | Habashita et al. |
| 2007/0099938 | A1 | 5/2007 | Ohmoto et al. |

FOREIGN PATENT DOCUMENTS

| EP | 0612524 B1 | 8/1998 |
| EP | 1054005 A1 | 11/2000 |
| EP | 1132376 A1 | 9/2001 |
| EP | 1295867 A1 | 3/2003 |
| WO | 91/03443 A1 | 3/1991 |
| WO | 9501326 A1 | 1/1995 |
| WO | 9630343 A1 | 10/1996 |
| WO | 9736591 A1 | 10/1997 |
| WO | 9917777 A1 | 4/1999 |
| WO | 0042011 A1 | 7/2000 |
| WO | 0119788 A2 | 3/2001 |
| WO | 0121577 A5 | 3/2001 |
| WO | 0164642 A2 | 9/2001 |
| WO | 02089738 A2 | 11/2002 |
| WO | 03006628 A2 | 1/2003 |
| WO | 03/032970 A1 | 4/2003 |
| WO | 03/032972 A1 | 4/2003 |
| WO | 03/032980 A1 | 4/2003 |
| WO | 03062392 A2 | 7/2003 |
| WO | 03068747 A1 | 8/2003 |
| WO | 2004041789 A1 | 5/2004 |
| WO | 2004043335 A2 | 5/2004 |
| WO | 2004083174 A2 | 9/2004 |
| WO | 2004/089874 A1 | 10/2004 |
| WO | 2004/089876 A1 | 10/2004 |
| WO | 2004089296 A2 | 10/2004 |
| WO | 2005009539 A2 | 2/2005 |
| WO | 2005021721 A2 | 3/2005 |
| WO | 2005023761 A2 | 3/2005 |
| WO | 2005065361 A2 | 7/2005 |
| WO | 2005086661 A2 | 9/2005 |
| WO | 2006001958 A2 | 1/2006 |
| WO | 2006014012 A2 | 2/2006 |
| WO | 2006037335 A2 | 4/2006 |
| WO | 2006047528 A2 | 5/2006 |
| WO | 2006/083271 A2 | 8/2006 |

(Continued)

OTHER PUBLICATIONS

Ishida et al; Involvement of p38 signaling pathway in interferon-a-mediated antiviral activity toward hepatitis C virus; Biochemical and Biophysical Research Communications; 2004; 321; 722-727.

(Continued)

*Primary Examiner* — Kahsay T Habte

(57) ABSTRACT

Use of a compound which is a biphenyl derivative of formula (I), or a pharmaceutically acceptable salt thereof, for the treatment of Hepatitis C

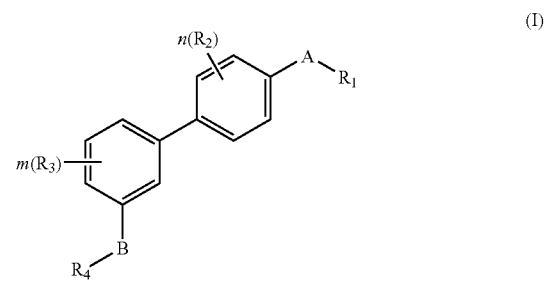

wherein the variables are described herein.

20 Claims, No Drawings

FOREIGN PATENT DOCUMENTS

| | | |
|---|---|---|
| WO | 2006/091858 A1 | 8/2006 |
| WO | 2006102760 A1 | 10/2006 |
| WO | 2007009083 A2 | 1/2007 |
| WO | 2007087441 A2 | 8/2007 |
| WO | 2007088996 A1 | 8/2007 |
| WO | 2007103162 A2 | 9/2007 |
| WO | 2007138242 A1 | 12/2007 |
| WO | 2008044667 A1 | 4/2008 |
| WO | 2008046216 A1 | 4/2008 |
| WO | 2008073670 A2 | 6/2008 |
| WO | 2008092006 A2 | 7/2008 |
| WO | 2008147864 A2 | 12/2008 |
| WO | 2009034390 A1 | 3/2009 |

OTHER PUBLICATIONS

Carter; Diphenylcarboxamides As Inhibitors of HCV Non-structural Protein NS5A, presentation at 23rd ICAR (Apr. 26, 2010).
Carter et al; Diphenylcarboxamides As Inhibitors of HCV Non-structural Protein NS5A, poster at 23rd ICAR (Apr. 26, 2010).

BIPHENYL DERIVATIVES AND THEIR USE IN TREATING HEPATITIS C

CROSS-REFERENCE TO RELATED APPLICATIONS

This application is a US National Stage under 35 U.S.C §371 of International Application No. PCTGB2006/003469 (filed Sep. 18, 2006) which claims priority under 35 U.S.C. §119(a)-(d) to Application No. GB0518971.7 filed on Sep. 16, 2005, Application No. GB0610663.7 filed on May 30, 2006, and Application No. GB0610664.5 filed on May 30, 2006. The entire teachings of PCT/GB2006/003469, GB0518971.7, GB0610663.7 and GB0610664.5 are incorporated herein by reference.

The present invention relates to a series of biphenyl derivatives which are useful in treating or preventing a hepatitis C viral (HCV) infection. The present invention provides, in a first embodiment, the use of a compound which is a biphenyl derivative of formula (I), or a pharmaceutically acceptable salt thereof, in the manufacture of a medicament for use in treating or alleviating HCV

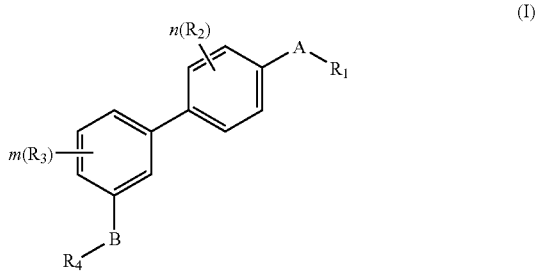

(I)

wherein:
$R_1$ is a $C_1$-$C_6$ alkyl group or a moiety -$A_1$, -$L_1$-$A_1$, -$A_1$-$A_1'$, -$L_1$-$A_1$-$A_1'$, -$A_1$-$L_1$-$A_1'$, -$A_1$-$Y_1$-$A_1'$, -$A_1$-$Het_1$-$A_1'$, -$L_1$-$A_1$-$Y_1$-$A_1'$, -$L_1$-$A_1$-$Het_1$-$A_1'$, -$L_1$-$Het_1$-$A_1$, -$L_1$-$Y_1$-$A_1$, -$L_1$-$Y_1$-$Het_1$-$A_1$, -$L_1$-$Het_1$-$Y_1$-$A_1$, -$L_1$-$Y_1$-$Het_1$-$L_1'$, -$A_1$-$Y_1$-$Het_1$-$A_1'$, -$A_1$-$Het_1$-$Y_1$-$A_1'$, -$A_1$-$Het_1$-$L_1$-$A_1'$, -$A_1$-$L_1$-$Het_1$-$A_1'$ or -$L_1$-$Het_1$-$L_1'$;

A and B are the same or different and each represent a direct bond or a —CO—NR'—, —NR'—CO—, —NR'—$CO_2$—, —CO—, —NR'—CO—NR"—, —NR'—S(O)$_2$—, —S(O)$_2$—NR'—, —$SO_2$—, —NR'—, —NR'—CO—CO—, —CO—O—, —O—CO—, —($C_1$-$C_2$ alkaline)-NR'— or —($C_1$-$C_2$ hydroxyalkylene)-NR'— moiety, wherein R' and R" are the same or different and each represent hydrogen or $C_1$-$C_4$ alkyl;

$R_2$ and $R_3$ are the same or different and each represent $C_1$-$C_4$ alkyl, $C_1$-$C_4$ alkoxy, $C_1$-$C_4$ haloalkyl, $C_1$-$C_4$ haloalkoxy or halogen;

n and m are the same or different and each represent 0 or 1;

$R_4$ is a $C_1$-$C_6$ alkyl group or a moiety -$A_4$, -$L_4$-$A_4$, -$A_4$-$A_4'$, -$L_4$-$A_4$-$A_4'$, -$A_4$-$L_4$-$A_4'$, -$A_4$-$Y_4$-$A_4'$, -$A_4$-$Het_4$-$A_4'$, -$L_4$-$A_4$-$Y_4$-$A_4'$, -$L_4$-$A_4$-$Het_4$-$A_4'$, -$L_4$-$Het_4$-$A_4$, -$L_4$-$Y_4$-$A_4$, -$L_4$-$Y_4$-$Het_4$-$A_4$, -$L_4$-$Het_4$-$Y_4$-$A_4$, -$L_4$-$Y_4$-$Het_4$-$L_4'$, -$A_4$-$Y_4$-$Het_4$-$A_4'$, -$A_4$-$Het_4$-$Y_4$-$A_4'$, -$A_4$-$Het_4$-$L_4$-$A_4'$, -$A_4$-$L_4$-$Het_4$-$A_4'$ or -$L_4$-$Het_4$-$L_4'$, each $A_1$, $A_4$, $A_1'$ and $A_4'$ are the same or different and represent a phenyl, 5- to 10-membered heteroaryl, 5- to 10-membered heterocyclyl or $C_3$-$C_8$ carbocyclyl moiety;

each $L_1$ and $L_4$ is the same or different and represents a $C_1$-$C_4$ alkylene or a $C_1$-$C_4$ hydroxyalkylene group;

each $Y_1$ and $Y_4$ is the same or different and represents —CO—, —SO— or —S(O)$_2$—;

each $L_1'$ and $L_4'$ is the same or different and represents hydrogen or a $C_1$-$C_4$ alkyl group; and each $Het_1$ and $Het_4$ is the same or different and represents —O—, —S— or —NR'—, wherein R' is hydrogen or a $C_1$-$C_4$ alkyl group, the phenyl, heteroaryl, heterocyclyl and carbocyclyl moieties in $R_1$ and $R_4$ being optionally fused to a phenyl, 5- to 10-membered heteroaryl or 5- to 10-membered heterocyclyl ring; and the phenyl, heteroaryl, heterocyclyl and carbocyclyl moieties in $R_1$ and $R_4$ being unsubstituted or substituted by (a) a single unsubstituted substituent selected from -($C_1$-$C_4$ alkyl)-$X_1$, —$CO_2R'$, —$SO_2NR'R"$, —S(O)$_2$—R', —CONR'R", —NR'—CO—R''', —NR'—S(O)$_2$—R''', —CO—NR'—($C_1$-$C_4$ alkyl)-NR'R" and —CO—O—($C_1$-$C_4$ alkyl)-NR'R" and/or (b) 1, 2 or 3 unsubstituted substituents selected from —($C_1$-$C_4$ alkyl)-$X_2$, halogen, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, hydroxy, cyano, nitro and —NR'R", wherein $X_1$ is —$CO_2R'$, —$SO_2$—R', —NR'—$CO_2$—R", —NR'—S(O)$_2$—R''', —CONR'R" or —$SO_2$—NR'R", each $X_2$ is the same or different and is cyano, nitro or —NR'R", each R' and R" is the same or different and represents hydrogen or $C_1$-$C_4$ alkyl and each R''' is the same or different and represents $C_1$-$C_4$ alkyl.

As used herein, a $C_1$-$C_6$ alkyl moiety is a linear or branched alkyl moiety containing from 1 to 6 carbon atoms, such as a $C_1$-$C_5$ or $C_1$-$C_4$ alkyl moiety. Examples of $C_1$-$C_6$ alkyl moieties include methyl, ethyl, n-propyl, i-propyl, n-butyl, t-butyl, —CH(Et)$_2$ and —CH$_2$—CH$_2$—CH(CH$_3$)$_2$. For the avoidance of doubt, where two alkyl moieties are present in a substituent, the alkyl moieties may be the same or different.

As used herein, a $C_1$-$C_4$ alkylene or $C_1$-$C_2$ alkylene group is any divalent linear or branched $C_1$-$C_4$ or $C_1$-$C_2$ alkyl moiety. Linear $C_1$-$C_4$ alkylene groups are methylene, ethylene, n-propylene and n-butylene groups. Methylene, ethylene and n-propylene groups are preferred. Branched $C_1$-$C_4$ alkylene groups include —CH(CH$_3$)—, —CH(CH$_3$)—CH$_2$— and —CH$_2$—CH(CH$_3$)—.

As used herein, a $C_1$-$C_4$ hydroxyalkylene or $C_1$-$C_2$ hydroxyalkylene group is a said $C_1$-$C_4$ alkylene or $C_1$-$C_2$ alkylene group which is substituted by a single hydroxy group. Particularly preferred $C_1$-$C_4$ hydroxyalkylene groups are branched $C_1$-$C_4$ alkylene groups carrying a hydroxy substituent, which is preferably located on a terminal carbon atom.

As used herein, a halogen is chlorine, fluorine, bromine or iodine. A halogen is typically fluorine, chlorine or bromine.

As used herein, a $C_1$-$C_4$ alkoxy moiety is a said $C_1$-$C_4$ alkyl moiety attached to an oxygen atom. A preferred $C_1$-$C_4$ alkoxy moiety is methoxy. A $C_1$-$C_4$ hydroxyalkyl moiety is a said $C_1$-$C_4$ alkyl moiety substituted by a single hydroxyl moiety. Preferred hydroxyalkyl moieties are $C_1$-$C_2$ hydroxyalkyl moieties, for example —C(OH)—CH$_3$ and —CH$_2$OH.

A $C_1$-$C_4$ haloalkyl or $C_1$-$C_4$ haloalkoxy moiety is typically a said $C_1$-$C_4$ alkyl or $C_1$-$C_4$ alkoxy moiety substituted by one or more said halogen atoms. Typically, it is substituted by 1, 2 or 3 said halogen atoms. Preferred haloalkyl and haloalkoxy moieties are perhaloalkyl and perhaloalkoxy moieties such as —CX$_3$ and —OCX$_3$ wherein X is a said halogen atom, for example chlorine and fluorine. A particularly preferred haloalkyl moiety is —CF$_3$. A particularly preferred haloalkoxy moiety is —OCF$_3$.

Preferably, the phenyl, heteroaryl, heterocyclyl and carbocyclyl moieties in $R_1$ and $R_4$ are unsubstituted or substituted by (a) a single unsubstituted substituent selected from —($C_1$-$C_2$ alkyl)-$X_1$, —$CO_2R'''$, —$SO_2R'''$, —$SO_2NR'R''$, —CONR'R''', —NR'—CO—R''', —NR'—$SO_2$—R''' and —CO—NR'—($C_1$-$C_2$ alkyl)-NR''' and/or (b) 1, 2 or 3 unsubstituted substituents selected from —($C_1$-$C_2$ alkyl)-$X_2$, halogen, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, hydroxy, cyano and —NR'R'', wherein $X_1$ is —$CO_2R'''$, —NR'—$CO_2$—R''', —NR'—$S(O)_2$—R''' or —$SO_2NR'R'''$, each $X_2$ is the same or different and is cyano or —NR'R''', each R' and R'' are the same or different and represent hydrogen or $C_1$-$C_4$ alkyl and each R''' is the same or different and represents $C_1$-$C_4$ alkyl.

More preferably the phenyl, heteroaryl, heterocyclyl and carbocyclyl moieties in $R_1$ and $R_4$ are unsubstituted or substituted by (a) a single unsubstituted substituent selected from —$CH_2$—$X_1$, —$CO_2$—R''', —$SO_2R'''$, —$SO_2NR'R''$, —CONR'R''', —NR'—CO—R''', —NR'—$SO_2$—R''' and —CO—NR'—($C_1$-$C_2$ alkyl)-NR'R''' and/or (b) 1 or 2 unsubstituted substituents selected from —$CH_2$—$X_2$, halogen, $C_1$-$C_4$ alkyl, $C_1$-$C_4$ alkoxy, $C_1$-$C_2$ haloalkyl, $C_1$-$C_2$ haloalkoxy, $C_1$-$C_4$ hydroxyalkyl, hydroxy, cyano and —NR'R'', wherein $X_1$ is —$CO_2R'''$, —NR'—$CO_2$—R''' or —$SO_2NR'R'''$, each $X_2$ is the same or different and is cyano or —NR'R'', each R' and R'' are the same or different and represent hydrogen or $C_1$-$C_4$ alkyl and each R''' is the same or different and represents $C_1$-$C_4$ alkyl.

More typically, the phenyl, heteroaryl, heterocyclyl and carbocyclyl moieties in $R_1$ and $R_4$ are unsubstituted or substituted by (a) a single unsubstituted substituent selected from —$CH_2$—$X_1$, —$CO_2$—R''', —$SO_2NR'R''$, —CONR'R''', —NR'—CO—R''', —NR'—$SO_2$—R''' and —CO—NR'—($C_1$-$C_2$ alkyl)-NR'R''' and/or (b) 1 or 2 unsubstituted substituents selected from —$CH_2$—$X_2$, halogen, $C_1$-$C_4$ alkyl, $C_1$-$C_4$ alkoxy, $C_1$-$C_2$ haloalkyl, $C_1$-$C_2$ haloalkoxy, $C_1$-$C_4$ hydroxyalkyl, hydroxy, cyano and —NR'R'', wherein $X_1$ is —$CO_2R'''$, —NR'—$CO_2$—R''' or —$SO_2NR'R'''$, each $X_2$ is the same or different and is cyano or —NR'R'', each R' and R'' are the same or different and represent hydrogen or $C_1$-$C_4$ alkyl and each R''' is the same or different and represents $C_1$-$C_4$ alkyl.

As used herein, a 5- to 10-membered heteroaryl moiety is a monocyclic 5- to 10-membered aromatic ring, containing at least one heteroatom, for example 1, 2 or 3 heteroatoms, selected from O, S and N. Typically a 5- to 10-membered heteroaryl moiety is a 5- to 6-membered heteroaryl moiety. Examples include imidazolyl, isoxazolyl, pyrrolyl, thienyl, thiazolyl, furanyl, pyridyl, pyrazinyl, pyrimidinyl, pyridazinyl, oxadiazolyl, oxazolyl, isoxazolyl, thiazolyl, isothiazolyl, thiadiazolyl, pyrazolyl and triazolyl moieties. Imidazolyl, isoxazolyl, pyrrolyl, thienyl, thiazolyl, furanyl, pyridyl, pyrazinyl, oxadiazolyl, oxazolyl, isoxazolyl, thiazolyl, isothiazolyl, thiadiazolyl, pyrazolyl and triazolyl moieties are preferred.

A 5- to 10-membered heteroaryl moiety is optionally fused to a phenyl, 5- to 10-membered heteroaryl or 5- to 10-membered heterocyclyl ring. Preferably, it is non-fused or fused to a phenyl, 5- to 6-membered heteroaryl or 5- to 6-membered heterocyclyl ring. More preferably, it is non-fused or fused to a phenyl ring. Most preferably, it is a non-fused 5- to 6-membered ring as defined above, or is a quinoxalinyl moiety.

A said fused or non-fused heteroaryl moiety is unsubstituted or substituted as set out above. Preferably, it is unsubstituted or substituted by 1 or 2 unsubstituted substituents selected from —$CH_2$—$X_2$, halogen, $C_1$-$C_4$ alkyl, $C_1$-$C_4$ alkoxy, $C_1$-$C_2$ haloalkyl, $C_1$-$C_2$ haloalkoxy, $C_1$-$C_4$ hydroxyalkyl, hydroxy, cyano and —NR'R'', wherein each $X_2$ is the same or different and is cyano or —NR'R'', and each R' and R'' is the same or different and represents hydrogen or $C_1$-$C_4$ alkyl. Preferably, it is unsubstituted or substituted by 1 or 2 unsubstituted substituents selected from halogen, $C_1$-$C_4$ alkyl, $C_1$-$C_4$ alkoxy, $C_1$-$C_2$ haloalkyl, $C_1$-$C_2$ haloalkoxy and hydroxy.

As used herein, a 5- to 10-membered heterocyclyl moiety is a monocyclic non-aromatic, saturated or unsaturated $C_5$-$C_{10}$ carbocyclic ring, in which at least one, for example 1, 2 or 3, carbon atoms in the ring are replaced with a moiety selected from O, S, SO, $SO_2$, CO and N. Typically, it is a saturated $C_5$-$C_{10}$ ring (preferably a $C_5$-$C_6$ ring) in which 1, 2 or 3 of the carbon atoms in the ring are replaced with a moiety selected from O, S, $SO_2$, CO and NH. Preferably, a heterocyclyl moiety contains up to two CO moieties.

Preferably, a heterocyclyl moiety is a 5- to 6-membered ring. Examples include azetidinyl, pyrazolidinyl, piperidyl, piperidin-2,6-dionyl, piperidin-2-onyl, piperazinyl, morpholinyl, thiomorpholinyl, S-oxothiomorpholinyl, S,S-dioxothiomorpholinyl, 1,3-dioxolanyl, 1,4-dioxanyl, pyrrolidinyl, imidazolidinyl, imidazol-2-onyl, pyrrolidin-2-onyl, tetrahydrofuranyl, tetrahydrothienyl, dithiolanyl, thiazolidinyl, oxazolidinyl, tetrahydropyranyl and pyrazolinyl moieties. Typically, these examples of heterocyclyl moieties are selected from pyrazolidinyl, piperidyl, piperidin-2,6-dionyl, piperidin-2-onyl, piperazinyl, morpholinyl, thiomorpholinyl, S-oxothiomorpholinyl, S,S-dioxothiomorpholinyl, 1,3-dioxolanyl, 1,4-dioxanyl, pyrrolidinyl, imidazolidinyl, imidazol-2-onyl, pyrrolidin-2-onyl, tetrahydrofuranyl, tetrahydrothienyl, dithiolanyl, thiazolidinyl, oxazolidinyl, tetrahydropyranyl and pyrazolinyl moieties Piperidyl, piperidin-2,6-dionyl, piperidin-2-onyl, azetidinyl, piperazinyl, morpholinyl, thiomorpholinyl, S,S-dioxothiomorpholinyl, 1,3-dioxolanyl, pyrrolidinyl, imidazol-2-onyl, pyrrolidin-2-onyl, tetrahydrofuranyl and tetrahydropyranyl moieties are preferred heterocyclyl moieties. Typically, these preferred moieties are selected from piperidyl, piperidin-2,6-dionyl, piperidin-2-onyl, piperazinyl, morpholinyl, thiomorpholinyl, S,S-dioxothiomorpholinyl, 1,3-dioxolanyl, pyrrolidinyl, imidazol-2-onyl, pyrrolidin-2-onyl, tetrahydrofuranyl and tetrahydropyranyl moieties.

A 5- to 10-membered heterocyclyl moiety is optionally fused to a phenyl, 5- to 10-membered heteroaryl or 5- to 10-membered heterocyclyl ring. Preferably, it is non-fused or fused to a phenyl, 5- to 6-membered heteroaryl or 5- to 6-membered heterocyclyl ring. More preferably, it is non-fused or fused to a phenyl ring. Most preferably, it is a non-fused 5- to 6-membered ring as defined above.

A said fused or non-fused heterocyclyl moiety is unsubstituted or substituted as set out above. Typically, it is unsubstituted or substituted by (a) an unsubstituted —$SO_2R'''$ or —$SO_2$—NR'R'' substituent and/or (b) 1 or 2 unsubstituted substituents selected from —$CH_2$—$X_2$, halogen, $C_1$-$C_4$ alkyl, $C_1$-$C_4$ alkoxy, $C_1$-$C_2$ haloalkyl, $C_1$-$C_2$ haloalkoxy, $C_1$-$C_4$ hydroxyalkyl, hydroxy, cyano and —NR'R'', wherein each $X_2$ is the same or different and is cyano or —NR'R'', each R' and R'' is the same or different and represents hydrogen or $C_1$-$C_4$ alkyl and each R''' is $C_1$-$C_4$ alkyl. More typically, it is unsubstituted or substituted by (a) an unsubstituted —$SO_2$—($C_1$-$C_4$ alkyl) or —$SO_2$—NR'R'' substituent, wherein R' and R'' are the same or different and each represent hydrogen or $C_1$-$C_4$ alkyl and/or (b) 1 or 2 unsubstituted substituents selected from halogen, $C_1$-$C_4$ alkyl, $C_1$-$C_4$ alkoxy, $C_1$-$C_2$ haloalkyl, $C_1$-$C_2$ haloalkoxy and hydroxy. Most typically, it is unsubstituted or substituted by (a) an unsubstituted —$SO_2$—($C_1$-$C_4$ alkyl) or —SO$_2$—N(C$_1$-C$_4$ alkyl)$_2$ substituent and/or (b) 1 or 2 unsubstituted substituents selected from C$_1$-C$_4$ alkyl and hydroxy substituents.

In a further embodiment of the invention, a said fused or non-fused heterocyclyl moiety is unsubstituted or substituted by (a) an unsubstituted —SO$_2$R''' substituent and/or (b) 1 or 2 unsubstituted substituents selected from —CH$_2$—X$_2$, halogen, C$_1$-C$_4$ alkyl, C$_1$-C$_4$ alkoxy, C$_1$-C$_2$ haloalkyl, C$_1$-C$_2$ haloalkoxy, C$_1$-C$_4$ hydroxyalkyl, hydroxy, cyano and —NR'R'', wherein each X$_2$ is the same or different and is cyano or —NR'R'', each R' and R'' is the same or different and represents hydrogen or C$_1$-C$_4$ alkyl and each R''' is C$_1$-C$_4$ alkyl. More typically, it is unsubstituted or substituted by (a) an unsubstituted —SO$_2$—(C$_1$-C$_4$ alkyl) substituent and/or (b) 1 or 2 unsubstituted substituents selected from halogen, C$_1$-C$_4$ alkyl, C$_1$-C$_4$ alkoxy, C$_1$-C$_2$ haloalkyl, C$_1$-C$_2$ haloalkoxy and hydroxy. Most typically, it is unsubstituted or substituted by (a) an unsubstituted —SO$_2$—(C$_1$-C$_4$ alkyl) substituent and/or (b) 1 or 2 unsubstituted substituents selected from C$_1$-C$_4$ alkyl and hydroxy substituents.

In a further embodiment of the invention, a said fused or non-fused heterocyclyl moiety is unsubstituted or substituted by 1 or 2 unsubstituted substituents selected from —CH$_2$—X$_2$, halogen, C$_1$-C$_4$ alkyl, C$_1$-C$_4$ alkoxy, C$_1$-C$_2$ haloalkyl, C$_1$-C$_2$ haloalkoxy, C$_1$-C$_4$ hydroxyalkyl, hydroxy, cyano and —NR'R'', wherein each X$_2$ is the same or different and is cyano or —NR'R'', and each R' and R'' is the same or different and represents hydrogen or C$_1$-C$_4$ alkyl. Preferably, it is unsubstituted or substituted by 1 or 2 unsubstituted substituents selected from halogen, C$_1$-C$_4$ alkyl, C$_1$-C$_4$ alkoxy, C$_1$-C$_2$ haloalkyl, C$_1$-C$_2$ haloalkoxy and hydroxy. Most preferably, said preferred substituents are selected from C$_1$-C$_4$ alkyl and hydroxy substituents.

For the avoidance of doubt, although the above definitions of heteroaryl and heterocyclyl groups refer to an "N" moiety which can be present in the ring, as will be evident to a skilled chemist the N atom will be protonated (or will carry a substituent as defined above) if it is attached to each of the adjacent ring atoms via a single bond.

A said phenyl group is optionally fused to a phenyl, 5- to 10-membered heteroaryl or 5- to 10-membered heterocyclyl ring. Preferably, it is non-fused or fused to a phenyl, 5- to 6-membered heteroaryl or 5- to 6-membered heterocyclyl ring. More preferably, it is non-fused or fused to a 5- to 6-membered heteroaryl or heterocyclyl ring. Most preferably, it is non-fused or is a fused ring system which is an indazolyl, indolyl, benzimidazolyl, benzo[1,3]dioxolanyl, benzothiazolyl or 1H-benzo[d]imidazol-2(3H)-onyl moiety.

A said fused or non-fused phenyl group is unsubstituted or substituted as set out above. When a said phenyl group is fused to a phenyl, heteroaryl or heterocyclyl ring, the fused moiety is typically unsubstituted or substituted by 1 or 2 unsubstituted substituents selected from halogen, C$_1$-C$_2$ haloalkyl, C$_1$-C$_2$ alkyl and hydroxy groups. Most preferably, the fused moiety is unsubstituted or substituted by a halogen or C$_1$-C$_2$ haloalkyl substituent.

As used herein, a C$_3$-C$_8$ carbocyclic moiety is a monocyclic non-aromatic saturated or unsaturated hydrocarbon ring having from 3 to 8 carbon atoms. Preferably it is a saturated hydrocarbon ring (i.e. a cycloalkyl moiety) having from 3 to 7 carbon atoms. Examples include cyclopropyl, cyclobutyl, cyclopentyl, cyclohexyl and cycloheptyl.

A C$_3$-C$_8$ carbocyclyl group is optionally fused to a phenyl, 5- to 10-membered heteroaryl or 5- to 10-membered heterocyclyl group. Preferably, it is non-fused or fused to a phenyl, 5- to 6-membered heteroaryl or 5- to 6-membered heterocyclyl ring. More preferably, it is non-fused.

A said fused or non-fused carbocyclyl moiety is unsubstituted or substituted as set out above. Preferably, it is unsubstituted or substituted by 1 or 2 unsubstituted substituents selected from —CH$_2$—X$_2$, halogen, C$_1$-C$_4$ alkyl, C$_1$-C$_4$ alkoxy, C$_1$-C$_2$ haloalkyl, C$_1$-C$_2$ haloalkoxy, C$_1$-C$_4$ hydroxyalkyl, hydroxy, cyano and —NR'R'', wherein each X$_2$ is the same or different and is cyano or —NR'R'', and each R' and R'' is the same or different and represents hydrogen or C$_1$-C$_4$ alkyl. More preferably, it is unsubstituted or substituted by 1 or 2 unsubstituted substituents selected from C$_1$-C$_4$ alkyl, cyano and C$_1$-C$_2$ haloalkyl substituents.

Typically, each A$_1$ moiety is the same or different and represents a non-fused 5- to 6-membered heterocyclyl or C$_3$-C$_8$ carbocyclyl group, or a phenyl or 5- to 6-membered heteroaryl group which is optionally fused to a phenyl ring or to a 5- to 6-membered heteroaryl or 5- to 6-membered heterocyclyl group. More preferably, it is a non-fused group or an indazolyl, indolyl, benzimidazolyl, benzo[1,3]dioxolanyl, 1H-benzo[d]imidazol-2(3H)-onyl, benzothiazolyl or quinoxalinyl group. Most preferably, it is a phenyl, pyrrolidinyl, indazolyl, pyridyl, indolyl, benzimidazolyl, piperidinyl, thienyl, imidazolyl, furanyl, benzo[1,3]dioxolanyl, piperazinyl, benzothiazolyl, S,S-dioxo-thiomorpholinyl, 1H-benzo[d]imidazol-2(3H)-onyl, cyclopropyl or quinoxalinyl group.

A$_1$ is substituted or unsubstituted as set out above. However, when A$_1$ is other than a non-fused phenyl ring, it is typically unsubstituted or substituted by 1 or 2 unsubstituted substituents selected from —CH$_2$—X$_2$, halogen, C$_1$-C$_4$ alkyl, C$_1$-C$_4$ alkoxy, C$_1$-C$_2$ haloalkyl, C$_1$-C$_2$ haloalkoxy, C$_1$-C$_4$ hydroxyalkyl, hydroxy, cyano and —NR'R'', wherein each X$_2$ is the same or different and is cyano or —NR'R'', and each R' and R'' is the same or different and represents hydrogen or C$_1$-C$_4$ alkyl. Preferably, it is unsubstituted or substituted by 1 or 2 unsubstituted substituents selected from halogen, C$_1$-C$_4$ alkyl, C$_1$-C$_4$ alkoxy, C$_1$-C$_2$ haloalkyl, C$_1$-C$_2$ haloalkoxy and hydroxy.

Typically, each A$_1$' moiety is the same or different and represents a non-fused phenyl, C$_3$-C$_8$ carbocyclyl, 5- to 6-membered heteroaryl or 5- to 6-membered heterocyclyl group. More preferably, each A$_1$' moiety is the same or different and represents a phenyl, oxazolyl, piperazinyl, triazolyl, piperidinyl, piperidin-2-onyl, piperidin-2,6-dionyl, morpholinyl, pyrrolidinyl, pyrazolyl, isoxazolyl, cyclohexyl, thiomorpholinyl or S,S-dioxothiomorpholinyl group. More preferably, each A$_1$' moiety is the same or different and represents a morpholino, piperazinyl or S,S-dioxothiomorpholinyl group. Most preferably, each A$_1$' is a piperazinyl moiety.

Preferably, each A$_1$' moiety is unsubstituted or substituted by (a) an unsubstituted —SO$_2$—R''' or —SO$_2$NR'R'' substitutent and/or (b) 1 or 2 unsubstituted substituents selected from halogen, C$_1$-C$_4$ alkyl, C$_1$-C$_4$ alkoxy, C$_1$-C$_2$ haloalkyl, C$_1$-C$_2$ haloalkoxy, C$_1$-C$_4$ hydroxyalkyl, hydroxy and —NR'R'', wherein each R' and R'' are the same or different and are selected from hydrogen and C$_1$-C$_4$ alkyl and R''' represents C$_1$-C$_4$ alkyl. More preferably, each A$_1$' moiety is unsubstituted or substituted by (a) an unsubstituted —SO$_2$—(C$_1$-C$_4$ alkyl) or —SO$_2$—NR'R'' substituent, wherein R' and R'' are the same or different and each represent hydrogen or C$_1$-C$_4$ alkyl, and/or (b) 1 or 2 unsubstituted substituents selected from chlorine, fluorine, bromine, hydroxy, C$_1$-C$_2$ alkyl, C$_1$-C$_2$ haloalkyl and C$_1$-C$_2$ hydroxyalkyl.

In a further embodiment of the invention, each A$_1$' moiety is unsubstituted or substituted by (a) an unsubstituted —SO$_2$—R''' substituent and/or (b) 1 or 2 unsubstituted substituents selected from halogen, C$_1$-C$_4$ alkyl, C$_1$-C$_4$ alkoxy, C$_1$-C$_2$ haloalkyl, C$_1$-C$_2$ haloalkoxy, C$_1$-C$_4$ hydroxyalkyl, hydroxy and —NR'R'', wherein each R' and R'' are the same or different and are selected from hydrogen and $C_1$-$C_4$ alkyl and each R''' represents $C_1$-$C_4$ alkyl. More preferably, each $A_1$' moiety is unsubstituted or substituted by (a) an unsubstituted —$SO_2$—($C_1$-$C_4$ alkyl) substituent and/or (b) 1 or 2 unsubstituted substituents selected from chlorine, fluorine, bromine, hydroxy, $C_1$-$C_2$ alkyl, $C_1$-$C_2$ haloalkyl and $C_1$-$C_2$ hydroxyalkyl.

In a further embodiment of the invention each $A_1$' moiety is unsubstituted or substituted by 1 or 2 unsubstituted substituents selected from halogen, $C_1$-$C_4$ alkyl, $C_1$-$C_4$ alkoxy, $C_1$-$C_2$ haloalkyl, $C_1$-$C_2$ haloalkoxy, $C_1$-$C_4$ hydroxyalkyl, hydroxy and —NR'R'', wherein each R' and R'' are the same or different and are selected from hydrogen and $C_1$-$C_4$ alkyl. More preferably, each $A_1$' moiety is unsubstituted or substituted by 1 or 2 unsubstituted substituents selected from chlorine, fluorine, bromine, hydroxy, $C_1$-$C_2$ alkyl, $C_1$-$C_2$ haloalkyl and $C_1$-$C_2$ hydroxyalkyl.

It is particularly preferred that each $A_1$' moiety is the same or different and represents a group

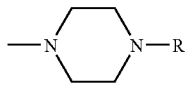

wherein R is $C_1$-$C_4$ alkyl, —$S(O)_2$—R' or —$S(O)_2$—NR'R'' wherein R' and R'' are the same or different and each represent hydrogen or $C_1$-$C_4$ alkyl. Preferably, R is $C_1$-$C_4$ alkyl or —$SO_2$—($C_1$-$C_4$ alkyl).

Typically, each $A_4$ moiety is the same or different and is a non-fused 5- to 6-membered heterocyclyl or $C_3$-$C_8$ carbocyclyl group, or a phenyl or 5- to 6-membered heteroaryl group which is optionally fused to a phenyl ring or to a 5- to 6-membered heteroaryl or 5- to 6-membered heterocyclyl group. Preferably, each $A_4$ moiety is the same or different and represents a non-fused 5- to 6-membered heteroaryl, 5- to 6-membered heterocyclyl or $C_3$-$C_8$ carbocyclyl group, or a phenyl group which is optionally fused to a 5- to 6-membered heteroaryl group. More preferably, each $A_4$ moiety is the same or different and represents phenyl, furanyl, imidazolyl, pyrazolyl, tetrahydrofuranyl, pyrrolidinyl, azetidinyl, piperazinyl, piperidinyl, pyrrolidin-2-onyl, thiadiazolyl, isothiazolyl, $C_3$-$C_8$ cycloalkyl, morpholinyl, thienyl, pyridyl, pyrrolyl, S,S-dioxo-thiomorpholinyl, tetrahydropyranyl, thiazolyl, oxadiazolyl or indazolyl. Most preferably, each $A_4$ moiety is the same or different and represents phenyl, furanyl, imidazolyl, pyrazolyl, tetrahydrofuranyl, piperazinyl, piperidinyl, pyrrolidin-2-onyl, thiadiazolyl, isothiazolyl, $C_3$-$C_8$ cycloalkyl, morpholinyl, thienyl, pyridyl, pyrrolyl, S,S-dioxo-thiomorpholinyl, tetrahydropyranyl, thiazolyl, oxadiazolyl or indazolyl.

Preferably, each $A_4$ moiety is unsubstituted or substituted by (a) a single unsubstituted substituent selected from —$CO_2$R''' and —CONR'R''' and/or (b) 1, 2 or 3 unsubstituted substituents selected from halogen, $C_1$-$C_4$ alkyl, $C_1$-$C_4$ alkoxy, —NR'R''', $C_1$-$C_4$ haloalkyl, $C_1$-$C_4$ haloalkoxy and cyano, wherein R' represents hydrogen or $C_1$-$C_4$ alkyl and R''' represents $C_1$-$C_4$ alkyl. More preferably, each $A_4$ moiety is unsubstituted or substituted by (a) a single unsubstituted —CONR'R''' substituent and/or (b) 1 or 2 unsubstituted substituents selected from fluorine, chlorine, bromine, —NR'R''', $C_1$-$C_4$ alkyl, $C_1$-$C_2$ alkoxy, $C_1$-$C_2$ haloalkyl and cyano, wherein R' is hydrogen or $C_1$-$C_4$ alkyl and R''' represents $C_1$-$C_4$ alkyl.

Typically, each $A_4$' moiety is the same or different and represents a non-fused phenyl, 5- to 6-membered heteroaryl, 5- to 6-membered heterocyclyl or $C_3$-$C_6$ carbocyclyl group. Preferably, each $A_4$' moiety is the same or different and represents a non-fused 5- to 6-membered heteroaryl, 5- to 6-membered heterocyclyl or $C_3$-$C_6$ cycloalkyl group. More preferably, each $A_4$' moiety is the same or different and is a morpholinyl, piperazinyl, isoxazolyl, pyrrolidinyl, S,S-dioxothiomorpholinyl, 2,6-dioxo-piperidinyl, triazolyl, piperidinyl, cyclopropyl or cyclohexyl group. Most preferably, each $A_4$' moiety is the same or different and is a morpholinyl, isoxazolyl, pyrrolidinyl, S,S-dioxothiomorpholinyl, 2,6-dioxo-piperidinyl, triazolyl, piperidinyl, cyclopropyl or cyclohexyl group.

Preferably, each $A_4$' moiety is unsubstituted or substituted by (a) an unsubstituted —$SO_2$—($C_1$-$C_4$ alkyl) substituent and/or (b) 1 or 2 unsubstituted substituents selected from halogen, $C_1$-$C_4$ alkyl, $C_1$-$C_4$ alkoxy, $C_1$-$C_2$ haloalkyl, $C_1$-$C_2$ haloalkoxy, $C_1$-$C_4$ hydroxyalkyl, hydroxy and —NR'R'', wherein each R' and R'' are the same or different and are selected from hydrogen and $C_1$-$C_4$ alkyl. More preferably, each A moiety is unsubstituted or substituted by (a) an unsubstituted —$SO_2$—($C_1$-$C_2$ alkyl) substituent and/or (b) 1 or 2 unsubstituted substituents selected from chlorine, fluorine, bromine, $C_1$-$C_2$ alkyl and $C_1$-$C_2$ haloalkyl. Most preferably, each $A_4$' moiety is unsubstituted or substituted by (a) an unsubstituted —$SO_2$—($C_1$-$C_2$ alkyl) substituent and/or (b) 1 or 2 unsubstituted $C_1$-$C_2$ alkyl groups.

In a further embodiment of the invention, each $A_4$' moiety is unsubstituted or substituted by 1 or 2 unsubstituted substituents selected from halogen, $C_1$-$C_4$ alkyl, $C_1$-$C_4$ alkoxy, $C_1$-$C_2$ haloalkyl, $C_1$-$C_2$ haloalkoxy, $C_1$-$C_4$ hydroxyalkyl, hydroxy and —NR'R'', wherein each R' and R'' are the same or different and are selected from hydrogen and $C_1$-$C_4$ alkyl. More preferably, each $A_4$' moiety is unsubstituted or substituted by 1 or 2 unsubstituted substituents selected from chlorine, fluorine, bromine, $C_1$-$C_2$ alkyl and $C_1$-$C_2$ haloalkyl. Most preferably, each $A_4$' moiety is unsubstituted or substituted by 1 or 2 unsubstituted $C_1$-$C_2$ alkyl groups.

Preferably, $L_1$ is a $C_1$-$C_3$ alkylene group or a $C_1$-$C_3$ hydroxyalkylene group. Preferably, $L_4$ is a $C_1$-$C_3$ alkylene group or a $C_1$-$C_3$ hydroxyalkylene group.

Preferably, $Y_1$ and $Y_4$ are each —CO—.

Preferably, each $L_1$' and $L_4$' are the same or different and represent hydrogen or a $C_1$-$C_2$ alkyl group. Preferably $L_1$' is as defined above and $L_4$' represents a $C_1$-$C_2$ alkyl group.

Preferably, each $Het_1$ and $Het_4$ are the same or different and represent —O—, —NR'— or —S—, wherein R' is hydrogen or $C_1$-$C_2$ alkyl. More preferably, $Het_1$ is as defined above and $Het_4$ represents —O— or —NH—. Most preferably, $Het_1$ is as defined above and $Het_4$ represents —O—.

Typically, $R_1$ is a $C_1$-$C_6$ alkyl group or a moiety -$A_1$, -$L_1$-$A_1$, -$A_1$-$A_1$', -$L_1$-$A_1$-$A_1$', -$A_1$-$L_1$-$A_1$', -$A_1$-$Y_1$-$A_1$', -$A_1$-$Het_1$-$A_1$', -$L_1$-$A_1$-$Het_1$-$A_1$', -$L_1$-$Y_1$-$Het_1$-$A_1$', -$L_1$-$Het_1$-$Y_1$-$A_1$', -$L_1$-$Y_1$-$Het_1$-$L_1$', -$A_1$-$Het_1$-$L_1$-$A_1$', -$A_1$-$L_1$-$Het_1$-$A_1$' or -$L_1$-$Het_1$-$L_1$', wherein $A_1$, $Het_1$, $L_1$, $Y_1$, $A_1$' and $L_1$' are as defined above. Preferably, $R_1$ is a $C_2$-$C_6$ alkyl group or a moiety -$A_1$, -$L_1$-$A_1$, -$A_1$-$A_1$', -$L_1$-$A_1$-$A_1$', -$A_1$-$L_1$-$A_1$', -$A_1$-$Y_1$-$A_1$', -$L_1$-$A_1$-$Het_1$-$A_1$', -$L_1$-$Het_1$-$Y_1$-$A_1$', -$L_1$-$Y_1$-$Het_1$-$L_1$', -$A_1$-$Het_1$-$L_1$-$A_1$', -$A_1$-$L_1$-$Het_1$-$A_1$' or -$L_1$-$Het_1$-$L_1$', wherein $A_1$, $Het_1$, $L_1$, $Y_1$, $A_1$' and $L_1$' are as defined above.

When $R_1$ is -$A_1$-$A_1$', $A_1$ is preferably a non-fused unsubstituted phenyl or piperazinyl group and $A_1$' is preferably a non-fused morpholinyl, S,S-dioxothiomorpholinyl, pyrazolyl, isoxazolyl, triazolyl, piperidin-2-onyl or phenyl group, which is unsubstituted or substituted with 1 or 2 unsubstituted substituents selected from halogen, hydroxy, $C_1$-$C_2$ alkyl and $C_1$-$C_2$ haloalkyl groups. More preferably, $A_1$' is a non-fused morpholinyl, pyrazolyl, isoxazolyl, triazolyl, piperidin-2- onyl or phenyl group, which is unsubstituted or substituted with 1 or 2 unsubstituted substituents selected from halogen, hydroxy, $C_1$-$C_2$ alkyl and $C_1$-$C_2$ haloalkyl groups.

Most preferably, when $R_1$ is -$A_1$-$A_1$' it is an unsubstituted non-fused -phenyl-morpholino group.

In a preferred embodiment of the invention, $R_1$ is -$A_1$-$L_1$-$A_1$'.

When $R_1$ is -$A_1$-$L_1$-$A_1$', $A_1$ is typically a non-fused unsubstituted phenyl group. $L_1$ is typically —$CH_2$— or —$CH_2$—$CH_2$—, more typically —$CH_2$—. $A_1$' is typically a non-fused 5- to 6-membered heterocyclyl group which is unsubstituted or substituted by (a) an unsubstituted —$SO_2$—($C_1$-$C_4$ alkyl) or —$SO_2$—NR'R" group, wherein R' and R" are the same or different and each represent hydrogen or $C_1$-$C_4$ alkyl and/or (b) 1 or 2 unsubstituted substituents selected from halogen, hydroxy, $C_1$-$C_2$ alkyl and $C_1$-$C_2$ alkoxy groups. More preferably, $A_1$' is a non-fused unsubstituted morpholinyl, thiomorpholinyl, S,S -dioxo-thiomorpholinyl, piperidinyl, pyrrolidinyl or piperazinyl group or $A_1$' is a piperazinyl group which is unsubstituted or substituted by (a) an unsubstituted —$SO_2$—($C_1$-$C_4$ alkyl) or —$SO_2$—NR'R" substituent, wherein R' and R" are the same or different and each represent hydrogen or $C_1$-$C_4$ alkyl, and/or (b) 1 or 2 unsubstituted $C_1$-$C_2$ alkyl groups. More preferably still, A' is a piperazinyl group which is unsubstituted or substituted by (a) an unsubstituted —$SO_2$—($C_1$-$C_4$ alkyl) or —$SO_2$—NR'R" substituent, wherein R' and R" are the same or different and each represent hydrogen or $C_1$-$C_4$ alkyl, and/or (b) 1 or 2 unsubstituted $C_1$-$C_2$ alkyl groups.

In a further embodiment of the invention, when $R_1$ is -$A_1$-$L_1$-$A_1$', $A_1$ is typically a non-fused unsubstituted phenyl group. $L_1$ is typically —$CH_2$—. $A_1$' is typically a non-fused 5- to 6-membered heterocyclyl group which is unsubstituted or substituted by (a) an unsubstituted —$SO_2$—($C_1$-$C_4$ alkyl) group and/or (b) 1 or 2 unsubstituted substituents selected from halogen, hydroxy, $C_1$-$C_2$ alkyl and $C_1$-$C_2$ alkoxy groups. More preferably, $A_1$' is a non-fused unsubstituted morpholinyl, thiomorpholinyl, S,S-dioxo -thiomorpholinyl, piperidinyl, pyrrolidinyl or piperazinyl group or $A_1$' is a piperazinyl group which carries a single unsubstituted —$S(O)_2$—($C_1$-$C_4$ alkyl) substituent.

In a further embodiment of the invention, when $R_1$ is -$A_1$-$L_1$-$A_1$', $A_1$ is typically a non-fused unsubstituted phenyl group. $L_1$ is typically —$CH_2$—. All is typically a non-fused 5- to 6-membered heterocyclyl group which is unsubstituted or substituted by 1 or 2 unsubstituted substituents selected from halogen, hydroxy, $C_1$-$C_2$ alkyl and $C_1$-$C_2$ alkoxy groups. More preferably, $A_1$' is a non-fused unsubstituted morpholinyl, thiomorpholinyl, S,S-dioxo-thiomorpholinyl, piperidinyl, pyrrolidinyl or piperazinyl group.

When $R_1$ is -$L_1$-$A_1$-$Het_1$-$A_1$', $L_1$ is typically —$CH_2$—. $A_1$ is typically a non-fused unsubstituted phenyl group. $Het_1$ is typically —O— or —S—, more typically —S—. $A_1$' is typically a non-fused phenyl group which is unsubstituted or substituted by 1 or 2 unsubstituted substituents selected from $C_1$-$C_2$ alkyl and $C_1$-$C_2$ hydroxyalkyl groups. Preferably, when $R_1$ is -$L_1$-$A_1$-$Het_1$-$A_1$', it is —$CH_2$— (phenyl)-S-(4-hydroxymethylphenyl).

When $R_1$ is -$L_1$-$A_1$-$A_1$', L is typically —$CH_2$—. $A_1$ is typically a non-fused unsubstituted phenyl group. All is typically a non-fused 5- to 6-membered heterocyclyl group which is unsubstituted or substituted by 1 or 2 unsubstituted substituents selected from $C_1$-$C_2$ alkyl groups. Preferably, $A_1$' is a morpholinyl or piperazinyl group which is unsubstituted or substituted by 1 or 2 unsubstituted substituents selected from $C_1$-$C_2$ alkyl groups.

When $R_1$ is -$A_1$-$Het_1$-$L_1$-$A_1$' or -$A_1$-$L_1$-$Het_1$-$A_1$', $L_1$ is typically —$CH_2$—. $A_1$ is typically a non-fused unsubstituted phenyl group. $Het_1$ is typically —O— or —NR'—, wherein R' is hydrogen or $C_1$-$C_2$ alkyl. $A_1$' is typically a non -fused phenyl or cyclohexyl group which is unsubstituted or substituted by 1 or 2 unsubstituted substituents selected from $C_1$-$C_2$ alkyl groups.

When $R_1$ is -$A_1$-$Y_1$-$A_1$', $A_1$ is typically a non-fused unsubstituted phenyl group. $Y_1$ is typically —CO—. $A_1$' is typically a non-fused phenyl or 5- to 6-membered heteroaryl group which is unsubstituted or substituted with 1 or 2 $C_1$-$C_2$ alkyl groups. Preferably, $A_1$' is an unsubstituted phenyl or pyridyl group.

When $R_1$ is -$L_1$-$Y_1$-$Het_1$-$L_1$', it is typically a moiety -$L_1$-$Y_1$-$Het_1$-H, wherein $L_1$, $Y_1$ and $Het_1$ are as defined above. Preferably, it is a moiety —$CH(CH_2OH)$—$CO_2H$.

When $R_1$ is -$L_1$-$Het_1$-$Y_1$-$A_1$, it is typically —$CH_2$—NH—CO-$A_1$', wherein $A_1$' is as defined above. Preferably, $A_1$' is a non-fused unsubstituted phenyl group.

When $R_1$ is -$L_1$-$Het_1$-$L_1$', $L_1$' is typically $C_1$-$C_4$ alkyl. Preferably, when $R_1$ is -$L_1$-$Het_1$-$L_1$', $R_1$ is a moiety —($C_1$-$C_4$ alkyl)-NR'—($C_1$-$C_4$ alkyl), wherein R_1 is hydrogen or $C_1$-$C_2$ alkyl.

For the avoidance of doubt, the left hand side of the A and B moieties depicted above are attached to the central biphenyl core. Thus, the right hand side of the depicted moieties are attached to $R_1$ or $R_4$.

Typically, A represents a —($C_1$-$C_2$ alkylene)-NR'—, —CO—NR'—, —NR'—CO—, —CO—, —CO—O— or —O—CO— group, in which R' is hydrogen or $C_1$-$C_2$ alkyl, preferably hydrogen.

Typically, B represents a direct bond, —CO—NR'—, —NR'—CO—, —NR'—$CO_2$—, —NR'—$S(O)_2$—, —$S(O)_2$—NR'—, —CO—, —NR'—, —($C_1$-$C_2$ alkylene)-NR'—, —NR'—CO—NR"— or —NR'—CO—CO—, wherein R' and R" are the same or different and represent hydrogen or $C_1$-$C_2$ alkyl, provided that when B represents a direct bond, $R_4$ is -$A_4$ or -$A_4$-$A_4$', wherein $A_4$ and $A_4$' are as defined above. More typically, B represents a direct bond, —CO—NR'—, —NR'—CO—, —NR'—$CO_2$—, —NR'—$S(O)_2$—, —CO—, —NR'—, —($C_1$-$C_2$ alkylene)-NR'—, —NR'—CO—NR"— or —NR'—CO—CO—, wherein R' and R" are the same or different and represent hydrogen or $C_1$-$C_2$ alkyl, provided that when B represents a direct bond, $R_4$ is -$A_4$ or -$A_4$-$A_4$', wherein $A_4$ and $A_4$' are as defined above. Preferably, B represents —CO—NH—, —NH—CO—, —NH—$CO_2$—, —NH—, —CO—, —NH—$S(O)_2$—, —$S(O)_2$—NH—, —($C_1$-$C_2$ alkylene)-NH—, —NH—CO—NH—, —N($CH_3$)—CO—, —NH—CO—CO— or a direct bond, provided that when B represents a direct bond, $R_4$ is -$A_4$ or -$A_4$-$A_4$', wherein $A_4$ and $A_4$' are as defined above. More preferably, B represents —CO—NH—, —NH—CO—, —NH—$CO_2$—, —NH—, —CO—, —NH—$S(O)_2$—, —($C_1$-$C_2$ alkylene)-NH—, —NH—CO—NH—, —N($CH_3$)—CO—, —NH—CO—CO— or a direct bond, provided that when B represents a direct bond, $R_4$ is -$A_4$ or -$A_4$-$A_4$', wherein $A_4$ and $A_4$' are as defined above. Most preferably, B represents —NH—CO—NH— or —($C_1$-$C_2$ alkylene)-NH—.

Typically, $R_2$ and $R_3$ are the same or different and represent halogen, $C_1$-$C_4$ alkyl, $C_1$-$C_4$ alkoxy, $C_1$-$C_2$ haloalkyl, $C_1$-$C_2$ haloalkoxy or halogen. Preferably, $R_2$ is present on a carbon atom ortho to the phenyl ring of the central biphenyl moiety.

Preferably, $R_3$ is as defined above and $R_2$ is chlorine, trifluoromethoxy or $C_1$-$C_4$ alkyl, more preferably $C_1$-$C_4$ alkyl, most preferably methyl. Typically, $R_3$ is present on a carbon atom ortho to the phenyl ring of the central biphenyl moiety (i.e is present at the 2-position).

In a further embodiment of the invention, $R_2$ is halogen, $C_1$-$C_4$ alkyl, $C_1$-$C_4$ alkoxy, $C_1$-$C_2$ haloalkyl, $C_1$-$C_2$ haloalkoxy or halogen and $R_3$ is chlorine, trifluoromethoxy or $C_1$-$C_4$ alkyl, more preferably $C_1$-$C_4$ alkyl, most preferably methyl.

Typically, $R_4$ is a $C_1$-$C_6$ alkyl group or a moiety -$A_4$, -$A_4$-$A_4$', -$L_4$-$A_4$, -$A_4$-$L_4$-$A_4$', -$A_4$-$Y_4$-$A_4$', -$A_4$-$Het_4$-$A_4$', -$L_4$-$A_4$-$A_4$', -$L_4$-$Het_4$-$A_4$' or -$L_4$-$Het_4$-$L_4$', wherein $A_4$, $A_4$', $L_4$, $Y_4$, $Het_4$ and $L_4$' are as defined above.

Preferably, $R_4$ is a $C_1$-$C_5$ alkyl group or a moiety -$A_4$, -$A_4$-A, -$L_4$-$A_4$, -$A_4$-$L_4$-$A_4$', -$A_4$-$Y_4$-$A_4$' or -$L_4$-$Het_4$-$L_4$' wherein $A_4$, $A_4$', $L_4$, $Y_4$ and $L_4$' are as defined above.

In a preferred embodiment of the invention, $R_4$ is -$A_4$ or -$A_4$-$L_4$-$A_4$'.

When $R_4$ is -$A_4$-$A_4$', $A_4$ is typically a non-fused phenyl or 5- to 6-membered heteroaryl moiety which is unsubstituted or substituted by 1 or 2 unsubstituted substituents selected from $C_1$-$C_2$ alkyl, halogen and $C_1$-$C_2$ haloalkyl substituents. Preferably, $A_4$ is a non-fused phenyl, pyridyl or oxadiazolyl group which is unsubstituted or substituted by 1 or 2 unsubstituted substituents selected from $C_1$-$C_2$ alkyl, halogen and $C_1$-$C_2$ haloalkyl substituents. $A_4$' is typically a non-fused 5- to 6-membered heteroaryl or heterocyclyl group, or a non-fused $C_3$-$C_6$ cycloalkyl group, and is unsubstituted or substituted by 1 or 2 unsubstituted $C_1$-$C_2$ alkyl groups. Preferably, $A_4$' is a non-fused morpholinyl, piperazinyl, isoxazolyl, triazolyl, piperidin-2,2-dionyl, cyclopropyl or cyclohexyl group, which is unsubstituted or substituted by an unsubstituted $C_1$-$C_2$ alkyl group.

In a further embodiment of the invention, when $R_4$ is -$A_4$-$A_4$', $A_4$ is typically a non-fused unsubstituted phenyl or 5- to 6-membered heteroaryl moiety. Preferably, $A_4$ is a non-fused unsubstituted phenyl, pyridyl or oxadiazolyl group. $A_4$' is typically a non-fused 5- to 6-membered heteroaryl or heterocyclyl group, or a non-fused $C_3$-$C_6$ cycloalkyl group, and is unsubstituted or substituted by 1 or 2 unsubstituted $C_1$-$C_2$ alkyl groups. Preferably, $A_4$' is a non-fused morpholinyl, isoxazolyl, triazolyl, piperidin -2,2-dionyl, cyclopropyl or cyclohexyl group, which is unsubstituted or substituted by an unsubstituted $C_1$-$C_2$ alkyl group.

Most preferably, when $R_4$ is -$A_4$-$A_4$', it is a non-fused unsubstituted -phenyl-morpholino group.

When $R_4$ is -$A_4$-$L_4$-$A_4$', $A_4$ is typically a non-fused unsubstituted phenyl group. $L_4$ is typically —$CH_2$—. $A_4$' is typically a non-fused 5- to 6-membered heterocyclyl group, preferably a piperazinyl group or a S,S-dioxo-thiomorpholinyl group, which is unsubstituted or substituted by an unsubstituted —$SO_2$—($C_1$-$C_2$ alkyl) substituent. More typically, $A_4$' is a non-fused unsubstituted 5- to 6-membered heterocyclyl group, preferably a S,S-dioxo-thiomorpholinyl group.

Preferably, when $R_4$ is -$A_4$-$L_4$-$A_4$' it is -phenyl-$CH_2$—(S,S-dioxothiomorpholino), wherein the cyclic moieties are non-fused and unsubstituted, or -phenyl-$CH_2$-piperazinyl-$SO_2$—($C_1$-$C_2$ alkyl).

When $R_4$ is -$A_4$-$Y_4$-$A_4$', $A_4$ is typically a non-fused unsubstituted phenyl group. $Y_4$ is typically —CO—. $A_4$' is typically a non-fused 5- to 6-membered heterocyclyl group which is unsubstituted or substituted by 1 or 2 unsubstituted $C_1$-$C_2$ alkyl groups. Preferably, $A_4$' is a non-fused unsubstituted morpholinyl or piperidinyl group.

When $R_4$ is -$L_4$-$Het_4$-$L_4$', $L_4$ is typically $C_1$-$C_2$ alkylene. $Het_4$ is typically —O— or —NR'—, wherein R' is hydrogen or $C_1$-$C_2$ alkyl. $L_4$' is typically $C_1$-$C_2$ alkylene, more preferably methyl. Preferably, when $R_4$ is -$L_4$-$Het_4$-$L_4$', it is a —($CH_2$)$_2$—O—$CH_3$ or —($C_1$-$C_2$ alkylene)-NR'R", wherein R' and R" are the same or different and each represent hydrogen or $C_1$-$C_4$ alkyl.

In one embodiment of the invention, either:

(a) $R_1$ is a $C_1$-$C_6$ alkyl group or a moiety -$A_1$, -$L_1$-$A_1$, -$A_1$-$A_1$', -$L_1$-$A_1$-$A_1$', -$A_1$-$Y_1$-$A_1$', -$A_1$-$Het_1$-$A_1$', -$L_1$-$A_1$-$Y_1$-$A_1$, -$L_1$-$A_1$-$Het_1$-$A_1$', -$L_1$-$Het_1$-$A_1$, -$L_1$-$Y_1$-$A_1$, -$L_1$-$Y_1$-$Het_1$-$A_1$, -$L_1$-$Het_1$-$Y_1$-$A_1$, -$L_1$-$Y_1$-$Het_1$-$L_1$', -$A_1$-$Y_1$-$Het_1$-$A_1$', -$A_1$-$Het_1$-$Y_1$-$A_1$', -$A_1$-$Het_1$-$L_1$-$A_1$', -$A_1$-$L_1$-$Het_1$-$A_1$' or -$L_1$-$Het_1$-$L_1$', wherein $A_1$, $L_1$, $A_1$', $Y_1$, $Het_1$ and $L_1$' are as defined above; or (b) A represents —NR'—$CO_2$—, —CO—, —$SO_2$—, —NR'—CO—CO—, —CO—O—, —O—CO—, —($C_1$-$C_2$ alkylene)-NR'— or —($C_1$-$C_2$ hydroxyalkylene) -NR'—, wherein R' represents hydrogen or $C_1$-$C_4$ alkyl; or (c) B represents —NR'—$CO_2$—, —CO—, —$SO_2$—, —NR'—CO—CO —, —CO—O—, —O—CO—, —($C_1$-$C_2$ alkylene)-NR'— or —($C_1$-$C_2$ hydroxyalkylene) -NR'—, wherein R' represents hydrogen or $C_1$-$C_4$ alkyl; or (d) $R_4$ represents -$L_4$-$A_4$, -$L_4$-$A_4$-$A_4$', -$A_4$-$Y_4$-$A_4$', -$A_4$-$Het_4$-$A_4$', -$L_4$-$A_4$-$Y_4$-$A_4$', -$L_4$-$A_4$-$Het_4$-$A_4$', -$L_4$-$Het_4$-$A_4$, -$L_4$-$Y_4$-$A_4$, -$L_4$-$Y_4$-$Het_4$-$A_4$, -$L_4$-$Het_4$-$Y_4$-$A_4$, -$L_4$-$Y_4$-$Het_4$-$L_4$', -$A_4$-$Y_4$-$Het_4$-$A_4$', -$A_4$-$Het_4$-$Y_4$-$A_4$', -$A_4$-$Het_4$-$L_4$-$A_4$' or -$A_4$-$L_4$-$Het_4$-$A_4$', wherein $L_4$, $A_4$, $A_4$', $Y_4$, $Het_4$ and $L_4$' are as defined above.

In option (a), $R_1$ is other than -$A_1$-$L_1$-$A_1$'.

In option (c), B typically represents —NR'—CO—CO— or —($C_1$-$C_2$ alkylene)-NR'—, wherein $R_1$ is hydrogen or $C_1$-$C_4$ alkyl. More preferably, B represents —($C_1$-$C_2$ alkylene)-NR'—.

In option (c), $R_4$ typically represents -$L_4$-$A_4$ or -$A_4$-$Y_4$-$A_4$'. Preferably, in this embodiment, either:

$R_1$ is other than -$A_1$-$L_1$-$A_1$', wherein $A_1$, $L_1$ and $A_1$' are as defined above; or B represents —NR'—CO—CO— or —($C_1$-$C_2$ alkylene)-NR'—; or $R_4$ represents -$L_4$-$A_4$ or -$A_4$-$Y_4$-$A_4$', wherein $L_4$, $A_4$, $Y_4$ and $A_4$' are as defined above.

More preferably, in this embodiment, $R_1$ is other than -$A_1$-$L_1$-$A_1$'.

Preferred compounds of formula (I) are those wherein:

$R_1$ is a $C_2$-$C_6$ alkyl group or a moiety -$A_1$, -$L_1$-$A_1$, -$A_1$-$A_1$', -$L_1$-$A_1$-$A_1$', -$A_1$-$L_1$-$A_1$', -$A_1$-$Y_1$-$A_1$', -L-$A_1$-$Het_1$-$A_1$', -$L_1$-$Het_1$-$Y_1$-$A_1$, -$L_1$-$Y_1$-$Het_1$-$L_1$', -$A_1$-$Het_1$-$L_1$-$A_1$', -$A_1$-$L_1$-$Het_1$-$A_1$' or -$L_1$-$Het_1$-$L_1$';

A represents a —($C_1$-$C_2$ alkylene)-NR'—, —CO—NR'—, —NR'—CO—, —CO—, —CO—O— or —O—CO— group, in which $R_1$ is hydrogen or $C_1$-$C_2$ alkyl;

B represents a direct bond, —CO—NR'—, —NR'—CO—, —NR'—$CO_2$—, —NR'—S(O)$_2$—, —S(O)$_2$—NR'—, —CO—, —NR'—, —($C_1$-$C_2$ alkylene) -NR'—, —NR'—CO—NR"— or —NR'—CO—CO—, wherein R' and R" are the same or different and represent hydrogen or $C_1$-$C_2$ alkyl, provided that when B represents a direct bond, $R_4$ is -$A_4$ or -$A_4$-$A_4$';

$R_2$ and $R_3$ are the same or different and each represents $C_1$-$C_4$ alkyl, $C_1$-$C_4$ alkoxy, $C_1$-$C_2$ haloalkyl, $C_1$-$C_2$ haloalkoxy or halogen;

n and m are the same or different and each represent 0 or 1;

$R_4$ is a $C_1$-$C_5$ alkyl group or a moiety -$A_4$, -$A_4$-$A_4$', -$L_4$-$A_4$, -$A_4$-$L_4$-$A_4$', -$A_4$-$Y_4$-$A_4$' or -$L_4$-$Het_4$-$L_4$';

each $A_1$, $A_4$, $A_1$' and $A_4$' are the same or different and represent a phenyl, 5- to 6-membered heteroaryl, 5- to 6-membered heterocyclyl or $C_3$-$C_8$ carbocyclyl moiety;

each $L_1$ and $L_4$ is the same or different and represents a $C_1$-$C_4$ alkylene or a $C_1$-$C_4$ hydroxyalkylene group;

each $Y_1$ and $Y_4$ is the same or different and represents —CO—;

each $L_1'$ and $L_4'$ is the same or different and represents hydrogen or a $C_1$-$C_2$ alkyl group; and each $Het_1$ and $Het_4$ is the same or different and represents —O—, —NR'— or —S—, wherein R' is hydrogen or $C_1$-$C_2$ alkyl, the phenyl, heteroaryl, heterocyclyl and carbocyclyl moieties in $R^1$ and $R^4$ being optionally fused to a phenyl, 5- to 6-membered heteroaryl or 5- to 6-membered heterocyclyl ring; and the phenyl, heteroaryl, heterocyclyl and carbocyclyl moieties in $R^1$ and $R^4$ being unsubstituted or substituted by (a) a single unsubstituted substituent selected from —CH$_2$—X$_1$, —CO$_2$—R''', —SO$_2$R''', —SO$_2$NR'R''', —CONR'R''', —NR'—CO—R''', —NR'—SO$_2$—R''' and —CO—NR'—(C$_1$-C$_2$ alkyl)-NR'R''', and/or (b) 1 or 2 unsubstituted substituents selected from —CH$_2$—X$_2$, halogen, C$_1$-C$_4$ alkyl, C$_1$-C$_4$ alkoxy, C$_1$-C$_2$ haloalkyl, C$_1$-C$_2$ haloalkoxy, C$_1$-C$_4$ hydroxyalkyl, hydroxy, cyano and —NR'R", wherein X$_1$ is —CO$_2$R''', —NR'—CO$_2$—R''' or —SO$_2$NR'R''', each X$_2$ is the same or different and is cyano or —NR'R", each R' and R" are the same or different and represent hydrogen or C$_1$-C$_4$ alkyl and each R''' is the same or different and represents C$_1$-C$_4$ alkyl.

Typically, in these preferred compounds of formula (I), B represents a direct bond, —CO—NR'—, —NR'—CO—, —NR'—CO$_2$—, —NR'—S(O)$_2$—, —CO—, —NR'—, —(C$_1$-C$_2$ alkylene)-NR'—, —NR'—CO—NR"— or —NR'—CO—CO—, wherein R' and R" are the same or different and represent hydrogen or C$_1$-C$_2$ alkyl, provided that when B represents a direct bond, R$_4$ is -A$_4$ or -A$_4$-A$_4'$;

Typically, in these preferred compounds of formula (I), the phenyl, heteroaryl, heterocyclyl and carbocyclyl moieties in R$^1$ and R$^4$ are unsubstituted or substituted by (a) an unsubstituted substituent selected from —CH$_2$—X$_1$, —CO$_2$—R''', —SO$_2$NR'R''', —CONR'R''', —NR'—CO—R''', —NR'—SO$_2$—R''' and —CO—NR'—(C$_1$-C$_2$ alkyl)-NR'R''', and/or (b) 1 or 2 unsubstituted substituents selected from —CH$_2$—X$_2$, halogen, C$_1$-C$_4$ alkyl, C$_1$-C$_4$ alkoxy, C$_1$-C$_2$ haloalkyl, C$_1$-C$_2$ haloalkoxy, C$_1$-C$_4$ hydroxyalkyl, hydroxy, cyano and —NR'R", wherein X$_1$ is —CO$_2$R''', —NR'—CO$_2$—R''' or —SO$_2$NR'R''', each X$_2$ is the same or different and is cyano or —NR'R", each R' and R" are the same or different and represent hydrogen or C$_1$-C$_4$ alkyl and each R''' is the same or different and represents C$_1$-C$_4$ alkyl.

Typically, in these preferred compounds of the invention, either:

(a) $R_1$ is a $C_2$-$C_6$ alkyl group or a moiety -A$_1$, -L$_1$-A$_1$, -A$_1$-A$_1'$, -L$_1$-A$_1$-A$_1'$, -A$_1$-Y$_1$-A$_1'$, -L-A$_1$-Het$_1$-A$_1'$, -L$_1$-Het$_1$-Y$_1$-A$_1'$, -L$_1$-Y$_1$-Het$_1$-Y$_1$-L$_1'$, -A$_1$-Het$_1$-L$_1$-A$_1'$, -A$_1$-L$_1$-Het$_1$-A$_1'$ or -L$_1$-Het$_1$-L$_1'$, wherein A$_1$, L$_1$, A$_1'$, Y$_1$, Het$_1$ and L$_1'$ are as defined above; or (b) A is —CO—, —CO—O, —O—CO— or —(C$_1$-C$_2$ alkylene) -NR'—, wherein R' is hydrogen or C$_1$-C$_2$ alkyl; or (c) B is —NR'—CO$_2$—, —CO—, —NR'—CO—CO— or —(C$_1$-C$_2$ alkylene)-NR'—, wherein R$_1$ is hydrogen or C$_1$-C$_2$ alkyl; or (d) R$_4$ is -L$_4$-A$_4$ or -A$_4$-Y$_4$-A$_4'$, wherein L$_4$, A$_4$, Y$_4$ and A$_4'$ are as defined above.

Further preferred compounds of formula (I) are those wherein:

$R_1$ is a $C_2$-$C_6$ alkyl group or a moiety -A$_1$, -L$_1$-A$_1$, -A$_1$-A$_1'$, -L$_1$-A$_1$-A$_1'$, -A$_1$-L$_1$-A$_1'$, -A$_1$CO-A$_1'$, -L$_1$-A$_1$-Het$_1$-A$_1'$, -L$_1$-Het$_1$-CO-A$_1'$, -L$_1$-CO-Het$_1$-L$_1'$, -A$_1$-Het$_1$-L$_1$-A$_1'$, -A$_1$-L$_1$-Het$_1$-A$_1'$ or -L-Het$_1$-L$_1'$;

A represents a —(C$_1$-C$_2$ alkylene)-NH—, —CO—NH—, —NH—CO—, —CO—, —CO—O— or —O—CO group;

B represents —CO—NH—, —NH—CO—, —NH—CO$_2$—, —NH—, —CO—, —NH—S(O)$_2$—, —S(O)$_2$—NH—, —(C$_1$-C$_2$ alkylene)-NH—, —NH—CO—NH—, —N(CH$_3$)—CO—, —NH—CO—CO— or a direct bond, provided that when B represents a direct bond, R$_4$ is -A$_4$ or -A$_4$-A;

$R_2$ is $C_1$-$C_4$ alkyl;

$R_3$ is $C_1$-$C_4$ alkyl, $C_1$-$C_4$ alkoxy, $C_1$-$C_2$ haloalkyl, $C_1$-$C_2$ haloalkoxy or halogen;

n and m are the same or different and each represent 0 or 1;

$R_4$ is a $C_1$-$C_5$ alkyl group or a moiety -A$_4$, -A$_4$-A$_4'$, -L$_4$-A$_4$, -A$_4$-L$_4$-A$_4'$, -A$_4$-CO-A$_4'$ or -L$_4$-Het$_4$-L$_4'$;

each $A_1$ moiety is the same or different and represents a non-fused 5- to 6-membered heterocyclyl or $C_3$-$C_8$ carbocyclyl group, or a phenyl or 5- to 6-membered heteroaryl group which is optionally fused to a phenyl ring or to a 5- to 6-membered heteroaryl or 5- to 6-membered heterocyclyl group, wherein (i) when A$_1$ is a non-fused phenyl ring it is unsubstituted or substituted by (a) a single unsubstituted substituent selected from —CH$_2$—X$_1$, —CO$_2$—R''', —SO$_2$NR'R''', —CONR''', —NR'—CO—R''', —NR'—SO$_2$—R''' and —CO—NR'—(C$_1$-C$_2$ alkyl)-NR'R''', and/or (b) 1 or 2 unsubstituted substituents selected from —CH$_2$—X$_2$, halogen, C$_1$-C$_4$ alkyl, C$_1$-C$_4$ alkoxy, C$_1$-C$_2$ haloalkyl, C$_1$-C$_2$ haloalkoxy, C$_1$-C$_4$ hydroxyalkyl, hydroxy, cyano and —NR'R", wherein X$_1$ is —CO$_2$R''', —NR'—CO$_2$—R''' or —SO$_2$—NR'R''', each X$_2$ is the same or different and is cyano or —NR'R", each R' and R" are the same or different and represent hydrogen or C$_1$-C$_4$ alkyl and each R''' is the same or different and represents C$_1$-C$_4$ alkyl and (ii) when A$_1$ is other than a non-fused phenyl group it is unsubstituted or substituted by 1 or 2 unsubstituted substituents selected from halogen, C$_1$-C$_4$ alkyl, C$_1$-C$_4$ alkoxy, C$_1$-C$_2$ haloalkyl, C$_1$-C$_2$ haloalkoxy and hydroxy;

each $A_1'$ moiety is the same or different and represents a non-fused phenyl, $C_3$-$C_8$ carbocyclyl, 5- to 6-membered heteroaryl or 5- to 6-membered heterocyclyl group which is unsubstituted or substituted by (a) an unsubstituted —SO$_2$—(C$_1$-C$_4$ alkyl) or —SO$_2$—NR'R" substituent, wherein R' and R" are the same or different and each represent hydrogen or C$_1$-C$_4$ alkyl, and/or (b) 1 or 2 unsubstituted substituents selected from chlorine, fluorine, bromine, hydroxy, C$_1$-C$_2$ alkyl, C$_1$-C$_2$ haloalkyl and C$_1$-C$_2$ hydroxyalkyl;

each $A_4$ moiety is the same or different and is a non-fused 5- to 6-membered heterocyclyl or $C_3$-$C_8$ carbocyclyl group, or a phenyl or 5- to 6-membered heteroaryl group which is optionally fused to a phenyl ring or to a 5- to 6-membered heteroaryl or 5- to 6-membered heterocyclyl group, each A$_4$ moiety being unsubstituted or substituted by (a) a single unsubstituted —CONR'R''' substituent and/or (b) 1 or 2 unsubstituted substituents selected from fluorine, chlorine, bromine, —NR'R''', C$_1$-C$_4$ alkyl, C$_1$-C$_2$ alkoxy, C$_1$-C$_2$ haloalkyl and cyano, wherein R$_1$ is hydrogen or C$_1$-C$_4$ alkyl and R''' represents C$_1$-C$_4$ alkyl;

each $A_4'$ moiety is the same or different and represents a non-fused 5- to 6-membered heteroaryl, 5- to 6-membered heterocyclyl or $C_3$-$C_6$ cycloalkyl group which is unsubstituted or substituted by (a) an unsubstituted —SO$_2$—(C$_1$-C$_2$ alkyl) substituent and/or (b) 1 or 2 unsubstituted substituents selected from chlorine, fluorine, bromine, $C_1$-$C_2$ alkyl and $C_1$-$C_2$ haloalkyl;

each $L_1$ and $L_4$ are the same or different and represent a $C_1$-$C_3$ alkylene group or a $C_1$-$C_3$ hydroxyalkylene group $L_1'$ represents hydrogen or a $C_1$-$C_2$ alkyl group;

$L_4'$ represents a $C_1$-$C_2$ alkyl group;

$Het_1$ represents —O—, —NR'— or —S—, wherein $R_1$ is hydrogen or $C_1$-$C_2$ alkyl; and $Het_4$ represents —O— or —NH—.

Additional preferred compounds of the formula (I) are those wherein:

$R_1$ is a $C_2$-$C_6$ alkyl group or a moiety -$A_1'$, -$L_1$-$A_1$, -$A_1$-$A_1'$, -$L_1$-$A_1$-$A_1'$, -$A_1$-$L_1$-$A_1'$, -A, —CO-$A_1'$, -$L_1$-$A_1$-$Het_1$-$A_1'$, -$L_1$-$Het_1$-CO-$A_1'$, -$L_1$-CO-$Het_1$-$L_1'$, -$A_1$-$Het_1$-$L_1$-$A_1'$, -$A_1$-$L_1$-$Het_1$-$A_1'$ or -$L_1$-$Het_1$-$L_1'$;

A represents a —($C_1$-$C_2$ alkylene)-NH—, —CO—NH—, —NH—CO—, —CO—, —CO—O— or —O—CO group;

B represents —CO—NH—, —NH—CO—, —NH—CO$_2$—, —NH—, —CO—, —NH—S(O)$_2$—, —($C_1$-$C_2$ alkylene)-NH—, —NH—CO—NH—, —N(CH$_3$)—CO—, —NH—CO—CO— or a direct bond, provided that when B represents a direct bond, $R_4$ is -$A_4$ or -$A_4$-$A_4'$;

$R_2$ is $C_1$-$C_4$ alkyl;

$R_3$ is $C_1$-$C_4$ alkyl, $C_1$-$C_4$ alkoxy, $C_1$-$C_2$ haloalkyl, $C_1$-$C_2$ haloalkoxy or halogen;

n and m are the same or different and each represent 0 or 1;

$R_4$ is a $C_1$-$C_5$ alkyl group or a moiety -$A_4$, -$A_4$-$A_4'$, -$L_4$-$A_4$, -$A_4$-$L_4$-$A_4'$, -$A_4$-CO-$A_4'$ or -$L_4$-O-$L_4'$;

each $A_1$ moiety is the same or different and represents a non-fused 5- to 6-membered heterocyclyl or $C_3$-$C_8$ carbocyclyl group, or a phenyl or 5- to 6-membered heteroaryl group which is optionally fused to a phenyl ring or to a 5- to 6-membered heteroaryl or 5- to 6-membered heterocyclyl group, wherein (i) when $A_1$ is a non-fused phenyl ring it is unsubstituted or substituted by (a) a single unsubstituted substituent selected from —CH$_2$—X$_1$, —CO$_2$—R''', —SO$_2$NR'R''', —CONR'R''', —NR'—CO—R''', —NR'—SO$_2$—R''' and —CO—NR'—(C$_1$-C$_2$ alkyl)-NR'R''', and/or (b) 1 or 2 unsubstituted substituents selected from —CH$_2$—X$_2$, halogen, $C_1$-$C_4$ alkyl, $C_1$-$C_4$ alkoxy, $C_1$-$C_2$ haloalkyl, $C_1$-$C_2$ haloalkoxy, $C_1$-$C_4$ hydroxyalkyl, hydroxy, cyano and —NR'R''', wherein X$_1$ is —CO$_2$R''', —NR'—CO$_2$—R''' or —SO$_2$—NR'R''', each X$_2$ is the same or different and is cyano or —NR'R''', each R' and R'' are the same or different and represent hydrogen or $C_1$-$C_4$ alkyl and each R''' is the same or different and represents $C_1$-$C_4$ alkyl and (ii) when $A_1$ is other than a non-fused phenyl group it is unsubstituted or substituted by 1 or 2 unsubstituted substituents selected from halogen, $C_1$-$C_4$ alkyl, $C_1$-$C_4$ alkoxy, $C_1$-$C_2$ haloalkyl, $C_1$-$C_2$ haloalkoxy and hydroxy;

each $A_1'$ moiety is the same or different and represents a non-fused phenyl, $C_3$-$C_8$ carbocyclyl, 5- to 6-membered heteroaryl or 5- to 6-membered heterocyclyl group which is unsubstituted or substituted by (a) a single unsubstituted —SO$_2$—Ry substituent and/or (b) 1 or 2 unsubstituted substituents selected from chlorine, fluorine, bromine, hydroxy, $C_1$-$C_2$ alkyl, $C_1$-$C_2$ haloalkyl and $C_1$-$C_2$ hydroxyalkyl;

each $A_4$ moiety is the same or different and is a non-fused 5- to 6-membered heterocyclyl or $C_3$-$C_8$ carbocyclyl group, or a phenyl or 5- to 6-membered heteroaryl group which is optionally fused to a phenyl ring or to a 5- to 6-membered heteroaryl or 5- to 6-membered heterocyclyl group, each $A_4$ moiety being unsubstituted or substituted by (a) a single unsubstituted —CONR'R''' substituent and/or (b) 1 or 2 unsubstituted substituents selected from fluorine, chlorine, bromine, —NR'R''', $C_1$-$C_4$ alkyl, $C_1$-$C_2$ alkoxy, $C_1$-$C_2$ haloalkyl and cyano, wherein R' is hydrogen or $C_1$-$C_4$ alkyl and R''' represents $C_1$-$C_4$ alkyl;

each $A_4'$ moiety is the same or different and represents a non-fused 5- to 6-membered heteroaryl, 5- to 6-membered heterocyclyl or $C_3$-$C_6$ cycloalkyl group which is unsubstituted or substituted by 1 or 2 unsubstituted substituents selected from chlorine, fluorine, bromine, $C_1$-$C_2$ alkyl and $C_1$-$C_2$ haloalkyl;

each $L_1$ and $L_4$ are the same or different and represent a $C_1$-$C_3$ alkylene group or a $C_1$-$C_3$ hydroxyalkylene group $L_1'$ represents hydrogen or a $C_1$-$C_2$ alkyl group;

$L_4'$ represents a $C_1$-$C_2$ alkyl group; and $Het_1$ represents —O—, —NR'— or —S—, wherein R' is hydrogen or $C_1$-$C_2$ alkyl.

Typically, in these additional preferred compounds of formula (I), each $A_1'$ moiety is the same or different and represents a non-fused phenyl, $C_3$-$C_8$ carbocyclyl, 5- to 6-membered heteroaryl or 5- to 6-membered heterocyclyl group which is unsubstituted or substituted by 1 or 2 unsubstituted substituents selected from chlorine, fluorine, bromine, hydroxy, $C_1$-$C_2$ alkyl, $C_1$-$C_2$ haloalkyl and $C_1$-$C_2$ hydroxyalkyl.

Typically, in these additional preferred compounds of the invention, either:

(a) $R_1$ is a $C_2$-$C_6$ alkyl group or a moiety -$A_1$, -$L_1$-$A_1$, -$A_1$-$A_1'$, -$L_1$-$A_1$-$A_1'$, -$A_1$-CO-$A_1'$, -$L_1$-$A_1$-$Het_1$-$A_1'$, -$L_1$-$Het_1$-CO-$A_1'$, -$L_1$-CO-$Het_1$-$L_1'$, -$A_1$-$Het_1$-$L_1$-$A_1'$, -$A_1$-$L_1$-$Het_1$-$A_1'$ or -$L_1$-$Het_1$-$L_1'$, wherein $A_1$, $L_1$, $A_1'$, $Het_1$ and $L_1'$ are as defined above; or (b) A is —($C_1$-$C_2$ alkylene)-NH—, —CO—, —CO—O— or —O—CO—; or (c) B is —NH—CO$_2$—, —CO—, —NH—CO—CO— or —($C_1$-$C_2$ alkylene)-NH—; or (d) $R_4$ is -$L_4$-$A_4$ or -$A_4$-CO-$A_4'$, wherein $L_4$, $A_4$ and $A_4'$ are as defined above.

Particularly preferred compounds of formula (I) are those wherein:

$R_1$ is a $C_2$-$C_6$ alkyl group or a moiety -$A_1$, -$L_1$-$A_1$, -$A_1$-$A_1'$, -$L_1$-$A_1$-$A_1'$, -$A_1$-$L_1$-$A_1'$, -$A_1$-CO-$A_1'$, -$L_1$-$A_1$-$Het_1$-$A_1'$, -$L_1$-$Het_1$-CO-$A_1'$, -$L_1$-CO-$Het_1$-$L_1'$, -A, -$Het_1$-$L_1$-$A_1'$, -$A_1$-$L_1$-$Het_1$-$A_1'$ or -$L_1$-$Het_1$-$L_1'$;

A represents a —($C_1$-$C_2$ alkylene)-NH—, —CO—NH—, —NH—CO—, —CO—, —CO—O— or —O—CO group;

B represents —CO—NH—, —NH—CO—, —NH—CO$_2$—, —NH—, —CO—, —NH—S(O)$_2$—, —S(O)$_2$—NH—, —($C_1$-$C_2$ alkylene)-NH—, —NH—CO—NH—, —N(CH$_3$)—CO—, —NH—CO—CO— or a direct bond, provided that when B represents a direct bond, $R_4$ is -$A_4$ or -$A_4$-$A_4'$;

$R_2$ is $C_1$-$C_4$ alkyl;

$R_3$ is $C_1$-$C_4$ alkyl, $C_1$-$C_4$ alkoxy, $C_1$-$C_2$ haloalkyl, $C_1$-$C_2$ haloalkoxy or halogen;

n and m are the same or different and each represent 0 or 1;

$R_4$ is a $C_1$-$C_5$ alkyl group or a moiety -$A_4$, -$A_4$-A, -$L_4$-$A_1$, -$A_1$-$L_4$-$A_4'$, -$A_4$-CO-$A_4'$ or -$L_4$-$Het_4$-$L_4'$;

each $A_1$ moiety is the same or different and represents a phenyl, pyrrolidinyl, indazolyl, pyridyl, indolyl, benzimidazolyl, piperidinyl, thienyl, imidazolyl, furanyl, benzo[1,3]dioxolanyl, piperazinyl, benzothiazolyl, S,S-dioxo-thiomorpholinyl, 1H-benzo[d]imidazol-2(3H)-onyl, cyclopropyl or quinoxalinyl group, wherein (i)

when $A_1$ is a phenyl ring it is unsubstituted or substituted by (a) a single unsubstituted substituent selected from —$CH_2$—$X_1$, —$CO_2$—R''', —$SO_2$NR'R''', —CONR'R''', —NR'—CO—R''', —NR'—$SO_2$—R''' and —CO—NR'—($C_1$-$C_2$ alkyl)-NR'R''', and/or (b) 1 or 2 unsubstituted substituents selected from —$CH_2$—$X_2$, halogen, $C_1$-$C_4$ alkyl, $C_1$-$C_4$ alkoxy, $C_1$-$C_2$ haloalkyl, $C_1$-$C_2$ haloalkoxy, $C_1$-$C_4$ hydroxyalkyl, hydroxy, cyano and —NR'R'', wherein $X_1$ is —$CO_2$R''', —NR'—$CO_2$—R''' or —$SO_2$—NR'R''', each $X_2$ is the same or different and is cyano or —NR'R'', each R' and R'' are the same or different and represent hydrogen or $C_1$-$C_4$ alkyl and each R''' is the same or different and represents $C_1$-$C_4$ alkyl and (ii) when $A_1$ is other than a phenyl group it is unsubstituted or substituted by 1 or 2 unsubstituted substituents selected from halogen, $C_1$-$C_4$ alkyl, $C_1$-$C_4$ alkoxy, $C_1$-$C_2$ haloalkyl, $C_1$-$C_2$ haloalkoxy and hydroxy;

each $A_1'$ moiety is the same or different and represents a phenyl, oxazolyl, piperazinyl, triazolyl, piperidinyl, piperidin-2-onyl, piperidin-2,6-dionyl, morpholinyl, pyrrolidinyl, pyrazolyl, isoxazolyl, cyclohexyl, thiomorpholinyl or S,S-dioxothiomorpholinyl group which is unsubstituted or substituted by (a) a single unsubstituted —$SO_2$—($C_1$-$C_4$ alkyl) or —$SO_2$—NR'R'' substituent, wherein R' and R'' are the same or different and each represent hydrogen or $C_1$-$C_4$ alkyl and/or (b) 1 or 2 unsubstituted substituents selected from chlorine, fluorine, bromine, hydroxy, $C_1$-$C_2$ alkyl, $C_1$-$C_2$ haloalkyl and $C_1$-$C_2$ hydroxyalkyl;

each $A_4$ moiety is the same or different and is phenyl, furanyl, imidazolyl, pyrazolyl, pyrrolidinyl, azetidinyl, tetrahydrofuranyl, piperazinyl, piperidinyl, pyrrolidin-2-onyl, thiadiazolyl, isothiazolyl, $C_3$-$C_8$ cycloalkyl, morpholinyl, thienyl, pyridyl, pyrrolyl, S,S-dioxo-thiomorpholinyl, tetrahydropyranyl, thiazolyl, oxadiazolyl or indazolyl group, each $A_4$ moiety being unsubstituted or substituted by (a) a single unsubstituted —CONR'R''' substituent and/or (b) 1 or 2 unsubstituted substituents selected from fluorine, chlorine, bromine, —NR'R''', $C_1$-$C_4$ alkyl, $C_1$-$C_2$ alkoxy, $C_1$-$C_2$ haloalkyl and cyano, wherein $R_1$ is hydrogen or $C_1$-$C_4$ alkyl and R''' represents $C_1$-$C_4$ alkyl;

each $A_4'$ moiety is the same or different and represents a morpholinyl, piperazinyl, isoxazolyl, pyrrolidinyl, S,S-dioxothiomorpholinyl, 2,6-dioxo-piperidinyl, triazolyl, piperidinyl, cyclopropyl or cyclohexyl group which is unsubstituted or substituted by (a) an unsubstituted —S(O)$_2$—($C_1$-$C_2$ alkyl) substituent and/or (b) 1 or 2 unsubstituted substituents selected from chlorine, fluorine, bromine, $C_1$-$C_2$ alkyl and $C_1$-$C_2$ haloalkyl;

each $L_1$ and $L_4$ are the same or different and represent a $C_1$-$C_3$ alkylene group or a $C_1$-$C_3$ hydroxyalkylene group $L_1'$ represents hydrogen or a $C_1$-$C_2$ alkyl group;

$L_4'$ represents a $C_1$-$C_2$ alkyl group;

$Het_1$ represents —O—, —NR'— or —S—, wherein $R_1$ is hydrogen or $C_1$-$C_2$ alkyl; and $Het_4$ represents —O— or —NH-Additional particularly preferred compounds of formula (I) are those wherein $R_1$ is a $C_2$-$C_6$ alkyl group or a moiety -$A_1$, -$L_1$-$A_1$, -$A_1$-$A_1'$, -$L_1$-$A_1$-$A_1'$, -$A_1$-$L_1$-$A_1'$, -$A_1$-CO-$A_1'$, -$L_1$-$A_1$-$Het_1$-$A_1$, -$L_1$-$Het_1$-CO-$A_1$, -$L_1$-CO-$Het_1$-$L_1'$, -$A_1$-$Het_1$-$L_1$-$A_1'$, -$A_1$-$L_1$-$Het_1$-$A_1'$ or -$L_1$-$Het_1$-$L_1'$;

A represents a —($C_1$-$C_2$ alkylene)-NH—, —CO—NH—, —NH—CO—, —CO—, —CO—O— or —O—CO group;

B represents —CO—NH—, —NH—CO—, —NH—$CO_2$—, —NH—, —CO—, —NH—S(O)$_2$—, —($C_1$-$C_2$ alkylene)-NH—, —NH—CO—NH—, —N($CH_3$)—CO—, —NH—CO—CO— or a direct bond, provided that when B represents a direct bond, $R_4$ is -$A_4$ or -$A_4$-A;

$R_2$ is $C_1$-$C_4$ alkyl;

$R_3$ is $C_1$-$C_4$ alkyl, $C_1$-$C_4$ alkoxy, $C_1$-$C_2$ haloalkyl, $C_1$-$C_2$ haloalkoxy or halogen;

n and m are the same or different and each represent 0 or 1;

$R_4$ is a $C_1$-$C_5$ alkyl group or a moiety -$A_4$, -$A_4$-$A_4'$, -$L_4$-$A_4$, -$A_4$-$L_4$-$A_4'$, -$A_4$-CO-$A_4'$ or -$L_4$-O-$L_4'$;

each $A_1$ moiety is the same or different and represents a phenyl, pyrrolidinyl, indazolyl, pyridyl, indolyl, benzimidazolyl, piperidinyl, thienyl, imidazolyl, furanyl, benzo[1,3]dioxolanyl, piperazinyl, benzothiazolyl, S,S-dioxo-thiomorpholinyl, 1H-benzo[d]imidazol-2(3H)-onyl, cyclopropyl or quinoxalinyl group, wherein (i) when $A_1$ is a phenyl ring it is unsubstituted or substituted by (a) a single unsubstituted substituent selected from —$CH_2$—$X_1$, —$CO_2$—R''', —$SO_2$NR'R''', —CONR'R''', —NR'—CO—R''', —NR'—$SO_2$—R''' and —CO—NR'—($C_1$-$C_2$ alkyl)-NR'R''', and/or (b) 1 or 2 unsubstituted substituents selected from —$CH_2$—$X_2$, halogen, $C_1$-$C_4$ alkyl, $C_1$-$C_4$ alkoxy, $C_1$-$C_2$ haloalkyl, $C_1$-$C_2$ haloalkoxy, $C_1$-$C_4$ hydroxyalkyl, hydroxy, cyano and —NR'R'', wherein $X_1$ is —$CO_2$R''', —NR'—$CO_2$—R''' or —$SO_2$—NR'R''', each $X_2$ is the same or different and is cyano or —NR'R'', each R' and R'' are the same or different and represent hydrogen or $C_1$-$C_4$ alkyl and each R''' is the same or different and represents $C_1$-$C_4$ alkyl and (ii) when $A_1$ is other than a phenyl group it is unsubstituted or substituted by 1 or 2 unsubstituted substituents selected from halogen, $C_1$-$C_4$ alkyl, $C_1$-$C_4$ alkoxy, $C_1$-$C_2$ haloalkyl, $C_1$-$C_2$ haloalkoxy and hydroxy;

each $A_1'$ moiety is the same or different and represents a phenyl, oxazolyl, piperazinyl, triazolyl, piperidinyl, piperidin-2-onyl, piperidin-2,6-dionyl, morpholinyl, pyrrolidinyl, pyrazolyl, isoxazolyl, cyclohexyl, thiomorpholinyl or S,S-dioxothiomorpholinyl group which is unsubstituted or substituted by (a) a single unsubstituted —$SO_2$—($C_1$-$C_4$ alkyl) substituent and/or (b) 1 or 2 unsubstituted substituents selected from chlorine, fluorine, bromine, hydroxy, $C_1$-$C_2$ alkyl, $C_1$-$C_2$ haloalkyl and $C_1$-$C_2$ hydroxyalkyl;

each $A_4$ moiety is the same or different and is phenyl, furanyl, imidazolyl, pyrazolyl, tetrahydrofuranyl, piperazinyl, piperidinyl, pyrrolidin-2-onyl, thiadiazolyl, isothiazolyl, $C_3$-$C_8$ cycloalkyl, morpholinyl, thienyl, pyridyl, pyrrolyl, S,S-dioxo-thiomorpholinyl, tetrahydropyranyl, thiazolyl, oxadiazolyl or indazolyl group, each $A_4$ moiety being unsubstituted or substituted by (a) a single unsubstituted —CONR'R''' substituent and/or (b) 1 or 2 unsubstituted substituents selected from fluorine, chlorine, bromine, —NR'R''', $C_1$-$C_4$ alkyl, $C_1$-$C_2$ alkoxy, $C_1$-$C_2$ haloalkyl and cyano, wherein R' is hydrogen or $C_1$-$C_4$ alkyl and R''' represents $C_1$-$C_4$ alkyl;

each $A_4'$ moiety is the same or different and represents a morpholinyl, isoxazolyl, pyrrolidinyl, S,S-dioxothiomorpholinyl, 2,6-dioxo-piperidinyl, triazolyl, piperidinyl, cyclopropyl or cyclohexyl group which is unsubstituted or substituted by 1 or 2 unsubstituted substituents selected from chlorine, fluorine, bromine, $C_1$-$C_2$ alkyl and $C_1$-$C_2$ haloalkyl;

each $L_1$ and $L_4$ are the same or different and represent a $C_1$-$C_3$ alkylene group or a $C_1$-$C_3$ hydroxyalkylene group $L_1'$ represents hydrogen or a $C_1$-$C_2$ alkyl group;

$L_4'$ represents a $C_1$-$C_2$ alkyl group; and $Het_1$ represents —O—, —NR'— or —S—, wherein $R_1$ is hydrogen or $C_1$-$C_2$ alkyl.

Typically, in these additional particularly preferred compounds of formula (I), each $A_1'$ moiety is unsubstituted or substituted by 1 or 2 unsubstituted substituents selected from chlorine, fluorine, bromine, hydroxy, $C_1$-$C_2$ alkyl, $C_1$-$C_2$ haloalkyl and $C_1$-$C_2$ hydroxyalkyl.

Typically, in these additional particularly preferred compounds of the invention, either:

(a) $R_1$ is a $C_2$-$C_6$ alkyl group or a moiety -$A_1$, -$L_1$-$A_1$, -$A_1$-$A_1'$, -$L_1$-$A$-$A_1'$, -$A_1$-CO-$A_1'$, -$L_1$-$A_1$-$Het_1$-$A_1'$, -$L_1$-$Het_1$-CO-$A_1'$, -L-CO-$Het_1$-$L_1'$, -$A_1$-$Het_1$-$L_1$-$A_1'$, -$A_1$-$L_1$-$Het_1$-$A_1'$ or -$L_1$-$Het_1$-$L_1'$, wherein $A_1$, $L_1$, $A_1'$, $Het_1$ and $L_1'$ are as defined above; or (b) A is —($C_1$-$C_2$ alkylene)-NH—, —CO—, —CO—O— or —O—CO—; or (c) B is —NH—$CO_2$—, —CO—, —NH—CO—CO— or —($C_1$-$C_2$ alkylene)-NH—; or (d) $R_4$ is -$L_4$-$A_4$ or -$A_4$-CO-$A_4'$, wherein $L_4$, $A_4$ and $A_4'$ are as defined above.

The medicaments of the present invention are for use in treating or preventing a a hepatitis C viral infection in the human or animal body. Preferably, the medicaments are for use in humans.

Compounds of formula (I) containing one or more chiral centre may be used in enantiomerically or diastereoisomerically pure form, or in the form of a mixture of isomers. For the avoidance of doubt, the compounds of formula (I) can, if desired, be used in the form of solvates. Further, for the avoidance of doubt, the compounds of the invention may be used in any tautomeric form.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines.

Especially preferred compounds of the invention include:

1 6-Methyl-biphenyl-3,4'-dicarboxylic acid 4'-[(3-bromo -phenyl)-amide] 3-[(4-morpholin-4-yl-phenyl)-amide]

2 6-Methyl-biphenyl-3,4'-dicarboxylic acid 4'-[(6-methoxy -pyridin-3-yl)-amide] 3-[(4-morpholin-4-yl-phenyl)-amide]

3 6-Methyl-biphenyl-3,4'-dicarboxylic acid 4'-(3-methyl -benzylamide) 3-[(4-morpholin-4-yl-phenyl)-amide]

4 6-Methyl-biphenyl-3,4'-dicarboxylic acid 4'-[(3-methyl -butyl)-amide] 3-[(4-morpholin-4-yl-phenyl)-amide]

5 6-Methyl-biphenyl-3,4'-dicarboxylic acid 4'-(3-fluoro -benzylamide) 3-[(4-morpholin-4-yl-phenyl)-amide]

6 6-Methyl-biphenyl-3,4'-dicarboxylic acid 3-[(4-morpholin-4-yl-phenyl)-amide]4'-[(2-piperidin-1-yl-ethyl)-amide]

7 6-Methyl-biphenyl-3,4'-dicarboxylic acid 4'-[(4-bromo -phenyl)-amide] 3-[(4-morpholin-4-yl-phenyl)-amide]

8 6-Methyl-biphenyl-3,4'-dicarboxylic acid 4'-[(3-benzyloxy -phenyl)-amide] 3-[(4-morpholin-4-yl-phenyl)-amide]

9 6-Methyl-biphenyl-3,4'-dicarboxylic acid 3-{[3-(4-methyl-piperazin-1-yl)-propyl]-amide} 4'-[(4-morpholin-4-yl-phenyl)-amide]

10 6-Methyl-biphenyl-3,4'-dicarboxylic acid 3-[(4-morpholin-4-yl-phenyl)-amide] 4'-(3-trifluoromethyl-benzylamide)

11 6-Methyl-biphenyl-3,4'-dicarboxylic acid 3-[(4-morpholin-4-yl-phenyl)-amide] 4'-[(2-thiophen-2-yl-ethyl)-amide]

12 6-Methyl-biphenyl-3,4'-dicarboxylic acid 4'-[(1H-indazol -6-yl)-amide] 3-[(4-morpholin-4-yl-phenyl)-amide]

13 6-Methyl-biphenyl-3,4'-dicarboxylic acid 4'-{[2-(3H-imidazol-4-yl)-ethyl]-amide} 3-[(4-morpholin-4-yl-phenyl)-amide]

14 6-Methyl-biphenyl-3,4'-dicarboxylic acid 4'-[(5-methyl -furan-2-ylmethyl)-amide] 3-[(4-morpholin-4-yl-phenyl)-amide]

15 6-Methyl-4'-(pyrrolidine-1-carbonyl)-biphenyl-3-carboxylic acid (4-morpholin-4-yl-phenyl)-amide 16 6-Methyl-biphenyl-3,4'-dicarboxylic acid 4'-benzo[1,3]dioxol-5-ylamide 3-[(4-morpholin-4-yl-phenyl)-amide]

17 6-Methyl-biphenyl-3,4'-dicarboxylic acid 3-cyclopropylamide 4'-[(4-morpholin-4-yl-phenyl)-amide]

18 Furan-2-carboxylic acid [6-methyl-4'-(4-morpholin-4-yl-phenylcarbamoyl)-biphenyl-3-yl]-amide 19 6-Methyl-biphenyl-3,4'-dicarboxylic acid 4'-[(3-benzoyl -phenyl)-amide] 3-[(4-morpholin-4-yl-phenyl)-amide]

20 6-Methyl-biphenyl-3,4'-dicarboxylic acid 4'-(4-morpholin-4-yl-benzylamide) 3-[(4-morpholin-4-yl-phenyl)-amide]

21 6-Methyl-biphenyl-3,4'-dicarboxylic acid 4'-[(3-butylsulfamoyl-phenyl)-amide] 3-[(4-morpholin-4-yl-phenyl)-amide]

22 6-Methyl-biphenyl-3,4'-dicarboxylic acid 4'-[(3,4-dichloro-phenyl)-amide] 3-[(4-morpholin-4-yl-phenyl)-amide]

23 6-Methyl-biphenyl-3,4'-dicarboxylic acid 3-[(4-morpholin-4-yl-phenyl)-amide] 4'-[(3-trifluoromethyl-phenyl)-amide]

24 6-Methyl-biphenyl-3,4'-dicarboxylic acid 4'-[(4-cyanophenyl)-amide] 3-[(4-morpholin-4-yl-phenyl)-amide]

25 6-Methyl-biphenyl-3,4'-dicarboxylic acid 3-[(4-morpholin-4-yl-phenyl)-amide] 4'-[(3-trifluoromethoxy-phenyl)-amide]

26 6-Methyl-biphenyl-3,4'-dicarboxylic acid 4'-{[3-(1-methyl-1H-pyrazol-3-yl)-phenyl]-amide} 3-[(4-morpholin-4-yl-phenyl)-amide]

27 6-Methyl-biphenyl-3,4'-dicarboxylic acid 4'-[(3-fluoro -phenyl)-amide] 3-[(4-morpholin-4-yl-phenyl)-amide]

28 6-Methyl-biphenyl-3,4'-dicarboxylic acid 4'-[(4-isoxazol -5-yl-phenyl)-amide] 3-[(4-morpholin-4-yl-phenyl)-amide]

29 6-Methyl-biphenyl-3,4'-dicarboxylic acid 4'-[(4-methylsulfamoyl-phenyl)-amide] 3-[(4-morpholin-4-yl-phenyl)-amide]

30 6-Methyl-biphenyl-3,4'-dicarboxylic acid 4'-[(4-bromo-3-chloro-phenyl)-amide] 3-[(4-morpholin-4-yl-phenyl)-amide]

31  6-Methyl-biphenyl-3,4'-dicarboxylic acid 4'-{[3-(1-hydroxy-ethyl)-phenyl]-amide} 3-[(4-morpholin-4-yl-phenyl)-amide]
32  3-{[2'-Methyl-5'-(4-morpholin-4-yl-phenylcarbamoyl)-biphenyl-4-carbonyl]-amino}-benzoic acid ethyl ester
33  6-Methyl-biphenyl-3,4'-dicarboxylic acid 4'-[(3-methoxy-phenyl)-amide] 3-[(4-morpholin-4-yl-phenyl)-amide]
34  6-Methyl-biphenyl-3,4'-dicarboxylic acid 4'-[(3,4-dimethoxy-phenyl)-amide] 3-[(4-morpholin-4-yl-phenyl)-amide]
35  6-Methyl-biphenyl-3,4'-dicarboxylic acid 4'-({2-[(cyclohexyl-methyl-amino)-methyl]-phenyl}-amide) 3-[(4-morpholin-4-yl-phenyl)-amide]
36  6-Methyl-biphenyl-3,4'-dicarboxylic acid 3-[(4-morpholin-4-yl-phenyl)-amide] 4'-pyridin-3-ylamide
37  4'-[4-(2,3-Dichloro-phenyl)-piperazine-1-carbonyl]-6-methyl-biphenyl-3-carboxylic acid (4-morpholin-4-yl-phenyl)-amide
38  6-Methyl-biphenyl-3,4'-dicarboxylic acid 3-[(4-morpholin-4-yl-phenyl)-amide] 4'-[(2-trifluoromethyl-1H-benzoimidazol-5-yl)-amide]
39  6-Methyl-biphenyl-3,4'-dicarboxylic acid 4'-[(4-cyanomethyl-phenyl)-amide] 3-[(4-morpholin-4-yl-phenyl)-amide]
40  6-Methyl-biphenyl-3,4'-dicarboxylic acid 3-[(4-morpholin-4-yl-phenyl)-amide] 4'-[(thiophen-3-ylmethyl)-amide]
41  6-Methyl-biphenyl-3,4'-dicarboxylic acid 3-[(4-morpholin-4-yl-phenyl)-amide] 4'-(3-trifluoromethoxy-benzylamide)
42  6-Methyl-biphenyl-3,4'-dicarboxylic acid 4'-(4-chloro-3-trifluoromethyl-benzylamide) 3-[(4-morpholin-4-yl-phenyl)-amide]
43  6-Methyl-biphenyl-3,4'-dicarboxylic acid 4'-(3-chloro-4-methyl-benzylamide) 3-[(4-morpholin-4-yl-phenyl)-amide]
44  6-Methyl-biphenyl-3,4'-dicarboxylic acid 4'-[(1H-indol-6-yl)-amide] 3-[(4-morpholin-4-yl-phenyl)-amide]
45  6-Methyl-biphenyl-3,4'-dicarboxylic acid 4'-[(1H-indol-5-yl)-amide] 3-[(4-morpholin-4-yl-phenyl)-amide]
46  6-Methyl-biphenyl-3,4'-dicarboxylic acid 4'-benzothiazol-6-ylamide 3-[(4-morpholin-4-yl-phenyl)-amide]
47  [3-({[2'-Methyl-5'-(4-morpholin-4-yl-phenylcarbamoyl)-biphenyl-4-carbonyl]-amino}-methyl)-benzyl]-carbamic acid tert-butyl ester
48  6-Methyl-biphenyl-3,4'-dicarboxylic acid 4'-[(1H-indol-7-yl)-amide] 3-[(4-morpholin-4-yl-phenyl)-amide]
49  6-Methyl-biphenyl-3,4'-dicarboxylic acid 4'-[2-(2-hydroxymethyl-phenylsulfanyl)-benzylamide] 3-[(4-morpholin-4-yl-phenyl)-amide]
50  6-Methyl-biphenyl-3,4'-dicarboxylic acid 4'-{[4-(1,1-dioxo-1lambda*6*-thiomorpholin-4-ylmethyl)-phenyl]-amide} 3-[(4-morpholin-4-yl-phenyl)-amide]
51  6-Methyl-biphenyl-3,4'-dicarboxylic acid 4'-{[(S)-1-hydroxymethyl-2-(1H-indol-3-yl)-ethyl]-amide} 3-[(4-morpholin-4-yl-phenyl)-amide]
52  6-Methyl-biphenyl-3,4'-dicarboxylic acid 4'-(3-bromo-benzylamide) 3-[(4-morpholin-4-yl-phenyl)-amide]
53  6-Methyl-biphenyl-3,4'-dicarboxylic acid 4'-[(4-amino-phenyl)-amide] 3-[(4-morpholin-4-yl-phenyl)-amide]
54  6-Methyl-biphenyl-3,4'-dicarboxylic acid 4'-[(4-methylsulfamoylmethyl-phenyl)-amide] 3-[(4-morpholin-4-yl-phenyl)-amide]
55  6-Methyl-biphenyl-3,4'-dicarboxylic acid 4'-[(5-bromo-1H-indol-7-yl)-amide] 3-[(4-morpholin-4-yl-phenyl)-amide]
56  6-Methyl-biphenyl-3,4'-dicarboxylic acid 3-[(4-morpholin-4-yl-phenyl)-amide] 4'-{[4-(1H-pyrazol-3-yl)-phenyl]-amide}
57  6-Methyl-biphenyl-3,4'-dicarboxylic acid 4'-(3-chloro-2-fluoro-benzylamide) 3-[(4-morpholin-4-yl-phenyl)-amide]
58  6-Methyl-biphenyl-3,4'-dicarboxylic acid 3-[(4-morpholin-4-yl-phenyl)-amide] 4'-{[4-(piperidine-1-carbonyl)-phenyl]-amide}
59  Biphenyl-3,4'-dicarboxylic acid 4'-[(1H-indol-5-yl)-amide] 3-[(4-morpholin-4-yl-phenyl)-amide]
60  Biphenyl-3,4'-dicarboxylic acid 4'-[(1H-indol-6-yl)-amide] 3-[(4-morpholin-4-yl-phenyl)-amide]
61  6-Methyl-biphenyl-3,4'-dicarboxylic acid 4'-[(3-acetylamino-phenyl)-amide] 3-[(4-morpholin-4-yl-phenyl)-amide]
62  2'-Methyl-biphenyl-3,4'-dicarboxylic acid 3-[(3-methoxy-phenyl)-amide] 4'-[(4-morpholin-4-yl-phenyl)-amide]
63  2'-Methyl-biphenyl-3,4'-dicarboxylic acid 3-[(1H-indazol-6-yl)-amide] 4'-[(4-morpholin-4-yl-phenyl)-amide]
64  2'-Methyl-biphenyl-3,4'-dicarboxylic acid 3-[(3-bromo-phenyl)-amide] 4'-[(4-morpholin-4-yl-phenyl)-amide]
65  2'-Methyl-biphenyl-3,4'-dicarboxylic acid 3-[(4-isoxazol-5-yl-phenyl)-amide] 4'-[(4-morpholin-4-yl-phenyl)-amide]
66  2'-Methyl-biphenyl-3,4'-dicarboxylic acid 3-(3-chloro-benzylamide) 4'-[(4-morpholin-4-yl-phenyl)-amide]
67  6-Methyl-biphenyl-3,4'-dicarboxylic acid 4'-[(1H-indazol-6-yl)-amide] 3-[(4-morpholin-4-yl-phenyl)-amide]
68  2'-Methyl-5'-(4-morpholin-4-yl-benzoylamino)-biphenyl-4-carboxylic acid (3-trifluoromethoxy-phenyl)-amide
69  6-Methyl-biphenyl-3,4'-dicarboxylic acid 3-[(4-morpholin-4-yl-phenyl)-amide] 4'-[(3-thiomorpholin-4-ylmethyl-phenyl)-amide]
70  6-Methyl-biphenyl-3,4'-dicarboxylic acid 4'-[(4-dimethylcarbamoyl-phenyl)-amide] 3-[(4-morpholin-4-yl-phenyl)-amide]
71  6-Methyl-biphenyl-3,4'-dicarboxylic acid 4'-{[4-(3-ethyl-6-hydroxy-2-oxo-piperidin-3-yl)-phenyl]-amide} 3-[(4-morpholin-4-yl-phenyl)-amide]
72  6-Methyl-biphenyl-3,4'-dicarboxylic acid 4'-[(3-acetylamino-phenyl)-amide] 3-[(4-morpholin-4-yl-phenyl)-amide]
73  6-Methyl-biphenyl-3,4'-dicarboxylic acid 3-[(4-morpholin-4-yl-phenyl)-amide] 4'-[(4-piperidin-1-ylmethyl-phenyl)-amide]
74  6-Methyl-biphenyl-3,4'-dicarboxylic acid 4'-[(4-morpholin-4-ylmethyl-phenyl)-amide] 3-[(4-morpholin-4-yl-phenyl)-amide]
75  6-Methyl-biphenyl-3,4'-dicarboxylic acid 3-[(4-morpholin-4-yl-phenyl)-amide] 4'-[(4-pyrrolidin-1-ylmethyl-phenyl)-amide]
76  6-Methyl-biphenyl-3,4'-dicarboxylic acid 4'-({4-[(methyl-propyl-amino)-methyl]-phenyl}-amide) 3-[(4-morpholin-4-yl-phenyl)-amide]
77  6-Methyl-biphenyl-3,4'-dicarboxylic acid 4'-[(3-acetylamino-4-methyl-phenyl)-amide] 3-[(4-morpholin-4-yl-phenyl)-amide]
78  6-Methyl-biphenyl-3,4'-dicarboxylic acid 4'-[(3-methanesulfonylamino-phenyl)-amide] 3-[(4-morpholin-4-yl-phenyl)-amide]

79 6-Methyl-biphenyl-3,4'-dicarboxylic acid 3-[(4-morpholin-4-yl-phenyl)-amide] 4'-[(2-oxo-2,3-dihydro-1H-benzoimidazol-5-yl)-amide]

80 6-Methyl-biphenyl-3,4'-dicarboxylic acid 3-[(4-morpholin-4-yl-phenyl)-amide] 4'-[(2-piperidin-1-ylmethyl-phenyl)-amide]

81 6-Methyl-biphenyl-3,4'-dicarboxylic acid 4'-[(4-hydroxymethyl-phenyl)-amide] 3-[(4-morpholin-4-yl-phenyl)-amide]

82 6-Methyl-biphenyl-3,4'-dicarboxylic acid 3-[(4-morpholin-4-yl-phenyl)-amide] 4'-[(4-piperazin-1-ylmethyl-phenyl)-amide]

83 6-Methyl-biphenyl-3,4'-dicarboxylic acid 4'-(3-chloro-benzylamide) 3-[(4-morpholin-4-yl-phenyl)-amide]

84 2'-Methyl-5'-(4-morpholin-4-yl-phenylcarbamoyl)-biphenyl-4-carboxylic acid ethyl ester 85 2'-Methyl-5'-(4-morpholin-4-yl-benzoylamino)-biphenyl-4-carboxylic acid (2-trifluoromethyl-1H-benzoimidazol-5-yl)-amide 86 2'-Methyl-5'-(4-morpholin-4-yl-benzoylamino)-biphenyl-4-carboxylic acid (4-acetylamino-phenyl)-amide 87 2'-Methyl-5'-(4-morpholin-4-yl-benzoylamino)-biphenyl-4-carboxylic acid [4-(1,1-dioxo-1lambda*6*-thiomorpholin-4-yl-ethyl)-phenyl]-amide 88 2'-Methyl-5'-(4-morpholin-4-yl-benzoylamino)-biphenyl-4-carboxylic acid 3-bromo-benzylamide 89 2'-Methyl-5'-(4-morpholin-4-yl-benzoylamino)-biphenyl-4-carboxylic acid 3-methyl-benzylamide 90 2'-Methyl-5'-(4-morpholin-4-yl-benzoylamino)-biphenyl-4-carboxylic acid (4-bromo-3-chloro-phenyl)-amide 91 2'-Methyl-5'-(4-morpholin-4-yl-benzoylamino)-biphenyl-4-carboxylic acid (3-methoxy-phenyl)-amide 92 2'-Methyl-5'-(4-morpholin-4-yl-benzoylamino)-biphenyl-4-carboxylic acid 3-trifluoromethoxy-benzylamide 93 2'-Methyl-5'-(4-morpholin-4-yl-benzoylamino)-biphenyl-4-carboxylic acid (1H-indol-6-yl)-amide 94 2'-Methyl-5'-(4-morpholin-4-yl-benzoylamino)-biphenyl-4-carboxylic acid 3-chloro-benzylamide 95 5'-{[1-Hydroxymethyl-2-(3H-imidazol-4-yl)-ethylamino]-methyl}-2'-methyl-biphenyl-4-carboxylic acid (4-morpholin-4-yl-phenyl)-amide 96 4'-[(3-Chloro-benzylamino)-methyl]-6-methyl-biphenyl-3-carboxylic acid (4-morpholin-4-yl-phenyl)-amide 97 4'-[(1H-Indazol-6-ylamino)-methyl]-6-methyl-biphenyl-3-carboxylic acid (4-morpholin-4-yl-phenyl)-amide 98 4'-Cyclopropylaminomethyl-6-methyl-biphenyl-3-carboxylic acid (4-morpholin-4-yl-phenyl)-amide 99 (S)-3-Hydroxy-2-{[2'-methyl-5'-(4-morpholin-4-yl-phenylcarbamoyl)-biphenyl-4-ylmethyl]-amino}-propionic acid 100 4'-{[2-(3H-imidazol-4-yl)-ethylamino]-methyl}-6-methyl-biphenyl-3-carboxylic acid (4-morpholin-4-yl-phenyl)-amide 101 4'-{[1-Hydroxymethyl-2-(3H-imidazol-4-yl)-ethylamino]-methyl}-6-methyl-biphenyl-3-carboxylic acid (4-morpholin-4-yl-phenyl)-amide 102 4'-[(2-Dimethylamino-ethylamino)-methyl]-6-methyl-biphenyl-3-carboxylic acid (4-morpholin-4-yl-phenyl)-amide 103 4'-(3-Bromo-benzoylamino)-6-methyl-biphenyl-3-carboxylic acid (4-morpholin-4-yl-phenyl)-amide 104 3-Hydroxy-quinoxaline-2-carboxylic acid [2'-methyl-5'-(4-morpholin-4-yl-phenylcarbamoyl)-biphenyl-4-yl]-amide 105 4'-(2-Benzoylamino-acetylamino)-6-methyl-biphenyl-3-carboxylic acid (4-morpholin-4-yl-phenyl)-amide 106 4'-[2-(3-Chloro-phenyl)-acetylamino]-6-methyl-biphenyl-3-carboxylic acid (4-morpholin-4-yl-phenyl)-amide 107 4'-(3-Methoxy-benzoylamino)-6-methyl-biphenyl-3-carboxylic acid (4-morpholin-4-yl-phenyl)-amide 108 1H-Pyrazole-4-carboxylic acid [6-methyl-4'-(4-morpholin-4-yl-phenylcarbamoyl)-biphenyl-3-yl]-amide 109 4'-(2-Hydroxy-benzoylamino)-6-methyl-biphenyl-3-carboxylic acid (4-morpholin-4-yl-phenyl)-amide 110 4'-(3,4-Dimethoxy-benzoylamino)-6-methyl-biphenyl-3-carboxylic acid (4-morpholin-4-yl-phenyl)-amide 111 N-[2'-Methyl-5'-(4-morpholin-4-yl-phenylcarbamoyl)-biphenyl-4-yl]-4-trifluoromethyl-nicotinamide 112 4'-(3-Methoxy-benzoylamino)-6-methyl-biphenyl-3-carboxylic acid (4-morpholin-4-yl-phenyl)-amide 113 4'-(Cyclopropanecarbonyl-amino)-2'-methyl-biphenyl-3-carboxylic acid (4-morpholin-4-yl-phenyl)-amide 114 Furan-2-carboxylic acid [2-methyl-3'-(4-morpholin-4-yl-phenylcarbamoyl)-biphenyl-4-yl]-amide 115 4'-(2-Methoxy-benzoylamino)-2'-methyl-biphenyl-3-carboxylic acid (4-morpholin-4-yl-phenyl)-amide 116 4'-(3-Methoxy-benzoylamino)-2'-methyl-biphenyl-3-carboxylic acid (4-morpholin-4-yl-phenyl)-amide 117 4'-(4-Dimethylaminomethyl-benzoylamino)-6-methyl-biphenyl-3-carboxylic acid (4-morpholin-4-yl-phenyl)-amide 118 6-Methyl-4'-(4-morpholin-4-ylmethyl-benzoylamino)-biphenyl-3-carboxylic acid (4-morpholin-4-yl-phenyl)-amide 119 6-Methyl-4'-(4-morpholin-4-yl-benzoylamino)-biphenyl-3-carboxylic acid (4-morpholin-4-yl-phenyl)-amide 120 Biphenyl-3,4'-dicarboxylic acid 4'-{[4-(1,1-dioxo-1lambda*6*-thiomorpholin-4-ylmethyl)-phenyl]-amide} 3-[(4-morpholin-4-yl-phenyl)-amide]

121 6-Methyl-biphenyl-3,4'-dicarboxylic acid 3-cyclopropylamide 4'-{[4-(1,1-dioxo-1lambda*6*-thiomorpholin-4-ylmethyl)-phenyl]-amide}

122 6-Methyl-biphenyl-3,4'-dicarboxylic acid 4'-{[4-(1,1-dioxo-1lambda*6*-thiomorpholin-4-ylmethyl)-phenyl]-amide} 3-[(3-methyl-butyl)-amide]

123 6-Methyl-biphenyl-3,4'-dicarboxylic acid 4'-{[4-(1,1-dioxo-1lambda*6*-thiomorpholin-4-ylmethyl)-phenyl]-amide} 3-(3-fluoro-benzylamide)

124 6-Methyl-biphenyl-3,4'-dicarboxylic acid 4'-{[4-(1,1-dioxo-1lambda*6*-thiomorpholin-4-ylmethyl)-phenyl]-amide} 3-[(tetrahydro-furan-2-ylmethyl)-amide]

125 6-Methyl-biphenyl-3,4'-dicarboxylic acid 4'-{[4-(1,1-dioxo-1lambda*6*-thiomorpholin-4-ylmethyl)-phenyl]-amide} 3-[(2-piperidin-1-yl-ethyl)-amide]

126 6-Methyl-biphenyl-3,4'-dicarboxylic acid 4'-{[4-(1,1-dioxo-1lambda*6*-thiomorpholin-4-ylmethyl)-phenyl]-amide} 3-[(2-methoxy-ethyl)-amide]

127 6-Methyl-biphenyl-3,4'-dicarboxylic acid 4'-{[4-(1,1-dioxo-1lambda*6*-thiomorpholin-4-ylmethyl)-phenyl]-amide} 3-{[2-(3H-imidazol-4-yl)-ethyl]-amide}

128 2'-Methyl-5'-(4-pyrrolidin-1-yl-piperidine-1-carbonyl)-biphenyl-4-carboxylic acid [4-(1,1-dioxo-1lambda*6*-thiomorpholin-4-ylmethyl)-phenyl]-amide 129 6-Methyl-biphenyl-3,4'-dicarboxylic acid bis-{[4-(1,1-dioxo-1lambda*6*-thiomorpholin-4-ylmethyl)-phenyl]-amide}

130 6-Methyl-biphenyl-3,4'-dicarboxylic acid 3-[(4-dimethylamino-phenyl)-amide] 4'-{[4-(1,1-dioxo-1lambda*6*-thiomorpholin-4-ylmethyl)-phenyl]-amide}

131 4'-(Cyclopropanecarbonyl-amino)-2'-methyl-biphenyl-3-carboxylic acid [4-(1,1-dioxo-1lambda*6*-thiomorpholin-4-ylmethyl)-phenyl]-amide 132 5'-(Cyclopropanecarbonyl-amino)-2'-methyl-biphenyl-4-carboxylic acid [4-(1,1-dioxo-1lambda*6*-thiomorpholin-4-ylmethyl)-phenyl]-amide 133 Furan-2-carboxylic acid {3'-[4-(1,1-dioxo-1lambda*6*-thiomorpholin-4-ylmethyl)-phenylcarbamoyl]-2-methyl-biphenyl-4-yl}-amide 134 4'-(2-Methoxy-benzoylamino)-2'-methyl-biphenyl-3-carboxylic acid [4-(1,1-dioxo-1lambda*6*-thiomorpholin-4-ylmethyl)-phenyl]-amide 135 2'-Methyl-biphenyl-3,4'-dicarboxylic acid 3-{[4-(1,1-dioxo-1lambda*6*-thiomorpholin-4-ylmethyl)-phenyl]-amide} 4'-[(4-morpholin-4-yl-phenyl)-amide]

136 6-Methyl-biphenyl-3,4'-dicarboxylic acid 4'-{[3-(1,1-dioxo-1lambda*6*-thiomorpholin-4-ylmethyl)-phenyl]-amide} 3-[(4-morpholin-4-yl -phenyl)-amide]

137 6-Methyl-biphenyl-3,4'-dicarboxylic acid 4'-{[4-(1,1-dioxo-1lambda*6*-thiomorpholin-4-ylmethyl)-phenyl]-amide} 3-{[3-(2-oxo -pyrrolidin-1-yl)-propyl]-amide}

138 6-Methyl-biphenyl-3,4'-dicarboxylic acid 4'-{[4-(1,1-dioxo-1lambda*6*-thiomorpholin-4-ylmethyl)-phenyl]-amide} 3-{[4-(3-ethyl-2,6-dioxo-piperidin-3-yl)-phenyl]-amide}

139 6-Methyl-biphenyl-3,4'-dicarboxylic acid 4'-{[4-(1,1-dioxo-1lambda*6*-thiomorpholin-4-ylmethyl)-phenyl]-amide} 3-[(4-[1,2,4]triazol-1-yl-phenyl)-amide]

140 6-Methyl-biphenyl-3,4'-dicarboxylic acid 4'-{[4-(1,1-dioxo-1lambda*6*-thiomorpholin-4-ylmethyl)-phenyl]-amide} 3-{[4-(morpholine-4-carbonyl)-phenyl]-amide}

141 6-Methyl-biphenyl-3,4'-dicarboxylic acid 4'-{[4-(1,1-dioxo-1lambda*6*-thiomorpholin-4-ylmethyl)-phenyl]-amide} 3-[(4-methylcarbamoyl -phenyl)-amide]

142 6-Methyl-biphenyl-3,4'-dicarboxylic acid 3-[(4-dimethylcarbamoyl-phenyl)-amide] 4'-{[4-(1,1-dioxo-1lambda*6*-thiomorpholin-4-ylmethyl)-phenyl]-amide}

143 6-Methyl-biphenyl-3,4'-dicarboxylic acid 4'-{[4-(1,1-dioxo-1lambda*6*-thiomorpholin-4-ylmethyl)-phenyl]-amide} 3-[(5-ethyl-[1,3,4]thiadiazol-2-yl)-amide]

144 6-Methyl-biphenyl-3,4'-dicarboxylic acid 4'-{[4-(1,1-dioxo-1lambda*6*-thiomorpholin-4-ylmethyl)-phenyl]-amide} 3-{[4-(piperidine-1-carbonyl)-phenyl]-amide}

145 6-Methyl-biphenyl-3,4'-dicarboxylic acid 4'-{[4-(1,1-dioxo-1lambda*6*-thiomorpholin-4-ylmethyl)-phenyl]-amide} 3-[(3-methyl-isothiazol-5-yl)-amide]

146 6-Methyl-biphenyl-3,4'-dicarboxylic acid 3-cyclohexylmethyl-amide 4'-{[4-(1,1-dioxo-1lambda*6*-thiomorpholin-4-yl-ethyl)-phenyl]-amide}

147 6-Methyl-biphenyl-3,4'-dicarboxylic acid 3-cycloheptylamide 4'-{[4-(1,1-dioxo-1lambda*6*-thiomorpholin-4-ylmethyl)-phenyl]-amide}

148 6-Methyl-biphenyl-3,4'-dicarboxylic acid 3-cyclopentylamide 4'-{[4-(1,1-dioxo-1lambda*6*-thiomorpholin-4-ylmethyl)-phenyl]-amide}

149 N-[5'-(Cyclopropanecarbonyl-amino)-2'-methyl-biphenyl-4-yl]-4-(1,1-dioxo-1lambda*6*-thiomorpholin-4-ylmethyl)-benzamide 150 N-[5'-(Cyclohexanecarbonyl-amino)-2'-methyl-biphenyl-4-yl]-4-(1,1-dioxo-1lambda*6*-thiomorpholin-4-ylmethyl)-benzamide 151 4'-[4-(1,1-Dioxo-1lambda*6*-thiomorpholin-4-ylmethyl)-benzoylamino]-6-methyl-biphenyl-3-carboxylic acid (4-morpholin-4-yl-phenyl)-amide 152 Morpholine-4-carboxylic acid {4'-[4-(1,1-dioxo-1lambda*6*-thiomorpholin-4-ylmethyl)-phenylcarbamoyl]-6-methyl-biphenyl-3-yl}-amide 153 Furan-2-carboxylic acid {4'-[4-(1,1-dioxo-1lambda*6*-thiomorpholin-4-ylmethyl)-phenylcarbamoyl]-6-methyl-biphenyl-3-yl}-amide 154 5'-(4-Bromo-benzoylamino)-2'-methyl-biphenyl-4-carboxylic acid [4-(1,1-dioxo-lambda*6*-thiomorpholin-4-ylmethyl)-phenyl]-amide 155 Thiophene-2-carboxylic acid {4'-[4-(1,1-dioxo-1lambda*6*-thiomorpholin-4-ylmethyl)-phenylcarbamoyl]-6-methyl-biphenyl-3-yl}-amide 156 N-{4'-[4-(1,1-Dioxo-1lambda*6*-thiomorpholin -4-ylmethyl)-phenylcarbamoyl]-6-methyl-biphenyl-3-yl}-nicotinamide 157 1-Methyl-1H-pyrrole-2-carboxylic acid {4'-[4-(1,1-dioxo-1lambda*6*-thiomorpholin-4-ylmethyl)-phenylcarbamoyl]-6-methyl-biphenyl-3-yl}-amide 158 5'-(Cyclohexanecarbonyl-amino)-2'-methyl-biphenyl-4-carboxylic acid [4-(1,1-dioxo-1lambda*6*-thiomorpholin-4-ylmethyl)-phenyl]-amide 159 7,7'-Dimethyl-N*4*-(4-morpholin-4-yl-phenyl)-N*4'*-(4-[1,2,4]triazol-1-yl-phenyl)-[6,6']biquinazolinyl-4,4'-diamine 160 2'-Methyl-5'-(4-methyl-benzoylamino)-biphenyl-4-carboxylic acid [4-(1,1-dioxo-1lambda*6*-thiomorpholin-4-ylmethyl)-phenyl]-amide 161 5'-[4-(1,1-Dioxo-1lambda*6*-thiomorpholin-4-ylmethyl)-benzoylamino]-2'-methyl-biphenyl-4-carboxylic acid [4-(1,1-dioxo-1lambda*6*-thiomorpholin-4-ylmethyl)-phenyl]-amide 162 5'-[4-(1,1-Dioxo-1lambda*6*-thiomorpholin-4-ylmethyl)-benzoylamino]-2'-methyl-biphenyl-4-carboxylic acid 3-chloro-benzylamide 163 5'-(3-Cyclohexyl-propionylamino)-2'-methyl-biphenyl-4-carboxylic acid [4-(1,1-dioxo-1lambda*6*-thiomorpholin-4-ylmethyl)-phenyl]-amide 164 5'-(Cycloheptanecarbonyl-amino)-2'-methyl-biphenyl-4-carboxylic acid [4-(1,1-dioxo-1lambda*6*-thiomorpholin-4-ylmethyl)-phenyl]-amide 165 5'-(2-Cyclohexyl-acetylamino)-2'-methyl-biphenyl-4-carboxylic acid [4-(1,1-dioxo-1lambda*6*-thiomorpholin-4-ylmethyl)-phenyl]-amide 166 5'-(2-Cyclopentyl-acetylamino)-2'-methyl-biphenyl-4-carboxylic acid [4-(1,1-dioxo-1lambda*6*-thiomorpholin-4-ylmethyl)-phenyl]-amide 167 5'-(Cyclopentanecarbonyl-amino)-2'-methyl-biphenyl-4-carboxylic acid [4-(1,1-dioxo-1lambda*6*-thiomorpholin-4-ylmethyl)-phenyl]-amide 168 3'-(Cyclopropanecarbonyl-amino)-biphenyl-4-carboxylic acid [4-(1,1-dioxo-1lambda*6*-thiomorpholin-4-ylmethyl)-phenyl]-amide 169 3'-(Cyclobutanecarbonyl-amino)-biphenyl-4-carboxylic acid [4-(1,1-dioxo-1lambda*6*-thiomorpholin-4-ylmethyl)-phenyl]-amide 170 Tetrahydro-pyran-4-carboxylic acid {4'-[4-(1,1-dioxo-1lambda*6*-thiomorpholin-4-ylmethyl)-phenylcarbamoyl]-6-methyl-biphenyl-3-yl}-amide 171 2'-Methyl-5'-(2-tetrahydro-pyran-4-yl-acetylamino) -biphenyl-4-carboxylic acid [4-(1,1-dioxo-1lambda*6*-thiomorpholin-4-ylmethyl)-phenyl]-amide 172 3'-(Cyclopropanecarbonyl-amino)-2,4'-dimethyl-biphenyl-4-carboxylic acid [4-(1,1-dioxo-1lambda*6*-thiomorpholin-4-yl-methyl)-phenyl]-amide 173 2'-Methyl-5'-[(1-trifluoromethyl-cyclopropanecarbonyl)-amino]-biphenyl-4-carboxylic acid [4-(1,1-dioxo-1lambda*6*-thiomorpholin-4-ylmethyl)-phenyl]-amide 174 5'-[(1-Cyano-cyclopropanecarbonyl)-amino]-2'-methyl-biphenyl-4-carboxylic acid [4-(1,1-dioxo-1lambda*6*-thiomorpholin-4-ylmethyl)-phenyl]-amide 175 2'-Methyl-5'-[(1-methyl-cyclopropanecarbonyl)-amino]-biphenyl-4-carboxylic acid [4-(1,1-dioxo-1lambda*6*-thiomorpholin-4-ylmethyl)-phenyl]-amide 176 5'-(Cyclopropanecarbonyl-amino)-2'-methyl-biphenyl-4-carboxylic acid [4-(1,1-dioxo-1lambda*6*-thiomorpholin-4-ylmethyl)-phenyl]-amide 177 Thiazole-4-carboxylic acid {4'-[4-(1,1-dioxo-1lambda*6*-thiomorpholin-4-ylmethyl)-phenylcarbamoyl]-6-methyl-biphenyl-3-yl}-amide 178 5'-(2-Cyclopropyl-acetylamino)-2'-methyl-biphenyl-4-carboxylic acid [4-(1,1-dioxo-1lambda*6*-thiomorpholin-4-ylmethyl)-phenyl]-amide 179 Thiazole-5-carboxylic acid {4'-[4-(1,1-dioxo-1lambda*6*-thiomorpholin-4-ylmethyl)-phenylcarbamoyl]-6-methyl-biphenyl-3-yl}-amide 180 5'-Acetylamino-2'-methyl-biphenyl-4-carboxylic acid [4-(1,1-dioxo-1lambda*6*-thiomorpholin-4-ylmethyl)-phenyl]-amide 181 5'-(2-Ethyl-butyrylamino)-2'-methyl-biphenyl-4-carboxylic acid [4-(1,1-dioxo-1lambda*6*-thiomorpholin-4-ylmethyl)-phenyl]-amide 182 5'-Butyrylamino-2'-methyl-biphenyl-4-carboxylic acid [4-(1,1-dioxo-1lambda*6*-thiomorpholin-4-ylmethyl)-phenyl]-amide 183 5'-Isobutyrylamino-2'-methyl-biphenyl-4-carboxylic acid [4-(1,1-dioxo-1lambda*6*-thiomorpholin-4-yl-methyl)-phenyl]-amide 184 5'-(2,2-Dimethyl-propionylamino)-2'-methyl-biphenyl-4-carboxylic acid [4-(1,1-dioxo-1lambda*6*-thiomorpholin-4-ylmethyl)-phenyl]-amide 185 5'-(Cyclopropanecarbonyl-amino)-2'-trifluoromethoxy-biphenyl-4-carboxylic acid [4-(1,1-dioxo-1lambda*6*-thiomorpholin-4-ylmethyl)-phenyl]-amide 186 5'-(Cyclopropanecarbonyl-amino)-2'-methoxy-biphenyl-4-carboxylic acid [4-(1,1-dioxo-1lambda*6*-thiomorpholin-4-ylmethyl)-phenyl]-amide 187 5'-(Cyclohexanecarbonyl-amino)-2'-methoxy-biphenyl-4-carboxylic acid [4-(1,1-dioxo-1lambda*6*-thiomorpholin-4-ylmethyl)-phenyl]-amide 188 5'-(3-Ethyl-ureido)-2'-methyl-biphenyl-4-carboxylic acid [4-(1,1-dioxo-lambda*6*-thiomorpholin-4-ylmethyl)-phenyl]-amide 189 5'-(3-Cyclohexyl-ureido)-2'-methyl-biphenyl-4-carboxylic acid [4-(1,1-dioxo-1lambda*6*-thiomorpholin-4-ylmethyl)-phenyl]-amide 190 2'-Methyl-5'-(2-oxo-propionylamino)-biphenyl-4-carboxylic acid [4-(1,1-dioxo-1lambda*6*-thiomorpholin-4-ylmethyl)-phenyl]-amide 191 5'-(Cyclohexanecarbonyl-amino)-2'-fluoro-biphenyl-4-carboxylic acid [4-(1,1-dioxo-1lambda*6*-thiomorpholin-4-ylmethyl)-phenyl]-amide 192 5'-(Cyclohexanecarbonyl-amino)-2'-trifluoromethoxy-biphenyl-4-carboxylic acid [4-(1,1-dioxo-1lambda*6*-thiomorpholin-4-ylmethyl)-phenyl]-amide 193 2'-Chloro-5'-(cyclohexanecarbonyl-amino)-biphenyl-4-carboxylic acid [4-(1,1-dioxo-1lambda*6*-thiomorpholin-4-ylmethyl)-phenyl]-amide 194 2'-Chloro-5'-(cyclopropanecarbonyl-amino)-biphenyl-4-carboxylic acid [4-(1,1-dioxo-1lambda*6*-thiomorpholin-4-ylmethyl)-phenyl]-amide 195 5'-(Cyclobutanecarbonyl-amino)-2'-methyl-biphenyl-4-carboxylic acid [4-(1,1-dioxo-1lambda*6*-thiomorpholin-4-ylmethyl)-phenyl]-amide 196 3'-(Cyclohexanecarbonyl-amino)-biphenyl-4-carboxylic acid [4-(1,1-dioxo-1lambda*6*-thiomorpholin-4-ylmethyl)-phenyl]-amide 197 5'-[(1H-Indazol-6-ylamino)-methyl]-2'-methyl-biphenyl-4-carboxylic acid [4-(1,1-dioxo-1lambda*6*-thiomorpholin-4-ylmethyl)-phenyl]-amide 198 5'-[(3-Bromo-phenylamino)-methyl]-2'-methyl-biphenyl-4-carboxylic acid [4-(1,1-dioxo-1lambda*6*-thiomorpholin-4-ylmethyl)-phenyl]-amide 199 5'-[(3-Chloro-benzylamino)-methyl]-2'-methyl-biphenyl-4-carboxylic acid [4-(1,1-dioxo-1lambda*6*-thiomorpholin-4-ylmethyl)-phenyl]-amide 200 5'-{[1-Hydroxymethyl-2-(3H-imidazol-4-yl)-ethylamino]-methyl}-2'-methyl-biphenyl-4-carboxylic acid [4-(1,1-dioxo-1lambda*6*-thiomorpholin-4-ylmethyl)-phenyl]-amide 201 5'-[(1H-Indazol-6-ylamino)-methyl]-2'-methyl-biphenyl-4-carboxylic acid [4-(1,1-dioxo-1lambda*6*-thiomorpholin-4-ylmethyl)-phenyl]-amide 202 5'-(4-Chloro-benzenesulfonylamino)-2'-methyl-biphenyl-4-carboxylic acid [4-(1,1-dioxo-1lambda*6*-thiomorpholin-4-ylmethyl)-phenyl]-amide 203 2'-Methyl-5'-(6-morpholin-4-yl-pyridine-3-sulfonylamino)-biphenyl-4-carboxylic acid [4-(1,1-dioxo-1lambda*6*-thiomorpholin-4-ylmethyl)-phenyl]-amide 204 5'-(5-Chloro-thiophene-2-sulfonylamino)-2'-methyl-biphenyl-4-carboxylic acid [4-(1,1-dioxo-1lambda*6*-thiomorpholin-4-ylmethyl)-phenyl]-amide 205 5'-(5-Cyclopropyl-[1,2,4]oxadiazol-3-yl)-2'-methyl-biphenyl-4-carboxylic acid [4-(1,1-dioxo-1lambda*6*-thiomorpholin-4-yl-ethyl)-phenyl]-amide 206 5'-(5-Cyclohexyl-[1,2,4]oxadiazol-3-yl)-2'-methyl-biphenyl-4-carboxylic acid [4-(1,1-dioxo-1lambda*6*-thiomorpholin-4-ylmethyl)-phenyl]-amide 207 5'-(5-Isopropyl-[1,2,4]oxadiazol-3-yl)-2'-methyl-biphenyl-4-carboxylic acid [4-(1,1-dioxo-1lambda*6*-thiomorpholin-4-ylmethyl)-phenyl]-amide 208 6-Methyl-biphenyl-3,4'-dicarboxylic acid 3-cyclopropylamide 4'-{[4-(2-diethylamino-ethylcarbamoyl)-phenyl]-amide}

209 Furan-2-carboxylic acid [4'-(3-chloro-benzylcarbamoyl)-6-methyl-biphenyl-3-yl]-amide 210 5'-tert-Butoxycarbonylamino-2'-methyl-biphenyl-4-carboxylic acid ethyl ester 211 5'-(4-Bromo-benzoylamino)-2'-methyl-biphenyl-4-carboxylic acid (1H-indazol-6-yl)-amide 212 5'-(4-Bromo-benzoylamino)-2'-methyl-biphenyl-4-carboxylic acid (4-oxazol-5-yl-phenyl)-amide 213 Thiophene-2-carboxylic acid [4'-(1H-indazol-6-ylcarbamoyl)-6-methyl-biphenyl-3-yl]-amide 214 1H-Pyrazole-4-carboxylic acid [6-methyl-4'-(3-methyl-benzylcarbamoyl)-biphenyl-3-yl]-amide 215 N-[6-Methyl-4'-(3-methyl-benzylcarbamoyl)-biphenyl-3-yl]-isonicotinamide 216 5'-(Cyclopropanecarbonyl-amino)-2'-methyl-biphenyl-4-carboxylic acid 3-chloro-benzylamide 217 5'-(Cyclopropanecarbonyl-amino)-2'-methyl-biphenyl-4-carboxylic acid 4-(4-methyl-piperazin-1-yl)-benzylamide 218 5'-(Cyclopropanecarbonyl-amino)-2'-methyl-biphenyl-4-carboxylic acid (4-[1,2,4]triazol-1-yl-phenyl)-amide 219 5'-(Cyclohexanecarbonyl-amino)-2'-methyl-biphenyl-4-carboxylic acid (4-[1,2,4]triazol-1-yl-phenyl)-amide 220 5'-(Cyclopropanecarbonyl-amino)-2'-methyl-biphenyl-4-carboxylic acid [4-(3-ethyl-2,6-dioxo-piperidin-3-yl)-phenyl]-amide 221 5'-(Cyclohexanecarbonyl-amino)-2'-methyl-biphenyl-4-carboxylic acid [4-(3-ethyl-2,6-dioxo-piperidin-3-yl)-phenyl]-amide 222 5'-(Cyclohexanecarbonyl-amino)-2'-methyl-biphenyl-4-carboxylic acid (4-dimethylaminomethyl-phenyl)-amide 223 5'-(Cyclopropanecarbonyl-amino)-2'-methyl-biphenyl-4-carboxylic acid (4-dimethylaminomethyl-phenyl)-amide
224 5'-(Cyclopropanecarbonyl-amino)-2'-methyl-biphenyl-4-carboxylic acid (2-piperidin-1-ylmethyl-phenyl)-amide
225 5'-(Cyclopropanecarbonyl-amino)-2'-methyl-biphenyl-4-carboxylic acid (3-dimethylaminomethyl-phenyl)-amide
226 5'-(Cyclohexanecarbonyl-amino)-2'-methyl-biphenyl-4-carboxylic acid (4-morpholin-4-ylmethyl-phenyl)-amide
227 5'-(Cyclohexanecarbonyl-amino)-2'-methyl-biphenyl-4-carboxylic acid (4-pyrrolidin-1-ylmethyl-phenyl)-amide
228 5'-(Cyclopropanecarbonyl-amino)-2'-methyl-biphenyl-4-carboxylic acid (4-piperidin-1-ylmethyl-phenyl)-amide
229 5'-(Cyclopropanecarbonyl-amino)-2'-methyl-biphenyl-4-carboxylic acid (4-piperidin-1-ylmethyl-phenyl)-amide
230 5'-(Cyclopropanecarbonyl-amino)-2'-methyl-biphenyl-4-carboxylic acid (4-pyrrolidin-1-ylmethyl-phenyl)-amide
231 5'-(Cyclohexanecarbonyl-amino)-2'-methyl-biphenyl-4-carboxylic acid (4-isoxazol-5-yl-phenyl)-amide
232 5'-(Cyclohexanecarbonyl-amino)-2'-methyl-biphenyl-4-carboxylic acid (4-hydroxymethyl-phenyl)-amide
233 Furan-2-carboxylic acid [4'-(1H-indol-6-ylcarbamoyl)-6-methyl-biphenyl-3-yl]-amide,
234 (R)-Piperidine-2-carboxylic acid (4'-{4-[4-(propane-1-sulfonyl)-piperazin-1-ylmethyl]-phenylcarbamoyl}-6-trifluoromethoxy-biphenyl-3-yl)-amide,
235 5'-(3-Cyclohexyl-ureido)-2'-trifluoromethoxy-biphenyl-4-carboxylic acid [4-(4-methanesulfonyl-piperazin-1-ylmethyl)-phenyl]-amide
236 (S)-Pyrrolidine-2-carboxylic acid (4'-{4-[4-(propane-1-sulfonyl)-piperazin-1-ylmethyl]-phenylcarbamoyl}-6-trifluoromethoxy-biphenyl-3-yl)-amide
237 5'-(Cyclopropanecarbonyl-amino)-2'-trifluoromethoxy-biphenyl-4-carboxylic acid {4-[4-(propane-1-sulfonyl)-piperazin-1-ylmethyl]-phenyl}-amide.
238 (S)-Piperidine-2-carboxylic acid (4'-{4-[4-(propane-1-sulfonyl)-piperazin-1-ylmethyl]-phenylcarbamoyl}-6-trifluoromethoxy-biphenyl-3-yl)-amide.
239 4-Methyl-piperazine-1-carboxylic acid {4'-[4-(4-methanesulfonyl-piperazin-1-ylmethyl)-phenylcarbamoyl]-6-trifluoromethoxy-biphenyl-3-yl}-amide
240 5'-(2-Methylamino-acetylamino)-2'-trifluoromethoxy-biphenyl-4-carboxylic acid [4-(4-dimethylsulfamoyl-piperazin-1-ylmethyl)-phenyl]-amide
241 (S)-2-{4'-[4-(4-Methanesulfonyl-piperazin-1-ylmethyl)-phenylcarbamoyl]-6-trifluoromethoxy-biphenyl-3-ylcarbamoyl}-azetidine-1-carboxylic acid
242 5'-(Cyclohexanecarbonyl-amino)-2'-methyl-biphenyl-4-carboxylic acid {4-[2-(1,1-dioxo-1lambda*6*-thiomorpholin-4-yl)-ethyl]-phenyl}-amide
243 5'-(Cyclopropanecarbonyl-amino)-2'-methyl-biphenyl-4-carboxylic acid [4-(4-propane-1-sulfonyl-piperazin-1-ylmethyl)-phenyl]-amide
244 2'-Methoxy-5'-(4-morpholin-4-yl-phenylsulfamoyl)-biphenyl-4-carboxylic acid [4-(1,1-dioxo-1lambda*6*-thiomorpholin-4-ylmethyl)-phenyl]-amide
245 2'-Methoxy-5'-(4-morpholin-4-yl-phenylsulfamoyl)-biphenyl-4-carboxylic acid [4-(4-methanesulfonyl-piperazin-1-ylmethyl)-phenyl]-amide
246 2'-Methoxy-5'-(4-morpholin-4-yl-phenylsulfamoyl)-biphenyl-4-carboxylic acid [4-(4-propane-2-sulfonyl-piperazin-1-ylmethyl)-phenyl]-amide
247 2'-Methoxy-5'-(4-morpholin-4-yl-phenylsulfamoyl)-biphenyl-4-carboxylic acid [4-(4-dimethylsulfamoyl-piperazin-1-ylmethyl)-phenyl]-amide
248 2'-Methoxy-5'-(4-morpholin-4-yl-phenylsulfamoyl)-biphenyl-4-carboxylic acid [4-(4-propane-1-sulfonyl-piperazin-1-ylmethyl)-phenyl]-amide
249 2'-Chloro-5'-(cyclohexanecarbonyl-amino)-biphenyl-4-carboxylic acid [4-(4-methyl-piperazin-1-ylmethyl)-phenyl]-amide
250 (R)-Pyrrolidine-2-carboxylic acid {6-chloro-4'-[4-(4-methanesulfonyl-piperazin-1-ylmethyl)-phenylcarbamoyl]-biphenyl-3-yl}-amide
251 (R)-Piperidine-2-carboxylic acid {6-chloro-4'-[4-(4-(propane-1-sulfonyl)-piperazin-1-ylmethyl)-phenylcarbamoyl]-biphenyl-3-yl}-amide
252 2'-Chloro-5'-(2-methylamino-acetylamino)-biphenyl-4-carboxylic acid [4-(4-methanesulfonyl-piperazin-1-ylmethyl)-phenyl]-amide
253 2'-Chloro-5'-(3-cyclohexyl-ureido)-biphenyl-4-carboxylic acid {4-[4-(propane-1-sulfonyl)-piperazin-1-ylmethyl]-phenyl}-amide
254 2'-Chloro-5'-(3-cyclohexyl-ureido)-biphenyl-4-carboxylic acid {4-[4-(propane-2-sulfonyl)-piperazin-1-ylmethyl]-phenyl}-amide
255 2'-Chloro-5'-(3-cyclohexyl-ureido)-biphenyl-4-carboxylic acid [4-(4-dimethylsulfamoyl-piperazin-1-ylmethyl)-phenyl]-amide
256 6-Trifluoromethoxy-biphenyl-3,4'-dicarboxylic acid 4'-{[4-(4-methanesulfonyl-piperazin-1-ylmethyl)-phenyl]-amide} 3-[(4-morpholin-4-yl-phenyl)-amide]
257 6-Methoxy-biphenyl-3,4'-dicarboxylic acid 3-[(4-morpholin-4-yl-phenyl)-amide] 4'-({4-[4-(propane-1-sulfonyl)-piperazin-1-ylmethyl]-phenyl}-amide)
258 6-Methoxy-biphenyl-3,4'-dicarboxylic acid 3-[(4-morpholin-4-yl-phenyl)-amide] 4'-({4-[4-(propane-2-sulfonyl)-piperazin-1-ylmethyl]-phenyl}-amide)
259 6-Methoxy-biphenyl-3,4'-dicarboxylic acid 4'-{[4-(4-dimethylsulfamoyl-piperazin-1-ylmethyl)-phenyl]-amide} 3-[(4-morpholin-4-yl-phenyl)-amide]
260 6-Methoxy-biphenyl-3,4'-dicarboxylic acid 3-[(2-methyl-4-morpholin-4-yl-phenyl)-amide] 4'-({4-[4-(propane-1-sulfonyl)-piperazin-1-ylmethyl]-phenyl}-amide)
261 6-Methoxy-biphenyl-3,4'-dicarboxylic acid 3-{[4-(4-(1,1-dioxo-1lambda*6*-thiomorpholin-4-yl)-phenyl]-amide} 4'-{[4-(4-methyl-piperazin-1-yl)-phenyl]-amide}
262 6-Methoxy-biphenyl-3,4'-dicarboxylic acid 4'-{[4-(1,1-dioxo-1lambda*6*-thiomorpholin-4-ylmethyl)-phenyl]-amide} 4'{[4-(4-methanesulfonyl-piperazin-1-ylmethyl)-phenyl]-amide}
263 6-Chloro-biphenyl-3,4'-dicarboxylic acid 4'-({4-[4-(butane-1-sulfonyl)piperazin-1-ylmethyl]-phenyl}-amide) 3-[(4-morpholin-4-yl-phenyl)-amide]
264 6-Chloro-biphenyl-3,4'-dicarboxylic acid 3-[(3-fluoro-4-morpholin-4-yl-phenyl)-amide] 4'-({4-[4-(propane-1-sulfonyl)-piperazin-1-ylmethyl]-phenyl}-amide)
265 6-Chloro-biphenyl-3,4'-dicarboxylic acid 3-{[4-(4-methanesulfonyl-piperazin-1-ylmethyl)-phenyl]-amide} 4'-[(4-morpholin-4-yl-phenyl)-amide] and pharmaceutically acceptable salts thereof.

The compounds of formula (I) may be prepared by analogy with known methods. For example, they can be prepared by the following reactions:

scheme (1)

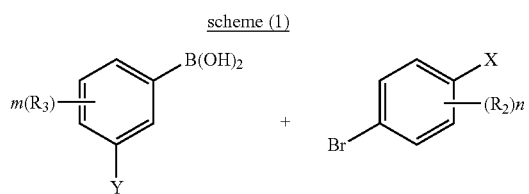

scheme (2)

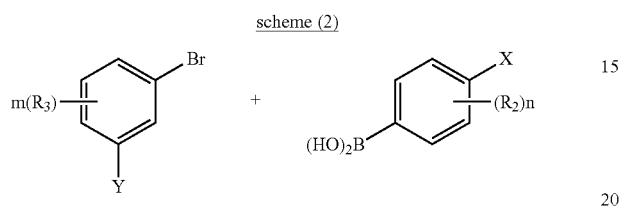

wherein $R_2$, $R_3$, n and m are as defined above, and either X and Y are, respectively, -A-$R_1$ or —B—$R_4$, wherein A, B, $R_1$ and $R_4$ are as defined above, or X and Y represent groups which can be further reacted by standard techniques to yield the moieties -A-$R_1$ or —B—$R_4$, for example amino groups or carbocyclic acid groups.

The coupling reactions shown in schemes (1) and (2) can be effected by known methods, for example cesium carbonate and palladium catalyst in aqueous DMF at reflux. The starting materials used in schemes (1) and (2) are known compounds or can be prepared by analogy with known methods.

Methods for converting the moieties X and Y into moieties -A-$R_1$ and —B—$R_4$, and for converting moieties -A-$R_1$ and —B—$R_4$ into other moieties set out in the definitions of -A-$R_1$ and —B—$R_4$, are known to those of skill in the art. By way of example, some representative techniques are set out below.

Examples of Suzuki Coupling Reaction.

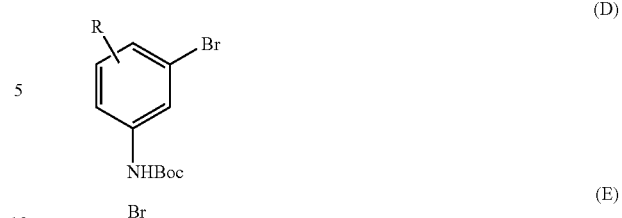

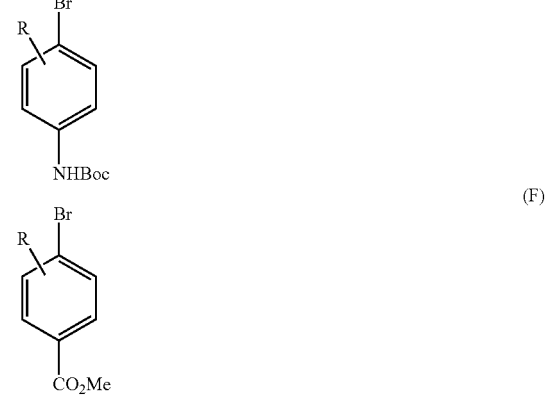

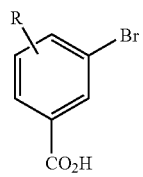

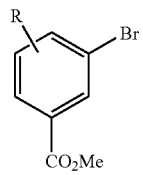

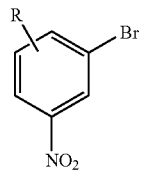

The above aryl bromides and boronic acids/esters can be coupled under standard conditions (cesium carbonate and palladium catalyst in aqueous DME at reflux) to provide a number of diverse biphenyl cores. These may have two carbonyl functionalities, two amino functionalities or one of both types. Some products from these reactions are shown below (for the sake of brevity, a substituent on the aromatic ring is either shown as "C" or "N" and the $R_2$ and $R_3$ substituents are simply shown as 'R').

Product of:

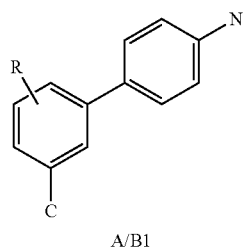
A/B1

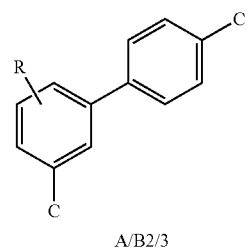
A/B2/3

Product of:

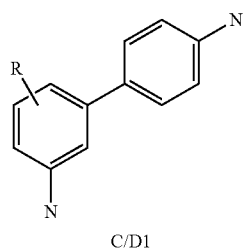
C/D1

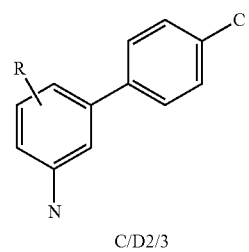
C/D2/3

Product of:

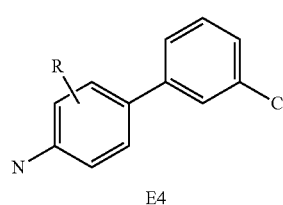
E4

By careful usage of monomers i.e. esters vs. acids and nitro groups vs. protected amines it can be seen that amide and reverse amide groups may be placed selectively at either end of the biphenyl core. The initial amide coupling reactions may be carried out by reaction of amines with acid chlorides, or by reaction with carboxylic acids and a suitable coupling reagent e.g. HBTU or EDAC/HOBT. Subsequent to this and dependent on the second functionality to be converted to the second amide, a hydrolysis of an ester, a deprotection of a protected amine, or a hydrogenation of a nitro-group will then furnish intermediates which are readily coupled as described above to give the final compounds shown below.

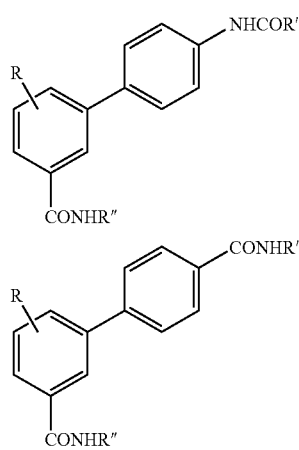

-continued

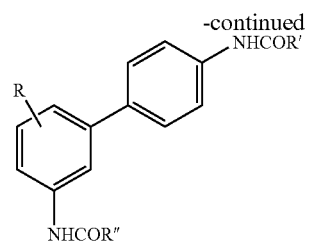

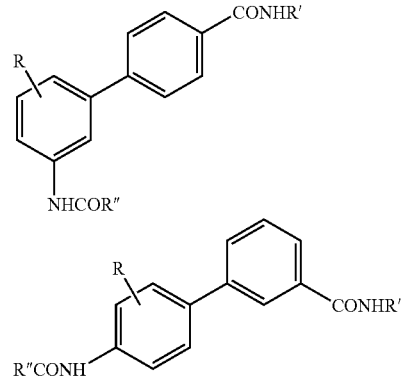

Analogues in which one of the amides has been replaced by a ring structure may be prepared, for example, via dehydration of a primary amide into a nitrile. Suitable adaptation of the nitrile furnishes compounds with heteroaromatic rings, e.g. 1,2,4-oxadiazoles or 1,2,4-triazoles. Replacement of the amide with aryl, carbocyclyl and heterocyclyl groups may be performed by analogy.

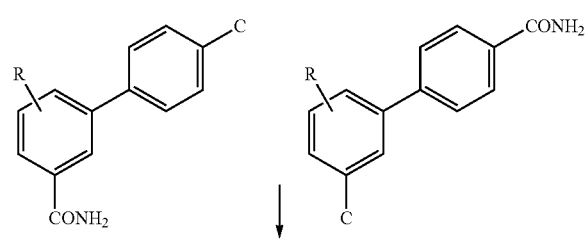

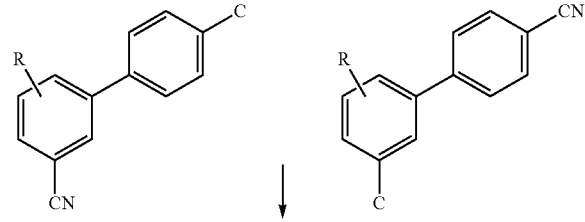

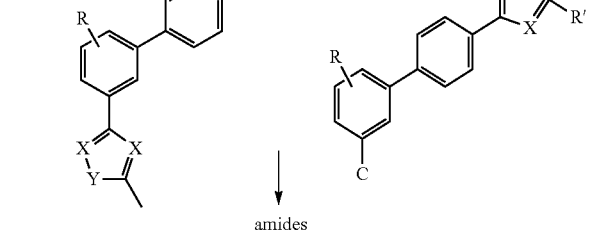
amides

X = N, Y = O or N

In some analogues one of the amide groups is reduced to the amine. These compounds can be prepared via reduction of an acid, usually with an organometallic reagent such as lithium borohydride, followed by oxidation to the aldehyde with manganese dioxide and then subsequent reductive amination. This final step is routinely carried out in the presence of a mild reducing agent such as sodium tri(acetoxy) borohydride:

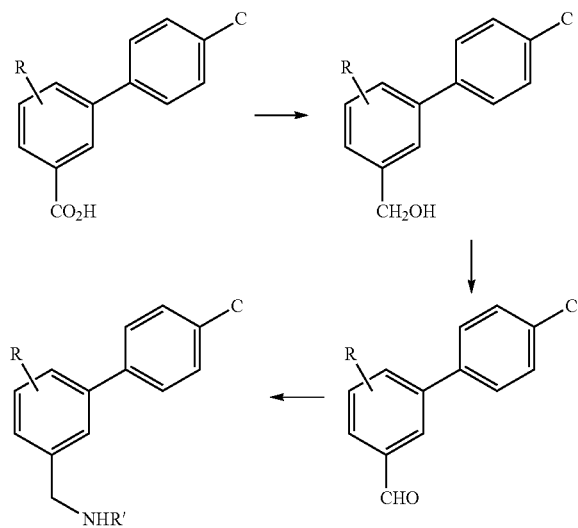

As explained above, the compounds of the invention are active against hepatitis C virus. The present invention therefore provides a method for treating a patient suffering from or susceptible to a hepatitis C infection, which method comprises administering to said patient an effective amount of a biphenyl derivative of formula (I), as defined above, or a pharmaceutically acceptable salt thereof. Also provided is a method for alleviating or reducing the incidence of a hepatitis C infection in a patient, which method comprises administering to said patient an effective amount of a compound of formula (I), as defined above, or a pharmaceutically acceptable salt thereof.

The present invention further provides a biphenyl derivative of formula (I), as defined above, or a pharmaceutically acceptable salt thereof, for the treatment of the human or animal body.

Compounds of formula (I) are also believed to be novel. The present invention therefore also provides a biphenyl derivative of formula (I), or a pharmaceutically acceptable salt thereof.

Yet further the present invention provides a pharmaceutical composition comprising a biphenyl derivative of formula (I) or a pharmaceutically acceptable salt thereof, and a pharmaceutically acceptable diluent or carrier. Said pharmaceutical composition typically contains up to 85 wt % of a compound of the invention. More typically, it contains up to 50 wt % of a compound of the invention. Preferred pharmaceutical compositions are sterile and pyrogen free. Further, the pharmaceutical compositions of the invention typically contain a compound of the invention which is a substantially pure optical isomer.

The compounds of the invention may be administered in a variety of dosage forms. Thus, they can be administered orally, for example as tablets, troches, lozenges, aqueous or oily suspensions, dispersible powders or granules. The compounds of the invention may also be administered parenterally, whether subcutaneously, intravenously, intramuscularly, intrasternally, transdermally or by infusion techniques. The compounds may also be administered as suppositories.

The compounds of the invention are typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

Compounds of the present invention may be used in conjunction with known anti-viral agents. Preferred known anti-viral agents in this regard are interferon and ribavirin, which are known for the treatment of hepatitis C (Clinical Microbiology Reviews, January 2000, 67-82). The said medicament therefore typically further comprises interferon and/or ribavirin. Further, the present invention provides a pharmaceutical composition comprising:

(a) a biphenyl derivative of the formula (I), as defined above, or a pharmaceutically acceptable salt thereof;
(b) interferon and/or ribavirin; and
(c) a pharmaceutically acceptable carrier or diluent.

Also provided is a product comprising:

(a) a biphenyl derivative of the formula (I), as defined above, or a pharmaceutically acceptable salt thereof; and
(b) interferon and/or ribavirin,
for separate, simultaneous or sequential use in the treatment of the human or animal body.

A therapeutically effective amount of a compound of the invention is administered to a patient. A typical dose is from about 0.01 to 100 mg per kg of body weight, according to the activity of the specific compound, the age, weight and conditions of the subject to be treated, the type and severity of the disease and the frequency and route of administration. Preferably, daily dosage levels are from 0.05 to 16 mg per kg of body weight, more preferably, from 0.05 to 1.25 mg per kg of body weight.

The following Examples illustrate the invention. They do not however, limit the invention in any way. In this regard, it is important to understand that the particular assay used in the Examples section is designed only to provide an indication of anti-hepatitis C activity. There are many assays available to determine such activity, and a negative result in any one particular assay is therefore not determinative.

EXAMPLES

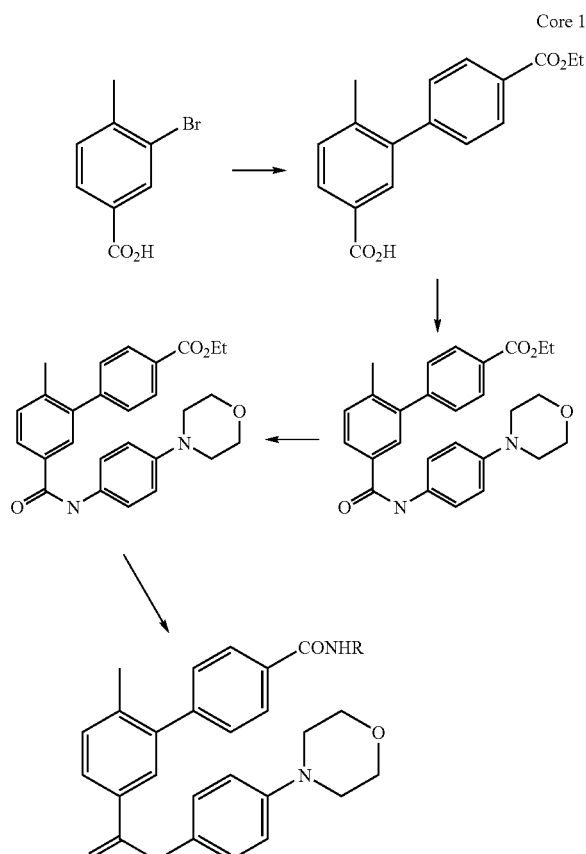

Intermediate 1

6-Methyl-biphenyl-3,4'-dicarboxylic acid 4'-ethyl ester

A mixture of 3-bromo-4-methyl benzoic acid (7.50 g), 4-(ethoxycarbonylphenyl) boronic acid (6.82 g), cesium carbonate (11.34 g) and tetrakis(triphenylphosphine) palladium (0), 5 mol % (2.01 g) was heated to reflux under nitrogen in DME (150 ml) for 18 h. The reaction mixture was then cooled to room temperature and filtered. The resulting filtrate was then evaporated and purified on silica gel, eluting with 0-30% 20:8:1 $CH_2Cl_2$/EtOH/$NH_3$ in $CH_2Cl_2$ gave the title compound as a white solid 2.5 g.

Intermediate 2

2'-Methyl-5'-(4-morpholin-4-yl-phenylcarbamoyl)-biphenyl-4-carboxylic acid ethyl ester 6-Methyl-biphenyl-3,4'-dicarboxylic acid 4'-ethyl ester (3.54 g) in toluene (70 ml) was treated with oxalyl chloride (4 ml) followed by DMF (3 drops). The reaction was stirred at room temperature for 2 hours and then evaporated to dryness. The resulting residue was redissolved in toluene (30 ml) and evaporated to dryness twice to yield the acid chloride.

A solution of triethylamine (0.25 g) in dichloromethane (5 ml) was added to 4-morpholin-4-yl-phenylamine (0.44 g). Then a solution of the above acid chloride (0.75 g) in dichloromethane (7 ml) was added and the reaction mixture stirred for 18 h. The mixture was then partitioned between 1M HCl and dichloromethane. The dried extracts were evaporated giving a colourless solid, used without further purification in the next synthetic step Intermediate 3

2'-Methyl-5'-(4-morpholin-4-yl-phenylcarbamoyl)-biphenyl-4-carboxylic acid

2'-Methyl-5'-(4-morpholin-4-yl-phenylcarbamoyl)-biphenyl-4-carboxylic acid ethyl ester (0.89 g) in THF (10 ml) and 0.5M NaOH (15 m) was heated to 100° C. for 3 hours then cooled to room temperature. THF was evaporated and the residue extracted with dichloromethane. The aqueous layer was acidified to pH 1 and a grey solid precipitated which was collected by filtration and dried (0.74 g).

$^1$H NMR (DMSO, δ) 2.33 (s, 3H) 3.26 (br s, 4H) 3.87 (br s, 4H) 7.26 (br d, 2H) 7.50 (d, 1H) 7.58 (d, 2H) 7.75 (d, 2H) 7.89 (s, 1H) 7.94 (d, 1H) 8.06 (d, 2H) 10.23 (s, 1H)

Example 1

6-Methyl-biphenyl-3,4'-dicarboxylic acid 4'-[(3-bromo-phenyl)-amide]-[(4 morpholin-4-yl-phenyl)-amide]

2'-Methyl-5'-(4-morpholin-4-yl-phenylcarbamoyl)-biphenyl-4-carboxylic acid (Intermediate 3) (54 mg), EDAC.HCl (25 mg), HOBT.$H_2O$ (17 mg) and N-methylmorpholine (26 mg) were stirred in DMF (1 ml). The mixture was then treated with 3-bromo-phenylamine (22 mg) and the whole reaction mixture was stirred at 20 C overnight. The reaction mixture was evaporated to dryness. The residue was redissolved in acetonitrile (0.5 ml) and water (3 mL) was added. The resulting brown solid was filtered and dried (55 mg).

$^1$H NMR (DMSO, δ) 2.35 (s, 3H) 3.10-3.06 (m, 4H) 3.73-3.77 (m, 4H) 6.95 (d, 2H) 7.33-7.39 (m, 2H) 7.50 (d, 1H) 7.62-7.66 (m, 4H) 7.81 (dd, 1H) 7.89 (s, 1H) 7.93 (d, 1H) 8.09 (d, 2H) 8.17 (s, 1H) 10.08 (s, 1H) 10.49 (s, 1H)

LC-MS ES+=570

Examples 2 to 8 were prepared in an analogous fashion to Example 1 using Intermediate 3:

Example 2

6-Methyl-biphenyl-3,4'-dicarboxylic acid 4'-[(6-methoxy-pyridin-3-yl)-amide] 3-[(4-morpholin-4-yl-phenyl)-amide]

$^1$H NMR (DMSO, δ) 2.35 (s, 3H) 3.06-3.10 (m, 4H) 3.77-3.73 (m, 4H) 3.86 (s, 3H) 6.88 (d, 1H) 6.95 (d, 2H) 7.50 (d, 1H) 7.61-7.66 (m, 4H) 7.89 (s, 1H) 7.93 (d, 1H) 8.09 (d, 3H) 8.57 (d, 1H) 10.09 (s, 1H) 10.40 (s, 1H)

LC-MS ES+=523

Example 3

6-Methyl-biphenyl-3,4'-dicarboxylic acid 4'-(3-methyl-benzylamide) 3-[(4-morpholin-4-yl-phenyl)-amide]

Example 4

6-Methyl-biphenyl-3,4'-dicarboxylic acid 4'-[(3-methyl-butyl)-amide] 3-[(4-morpholin-4-yl-phenyl)-amide]

$^1$H NMR (DMSO, δ) 0.93 (d, 6H) 1.47 (dt, 2H) 1.66 (septet, 1H) 2.32 (s, 3H) 3.08 (m, 4H) 3.34 (m, 2H) 3.75 (m, 4H) 6.94 (d, 2H) 7.46-7.51 (m, 3H) 7.63 (d, 2H) 7.86-7.97 (m, 4H) 8.51 (t, 1H) 10.06 (s, 1H)

LC-MS ES+=486

Example 5

6-Methyl-biphenyl-3,4'-dicarboxylic acid 4'-(3-fluoro-benzylamide) 3-[(4-morpholin-4-yl-phenyl)-amide]

Example 6

6-Methyl-biphenyl-3,4'-dicarboxylic acid 3-[(4-morpholin-4-yl-phenyl)-amide] 4'-[(2-piperidin-1-yl-ethyl)-amide]

Example 7

6-Methyl-biphenyl-3,4'-dicarboxylic acid 4'-[(4-bromo-phenyl)-amide] 3-[(4-morpholin-4-yl-phenyl)-amide]

Example 8

6-Methyl-biphenyl-3,4'-dicarboxylic acid 4'-[(3-benzyloxy-phenyl)-amide] 3-[(4-morpholin-4-yl-phenyl)-amide]

Example 9

6-Methyl-biphenyl-3,4'-dicarboxylic acid 3-{[3-(4-methyl-piperazin-1-yl)-propyl]-amide} 4'-[(4-morpholin-4-yl-phenyl)-amide]

This compound was prepared in by analogous methods from Intermediate 1.

Examples 10-16 were prepared in an analogous fashion to Example 1.

Example 10

6-Methyl-biphenyl-3,4'-dicarboxylic acid 3-[(4-morpholin-4-yl-phenyl)-amide] 4'-(3-trifluoromethyl-benzylamide)

$^1$H NMR (DMSO, δ) 2.33 (s, 3H) 3.06-3.1 (m, 4H) 3.73-3.77 (m, 4H) 4.61 (d, 2H) 6.94 (d, 2H) 7.48 (d, 1H) 7.60 (d, 1H) 7.63-7.67 (m, 5H) 7.71 (s, 1H) 7.86 (m, 1H) 7.91 (dd, 1H) 8.03 (d, 2H) 8.25 (m, 1H) 9.27 (t, 1H) 10.08 (s, 1H)

LC-MS ES+=574

Example 11

6-Methyl-biphenyl-3,4'-dicarboxylic acid 3-[(4-morpholin-4-yl-phenyl)-amide] 4'-[(2-thiophen-2-yl-ethyl)-amide]

Example 12

6-Methyl-biphenyl-3,4'-dicarboxylic acid 4'-[(1H-indazol-6-yl)-amide] 3-[(4-morpholin-4-yl-phenyl)-amide]

Example 13

6-Methyl-biphenyl-3,4'-dicarboxylic acid 4'-{[2-(3H-imidazol-4-yl)-ethyl]-amide} 3-[(4-morpholin-4-yl-phenyl)-amide]

Example 14

6-Methyl-biphenyl-3,4'-dicarboxylic acid 4'-[(5-methyl-furan-2-ylmethyl)-amide] 3-[(4-morpholin-4-yl-phenyl)-amide]

Example 15

6-Methyl-4'-pyrrolidine-1-carbonyl)-biphenyl-3-carboxylic acid (4-morpholin-4-yl-phenyl)-amide

Example 16

6-Methyl-biphenyl-3,4'-dicarboxylic acid 4'-benzo[1,3]dioxol-5-ylamide 3-[(4-morpholin-4-yl-phenyl)-amide]

Example 17

6-Methyl-biphenyl-3,4'-dicarboxylic acid 3-cyclopropylamide 4'-[(4-morpholin-4-yl-phenyl)-amide]

This compound was prepared by analogous methods using Intermediate 1.

Example 18

Furan-2-carboxylic acid [6-methyl-4'-(4-morpholin-4-yl-phenylcarbamoyl)-biphenyl-3-yl]-amide This compound was prepared by analogous methods using Intermediate 23

Examples 19-59 were prepared in an analogous fashion to Example 1.

Example 19

6-Methyl-biphenyl-3,4'-dicarboxylic acid 4'-[(3-benzoyl-phenyl)-amide] 3-[(4-morpholin-4-yl-phenyl)-amide]

Example 20

6-Methyl-biphenyl-3,4'-dicarboxylic acid 4'-(4-morpholin-4-yl-benzylamide) 3-[(4-morpholin-4-yl-phenyl)-amide]

Example 21

6-Methyl-biphenyl-3,4'-dicarboxylic acid 4'-[(3-butylsulfamoyl-phenyl)-amide] 3-[(4-morpholin-4-yl-phenyl)-amide]

Example 22

6-Methyl-biphenyl-3,4'-dicarboxylic acid 4'-[(3,4-dichloro-phenyl)-amide] 3-[(4-morpholin-4-yl-phenyl)-amide]

Example 23

6-Methyl-biphenyl-3,4'-dicarboxylic acid 3-[(4-morpholin-4-yl-phenyl)-amide] 4'-[(3-trifluoromethyl-phenyl)-amide]

Example 24

6-Methyl-biphenyl-3,4'-dicarboxylic acid 4'-[(4-cyano-phenyl)-amide] 3-[(4-morpholin-4-yl-phenyl)-amide]

Example 25

6-Methyl-biphenyl-3,4'-dicarboxylic acid 3-[(4-morpholin-4-yl-phenyl)-amide] 4'-[(3-trifluoromethoxy-phenyl)-amide]

Example 26

6-Methyl-biphenyl-3,4'-dicarboxylic acid 3-[(4-morpholin-4-yl-phenyl)-amide] 4'-[(3-trifluoromethoxy-phenyl)-amide]

Example 27

6-Methyl-biphenyl-3,4'-dicarboxylic acid 3-[(4-morpholin-4-yl-phenyl)-amide] 4'-[(3-trifluoromethoxy-phenyl)-amide]

Example 28

6-Methyl-biphenyl-3,4'-dicarboxylic acid 4'-[(4-isoxazol-5-yl-phenyl)-amide] 3-[(4-morpholin-4-yl-phenyl)-amide]

$^1$H NMR (DMSO, δ) 2.36 (s, 3H) 3.06-3.1 (m, 4H) 3.73-3.77 (m, 4H) 6.96-6.98 (m, 3H) 7.50 (d, 2H) 7.64 (d, 4H) 7.92 (dd, 4H) 8.11 (d, 2H, d) 8.65 (d, 1H, d) 10.1 (s, 1H) 10.61 (s, 1H)
LC-MS ES+=559

Example 29

6-Methyl-biphenyl-3,4'-dicarboxylic acid 4'-[(4-methylsulfamoyl-phenyl)-amide] 3-[(4-morpholin-4-yl-phenyl)-amide]

$^1$H NMR (DMSO, δ) 2.49 (s, 3H) 2.57 (d, 3H) 3.20-3.24 (m, 4H) 3.87-3.91 (m, 4H) 7.09 (d, 2H) 7.52 (q, 1H) 7.64 (d, 1H) 7.78 (d, 4H) 7.93 (d, 2H) 8.03-8.08 (m, 2H) 8.22 (dd, 4H) 10.23 (s, 1H) 10.86 (s, 1H)
LC-MS ES+=585

Example 30

6-Methyl-biphenyl-3,4'-dicarboxylic acid 4'-[(4-bromo-3-chloro-phenyl)-amide] 3-[(4-morpholin-4-yl-phenyl)-amide]

Example 31

6-Methyl-biphenyl-3,4'-dicarboxylic acid 4'-{[3-(1-hydroxy-ethyl)-phenyl]-amide} 3-[(4-morpholin-4-yl-phenyl)-amide]

Example 32

3-{[2'-Methyl-5'-(4-morpholin-4-yl-phenylcarbamoyl)-biphenyl-4-carbonyl]-amino}-benzoic acid ethyl ester

Example 33

6-Methyl-biphenyl-3,4'-dicarboxylic acid 4'-[(3-methoxy-phenyl)-amide] 3-[(4-morpholin-4-yl-phenyl)-amide]

Example 34

6-Methyl-biphenyl-3,4'-dicarboxylic acid 4'-[(3,4-dimethoxy-phenyl)-amide] 3-[(4-morpholin-4-yl-phenyl)-amide]

Example 35

6-Methyl-biphenyl-3,4'-dicarboxylic acid 4'-({2-[(cyclohexyl-methyl-amino)-methyl]-phenyl}-amide) 3-[(4-morpholin-4-yl-phenyl)-amide]

Example 36

6-Methyl-biphenyl-3,4'-dicarboxylic acid 3-[(4-morpholin-4-yl-phenyl)-amide] 4'-pyridin-3-ylamide

Example 37

4'-[4-(2,3-Dichloro-phenyl)-piperazine-1-carbonyl]-6-methyl-biphenyl-3-carboxylic acid (4-morpholin-4-yl-phenyl)-amide

Example 38

6-Methyl-biphenyl-3,4'-dicarboxylicacid 3-[(4-morpholin-4-yl-phenyl)-amide] 4'-[(2-trifluoromethyl-1H-benzoimidazol-5-yl)-amide]

$^1$H NMR (DMSO, δ) 2.36 (s, 3H) 3.06-3.1 (m, 4H) 3.73-3.77 (m, 4H) 6.95 (d, 2H) 7.50 (d, 1H) 7.62-7.66 (m, 4H) 7.74 (s, 2H) 7.90 (d, 1H) 7.95 (d, 1H) 8.12 (d, 2H) 8.39 (s, 1H) 10.1 (s, 1H) 10.52 (s, 1H) 13.85 (br s, 1H)
LC-MS ES+=600

Example 39

6-Methyl-biphenyl-3,4'-dicarboxylic acid 4'-[(4-cyanomethyl-phenyl)-amide] 3-[(4-morpholin-4-yl-phenyl)-amide]

Example 40

6-Methyl-biphenyl-3,4'-dicarboxylic acid 3-[(4-morpholin-4-yl-phenyl)-amide] 4'-[(thiophen-3-ylmethyl)-amide]

Example 41

6-Methyl-biphenyl-3,4'-dicarboxylic acid 3-[(4-morpholin-4-yl-phenyl)-amide] 4'-(3-trifluoromethoxy-benzylamide)

Example 42

6-Methyl-biphenyl-3,4'-dicarboxylic acid 4'-(4-chloro-3-trifluoromethyl-benzylamide) 3-[(4-morpholin-4-yl-phenyl)-amide]

Example 43

6-Methyl-biphenyl-3,4'-dicarboxylic acid 4'-(3-chloro-4-methyl-benzylamide) 3-[(4-morpholin-4-yl-phenyl)-amide]

Example 44

6-Methyl-biphenyl-3,4'-dicarboxylic acid 4'-[(1H-indol-6-yl)-amide] 3-[(4-morpholin-4-yl-phenyl)-amide]

$^1$H NMR (DMSO, δ) 2.36 (s, 3H) 3.06-3.08 (m, 4H) 3.73-3.77 (m, 4H) 6.40 (br s, 1H) 6.95 (d, 2H) 7.31-7.35 (m, 2H) 7.50 (d, 2H) 7.60-7.66 (m, 4H) 7.90-7.97 (m, 2H) 8.09-8.13 (m, 3H) 10.1 (s, 1H) 10.27 (s, 1H) 11.1 (s, 1H)
LC-MS ES+=53

Example 45

6-Methyl-biphenyl-3,4'-dicarboxylic acid 4'-[(1H-indol-5-yl)-amide] 3-[(4-morpholin-4-yl-phenyl)-amide]

Example 46

6-Methyl-biphenyl-3,4'-dicarboxylic acid 4'-benzothiazol-6-ylamide 3-[(4-morpholin-4-yl-phenyl)-amide]

Example 47

[3-({[2'-Methyl-5'-(4-morpholin-4-yl-phenylcarbamoyl)-biphenyl-4-carbonyl]-amino}-methyl)-benzyl]-carbamic acid tert-butyl ester

Example 48

6-Methyl-biphenyl-3,4'-dicarboxylic acid 4'-[(1H-indol-7-yl)-amide] 3-[(4-morpholin-4-yl-phenyl)-amide]

Example 49

6-Methyl-biphenyl-3,4'-dicarboxylic acid 4'-[2-(2-hydroxymethyl-phenylsulfanyl)-benzylamide] 3-[(4-morpholin-4-yl-phenyl)-amide]

Example 50

6-Methyl-biphenyl-3,4'-dicarboxylic acid 4'-{[4-(1,1-dioxo-1lambda*6*-thiomorpholin-4-ylmethyl)-phenyl]-amide} 3-[(4-morpholin-4-yl-phenyl)-amide]

Example 51

6-Methyl-biphenyl-3,4'-dicarboxylic acid 4'-{[(S)-1-hydroxymethyl-2-(1H-indol-3-yl)-ethyl]-amide} 3-[(4-morpholin-4-yl-phenyl)-amide]

Example 52

6-Methyl-biphenyl-3,4'-dicarboxylic acid 4'-(3-bromo-benzylamide) 3-[(4-morpholin-4-yl-phenyl)-amide]

Example 53

6-Methyl-biphenyl-3,4'-dicarboxylic acid 4'-[(4-amino-phenyl)-amide] 3-[(4-morpholin-4-yl-phenyl)-amide]

Example 54

6-Methyl-biphenyl-3,4'-dicarboxylic acid 4'-[(4-methylsulfamoylmethyl-phenyl)-amide] 3-[(4-morpholin-4-yl-phenyl)-amide]

Example 55

6-Methyl-biphenyl-3,4'-dicarboxylic acid 4'-[(5-bromo-1H-indol-7-yl)-amide] 3-[(4-morpholin-4-yl-phenyl)-amide]

Example 56

6-Methyl-biphenyl-3,4'-dicarboxylic acid 3-[(4-morpholin-4-yl-phenyl)-amide] 4'-f{[4-(1H-pyrazol-3-yl)-phenyl]-amide}

Example 57

6-Methyl-biphenyl-3,4'-dicarboxylic acid 4'-(3-chloro-2-fluoro-benzylamide) 3-[(4-morpholin-4-yl-phenyl)-amide]

Example 58

6-Methyl-biphenyl-3,4'-dicarboxylic acid 3-[(4-morpholin-4-yl-phenyl)-amide] 4'-{[4-(piperidine-1-carbonyl)-phenyl]-amide}

Example 59

Biphenyl-3,4'-dicarboxylic acid 4'-[(1H-indol-5-yl)-amide] 3-[(4-morpholin-4-yl-phenyl)-amide]

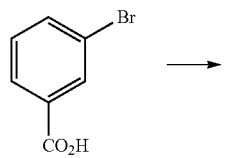

Core 2

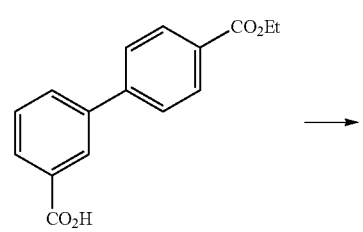

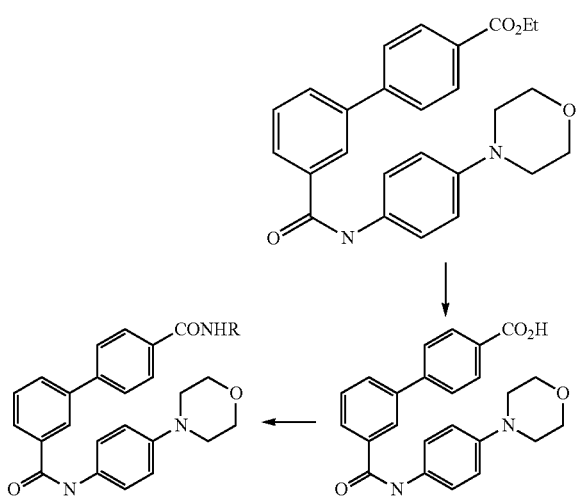

Intermediate 4

Biphenyl-3,4'-dicarboxylic acid 4'-ethyl ester

A mixture of 3-bromo-benzoic acid (4.02 g) and 4-ethoxycarbonyl-phenyl boronic acid (3.88 g) in DME (100 ml) containing cesium carbonate (6.5 g) and tetrakis(triphenylphosphine) palladium (0) (1.15 g) was heated to reflux for 24 h. The cooled mixture was then filtered through celite and evaporated giving the crude title compound as a white solid which was used without purification in the next synthetic step.

Intermediate 5

3'-(4-Morpholin-4-yl-phenylcarbamoyl)-biphenyl-4-carboxylic acid ethyl ester

Biphenyl-3,4'-dicarboxylic acid 4'-ethyl ester (660 mg) in toluene (10 ml) was treated with oxalyl chloride (1 ml) followed by DMF (2 drops). The reaction was stirred at room temperature for 2 hours and then evaporated to dryness. The resulting residue was redissolved in toluene (30 ml) and evaporated to dryness twice to yield the acid chloride.

A solution of triethylamine (494 mg) in dichloromethane (10 ml) was added to 4-morpholin-4-yl-phenylamine (435 mg). Then a solution of the above acid chloride in dichloromethane (7 ml) was added and the reaction mixture stirred for 18 h. The mixture was then partitioned between 1M HCl and dichloromethane. The dried extracts were evaporated giving a colourless solid, used without further purification in the next synthetic step Intermediate 6

3'-(4-Morpholin-4-yl-phenylcarbamoyl)-biphenyl-4-carboxylic acid

3'-(4-Morpholin-4-yl-phenylcarbamoyl)-biphenyl-4-carboxylic acid ethyl ester (850 mg) in THF (12 ml) and 1M NaOH (25 m) was heated to 100° C. for 3 hours then cooled to room temperature. THF was evaporated and the residue extracted with dichloromethane. The aqueous layer was acidified to pH 1 and a grey solid precipitated which was collected by filtration and dried (793 mg)

Example 60

Biphenyl-3,4'-dicarboxylic acid 4'-[(1H-indol-6-yl)-amide] 3-[(4-morpholin-4-yl-phenyl)-amide]

3'-(4-Morpholin-4-yl-phenylcarbamoyl)-biphenyl-4-carboxylic acid (30 mg) (Intermediate 6), EDAC.HCl (14 mg), HOBT.H$_2$O (10 mg) and N-methylmorpholine (15 mg) were stirred in DMF (0.5 ml). The mixture was then treated with 1H-indol-6-ylamine (10 mg) and the whole reaction mixture was stirred at 20 C overnight. The reaction mixture was diluted with water and the solid collected by filtration. This was then recrystallised from 3:1 EtOH:H$_2$O at 140 C (in microwave) giving the title compound as an off-white solid (5 mg).

$^1$H NMR (DMSO, δ) 3.10 (t, 4H) 3.76 (t, 4H) 6.41 (s, 1H) 6.98 (d, 2H) 7.31-7.35 (m, 2H) 7.51 (m, 1H) 7.63-7.72 (m, 3H) 7.95-8.00 (m, 4H) 8.13-8.17 (m, 3H) 8.32-8.35 (m, 1H) 10.24 (s, 1H) 10.26 (s, 1H) 11.10 (s, 1H)

LC-MS ES+=517.

Example 61

6-Methyl-biphenyl-3,4'-dicarboxylic acid 4'-[(3-acetylamino-phenyl)-amide] 3-[(4-morpholin-4-yl-phenyl)-amide]

This compound was prepared in an analogous fashion to Example 1.

Examples 62 to 66 were prepared from Intermediates generated from the coupling reaction F4 and are prepared in an analogous fashion to Example 1.

Example 62

2'-Methyl-biphenyl-3,4'-dicarboxylic acid 3-[(3-methoxy -phenyl)-amide] 4'-[(4-morpholin-4-yl-phenyl)-amide]

Example 63

2'-Methyl-biphenyl-3,4'-dicarboxylic acid 3-[(1H-indazol-6-yl)-amide] 4'-[(4-morpholin-4-yl-phenyl)-amide]

Example 64

2'-Methyl-biphenyl-3,4'-dicarboxylic acid 3-[(3-bromo -phenyl)-amide] 4'-[(4-morpholin-4-yl-phenyl)-amide]

Example 65

2'-Methyl-biphenyl-3,4'-dicarboxylic acid 3-[(4-isoxazol-5-yl-phenyl)-amide] 4'-[(4-morpholin-4-yl-phenyl)-amide]

Example 66

2'-Methyl-biphenyl-3,4'-dicarboxylic acid 3-(3-chloro -benzylamide) 4'-[(4-morpholin-4-yl-phenyl)-amide]

Examples 67 to 84 were prepared in an analogous fashion to Example 1.

Example 67

6-Methyl-biphenyl-3,4'-dicarboxylic acid 4'-[(1H-indazol-6-yl)-amide] 3-[(4-morpholin-4-yl-phenyl)-amide]

Example 68

2'-Methyl-5'-(4-morpholin-4-yl-benzoylamino)-biphenyl-4-carboxylic acid (3-trifluoromethoxy-phenyl)-amide

Example 69

6-Methyl-biphenyl-3,4'-dicarboxylic acid 3-[(4-morpholin-4-yl-phenyl)-amide] 4'-[(3-thiomorpholin-4-ylmethyl-phenyl)-amide]

Example 70

6-Methyl-biphenyl-3,4'-dicarboxylic acid 4'-[(4-dimethylcarbamoyl-phenyl)-amide] 3-[(4-morpholin-4-yl-phenyl)-amide]

Example 71

6-Methyl-biphenyl-3,4'-dicarboxylic acid 4'-{[4-(3-ethyl-6-hydroxy-2-oxo-piperidin-3-yl)-phenyl]-amide} 3-[(4-morpholin-4-yl-phenyl)-amide]

Example 72

6-Methyl-biphenyl-3,4'-dicarboxylic acid 4'-[(3-acetylamino -phenyl)-amide] 3-[(4-morpholin-4-yl-phenyl)-amide]

Example 73

6-Methyl-biphenyl-3,4'-dicarboxylic acid 3-[(4-morpholin-4-yl-phenyl)-amide] 4'-[(4-piperidin-1-ylmethyl-phenyl)-amide]

Example 74

6-Methyl-biphenyl-3,4'-dicarboxylic acid 4'-[(4-morpholin-4-ylmethyl-phenyl)-amide] 3-[(4-morpholin-4-yl-phenyl)-amide]

Example 75

6-Methyl-biphenyl-3,4'-dicarboxylic acid 3-[(4-morpholin-4-yl-phenyl)-amide] 4'-[(4-pyrrolidin-1-ylmethyl-phenyl)-amide]

Example 76

6-Methyl-biphenyl-3,4'-dicarboxylic acid 4'-({4-[(methyl -propyl-amino)-methyl]-phenyl}-amide) 3-[(4-morpholin-4-yl-phenyl)-amide]

Example 77

6-Methyl-biphenyl-3,4'-dicarboxylic acid 4'-[(3-acetylamino -4-methyl-phenyl)-amide] 3-[(4-morpholin-4-yl-phenyl)-amide]

Example 78

6-Methyl-biphenyl-3,4'-dicarboxylic acid 4'-[(3-methanesulfonylamino-phenyl)-amide] 3-[(4-morpholin-4-yl-phenyl)-amide]

Example 79

6-Methyl-biphenyl-3,4'-dicarboxylic acid 3-[(4-morpholin-4-yl-phenyl)-amide] 4'-[(2-oxo-2,3-dihydro-1H-benzoimidazol-5-yl)-amide]

Example 80

6-Methyl-biphenyl-3,4'-dicarboxylic acid 3-[(4-morpholin-4-yl-phenyl)-amide] 4'-[(2-piperidin-1-ylmethyl-phenyl)-amide]

Example 81

6-Methyl-biphenyl-3,4'-dicarboxylic acid 4'-[(4-hydroxymethyl-phenyl)-amide] 3-[(4-morpholin-4-yl-phenyl)-amide]

Example 82

6-Methyl-biphenyl-3,4'-dicarboxylic acid 3-[(4-morpholin-4-yl-phenyl)-amide] 4'-[(4-piperazin-1-ylmethyl-phenyl)-amide]

Example 83

6-Methyl-biphenyl-3,4'-dicarboxylic acid 4'-(3-chloro -benzylamide) 3-[(4-morpholin-4-yl-phenyl)-amide]

Example 84

2'-Methyl-5'-(4-morpholin-4-yl-phenylcarbamoyl)-biphenyl-4-carboxylic acid ethyl ester

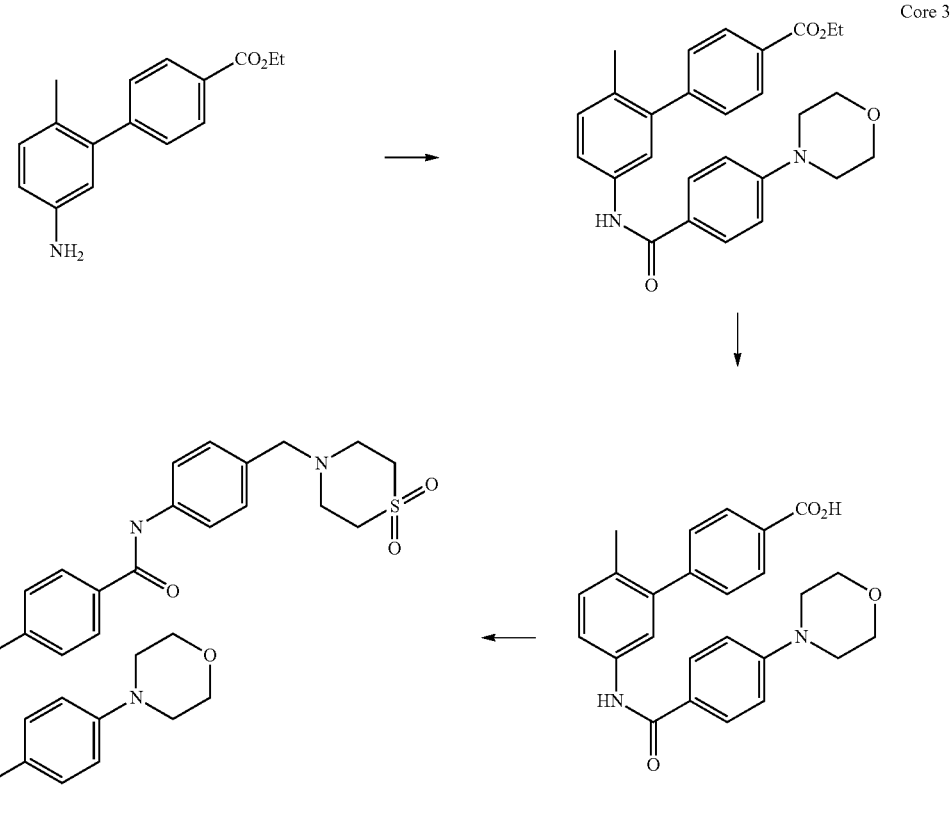

Intermediate 7

2'-Methyl-5'-(4-morpholin-4-yl-benzoylamino)-biphenyl-4-carboxylic acid ethyl ester 5'-Amino-2'-methyl-biphenyl-4-carboxylic acid ethyl ester (2.15 g), 4-morpholin-4-yl benzoic acid (1.27 g), N-methylmorpholine (2.05 ml), 1-hydroxybenzotriazole (826 mg) and 1-ethyl-3-(3-(dimethylaminopropyl)carbodiimide hydrochloride (1.17 g) in dry DMF (30 ml) was stirred at 20 C for 18 h. Then the DMF was evaporated and the residue partitioned between water and dichloromethane. The dried extracts were evaporated and the residue purified on silica gel. Elution with 1-2% methanol in dichloromethane gave a colourless solid (2.4 g)

Intermediate 8

2'-Methyl-5'-(4-morpholin-4-yl-benzoylamino)-biphenyl-4-carboxylic acid

2'-Methyl-5'-(4-morpholin-4-yl-benzoylamino)-biphenyl-4-carboxylic acid ethyl ester (2.4 g) was stirred in a mixture of THF (25 ml) and 1M sodium hydroxide (50 ml) at 10° C. for 4 h. The mixture was allowed to cool and the THF was evaporated. The residue was acidified and the resultant colourless precipitate collected by filtration and dried (1.98 g).

Examples 85 and 86 were prepared in an analogous fashion to Example 87

Example 85

2'-Methyl-5'-(4-morpholin-4-yl-benzoylamino)-biphenyl-4-carboxylic acid (2-trifluoromethyl-1H-benzoimidazol-5-yl)-amide

Example 86

2'-Methyl-5'-(4-morpholin-4-yl-benzoylamino)-biphenyl-4-carboxylic acid (4-acetylamino-phenyl)-amide

Example 87

2'-Methyl-5'-(4-morpholin-4-yl-benzoylamino)-biphenyl-4-carboxylic acid [4-(1,1-dioxo-1lambda*6*-thiomorpholin-4-ylmethyl)-phenyl]-amide 2'-Methyl-5'-(4-morpholin-4-yl-benzoylamino)-biphenyl-4-carboxylic acid (60 mg) 4-(1,1-dioxo-1lambda*6*-thiomorpholin-4-ylmethyl)-phenylamine (35 mg), N-methyl-morpholine (0.035 ml), 1-hydroxybenzotriazole (20 mg) and 1-ethyl-3-(3-(dimethylaminopropyl)carbodiimide hydrochloride (29 mg) in dry DMF (2 ml) was stirred at 20 C for 18 h. Water was then added and the resultant precipitate collected by filtration and dried (44 mg).

$^1$H NMR (DMSO, δ) 2.24 (s, 3H) 2.88 (m, 4H) 3.12 (m, 4H) 3.27 (m, 4H) 3.66 (s, 2H) 3.76 (m, 4H) 6.95 (d, 2H) 7.28-7.7.42 (m, 3H) 7.52 (d, 2H) 7.74-7.78 (m, 4H) 7.91 (d, 2H) 8.05 (d, 2H) 10.05 (s, 1H) 10.39 (s, 1H).

LC-MS ES+=639.

Example 88

2'-Methyl-5'-(4-morpholin-4-yl-benzoylamino)-biphenyl-4-carboxylic acid 3-bromo-benzylamide Example 89

2'-Methyl-5'-(4-morpholin-4-yl-benzoylamino)-biphenyl-4-carboxylic acid 3-methyl-benzylamide Example 90

2'-Methyl-5'-(4-morpholin-4-yl-benzoylamino)-biphenyl-4-carboxylic acid (4-bromo-3-chloro-phenyl)-amide Example 91

2'-Methyl-5'-(4-morpholin-4-yl-benzoylamino)-biphenyl-4-carboxylic acid (3-methoxy-phenyl)-amide Example 92

2'-Methyl-5'-(4-morpholin-4-yl-benzoylamino)-biphenyl-4-carboxylic acid 3-trifluoromethoxy-benzylamide Example 93

2'-Methyl-5'-(4-morpholin-4-yl-benzoylamino)-biphenyl-4-carboxylic acid (1H-indol-6-yl)-amide Example 94

2'-Methyl-5'-(4-morpholin-4-yl-benzoylamino)-biphenyl-4-carboxylic acid 3-chloro-benzylamide Examples 95 to 102 are prepared by a reductive amination procedure, via an aldehyde intermediate, generated in analogous procedures to Intermediate 42 and Example 197

Example 95

5'-{[1-Hydroxymethyl-2-(3H-imidazol-4-yl)-ethylamino]-methyl}-2'-methyl-biphenyl-4-carboxylic acid (4-morpholin-4-yl-phenyl)-amide Example 96

4'-[(3-Chloro-benzylamino)-methyl]-6-methyl-biphenyl-3-carboxylic acid (4-morpholin-4-yl-phenyl)-amide Example 97

4'-[(1H-Indazol-6-ylamino)-methyl]-6-methyl-biphenyl-3-carboxylic acid (4-morpholin-4-yl-phenyl)-amide Example 98

4'-Cyclopropylaminomethyl-6-methyl-biphenyl-3-carboxylic acid (4-morpholin-4-yl-phenyl)-amide Example 99

(S)-3-Hydroxy-2-{[2'-methyl-5'-(4-morpholin-4-yl-phenylcarbamoyl)-biphenyl-4-ylmethyl]-amino}-propionic acid Example 100

4'-{[2-(3H-Imidazol-4-yl)-ethylamino]-methyl}-6-methyl-biphenyl-3-carboxylic acid (4-morpholin-4-yl-phenyl)-amide Example 101

4'-{[1-Hydroxymethyl-2-(3H-imidazol-4-yl)-ethylamino]-methyl}-6-methyl-biphenyl-3-carboxylic acid (4-morpholin-4-yl-phenyl)-amide Example 102

4'-[(2-Dimethylamino-ethylamino)-methyl]-6-methyl-biphenyl-3-carboxylic acid (4-morpholin-4-yl-phenyl)-amide

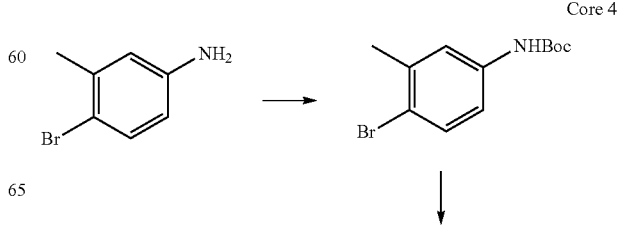

Core 4

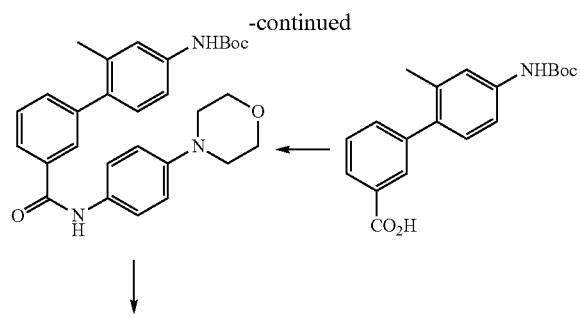

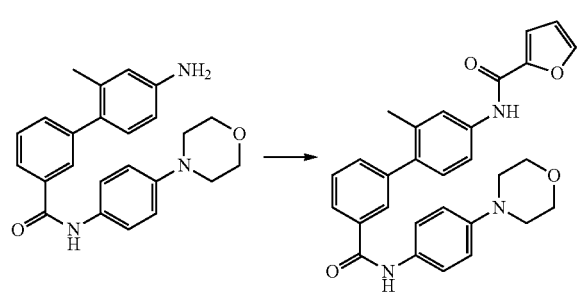

Intermediate 9

(4-Bromo-3-methyl-phenyl)-carbamic acid tert-butyl ester

A solution of 4-bromo-3-methyl aniline (500 mg) in methanol (20 ml) was treated with triethylamine (0.75 ml) and Boc anhydride (1.18 g) and was stirred at 20 C for 18 h. The solvent was then evaporated and the residue partitioned between water and dichloromethane. The dried extracts were then evaporated giving the title compound as a pale brown solid (770 mg).

Intermediate 10

4'-tert-Butoxycarbonylamino-2'-methyl-biphenyl-3-carboxylic acid

A mixture of (4-bromo-3-methyl-phenyl)-carbamic acid tert-butyl ester (765 mg), 3-carboxyphenyl boronic acid (446 mg), cesium carbonate (875 mg) and tetrakis(triphenylphosphine)palladium⁰ (catalytic quantity), in 1:2 aqueous DME (30 ml) was heated to reflux for 18 h. The mixture was then allowed to cool and was then partitioned between 1M HCl and dichloromethane. The dried extracts were then evaporated giving the title compound as a pale brown foam (785 mg).

Intermediate 11

[2-Methyl-3'-(4-morpholin-4-yl-phenylcarbamoyl)-biphenyl-4-yl]-carbamic acid tert-butyl ester A mixture of 4'-tert-butoxycarbonylamino-2'-methyl-biphenyl-3-carboxylic acid (436 mg), 4-morpholin-4-yl aniline (238 mg), triethylamine (0.55 ml) and O-benzotriazol-1-yl-N,N,N',N'-tetramethyluronium hexafluorophosphate (757 mg) in dry DMF (1 ml) was stirred at 20 C for 18 h. Water (50 ml) was then added and the resulting colourless precipitate was collected by filtration and dried (680 mg)

Intermediate 12

4'-Amino-2'-methyl-biphenyl-3-carboxylic acid (4-morpholin-4-yl-phenyl)-amide

[2-Methyl-3'-(4-morpholin-4-yl-phenylcarbamoyl)-biphenyl-4-yl]-carbamic acid tert-butyl ester (670 mg) was stirred in methanol (15 ml) and 5M HCl (5 ml) at 20 C for 2 days. TLC indicated that the reaction was progressing slowly and so the mixture was heated to reflux for 6 h. The reaction was allowed to cool and was then basified and extracted with dichloromethane. The dried extract was evaporated and the residue purified on silica gel. Elution with dichloromethane: ethanol:0.880 ammonia; 400:8:1 gave a colourless foam which crystallized on standing (354 mg).

Examples 103 to 112 were prepared from intermediates produced from coupling A/B1 and are synthesized in an analogous fashion to Example 114.

Example 113

4'-(Cyclopropanecarbonyl-amino)-2'-methyl-biphenyl-3-carboxylic acid (4-morpholin-4-yl-phenyl)-amide This was prepared in an analogous fashion to Example 114

Example 114

Furan-2-carboxylic acid [2-methyl-3'-(4-morpholin-4-yl -phenylcarbamoyl)-biphenyl-4-yl]-amide A solution of 4'-amino-2'-methyl-biphenyl-3-carboxylic acid (4-morpholin-4-yl-phenyl)-amide (40 mg) and triethylamine (0.4 ml) in dry DMF (3 ml) was treated with furan-2-carbonyl chloride (0.015 ml) and the mixture stirred at 20 C for 18 h. The mixture was then partitioned between water and dichloromethane. The dried extract was then evaporated and the residue purified on silica gel. Elution with dichloromethane:ethanol:0.880 ammonia; 400:8:1 gave a colourless foam (46 mg).

$^1$H NMR (DMSO, δ) 2.28 (s, 3H) 3.09 (t, 4H) 3.74 (t, 4H) 6.74 (m, 1H) 6.93 (d, 2H) 7.30-7.38 (m, 2H) 7.56-7.76 (m, 6H) 7.93-7.99 (m, 3H) 10.12 (s, 1H) 10.24 (s, 1H).

Examples 115 and 116 were prepared in an analogous fasion to Example 114

Example 115

4'-(2-Methoxy-benzoylamino)-2'-methyl-biphenyl-3-carboxylic acid (4-morpholin-4-yl-phenyl)-amide Example 116

4'-(3-Methoxy-benzoylamino)-2'-methyl-biphenyl-3-carboxylic acid (4-morpholin-4-yl-phenyl)-amide Examples 117 to 119 were prepared from intermediates produced from coupling A/B1 and are synthesised in an analogous fashion to Example 114.

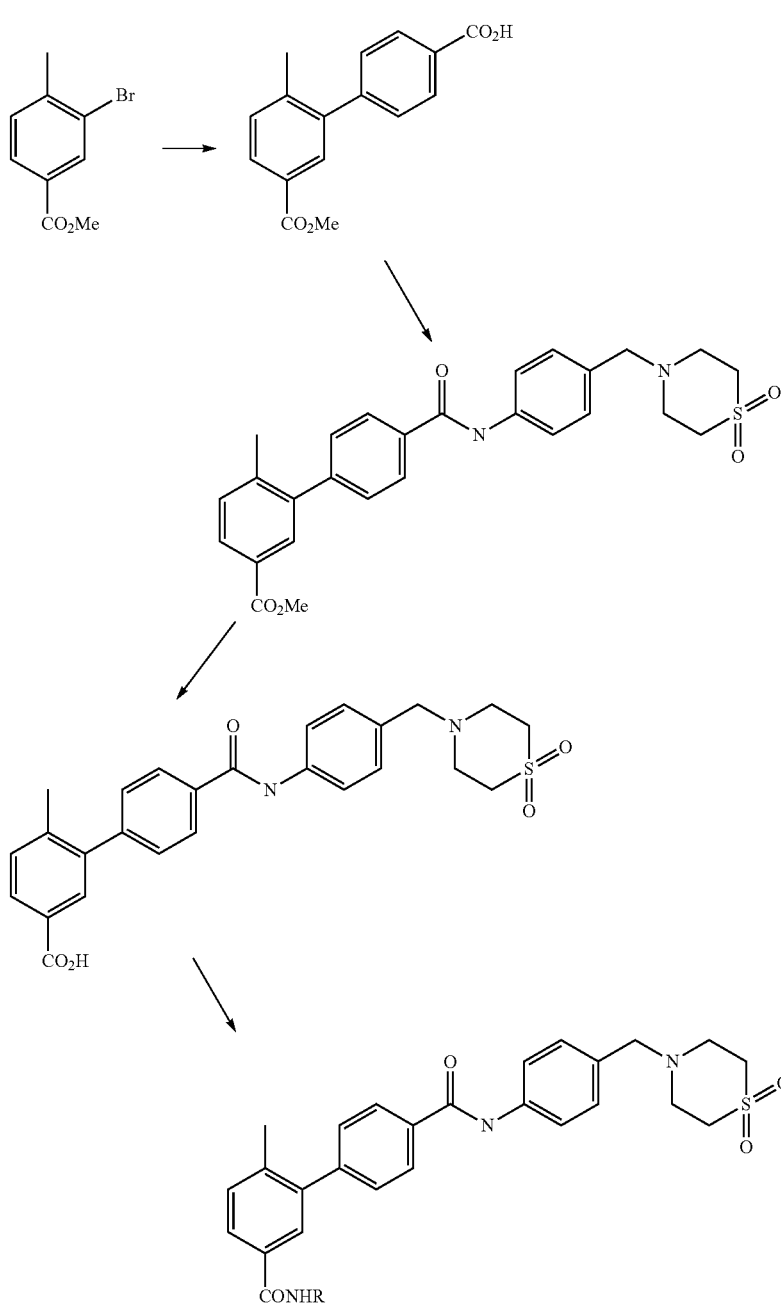

Core 5

Intermediate 13

6-Methyl-biphenyl-3,4'-dicarboxylic acid 3-methyl ester

A mixture of 3-bromo-4-methyl-benzoic acid methyl ester (3 g), 4-hydroxycarbonyl-phenyl boronic acid (2.21 g), cesium carbonate (4.26 g) and tetrakis(triphenylphosphine)palladium⁰ (catalytic quantity), in 1:2 aqueous DME (75 ml) was heated to reflux for 18 h. The cooled reaction was then evaporated to dryness and the residue purified on silica gel. Elution with dichloromethane:ethanol:0.880 ammonia; 800:8:1 to 100:8:1 gave a yellow crystalline solid (3.4 g)

Intermediate 14

4'-[4-(1,1-Dioxo-1lambda*6*-thiomorpholin-4-ylmethyl)-phenylcarbamoyl]-6-methyl-biphenyl-3-carboxylic acid methyl ester 6-Methyl-biphenyl-3,4'-dicarboxylic acid 3-methyl ester (1.59 g) in toluene (50 ml) was treated with oxalyl chloride (8 ml) and DMF (6 drops). The mixture was stirred at 20 C for 2 h. and then was evaporated to dryness. The residue was then dissolved in dichloromethane (50 ml) containing triethylamine (0.85 ml) and was treated with 4-(1,1-dioxo-1lambda*6*-thiomorpholin-4-ylmethyl)-phenylamine (1.4 g). This mixture was stirred at 20 C for 18 h. and was then partitioned between 1M sodium hydroxide and dichloromethane. The dried extracts were evaporated giving the title compound as a colourless foam (2.72 g).

Intermediate 15

4'-[4-(1,1-Dioxo-1lambda*6*-thiomorpholin-4-ylmethyl)-phenylcarbamoyl]-6-methyl-biphenyl-3-carboxylic acid 4'-[4-(1,1-Dioxo-1lambda*6*-thiomorpholin-4-ylmethyl)-phenylcarbamoyl]-6-methyl-biphenyl-3-carboxylic acid methyl ester (1.09 g) was heated to reflux in 1M sodium hydroxide (20 ml) and THF (20 ml) for 3 h. The mixture was then allowed to cool, and the THF evaporated. The aqueous residue was extracted with dichloromethane, and was then acidified. The resultant white solid was collected by filtration and dried (950 mg).

Example 120

Biphenyl-3,4'-dicarboxylic acid 4'-{[4-(1,1-dioxo-1lambda*6*-thiomorpholin-4-ylmethyl)-phenyl]-amide} 3-[(4-morpholin-4-yl-phenyl)-amide]

This compound was prepared by an analogous method to Example 121

Example 121

6-Methyl-biphenyl-3,4'-dicarboxylic acid 4'-cyclopropylamide 3-{[4-(1,1-dioxo-1lambda*6*-thiomorpholin-4-ylmethyl)-phenyl]-amide}

4'-[4-(1,1-Dioxo-1lambda*6*-thiomorpholin-4-ylmethyl)-phenylcarbamoyl]-6-methyl-biphenyl-3-carboxylic acid (35 mg) N-methylmorpholine (0.01 ml), 1-hydroxybenzotriazole (10 mg) cyclopropylamine (5 mg) and 1-ethyl-3-(3-(dimethylaminopropyl)carbodiimide hydrochloride (14 mg) in dry DMF (0.5 ml) was stirred at 20 C for 18 h. The mixture was then added to water (6 ml) and after a further 15 mins stirring, the solid was collected by filtration, washed (water 2×1 ml and pet ether 2×1 ml) and dried giving the title compound as a colourless solid (27 mg).

$^1$H NMR (DMSO, δ) 0.57-0.60 (m, 2H) 0.66-0.71 (m, 2H) 2.31 (s, 3H) 2.88-3.00 (m, 5H) 3.13 (m, 4H) 3.66 (s, 2H) 7.33 (d, 2H) 7.41-7.43 (m, 1H) 7.54-7.58 (d, 2H) 7.74-7.81 (m, 4H) 8.04 (d, 2H) 8.46 (d, 1H) 10.34 (s, 1H).
LC-MS ES+=518

Example 122

6-Methyl-biphenyl-3,4'-dicarboxylic acid 4'-{[4-(1,1-dioxo-1lambda*6*-thiomorpholin-4-ylmethyl)-phenyl]-amide} 3-[(3-methyl-butyl)-amide]

This compound was prepared by an analogous method to Example 121

Example 123

6-Methyl-biphenyl-3,4'-dicarboxylic acid 3-{[4-(1,1-dioxo-1lambda*6*-thiomorpholin-4-ylmethyl)-phenyl]-amide} 4'-(3-fluoro-benzylamide)

The following compound was prepared in an analogous fashion to Example 121 except that 3-fluorobenzylamine was used. The title compound was isolated as a colourless solid (11 mg)

$^1$H NMR (DMSO, δ) 2.33 (s, 3H) 2.90 (m, 4H) 3.12 (m, 4H) 3.66 (s, 2H) 4.51 (d, 2H) 7.05-7.19 (m, 4H) 7.32-7.48 (m, 3H) 7.58 (d, 2H) 7.78-7.88 (m, 4H) 8.06 (d, 2H) 9.14 (t, 1H) 10.35 (s, 1H)
LC-MS ES+=586

Examples 124 to 128 were prepared by an analogous method to Example 121

Example 124

6-Methyl-biphenyl-3,4'-dicarboxylic acid 4'-{[4-(1,1-dioxo-1lambda*6*-thiomorpholin-4-ylmethyl)-phenyl]-amide} 3-[(tetrahydro-furan-2-ylmethyl)-amide]

Example 125

6-Methyl-biphenyl-3,4'-dicarboxylic acid 4'-{[4-(1,1-dioxo-1lambda*6*-thiomorpholin-4-ylmethyl)-phenyl]-amide} 3-[(2-piperidin-1-yl-ethyl)-amide]

Example 126

6-Methyl-biphenyl-3,4'-dicarboxylic acid 4'-{[4-(1,1-dioxo-1lambda*6*-thiomorpholin-4-ylmethyl)-phenyl]-amide} 3-[(2-methoxy-ethyl)-amide]

Example 127

6-Methyl-biphenyl-3,4'-dicarboxylic acid 4'-{[4-(1,1-dioxo-1lambda*6*-thiomorpholin-4-ylmethyl)-phenyl]-amide} 3-{[2-(3H-imidazol-4-yl)-ethyl]-amide}

Example 128

2'-Methyl-5'-(4-pyrrolidin-1-yl-piperidine-1-carbonyl)-biphenyl-4-carboxylic acid [4-(1,1-dioxo-1lambda*6*-thiomorpholin-4-ylmethyl)-phenyl]-amide Example 129

6-Methyl-biphenyl-3,4'-dicarboxylic acid bis-{[4-(1,1-dioxo-1lambda*6*-thiomorpholin-4-ylmethyl)-phenyl]-amide}

The following compound was prepared in an analogous fashion to Example 123 except that 4-(1,1-dioxo-1lambda*6*-thiomorpholin-4-ylmethyl)-phenylamine was used. The title compound was isolated as a colourless solid (21 mg).

$^1$H NMR (DMSO, δ) 2.36 (s, 3H) 2.88 (m, 8H) 3.12 (m, 8H) 3.65 (m, 4H) 7.30-7.35 (m, 4H) 7.55 (d, 1H) 7.61 (d, 2H) 7.75-7.82 (m, 4H) 7.92-7.95 (m, 2H) 8.08 (d, 2H) 10.28 (s, 1H) 10.38 (s, 1H).
LC-MS ES+=701

Example 130

6-Methyl-biphenyl-3,4'-dicarboxylic acid 3-[(4-dimethylamino-phenyl)-amide] 4'-{[4-(1,1-dioxo-1lambda*6*-thiomorpholin-4-ylmethyl)-phenyl]-amide}

This compound was prepared by an analogous method to Example 121

Example 131
**4'-(Cyclopropanecarbonyl-amino)-2'-methyl-biphenyl-3-carboxylic acid [4-(1,1-dioxo-1lambda*6*-thiomorpholin-4-ylmethyl)-phenyl]-amide**
This compound was prepared from intermediates generated from coupling A/B1 and synthesised in an analogous fashion to example 114.
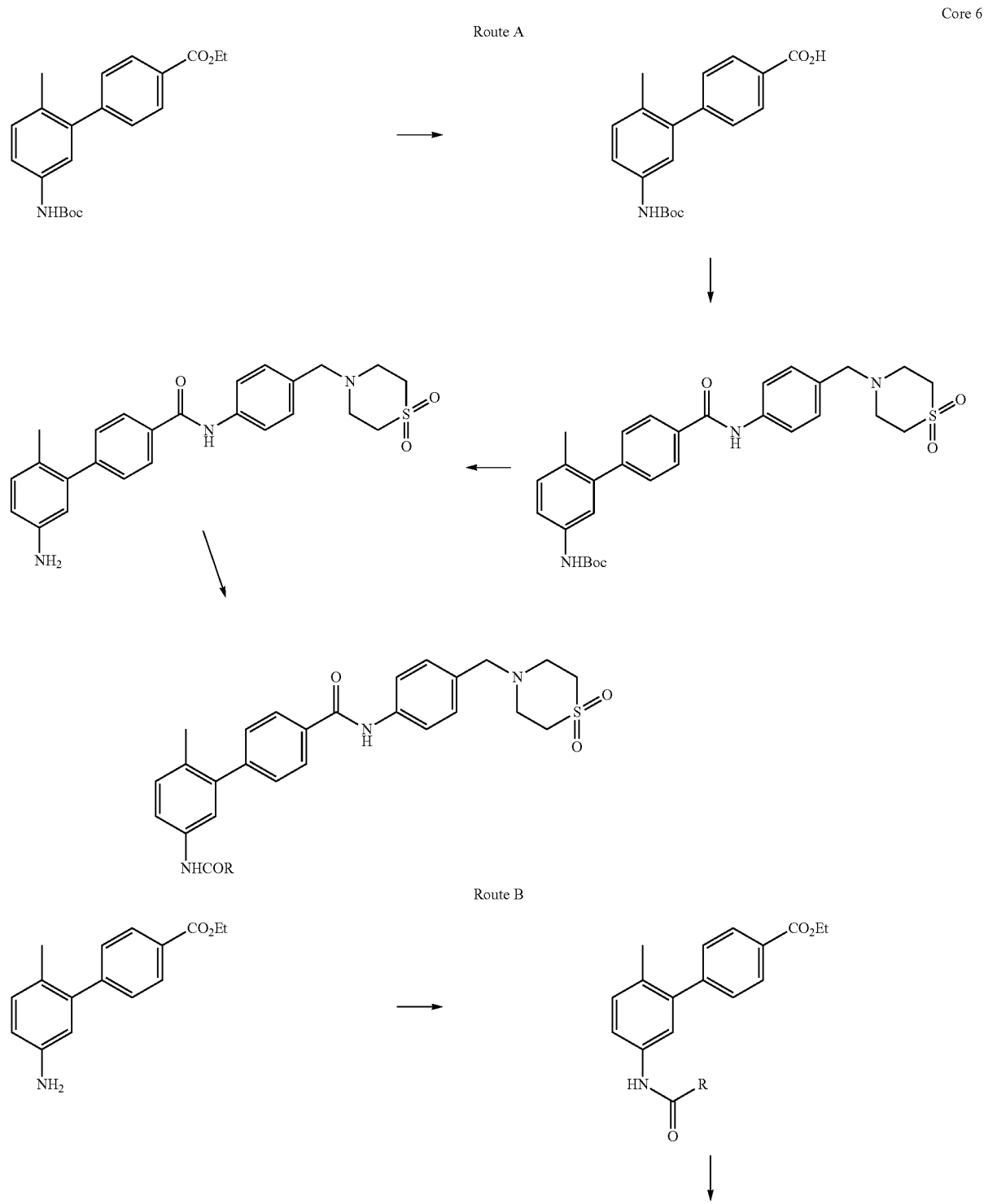

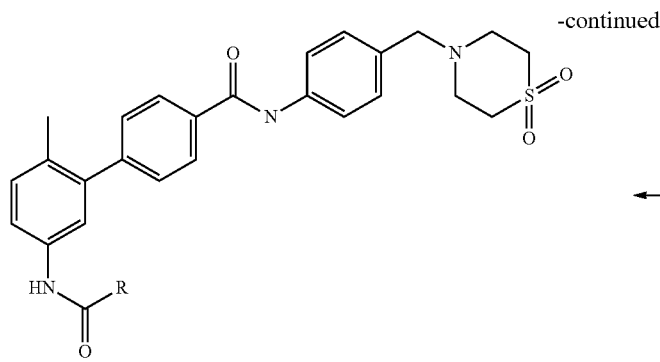 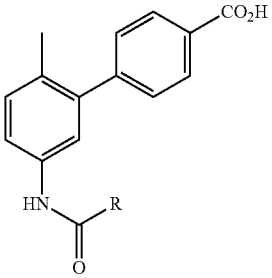

-continued

Intermediate 16

5'-tert-Butoxycarbonylamino-2'-methyl-biphenyl-4-carboxylic acid

5'-tert-Butoxycarbonylamino-2'-methyl-biphenyl-4-carboxylic acid ethyl ester (6.3 g) was stirred in ethanol (75 ml) and 1M sodium hydroxide (30 ml) at 20 C for 18 h. The mixture was then acidified and the ethanol evaporated. The pale beige solid thus formed was collected by filtration and dried (4.26 g)

Intermediate 17

**{4'-[4-(1,1-Dioxo-1lambda*6*-thiomorpholin-4-ylmethyl)-phenylcarbamoyl]-6-methyl-biphenyl-3-yl}-carbamic acid tert-butyl ester**

A mixture of 5'-tert-butoxycarbonylamino-2'-methyl-biphenyl-4-carboxylic acid (500 mg), 4-(1,1-dioxo-1lambda*6*-thiomorpholin-4-ylmethyl)-phenylamine (367 mg), triethylamine (0.64 ml) and O-benzotriazol-1-yl-N,N,N',N'-tetramethyluronium hexafluorophosphate (869 mg) in dry DMF (20 ml) was stirred at 20 C for 118 h. The mixture was then partitioned between water and dichloromethane. The dried extracts were evaporated and the residue purified on silica gel. Elution with ethyl acetate:petrol; 1:1 removed high Rf impurities and further elution with ethyl acetate gave the title compound as a pale yellow solid (693 mg).

Intermediate 18

**5'-Amino-2'-methyl-biphenyl-4-carboxylic acid [4-(1,1-dioxo-1 lambda*6*-thiomorpholin-4-ylmethyl)-phenyl]-amide**

A solution of {4'-[4-(1,1-dioxo-1lambda*6*-thiomorpholin-4-ylmethyl)-phenylcarbamoyl]-6-methyl-biphenyl-3-yl}-carbamic acid tert-butyl ester (685 mg) in ethanol (25 ml) and 6M HCl (25 ml) was stirred at 20 C for 18 h. The mixture was then basified and the ethanol evaporated. The colourless solid thus formed was collected by filtration and dried (434 mg).

Example 132

**5'-(Cyclopropanecarbonyl-amino)-2'-methyl-biphenyl-4-carboxylic acid [4-(1,1-dioxo-1lambda*6*-thiomorpholin-4-ylmethyl)-phenyl]-amide (Route A)**

A mixture of 5'-amino-2'-methyl-biphenyl-4-carboxylic acid [4-(1,1-dioxo-1lambda*6*-thiomorpholin-4-ylmethyl)-phenyl]1-amide (Intermediate 13)(50 mg) and triethylamine (11 mg) in dry dichloromethane (1 ml) was treated with cyclopropanecarbonyl chloride (12 mg) with stirring for 2 h. The mixture was then partitioned between water and dichloromethane. The dried extracts were then evaporated giving the title compound as a colourless solid (44 mg)

$^1$H NMR (DMSO, δ) 0.77-0.80 (m, 4H) 1.74-1.79 (m, 1H) 2.20 (s, 3H) 2.88 (m, 4H) 3.11 (m, 4H) 3.65 (s, 2H) 7.24 (d, 1H) 7.33 (d, 2H) 7.48-7.55 (m, 4H) 7.77 (d, 2H) 8.02 (d, 2H) 10.22 (s, 1H) 10.32 (s, 1H).

LC-MS ES+=518.

Examples 133 to 135 were prepared from intermediates generated from coupling A/B1 and synthesised in an analogous fashion to example 114.

Example 133

**Furan-2-carboxylic acid {3'-[4-(1,1-dioxo-1lambda*6*-thiomorpholin-4-ylmethyl)-phenylcarbamoyl]-2-methyl-biphenyl-4-yl}-amide**

Example 134

**4'-(2-Methoxy-benzoylamino)-2'-methyl-biphenyl-3-carboxylic acid [4-(1,1-dioxo-1lambda*6*-thiomorpholin-4-ylmethyl)-phenyl]-amide**

Example 135

**2'-Methyl-biphenyl-3,4'-dicarboxylic acid 3-{[4-(1,1-dioxo-1 lambda*6*-thiomorpholin-4-ylmethyl)-phenyl]-amide} 4'-[(4-morpholin-4-yl-phenyl)-amide]**

Examples 136 to 148 were prepared by an analogous method to Example 121

Example 136

6-Methyl-biphenyl-3,4'-dicarboxylic acid 4'-{[3-(1,1-dioxo-1lambda*6*-thiomorpholin-4-ylmethyl)-phenyl]-amide} 3-[(4-morpholin-4-yl-phenyl)-amide]

Example 137

6-Methyl-biphenyl-3,4'-dicarboxylic acid 4'-{[4-(1,1-dioxo-1lambda*6*-thiomorpholin-4-ylmethyl)-phenyl]-amide} 3-{[3-(2-oxo-pyrrolidin-1-yl)-propyl]-amide}

Example 138

6-Methyl-biphenyl-3,4'-dicarboxylic acid 4'-{[4-(1,1-dioxo-1lambda*6*-thiomorpholin-4-ylmethyl)-phenyl]-amide} 3-{[4-(3-ethyl-2,6-dioxo-piperidin-3-yl)-phenyl]-amide}

Example 139

6-Methyl-biphenyl-3,4'-dicarboxylic acid 4'-{[4-(1,1-dioxo-1lambda*6*-thiomorpholin-4-ylmethyl)-phenyl]-amide} 3-[(4-[1,2,4]triazol-1-yl-phenyl)-amide]

Example 140

6-Methyl-biphenyl-3,4'-dicarboxylic acid 4'-{[4-(1,1-dioxo-1lambda*6*-thiomorpholin-4-ylmethyl)-phenyl]-amide} 3-{[4-(morpholine-4-carbonyl)-phenyl]-amide}

Example 141

6-Methyl-biphenyl-3,4'-dicarboxylic acid 4'-{[4-(1,1-dioxo-1lambda*6*-thiomorpholin-4-ylmethyl)-phenyl]-amide} 3-[(4-methylcarbamoyl-phenyl)-amide]

Example 142

6-Methyl-biphenyl-3,4'-dicarboxylic acid 3-[(4-dimethylcarbamoyl-phenyl)-amide] 4'-{[4-(1,1-dioxo-1lambda*6*-thiomorpholin-4-ylmethyl)-phenyl]-amide}

Example 143

6-Methyl-biphenyl-3,4'-dicarboxylic acid 4'-{[4-(1,1-dioxo-1lambda*6*-thiomorpholin-4-ylmethyl)-phenyl]-amide} 3-[(5-ethyl-[1,3,4]thiadiazol-2-yl)-amide]

Example 144

6-Methyl-biphenyl-3,4'-dicarboxylic acid 4'-{[4-(1,1-dioxo-1lambda*6*-thiomorpholin-4-ylmethyl)-phenyl]-amide} 3-{[4-(piperidine-1-carbonyl)-phenyl]-amide}

Example 145

6-Methyl-biphenyl-3,4'-dicarboxylic acid 4'-{[4-(1,1-dioxo-1lambda*6*-thiomorpholin-4-ylmethyl)-phenyl]-amide} 3-[(3-methyl-isothiazol-5-yl)-amide]

Example 146

6-Methyl-biphenyl-3,4'-dicarboxylic acid 3-cyclohexylmethyl-amide 4'-{[4-(1,1-dioxo-1lambda*6*-thiomorpholin-4-ylmethyl)-phenyl]-amide}

Example 147

6-Methyl-biphenyl-3,4'-dicarboxylic acid 3-cycloheptylamide 4'-{[4-(1,1-dioxo-1lambda*6*-thiomorpholin-4-ylmethyl)-phenyl]-amide}

Example 148

6-Methyl-biphenyl-3,4'-dicarboxylic acid 3-cyclopentylamide 4'-{[4-(1,1-dioxo-lambda*6*-thiomorpholin-4-ylmethyl)-phenyl]-amide}

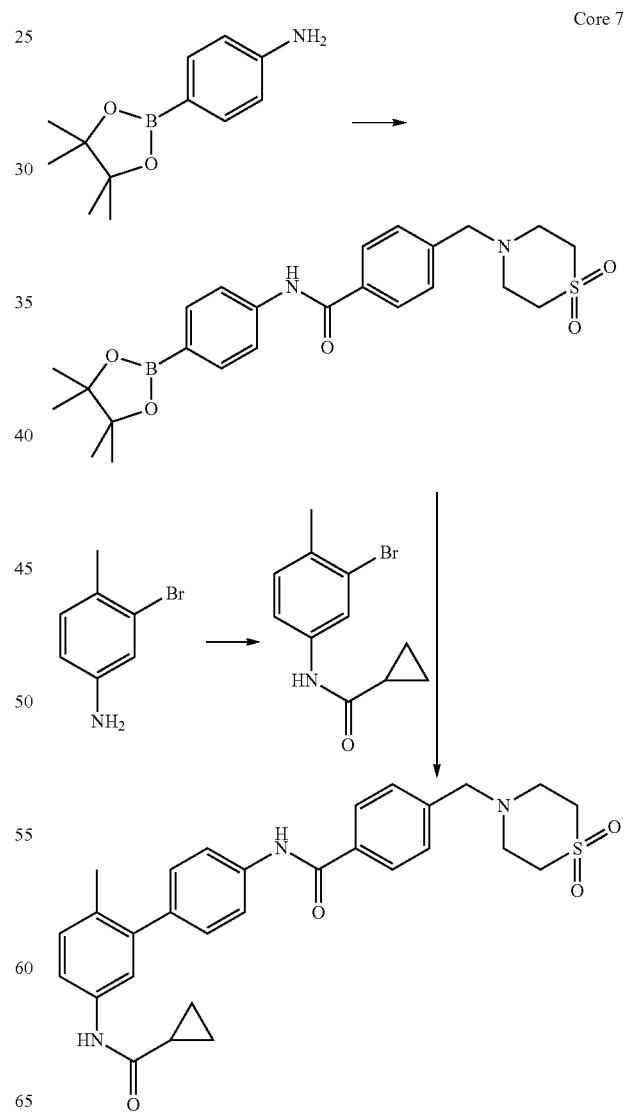

Core 7

Intermediate 19

4-(1,1-Dioxo-1lambda*6*-thiomorpholin-4-ylmethyl)-N-[4-(4,4,5,5-tetramethyl-[1,3,2]dioxaborolan-2-yl)-phenyl]-benzamide A mixture of 4-(4,4,5,5-tetramethyl-[1,3,2]dioxaboroloan-2-yl) -phenylamine (60 mg), 4-(1,1-dioxo-1lambda*6*-thiomorpholin-4-ylmethyl)-benzoic acid (73 mg), EDAC (53 mg), HOBT (37 mg) and N-methylmorpholine (0.06 ml) in dry DMF (2 ml) was stirred at 20 C for 18 h. The mixture was then diluted with water (6 ml) and the resulting colourless solid collected by filtration and dried (130 mg).

Intermediate 20

Cyclopropanecarboxylic acid (3-bromo-4-methyl-phenyl)-amide

A mixture of 3-bromo-4-methylaniline (100 mg), cyclopropanecarbonyl chloride (98 mg) and N-methylmorpholine (0.12 ml) in dry dichloromethane (2 ml) was stirred at 20 C for 18 h. The mixture was then partitioned between saturated sodium bicarbonate solution and dichloromethane. The dried extracts were evaporated giving a solid which was used without purification in the next synthetic step (120 mg).

Example 149

N-[5'-(Cyclopropanecarbonyl-amino)-2'methyl-biphenyl-4-yl]-4-(1,1-dioxo-1lambda*6*-thiomorpholin-4-ylmethyl)-benzamide A mixture of 4-(1,1-dioxo-1lambda*6*-thiomorpholin-4-ylmethyl) -N-[4-(4,4,5,5-tetramethyl-[1,3,2]dioxaborolan-2-yl)-phenyl]-benzamide (70 mg), cyclopropanecarboxylic acid (3-bromo-4-methyl-phenyl)-amide (38 mg) in DME (4 ml) and water (1.5 ml) containing cesium carbonate (50 mg) and tetrakis(triphenylphosphine) palladium (0) (10 mg) was heated to reflux for 18 h. The cooled mixture was then partitioned between water and ethyl acetate. The dried extracts were evaporated and the residue purified on silica gel. Elution with 0-30% DCM:EtOH:NH3; 20:8:1 in DCM gave the title compound as a tan solid (6 mg)

$^1$H NMR (DMSO, δ) 0.60-0.72 (m, 4H) 1.64-1.74 (m, 1H) 2.13 (s, 3H) 2.83 (m, 4H) 3.06 (m, 4H) 3.71 (s, 2H) 7.12 (d, 1H) 7.24 (d, 2H) 7.38-7.56 (m, 4H) 7.78 (d, 2H) 7.88 (d, 2H) 10.09 (s, 1H) 10.25 (s, 1H).

LC-MS ES+=518.

Examples 150 and 151 were prepared by analogous methods to Example 149

Example 150

N-[5'-(Cyclohexanecarbonyl-amino)-2'-methyl-biphenyl-4-yl]-4-(1,1-dioxo-1lambda*6*-thiomorpholin-4-ylmethyl)-benzamide

Example 151

4'-[4-(1,1-Dioxo-1lambda*6*-thiomorpholin-4-lmethyl)-benzoylamino]-6-methyl-biphenyl-3-carboxylic acid (4-morpholin-4-yl-phenyl)-amide

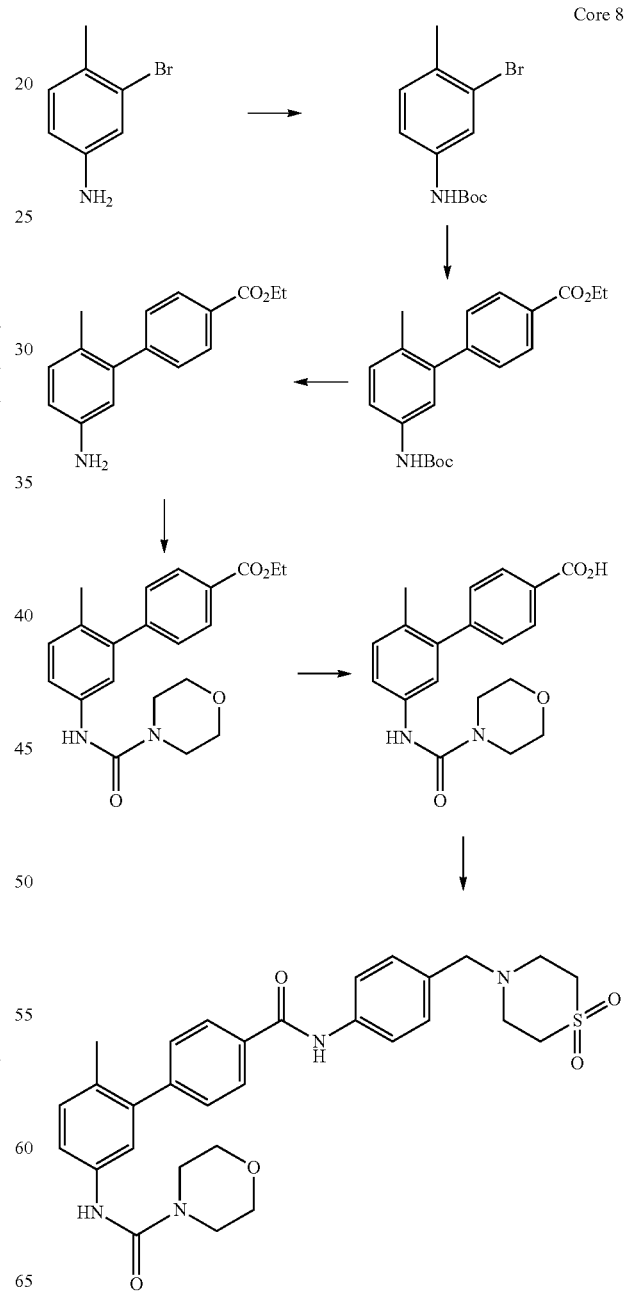

Core 8

Intermediate 21

(3-Bromo-4-methyl-phenyl)-carbamic acid tert-butyl ester

A solution of 3-bromo-4-methyl aniline (3.4 g) in methanol (100 ml) was treated with triethylamine (5.1 ml) and Boc anhydride (6.6 g) and was stirred at 20 C for 18 h. The solvent was then evaporated and the residue partitioned between water and dichloromethane. The dried extracts were then evaporated giving the title compound as a brown oil (5.47 g).

Intermediate 22

5'-tert-Butoxycarbonylamino-2'-methyl-biphenyl-4-carboxylic acid ethyl ester A mixture of (3-bromo-4-methyl-phenyl)-carbamic acid tert-butyl ester (5.3 g) 4-ethoxycarbonyl-phenyl boronic acid (3.54 g), cesium carbonate (5.95 g) and tetrakis(triphenylphosphine)palladium° (catalytic quantity), in 1:2 aqueous DME (120 ml) was heated to reflux for 18 h. The mixture was then allowed to cool and was then partitioned between 1M HCl and dichloromethane. The dried extracts were then evaporated giving the title compound as a yellow/orange foam (6.63 g).

Intermediate 23

5'-Amino-2'-methyl-biphenyl-4-carboxylic acid ethyl ester

5'-tert-Butoxycarbonylamino-2'-methyl-biphenyl-4-carboxylic acid ethyl ester (6.6 g) was stirred in ethanol (120 ml) and 6M HCl (50 ml) at 20 C for 2 days. The ethanol was evaporated and the residue basified and then extracted with dichloromethane. The dried extracts were evaporated giving the title compound as a pale brown crystalline solid (4 g).

Intermediate 24

2'-Methyl-5'-[(morpholine-4-carbonyl)-amino]-biphenyl-4-carboxylic acid ethyl ester A stirred solution of 5'-amino-2'-methyl-biphenyl-4-carboxylic acid ethyl ester (520 mg) in dry THF (25 ml) containing triethylamine (0.57 ml) was treated with 4-morpholinecarbonyl chloride (0.26 ml). After 18 h. the mixture was partitioned between water and dichloromethane. The dried extracts were evaporated and the residue purified on silica gel. Elution with ethyl acetate:petrol 1:1 gave the title compound as a yellow oil (416 mg).

$^1$H NMR (CDCl$_3$, δ) 1.39 (t, 3H) 2.18 (s, 3H) 3.46 (t, 4H) 3.73 (t, 4H) 4.38 (q, 2H) 6.28 (s, 1H) 7.17-7.31 (m, 3H) 7.36 (d, 2H) 8.04 (d, 2H).

Intermediate 25

2'-Methyl-5'-[(morpholine-4-carbonyl)-amino]-biphenyl-4-carboxylic acid

2'-Methyl-5'-[(morpholine-4-carbonyl)-amino]-biphenyl-4-carboxylic acid ethyl ester (416 mg) was stirred in ethanol (15 ml) and 1M sodium hydroxide (4 ml) at 20 C for 18 h. The mixture was then acidified and extracted with dichloromethane. The dried extracts were then evaporated giving the title compound as a beige solid (295 mg).

$^1$H NMR (DMSO, δ) 2.23 (s, 3H) 3.49 (m, 4H) 3.67 (m, 4H) 7.24 (d, 1H) 7.45-7.84 (m, 4H) 8.07 (d, 2H) 8.62 (s, 1H).

Example 152

Morpholine-4-carboxylic acid {4'-[4-(1,1-dioxo-1lambda*6*-thiomorpholin-4-ylmethyl)-phenylcarbamoyl]-6-methyl-biphenyl-3-yl}-amide A mixture of 2'-methyl-5'-[(morpholine-4-carbonyl)-amino]-biphenyl-4-carboxylic acid (40 mg), 4-(1,1-Dioxo-1lambda*6*-thiomorpholin-4-ylmethyl)-phenylamine (28 mg), triethylamine (0.033 ml) and O-benzotriazol-1-yl-N,N,N',N'-tetramethyluronium hexafluorophosphate (67 mg) in dry DMF (3 ml) was stirred at 20 C for 18 h. The mixture was then partitioned between water and dichloromethane. The dried extracts were evaporated and the residue purified on silica gel. Elution with dichloromethane:ethanol:0.880 ammonia; 200:8:1 gave an off-white solid (32 mg).

$^1$H NMR (DMSO, δ) 2.20 (s, 3H) 2.88 (m, 4H) 3.13 (m, 4H) 3.43 (m, 4H) 3.60-3.66 (m+s, 6H) 7.18 (d, 1H) 7.22 (d, 2H) 7.38-7.52 (m, 4H) 7.78 (d, 2H) 8.02 (d, 2H) 8.57 (s, 1H) 10.33 (s, 1H).

Examples 153 and 154 were prepared by analogous methods to Example 155.

Example 153

Furan-2-carboxylic acid {4'-[4-(1,1-dioxo-1lambda*6*-thiomorpholin-4-ylmethyl)-phenylcarbamoyl]-6-methyl-biphenyl-3-yl}-amide

Example 154

5'-(4-Bromo-benzoylamino)-2'-methyl-biphenyl-4-carboxylic acid [4-(1,1-dioxo-1lambda*6*-thiomorpholin-4-ylmethyl)-phenyl]-amide

Intermediate 26

2'-Methyl-5'-[(thiophene-2-carbonyl)-amino]-biphenyl-4-carboxylic acid ethyl ester A mixture of 5'-amino-2'-methyl-biphenyl-4-carboxylic acid ethyl ester (280 mg) and thiophene-2-carbonyl chloride (161 mg) in dichloromethane (5 ml) containing triethylamine (222 mg) was stirred at 20 C for 18 h. The mixture was then partitioned between water and dichloromethane. The dried extracts were then evaporated giving the title compound as a colourless solid (425 mg)

Intermediate 27

2'-Methyl-5'-[(thiophene-2-carbonyl)-amino]-biphenyl-4-carboxylic acid

2'-Methyl-5'-[(thiophene-2-carbonyl)-amino]-biphenyl-4-carboxylic acid ethyl ester (425 mg) in THF (10 ml) and sodium hydroxide (1M, 20 ml) was heated to reflux for 4 h. The solvent was then evaporated and the residue acidified. The resulting precipitate was collected by filtration and dried (321 mg).

Example 155

Thiophene-2-carboxylic acid {4'-[4-(1,1-dioxo-1lambda*6*-thiomorpholin-4-ylmethyl)-phenylcarbamoyl]-6-methyl-biphenyl-3-yl}-amide (Route B)

2'-Methyl-5'-[(thiophene-2-carbonyl)-amino]-biphenyl-4-carboxylic acid (45 mg), 4-(1,1-dioxo-1lambda*6*-thiomorpholin-4-ylmethyl)-phenylamine (32 mg), EDAC (25 mg), HOBT (18 mg) and N-methylmorpholine (27 mg) in dry DMF (0.5 ml) was stirred at 20 C for 18 h. The mixture was then diluted with water (6 ml) and the resulting colourless solid collected by filtration and dried (62 mg).

$^1$H NMR (DMSO, δ) 2.25 (s, 3H) 2.90 (m, 4H) 3.13 (m, 4H) 3.66 (s, 2H) 7.24 (m, 1H) 7.26-7.35 (m, 3H) 7.54 (d, 2H) 7.68-7.88 (m, 6H) 8.05 (d, 2H) 10.27 (s, 1H) 10.34 (s, 1H).

LC-MS ES+=560.

Example 156

N-{4'-[4-(1,1-Dioxo-1lambda*6*-thiomorpholin-4-ylmethyl)-phenylcarbamoyl]-6-methyl-biphenyl-3-yl}-nicotinamide This compound was prepared by an analogous method to Example 155.

Example 157

1-Methyl-1H-pyrrole-2-carboxylic acid {4'-[4-(1,1-dioxo-1lambda*6*-thiomorpholin-4-ylmethyl)-phenylcarbamoyl]-6-methyl-biphenyl-3-yl}-amide (Route B)

This material was prepared as described for Example 155 via the intermediates 2'-methyl-5'-[(1-methyl-1H-pyrrole-2-carbonyl)-amino]-biphenyl-4-carboxylic acid ethyl ester and 2'-methyl-5'-[(1-methyl-1H-pyrrole-2-carbonyl)-amino]-biphenyl-4-carboxylic acid. The title compound was isolated as a white solid (49 mg)
$^1$H NMR (DMSO, δ) 2.24 (s, 3H) 2.90 (m, 4H) 3.13 (m, 4H) 3.66 (s, 2H) 3.88 (s, 3H) 6.10 (dd, 1H) 7.01-7.05 (m, 2H) 7.25-7.35 (m, 3H) 7.53 (d, 2H) 7.67 (m, 2H) 7.79 (d, 2H) 8.04 (d, 2H) 9.78 (s, 1H) 10.34 (s, 1H).
LC-MS ES+=557.

Example 158

5'-(Cyclohexanecarbonyl-amino)-2'-methyl-biphenyl-4-carboxylic acid [4-(1,1-dioxo-1lambda*6*-thiomorpholin-4-ylmethyl)-phenyl]-amide (Route A)

This material was prepared as described for Example 132 except that cyclohexanecarbonyl chloride was used. The title compound was obtained as a colourless solid (35 mg)
$^1$H NMR (DMSO, δ) 1.15-1.4 (m, 6H) 1.65-1.85 (m, 4H) 2.20 (s, 3H) 2.28-2.32 (m, 1H) 2.74 (m, 4H) 3.13 (m, 4H) 3.66 (s, 2H) 7.24 (d, 1H) 7.33 (d, 2H) 7.48-7.55 (m, 4H) 7.78 (d, 2H) 8.03 (d, 2H) 9.84 (s, 1H) 10.34 (s, 1H).
LC-MS ES+=560.

Example 159

5'-(4-Fluoro-benzoylamino)-2'-methyl-biphenyl-4-carboxylic acid [4-(1,1-dioxo-1lambda*6*-thiomorpholin-4-ylmethyl)-phenyl]-amide This compound was prepared by an analogous method to compound 160

Example 160

2'-Methyl-5'-(4-methyl-benzoylamino)-biphenyl-4-carboxylic acid [4-(1,1-dioxo-1lambda*6*-thiomorpholin-4-ylmethyl)-phenyl]-amide (Route B)

This material was prepared as described for Example 155 via the intermediates 2'-methyl-5'-(4-methyl-benzoylamino)-biphenyl-4-carboxylic acid ethyl ester and 2'-methyl-5'-(4-methyl-benzoylamino)-biphenyl-4-carboxylic acid. The title compound was isolated as a white solid (15 mg)
$^1$H NMR (DMSO, δ) 2.25 (s, 3H) 2.40 (s, 3H) 2.88 (m, 4H) 3.13 (m, 4H) 3.66 (s, 2H) 7.30-7.36 (m, 5H) 7.54 (d, 2H) 7.74-7.91 (m, 6H) 8.04 (d, 2H) 10.21 (s, 1H) 10.35 (s, 1H).
LC-MS ES+=568.
Examples 160 and 162 were prepared by an analogous method to compound 160

Example 161

5'-[4-(1,1-Dioxo-1lambda*6*-thiomorpholin-4-ylmethyl)-benzoylamino]-2'-methyl-biphenyl-4-carboxylic acid [4-(1,1-dioxo-1lambda*6*-thiomorpholin-4-ylmethyl)-phenyl]-amide

Example 162

5'-[4-(1,1-Dioxo-1lambda*6*-thiomorpholin-4-ylmethyl)-benzoylamino]-2'-methyl-biphenyl-4-carboxylic acid 3-chloro-benzylamide

Example 163

5'-(3-Cyclohexyl-propionylamino)-2'-methyl-biphenyl-4-carboxylic acid [4-(1,1-dioxo-1lambda*6*-thiomorpholin-4-ylmethyl)-phenyl]-amide (Route B)

This material was prepared as described for Example 155 via the intermediates 5'-(3-cyclohexyl-propionylamino)-2'-methyl-biphenyl-4-carboxylic acid ethyl ester and 5'-(3-cyclohexyl-propionylamino)-2'-methyl-biphenyl-4-carboxylic acid. The title compound was isolated as a white solid (55 mg)
$^1$H NMR (DMSO, δ) 0.80-0.91 (m, 2H) 1.05-1.26 (m, 6H) 1.46 (q, 2H) 1.61-1.69 (m, 4H) 2.16 (s, 3H) 2.20-2.27 (m, 1H) 2.85 (m, 4H) 3.08 (m, 4H) 3.62 (s, 2H) 7.20 (d, 1H) 7.23 (d, 2H) 7.44-7.51 (m, 4H) 7.74 (d, 2H) 7.98 (d, 2H) 9.88 (s, 1H) 10.31 (s, 1H).
LC-MS ES+=588.
Examples 164 to 167 were prepared by analogous methods to Example 163

Example 164

5'-(Cycloheptanecarbonyl-amino)-2'-methyl-biphenyl-4-carboxylic acid [4-(1,1-dioxo-1lambda*6*-thiomorpholin-4-ylmethyl)-phenyl]-amide

Example 165

5'-(2-Cyclohexyl-acetylamino)-2'-methyl-biphenyl-4-carboxylic acid [4-(1,1-dioxo-1lambda*6*-thiomorpholin-4-ylmethyl)-phenyl]-amide

Example 166

5'-(2-Cyclopentyl-acetylamino)-2'-methyl-biphenyl-4-carboxylic acid [4-(1,1-dioxo-1lambda*6*-thiomorpholin-4-ylmethyl)-phenyl]-amide

Example 167

5'-(Cyclopentanecarbonyl-amino)-2'-methyl-biphenyl-4-carboxylic acid [4-(1,1-dioxo-1lambda*6*-thiomorpholin-4-ylmethyl)-phenyl]-amide Examples 168 and 169 were prepared in an analogous fashion to Example 60 using an intermediate analogous to the Intermediate 6.

Example 168

3'-(Cyclopropanecarbonyl-amino)-biphenyl-4-carboxylic acid [4-(1,1-dioxo-lambda*6*-thiomorpholin-4-ylmethyl)-phenyl]-amide

Example 169

3'-(Cyclobutanecarbonyl-amino)-biphenyl-4-carboxylic acid [4-(1,1-dioxo-1lambda*6*-thiomorpholin-4-ylmethyl)-phenyl]-amide Examples 170 and 171 were prepared by an analogous method to example 163

Example 170

Tetrahydro-pyran-4-carboxylic acid {4'-[4-(1,1-dioxo-1lambda*6*-thiomorpholin-4-ylmethyl)-phenylcarbamoyl]-6-methyl-biphenyl-3-yl}-amide

Example 171

2'-Methyl-5'-(2-tetrahydro-pyran-4-yl-acetylamino)-biphenyl-4-carboxylic acid [4-(1,1-dioxo-1lambda*6*-thiomorpholin-4-ylmethyl)-phenyl]-amide

Example 172

3'-(Cyclopropanecarbonyl-amino)-2,4'-dimethyl-biphenyl-4-carboxylic acid [4-(1,1-dioxo-1lambda*6*-thiomorpholin-4-ylmethyl)-phenyl]-amide Check
Examples 173 to 179 were prepared by analogous methods to example 163

Example 173

2'-Methyl-5'-[(1-trifluoromethyl-cyclopropanecarbonyl)-amino]-biphenyl-4-carboxylic acid [4-(1,1-dioxo-1lambda*6*-thiomorpholin-4-ylmethyl)-phenyl]-amide

Example 174

5'-[(1-Cyano-cyclopropanecarbonyl)-amino]-2'-methyl-biphenyl-4-carboxylic acid [4-(1,1-dioxo-1lambda*6*-thiomorpholin-4-ylmethyl)-phenyl]-amide

Example 175

2'-Methyl-5'-[(1-methyl-cyclopropanecarbonyl)-amino]-biphenyl-4-carboxylic acid [4-(1,1-dioxo-1lambda*6*-thiomorpholin-4-ylmethyl)-phenyl]-amide

Example 176

5'-(Cyclopropanecarbonyl-amino)-2'-methyl-biphenyl-4-carboxylic acid [4-(1,1-dioxo-1lambda*6*-thiomorpholin-4-ylmethyl)-phenyl]-amide

Example 177

Thiazole-4-carboxylic acid {4'-[4-(1,1-dioxo-1lambda*6*-thiomorpholin-4-ylmethyl)-phenylcarbamoyl]-6-methyl-biphenyl-3-yl}-amide

Example 178

5'-(2-Cyclopropyl-acetylamino)-2'-methyl-biphenyl-4-carboxylic acid [4-(1,1-dioxo-1lambda*6*-thiomorpholin-4-ylmethyl)-phenyl]-amide

Example 179

Thiazole-5-carboxylic acid {4'-[4-(1,1-dioxo-1lambda*6*-thiomorpholin-4-ylmethyl)-phenylcarbamoyl]-6-methyl-biphenyl-3-yl}-amide Examples 180 and 181 were prepared by analogous methods to example 182

Example 180

5'-Acetylamino-2'-methyl-biphenyl-4-carboxylic acid [4-(1,1-dioxo-1lambda*6*-thiomorpholin-4-ylmethyl)-phenyl]-amide

Example 181

5'-(2-Ethyl-butyrylamino)-2'-methyl-biphenyl-4-carboxylic acid [4-(1,1-dioxo-1lambda*6*-thiomorpholin-4-ylmethyl)-phenyl]-amide

Example 182

5'-Butyrylamino-2'-methyl-biphenyl-4-carboxylic acid [4-(1,1-dioxo-1lambda*6*-thiomorpholin-4-ylmethyl)-phenyl]-amide (Route A)

A mixture of 5'-amino-2'-methyl-biphenyl-4-carboxylic acid [4-(1,1-dioxo-1lambda*6*-thiomorpholin-4-ylmethyl)-phenyl]-amide (54 mg), butyric acid (11 mg), EDAC (24 mg), HOBT (16 mg) and N-methylmorpholine (24 mg) in dry DMF (1 ml) was stirred at 20 C for 18 h. The mixture was then diluted with water (6 ml) and the resulting colourless solid collected by filtration and dried (42 mg).

$^1$H NMR (DMSO, δ) 0.92 (t, 3H) 1.61 (q, 2H) 2.21 (s, 3H) 2.29 (t, 2H) 2.90 (m, 4H) 3.13 (m, 4H) 3.66 (s, 2H) 7.25 (d, 1H) 7.33 (d, 2H) 7.48-7.56 (m, 4H) 7.78 (d, 2H) 8.03 (d, 2H) 9.89 (s, 1H) 10.32 (s, 1H)

LC-MS ES+=520

Examples 183 and 184 were prepared by analogous methods to Example 182

Example 183

5'-Isobutyrylamino-2'-methyl-biphenyl-4-carboxylic acid [4-(1,1-dioxo-1lambda*6*-thiomorpholin-4-ylmethyl)-phenyl]-amide

Example 184

5'-(2,2-Dimethyl-propionylamino)-2'-methyl-biphenyl-4-carboxylic acid [4-(1,1-dioxo-1lambda*6*-thiomorpholin-4-ylmethyl)-phenyl]-amide

Intermediate 28

(3-Bromo-4-trifluoromethoxy-phenyl)-carbamic acid tert-butyl ester

A mixture of 3-bromo-4-trifluoromethoxy-phenylamine (250 mg) and Boc anhydride (430 mg) in methanol (4 ml) containing triethylamine (0.26 ml) was stirred at 20 C for 18 h. The mixture was then partitioned between 1M HCL and ethyl acetate. The dried extracts were then evaporated giving the title compound as an off-white solid (250 mg).

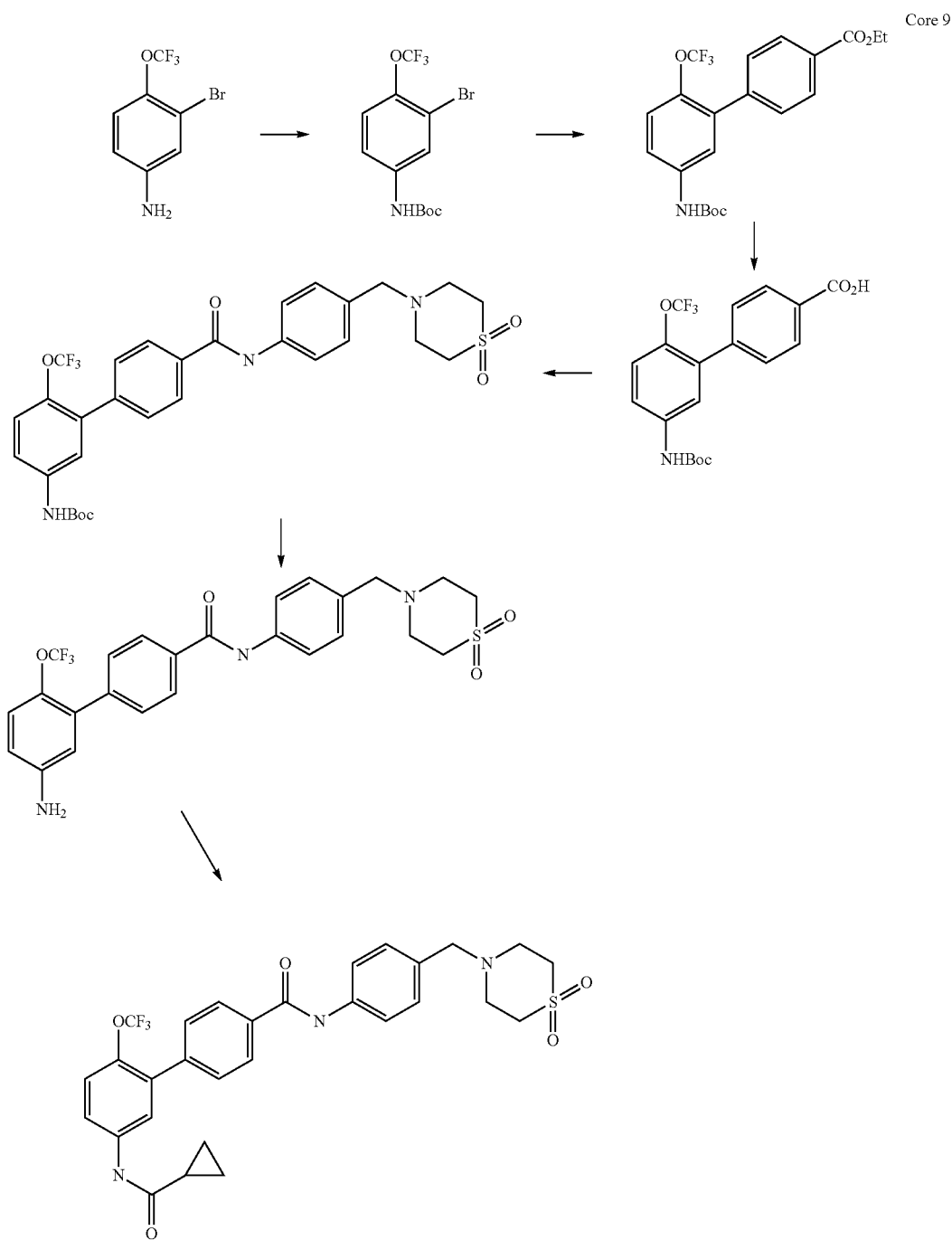

Intermediate 29

5'-tert-Butoxycarbonylamino-2'-trifluoromethoxy-biphenyl-4-carboxylic acid ethyl ester A mixture of (3-bromo-4-trifluoromethoxy-phenyl)-carbamic acid tert-butyl ester (250 mg), 4-ethoxycarbonyl-phenyl boronic acid (136 mg), cesium carbonate (228 mg) and tetrakis(triphenylphosphine)palladium⁰ (catalytic quantity), in 1:2 aqueous DME (15 ml) was heated to reflux for 18 h. The mixture was then cooled and partitioned between water and ethyl acetate. The dried extracts were evaporated and the residue purified on silica gel. Elution with 5-40% ethyl acetate:petrol gave a pale yellow solid (217 mg)

Intermediate 30

5'-tert-Butoxycarbonylamino-2'-trifluoromethoxy-biphenyl-4-carboxylic acid

5'-tert-Butoxycarbonylamino-2'-trifluoromethoxy-biphenyl-4-carboxylic acid ethyl ester (200 mg) in ethanol (7 ml) and 2M sodium hydroxide (4 ml) was stirred at 20 C for 18 h. The ethanol was then evaporated and the residue acidified. The solid thus formed was collected by filtration and dried (128 mg)

Intermediate 31

{4'-[4-(1,1-Dioxo-1lambda*6*-thiomorpholin-4-ylmethyl)-phenylcarbamoyl]-6-trifluoromethoxy-biphenyl-3-yl}-carbamic acid tert-butyl ester A mixture of 5'-tert-butoxycarbonylamino-2'-trifluoromethoxy-biphenyl-4-carboxylic acid (100 mg) 4-(1,1-dioxo-1lambda*6*-thiomorpholin-4-ylmethyl)-phenylamine (61 mg), N-methylmorpholine (0.06 ml), 1-hydroxybenzotriazole (34 mg) and 1-ethyl-3-(3-(dimethylaminopropyl)carbodiimide hydrochloride (48 mg) in dry DMF (2 ml) was stirred at 20 C for 18 h. The mixture was then added to water and the resulting colourless precipitate collected by filtration and dried (140 mg).

Intermediate 32

5'-Amino-2'-trifluoromethoxy-biphenyl-4-carboxylic acid [4-(1,1-dioxo-1lambda*6*-thiomorpholin-4-ylmethyl)-phenyl]-amide {4'-[4-(1,1-Dioxo-1lambda*6*-thiomorpholin-4-ylmethyl)-phenylcarbamoyl]-6-trifluoromethoxy-biphenyl-3-yl}-carbamic acid tert-butyl ester (140 mg) was stirred in 1:1 trifluoroacetic acid:dichloromethane (6 ml) at 20 C for 1 h. The mixture was then basified and extracted with ethyl acetate. The dried extracts were then evaporated giving a dark gum (105 mg).

Example 185

5'-(Cyclopropanecarbonyl-amino)-2'-trifluoromethoxy-biphenyl-4-carboxylic acid [4-(1,1-dioxo-1lambda*6*-thiomorpholin-4-ylmethyl)-phenyl]-amide 5'-Amino-2'-trifluoromethoxy-biphenyl-4-carboxylic acid [4-(1,1-dioxo-1lambda*6*-thiomorpholin-4-ylmethyl)-phenyl]-amide (50 mg) in dichloromethane (1 ml) containing N-methylmorpholine (0.03 ml) was treated with cyclopropanecarbonyl chloride (9 mg), the mixture being stirred for 18 h. The solvent was then evaporated and the residue purified on silica gel. Elution with dichloromethane:ethanol:0.880 ammonia; 800:8:1 to 100:8:1 gave a colourless solid (46 mg).
¹H NMR (DMSO, δ) 0.84 (d, 4H) 1.80-1.85 (m, 1H) 2.89 (m, 4H) 3.13 (m, 4H) 3.66 (s, 2H) 7.33 (d, 2H) 7.38 (m, 1H) 7.47 (d, 2H) 7.60-7.81 (m, 4H) 8.06 (d, 2H) 10.37 (s, 1H) 10.57 (s, 1H).
LC-MS ES+588

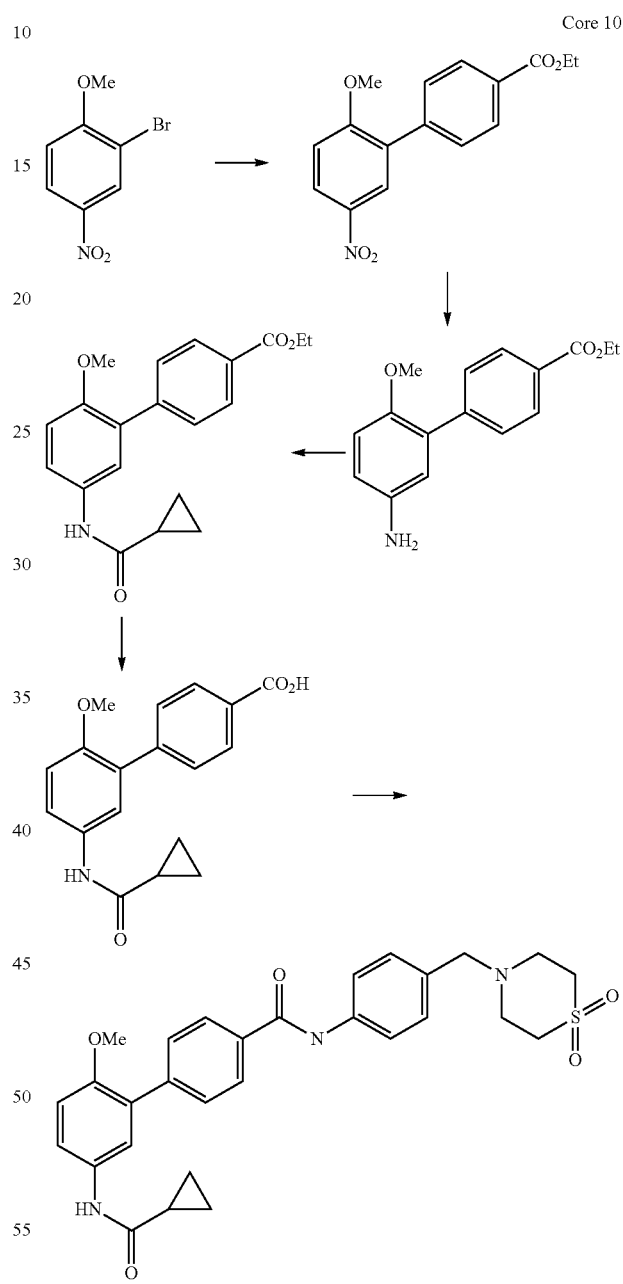

Core 10

Intermediate 33

2'-Methoxy-5'-nitro-biphenyl-4-carboxylic acid ethyl ester

A mixture of 2-bromo-1-methoxy-4-nitro-benzene (1 g), 4-ethoxycarbonyl-phenyl boronic acid (836 mg), cesium carbonate (1.4 g) and tetrakis(triphenylphosphine)palladium⁰ (catalytic quantity), in 1:2 aqueous DME (45 ml) was heated to reflux for 18 h. The mixture was then cooled and partitioned between water and ethyl acetate. The dried extracts were evaporated and the residue purified on silica gel. Elution with 5-40% ethyl acetate:petrol gave a yellow solid (997 mg).
Intermediate 34

5'-Amino-2'methoxy-biphenyl-4-carboxylic acid ethyl ester hydrochloride

2'-Methoxy-5'-nitro-biphenyl-4-carboxylic acid ethyl ester (600 mg) in ethanol 90 ml) and 2M HCl (2.5 ml) was hydrogenated at RTP for 3 h. The mixture was then filtered through celite and the solvent evaporated. The dark solid residue was dissolved in 1:1 aqueous acetonitrile, filtered through celite again and evaporated giving the title compound as a red solid (595 mg).
Intermediate 35

5'-(Cyclopropanecarbonyl-amino)-2'-methoxy-biphenyl-4-carboxylic acid ethyl ester A mixture of 5'-amino-2'methoxy-biphenyl-4-carboxylic acid ethyl ester hydrochloride (100 mg), N-methylmorpholine (0.1 ml) and cyclopropanecarbonyl chloride (29 mg) in dry THF (3 ml) was stirred at 20 C for 18 h. The mixture was then evaporated and the residue partitioned between sodium bicarbonate solution and ethyl acetate. The dried extracts were then evaporated giving the title compound as a dark oil (88 mg)
Intermediate 36

5'-(Cyclopropanecarbonyl-amino)-2'-methoxy-biphenyl-4-carboxylic acid

A mixture of 5'-(cyclopropanecarbonyl-amino)-2'-methoxy-biphenyl-4-carboxylic acid ethyl ester (88 mg) in ethanol (7 ml) and 2M sodium hydroxide (4 ml) was stirred at 20 C for 18 h. The ethanol was then evaporated and the residue acidified. The solid thus formed was collected by filtration and dried (55 mg)

Example 186

5'-(Cyclopropanecarbonyl-amino)-2'-methoxy-biphenyl-4-carboxylic acid [4-(1,1-dioxo-1lambda*6*-thiomorpholin-4-ylmethyl)-phenyl]-amide A mixture of 5'-(cyclopropanecarbonyl-amino)-2'-methoxy-biphenyl-4-carboxylic acid (50 mg), 4-(1,1-dioxo-1lambda*6*-thiomorpholin-4-ylmethyl)-phenylamine (38 mg), N-methylmorpholine (0.03 ml), 1-hydroxybenzotriazole (21 mg) and 1-ethyl-3-(3-(dimethylaminopropyl)carbodiimide hydrochloride (30 mg) in dry DMF (1 ml) was stirred at 20 C for 18 h. The mixture was then added to water and the resulting colourless precipitate collected by filtration and dried (38 mg).

$^1$H NMR (DMSO, δ) 0.74-0.81 (m, 4H) 1.70-1.80 (m, 1H) 2.88 (m, 4H) 3.13 (m, 4H) 3.36 (s, 3H) 3.66 (s, 2H) 7.10 (d, 1H) 7.36 (d, 2H) 7.56-7.65 (m, 4H) 7.70 (d, 2H) 8.00 (d, 2H) 10.16 (s, 1H) 10.29 (s, 1H).

LC-MS ES+=534

Example 187

5'-(Cyclohexanecarbonyl-amino)-2'-methoxy-biphenyl-4-carboxylic acid [4-(1,1-dioxo-1lambda*6*-thiomorpholin-4-ylmethyl)-phenyl]-amide This compound was prepared by an analogous method to Example 186

Example 188

5'-(3-Ethyl-ureido)-2'-methyl-biphenyl-4-carboxylic acid [4-(1,1-dioxo-1lambda*6*-thiomorpholin-4-ylmethyl)-phenyl]-amide This compound was prepared by an analogous method to Example 189

Example 189

5'-(3-Cyclohexyl-ureido)-2'-methyl-biphenyl-4-carboxylic acid [4-(1,1-dioxo-1lambda*6*-thiomorpholin-4-ylmethyl)-phenyl]-amide (Route A)

This material was prepared as described for Example 132 except that isocyanatocyclohexane was used. The title compound was obtained as a colourless solid (40 mg)

$^1$H NMR (DMSO, δ) 1.15-1.34 (m, 4H) 1.64-1.83 (m, 6H) 2.18 (s, 3H) 2.90 (m, 4H) 3.12 (m, 4H) 3.33 (m, 1H) 3.66 (s, 2H) 6.04 (d, 1H) 7.17 (d, 1H) 7.24-7.35 (m, 4H) 7.48 (d, 2H) 7.78 (d, 2H) 7.97-8.04 (2H) 8.30 (s, 1H) 10.30 (s, 1H)

LC-MS ES+=575.

Example 190

2'-Methyl-5'-(2-oxo-propionylamino)-biphenyl-4-carboxylic acid [4-(1,1-dioxo-1lambda*6*-thiomorpholin-4-ylmethyl)-phenyl]-amide This compound was prepared by an analogous method to Example 189

Example 191

5'-(Cyclohexanecarbonyl-amino)-2'-fluoro-biphenyl-4-carboxylic acid [4-(1,1-dioxo-1lambda*6*-thiomorpholin-4-ylmethyl)-phenyl]-amide This compound was prepared by an analogous method to Example 194 except that a fluorinated core was used.

Example 192

5'-(Cyclohexanecarbonyl-amino)-2'-trifluoromethoxy-biphenyl-4-carboxylic acid [4-(1,1-dioxo-1lambda*6*-thiomorpholin-4-ylmethyl)-phenyl]-amide This compound was prepared by an analogous method to Example 185.

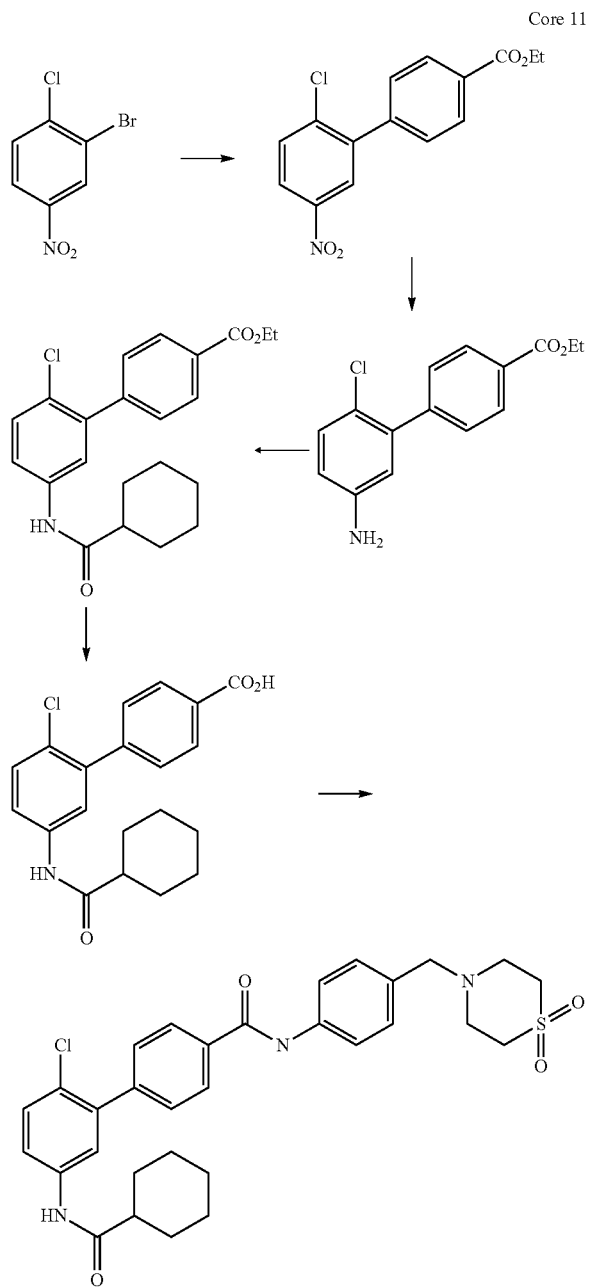

Intermediate 37

2'-Chloro-5'-nitro-biphenyl-4-carboxylic acid ethyl ester

A mixture of 2-bromo-1-chloro-4-nitro-benzene (2.5 g), 4-ethoxycarbonyl-phenyl boronic acid (2.05 g), cesium carbonate (3.44 g) and tetrakis(triphenylphosphine)palladium⁰ (catalytic quantity), in 1:2 aqueous DME (45 ml) was heated to reflux for 18 h. The mixture was then cooled and partitioned between water and ethyl acetate. The dried extracts were evaporated to give the product as a white solid (3.01 g). This material was used in the next stage without further purification.

Intermediate 38

5'-Amino-2'-chloro-biphenyl-4-carboxylic acid ethyl ester hydrochloride

2'-Chloro-5'-nitro-biphenyl-4-carboxylic acid ethyl ester (1.04 g) in ethanol 30 ml) and 2M HCl (5.0 ml) was hydrogenated at RTP for 3 h. The mixture was then filtered through celite and the solvent evaporated to give the title compound as a dark red solid (1.02 g) which was used in the next stage without further purification.

Intermediate 39

5'-(Cyclohexanecarbonyl-amino)-2'-chloro-biphenyl-4-carboxylic acid ethyl ester

A mixture of 5'-amino-2'-chloro-biphenyl-4-carboxylic acid ethyl ester hydrochloride (521 mg), triethylamine (0.49 ml) and cyclohexanecarbonyl chloride (0.26 ml) in dry THF (25 ml) was stirred at 20 C for 18 h. The mixture was then evaporated and the residue partitioned between water and dichloromethane. The organic layer was washed with water, dried (MgSO$_4$), filtered and evaporated under reduced pressure to give the product (714 mg) as a yellow oil.

Intermediate 40

5'-(Cyclohexanecarbonyl-amino)-2'-chloro-biphenyl-4-carboxylic acid

A mixture of 5'-(cyclohexanecarbonyl-amino)-2'-chloro-biphenyl-4-carboxylic acid ethyl ester (200 mg) in ethanol (15 ml) and 1M sodium hydroxide (7.5 ml) was stirred at 20 C for 18 h. The ethanol was then evaporated and the residue acidified. The solid thus formed was collected by filtration and dried (176 mg).

Example 193

5'-(Cyclohexanecarbonyl-amino)-2'-chloro-biphenyl-4-carboxylic acid [4-(1,1-dioxo-1lambda*6*-thiomorpholin-4-ylmethyl)-phenyl]-amide A mixture of 5'-(cyclohexanecarbonyl-amino)-2'-chloro-biphenyl-4-carboxylic acid (100 mg), 4-(1,1-dioxo-1lambda*6*-thiomorpholin-4-ylmethyl)-phenylamine (67 mg), triethylamine (0.098 ml) and HBTU (159 mg) in dry DMF (5 ml) was stirred at 20 C for 18 h. The mixture was then evaporated to dryness and purified via reversed-phase preparative HPLC (eluting with acetonitrile/water) to afford the title compound as an orange solid (35 mg).

$^1$H NMR (DMSO, δ) 0.90-1.40 (m, 6H), 1.42-1.73 (m, 4H), 2.09-2.24 (m, 1H), 2.65-2.78 (m, 4H), 2.90-3.00 (m, 4H), 3.49 (s, 1H), 7.18 (d, 2H), 7.30-7.54 (m, 5H), 7.58-7.69 (m, 2H), 7.88 (d, 2H), 9.89 (s, 1H), 10.19 (s, 1H).

Example 194

2'-Chloro-5'-(cyclopropanecarbonyl-amino)-biphenyl-4-carboxylic acid [4-(1,1-dioxo-1lambda*6*-thiomorpholin-4-ylmethyl)-phenyl]-amide This compound was prepared by an analogous method to Example 193.

Example 195

5'-(Cyclobutanecarbonyl-amino)-2'-methyl-biphenyl-4-carboxylic acid [4-(1,1-dioxo-lambda*6*-thiomorpholin-4-ylmethyl)-phenyl]-amide This compound was prepared by an analogous method to Example 165

Example 196
3'-(Cyclohexanecarbonyl-amino)-biphenyl-4-carboxylic acid [4-(1,1-dioxo-1lambda*6*-thiomorpholin-4-ylmethyl)-phenyl]-amide
This compound was prepared by an analogous method to Example 60 using an intermediate analogous to Intermediate 6.
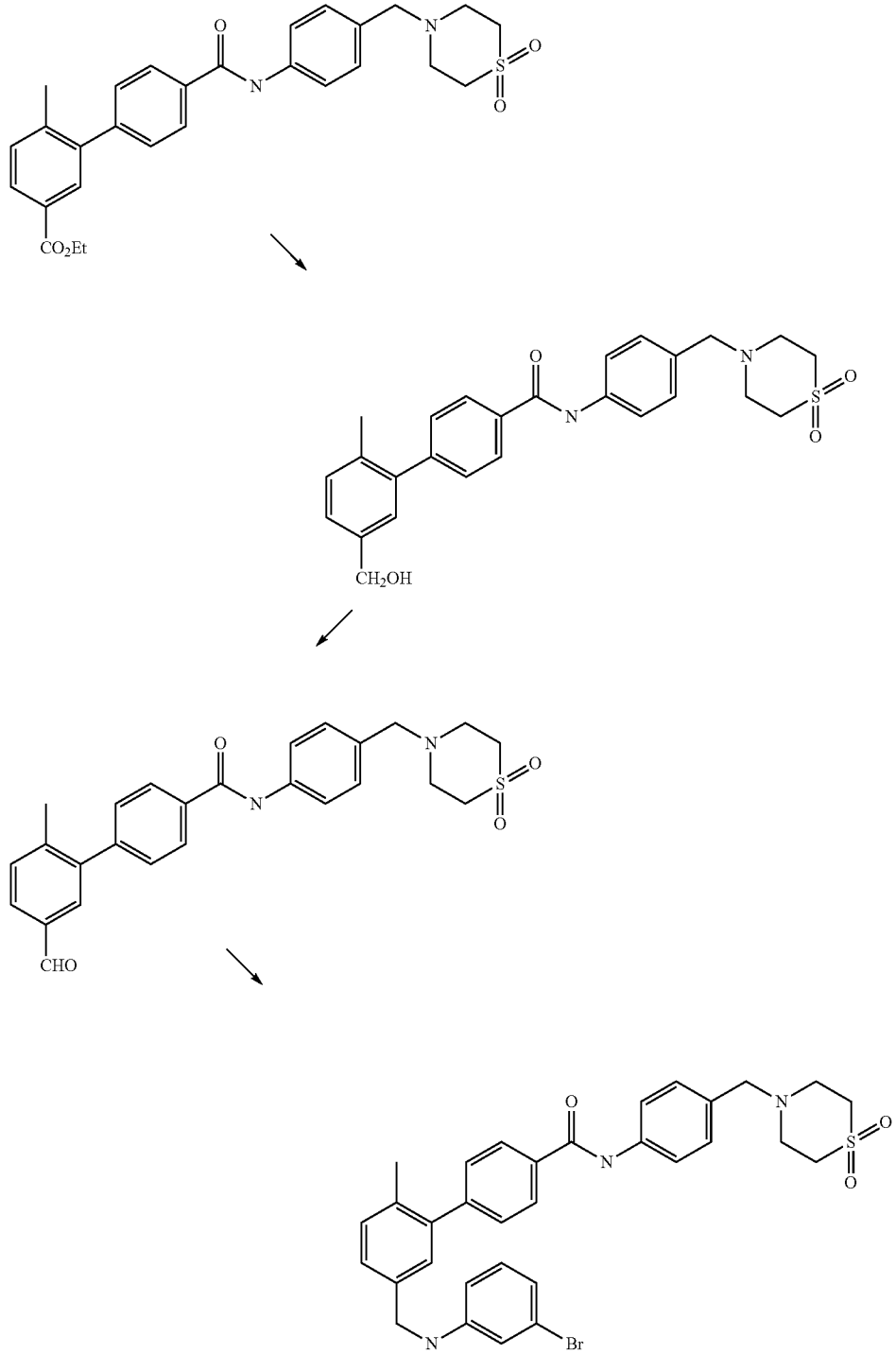
Core 12

Intermediate 41

5'-Hydroxymethyl-2'-methyl-biphenyl-4-carboxylic acid [4-(1,1-dioxo-1lambda*6*-thiomorpholin-4-ylmethyl)-phenyl]-amide 4'-[4-(1,1-Dioxo-1lambda*6*-thiomorpholin-4-ylmethyl)-phenylcarbamoyl]-6-methyl-biphenyl-3-carboxylic acid methyl ester (565 mg) in dry THF (6 ml) was treated with a solution of lithium borohydride (2M in THF, 3.5 ml). The mixture was stirred at 20 C for 18 h. and was then treated with methanol (5 ml). The mixture was then evaporated and the residue partitioned between water and ethyl acetate. The dried extracts were evaporated giving the title compound as a colourless crystalline solid (505 mg).

Intermediate 42

5'-Formyl-2'-methyl-biphenyl-4-carboxylic acid [4-(1,1-dioxo-1 lambda*6*-thiomorpholin-4-ylmethyl)-phenyl]-amide 5'-Hydroxymethyl-2'-methyl-biphenyl-4-carboxylic acid [4-(1,1-dioxo-1lambda*6*-thiomorpholin-4-ylmethyl)-phenyl]-amide (500 mg) in dichloromethane (30 ml) was treated with manganese dioxide (3 g) and the mixture stirred at 20 C for 18 h. The suspension was then filtered through celite and the mother liquor evaporated giving the title compound as a colourless oil (480 mg)

Example 197

5'-[(3-Bromo-phenylamino)-methyl]-2'-methyl-biphenyl-4-carboxylic acid [4-(1,1-dioxo-1lambda*6*-thiomorpholin-4-ylmethyl)-phenyl]-amide This compound was prepared by an analogous method to Example 198.

Example 198

5'-[(3-Bromo-phenylamino)-methyl]-2'methyl-biphenyl-4-carboxylic acid [4-(1,1-dioxo-1lambda*6*-thiomorpholin-4-ylmethyl)-phenyl]-amide 5'-Formyl-2'-methyl-biphenyl-4-carboxylic acid [4-(1,1-dioxo-1lambda*6*-thiomorpholin-4-ylmethyl)-phenyl]-amide (40 mg) and 3-bromo-aniline (18 mg) were stirred together in dry dichloromethane (10 ml) containing 3 A molecular sieves. The mixture was then heated to 40 C for 4 h. Sodium (triacetoxy)borohydride (50 mg) and glacial acetic acid (1 ml) were then added and stirring continued at 20 C for 18 h. The sieves were then removed by filtration and the mother liquor evaporated. The residue was purified on silica gel. Elution with dichloromethane:ethanol:0.880 ammonia; 200:8:1 gave the title compound as a pale yellow solid (32 mg).

$^1$H NMR (DMSO, δ) 2.25 (s, 3H) 2.88 (m, 4H) 3.13-3.18 (m, 4H) 3.66 (s, 2H) 4.29 (d, 2H) 6.57-6.67 (m, 3H) 6.76 (s, 1H) 6.96 (t, 1H) 7.25-7.35 (m, 5H) 7.49 (d, 2H) 7.78 (d, 2H) 8.02 (d, 2H) 10.33 (s, 1H)

LC-MS ES+=618

Examples 199 to 201 were prepared by analogous methods to Example 198

Example 199

5'-[(3-Chloro-benzylamino)-methyl]-2'-methyl-biphenyl-4-carboxylic acid [4-(1,1-dioxo-1lambda*6*-thiomorpholin-4-ylethyl)-phenyl]-amide Example 200

5'-{[1-Hydroxymethyl-2-(3H-imidazol-4-yl)-ethylamino]-methyl}-2'-methyl-biphenyl-4-carboxylic acid [4-(1,1-dioxo-1lambda*6*-thiomorpholin-4-ylmethyl)-phenyl]-amide Example 201

5'-[(1H-Indazol-6-ylamino)-methyl]-2'-methyl-biphenyl-4-carboxylic acid [4-(1,1-dioxo-1lambda*6*-thiomorpholin-4-ylmethyl)-phenyl]-amide Example 202

5'-(4-Chloro-benzenesulfonylamino)-2'-methyl-biphenyl-4-carboxylic acid [4-(1,1-dioxo-1lambda*6*-thiomorpholin-4-ylmethyl)-phenyl]-amide This compound was prepared by an analogous method to Example 203.

Example 203

2'-Methyl-5'-(6-morpholin-4-yl-pyridine-3-sulfonylamino)-biphenyl-4-carboxylic acid [4-(1,1-dioxo-1lambda*6*-thiomorpholin-4-ylmethyl)-phenyl]-amide (RouteB)

This material was prepared as described for Example 155. The title compound was isolated as a colourless solid (31 mg).

$^1$H NMR (DMSO, δ) 2.16 (s, 3H) 2.90 (m, 4H) 3.13 (m, 4H) 3.58-3.66 (m, 10H) 6.91-6.98 (m, 2H) 7.05-7.10 (m, 1H) 7.22 (d, 1H) 7.33 (d, 2H) 7.40 (d, 2H) 7.75-7.79 (m, 3H) 8.01 (d, 2H) 8.38 (dd, 1H) 10.14 (s, 1H) 10.33 (s, 1H).

LC-MS ES+=676

Example 204

5'-(5-Chloro-thiophene-2-sulfonylamino)-2'-methyl-biphenyl-4-carboxylic acid [4-(1,1-dioxo-1lambda*6*-thiomorpholin-4-ylmethyl)-phenyl]-aide This compound was prepared by an analogous method to Example 203

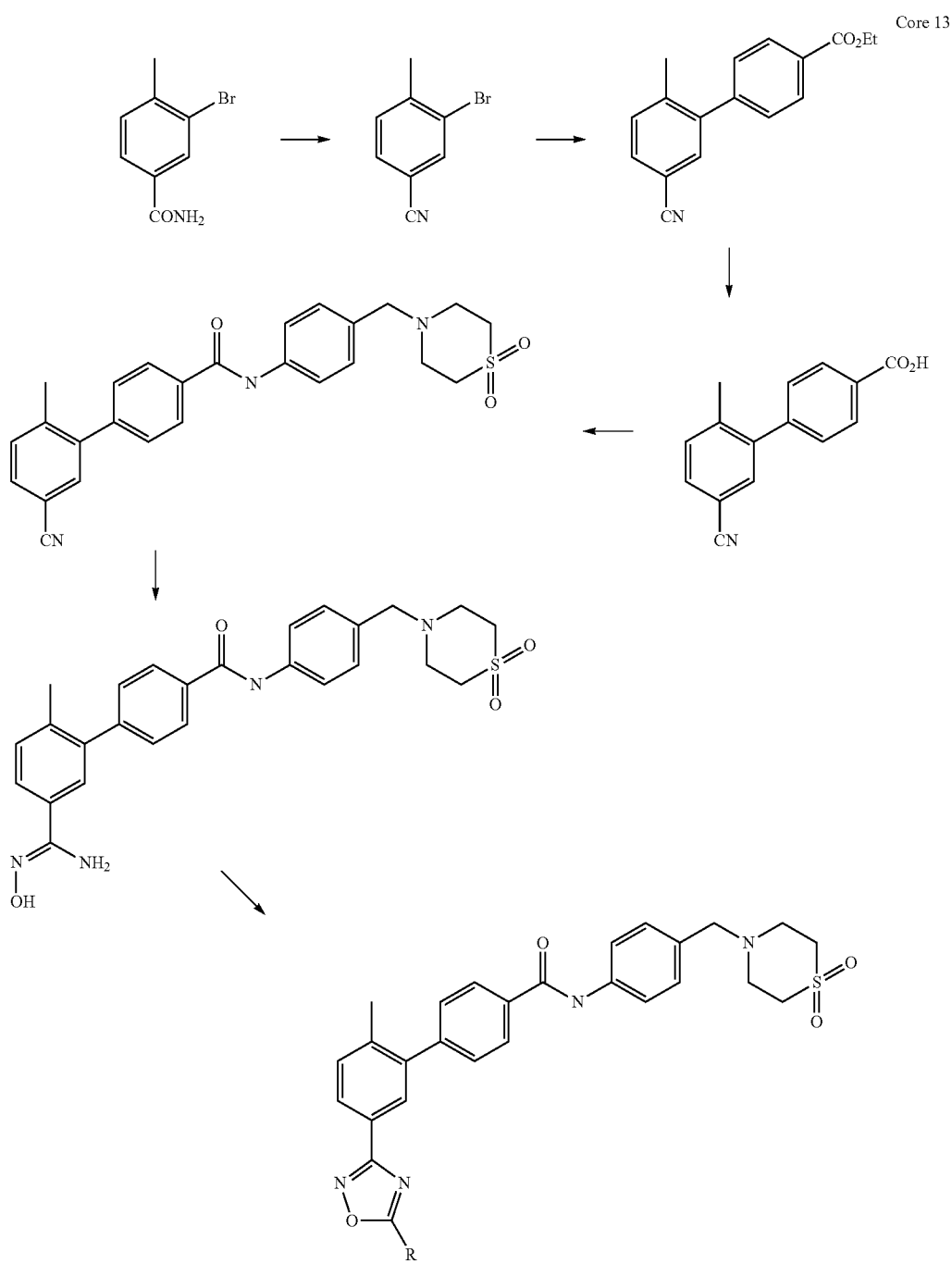

Intermediate 43

3-Bromo-4-methyl-benzonitrile

3-Bromo-4-methyl-benzoic acid (3 g) in toluene (75 ml) was treated with oxalyl chloride (10 ml) and DMF (4 drops). The mixture was then stirred at 20 C for 3 h. and then the solvent evaporated giving a yellow solid. This in turn was dissolved in THF (30 ml) containing N-methyl-morpholine (1.5 ml). Aqueous ammonia (0.880, 40 ml) was then added and the mixture stirred for 18 h. The THF was then evaporated and the resulting amide intermediate collected by filtration as a colourless solid (2.9 g). This material was then suspended in thionyl chloride (35 ml) and was heated to 85 C for 6 h. The excess reagent was then evaporated and the residue purified on silica gel. Elution with 5-50% ethyl acetate in hexane gave the title compound as a white solid (1.4 g)

Intermediate 44

5'-Cyano-2'-methyl-biphenyl-4-carboxylic acid ethyl ester

A mixture of 3-bromo-4-methyl-benzonitrile (600 mg), 4-(ethoxycarbonylphenyl) boronic acid (594 mg), cesium carbonate (995 mg) and tetrakis(triphenylphosphine) palladium (0), 5 mol % (180 mg) was heated to reflux under nitrogen in DME (30 ml) and water (15 ml) for 18 h. The reaction mixture was then cooled to room temperature and filtered. The resulting filtrate was then evaporated and purified on silica gel, gradient elution with 10-20% ethyl acetate in petrol gave the title compound as a pale yellow solid (867 mg).

Intermediate 45

5'-Cyano-2'-methyl-biphenyl-4-carboxylic acid

A mixture of 5'-Cyano-2'-methyl-biphenyl-4-carboxylic acid ethyl ester (850 mg) and sodium hydroxide (2M, 15 ml) in ethanol (30 ml) was stirred at 20 C for 18 h. The ethanol was then evaporated and the residue acidified. The resulting solid was collected by filtration and was then purified on silica gel. Gradient elution with 0-30% 20:8:1 $CH_2Cl_2/EtOH/NH_3$ in $CH_2Cl_2$ gave the title compound as a white solid (665 mg).

Intermediate 46

5'-Cyano-2'-methyl-biphenyl-4-carboxylic acid [4-(1,1-dioxo-1lambda*6*-thiomorpholin-4-ylmethyl)-phenyl]-amide A mixture of 5'-cyano-2'-methyl-biphenyl-4-carboxylic acid (100 mg), 4-(1,1-dioxo-1lambda*6*-thiomorpholin-4-ylmethyl)-phenylamine (101 mg), EDAC (81 mg), HOBT (57 mg) and N-methylmorpholine (0.09 ml) in dry DMF (2 ml) was stirred at 20 C for 18 h. Water (8 ml) was then added and the resulting solid collected by filtration and dried (160 mg).

Intermediate 47

5'-(N-Hydroxycarbamimidoyl)-2'-methyl-biphenyl-4-carboxylic acid [4-(1,1-dioxo-1lambda*6*-thiomorpholin-4-ylmethyl)-phenyl]-amide Hydroxylamine hydrochloride (47 mg) and sodium methoxide (37 mg) were stirred in methanol (5 ml) for 1 h. The mixture was filtered and the mother liquor treated with 5'-Cyano-2'-methyl-biphenyl-4-carboxylic acid [4-(1,1-dioxo-1lambda*6*-thiomorpholin-4-ylmethyl)-phenyl]-amide (155 mg). The mixture was then heated to reflux for 18 h. On cooling a colourless solid was formed which was collected by filtration and dried (138 mg).

Example 205

5'-(5-Cyclopropyl-[1,2,4]oxadiazol-3-yl)-2'-methyl-biphenyl-4-carboxylic acid [4-(1,1-dioxo-1lambda*6*-thiomorpholin-4-ylmethyl)-phenyl]-amide 5'-(N-Hydroxycarbamimidoyl)-2'-methyl-biphenyl-4-carboxylic acid [4-(1,1-dioxo-1lambda*6*-thiomorpholin-4-ylmethyl)-phenyl]-amide (50 mg) and cyclopropylcarbonyl chloride (0.02 ml) was heated in a microwave at 150 C for 40 min. The solvent was then evaporated and the residue purified on silica gel. Gradient elution with 0-30% 20:8:1 $CH_2Cl_2/EtOH/NH_3$ in $CH_2Cl_2$ gave the title compound as a white solid (24 mg).

$^1$H NMR (DMSO, δ) 1.18-1.32 (m, 4H) 2.34 (s, 3H) 2.34-2.43 (m, 1H) 2.89 (m, 4H) 3.12 (m, 4H) 3.66 (s, 2H) 7.33 (d, 2H) 7.52-7.60 (m, 3H) 7.78-7.81 (m, 3H) 7.92 (dd, 1H) 8.07 (d, 2H) 10.35 (s, 1H).

LC-MS ES+=543

Example 206

5'-(5-Cyclohexyl-[1,2,4]oxadiazol-3-yl)-2'-methyl-biphenyl-4-carboxylic acid [4-(1,1-dioxo-1lambda*6*-thiomorpholin-4-ylmethyl)-phenyl]-amide This material was prepared as described for Example 209 except that cyclohexanecarbonyl chloride was used. The title compound was obtained as a white solid (15 mg).

$^1$H NMR (DMSO, δ) 1.20-1.45 (m, 6H) 1.60-1.80 (m, 4H) 2.05-2.12 (m, 1H) 2.35 (s, 3H) 2.89 (m, 4H) 3.10 (m, 4H) 3.66 (s, 2H) 7.33 (d, 2H) 7.52-7.60 (m, 3H) 7.78-7.81 (m, 3H) 7.92 (dd, 1H) 8.07 (d, 2H) 10.35 (s, 1H).

LC-MS ES+=585.

Example 207

5'-(5-Isopropyl-[1,2,4]oxadiazol-3-yl)-2'-methyl-biphenyl-4-carboxylic acid [4-(1,1-dioxo-1lambda*6*-thiomorpholin-4-ylmethyl)-phenyl]-amide This material was prepared as described for Example 205 except that isobutyryl chloride was used. The title compound was obtained as a white solid (14 mg).

$^1$H NMR (DMSO, δ) 1.39 (d, 6H) 2.35 (s, 1H) 2.89 (m, 4H) 3.12 (m, 4H) 3.66 (s, 2H) 7.33 (d, 2H) 7.52-7.60 (m, 3H) 7.78-7.81 (m, 3H) 7.92 (dd, 1H) 8.07 (d, 2H) 10.35 (s, 1H).

Examples 208 to 233 can be prepared in an analogous fashion to Examples 1 or 87.

Example 208

6-Methyl-biphenyl-3,4'-dicarboxylic acid 3-cyclopropylamide 4'-{[4-(2-diethylamino-ethylcarbamoyl)-phenyl]-amide}

Example 209

Furan-2-carboxylic acid [4'-(3-chloro-benzylcarbamoyl)-6-methyl-biphenyl-3-yl]-amide Example 210

5'-tert-Butoxycarbonylamino-2'-methyl-biphenyl-4-carboxylic acid ethyl ester

Example 211

5'-(4-Bromo-benzoylamino)-2'-methyl-biphenyl-4-carboxylic acid (1H-indazol-6-yl)-amide Example 212

5'-(4-Bromo-benzoylamino)-2'-methyl-biphenyl-4-carboxylic acid (4-oxazol-5-yl-phenyl)-amide Example 213

Thiophene-2-carboxylic acid [4'-(1H-indazol-6-yl-carbamoyl)-6-methyl-biphenyl-3-yl]-amide Example 214

1H-Pyrazole-4-carboxylic acid [6-methyl-4'-(3-methyl-benzylcarbamoyl)-biphenyl-3-yl]-amide

Example 215

N-[6-Methyl-4'-(3-methyl-benzylcarbamoyl)-biphenyl-3-yl]-isonicotinamide

Example 216

5'-(Cyclopropanecarbonyl-amino)-2'-methyl-biphenyl-4-carboxylic acid 3-chloro-benzylamide

Example 217

5'-(Cyclopropanecarbonyl-amino)-2'-methyl-biphenyl-4-carboxylic acid 4-(4-methyl-piperazin-1-yl)-benzylamide

Example 218

5'-(Cyclopropanecarbonyl-amino)-2'-methyl-biphenyl-4-carboxylic acid (4-[1,2,4]triazol-1-yl-phenyl)-amide

Example 219

5'-(Cyclohexanecarbonyl-amino)-2'-methyl-biphenyl-4-carboxylic acid (4-[1,2,4]triazol-1-yl-phenyl)-amide

Example 220

5'-(Cyclopropanecarbonyl-amino)-2'-methyl-biphenyl-4-carboxylic acid [4-(3-ethyl-2,6-dioxo-piperidin-3-yl)-phenyl]-amide

Example 221

5'-(Cyclohexanecarbonyl-amino)-2'-methyl-biphenyl-4-carboxylic acid [4-(3-ethyl-2,6-dioxo-piperidin-3-yl)-phenyl]-amide

Example 222

5'-(Cyclohexanecarbonyl-amino)-2'-methyl-biphenyl-4-carboxylic acid (4-dimethylaminomethyl-phenyl)-amide

Example 223

5'-(Cyclopropanecarbonyl-amino)-2'-methyl-biphenyl-4-carboxylic acid (4-dimethylaminomethyl-phenyl)-amide

Example 224

5'-(Cyclopropanecarbonyl-amino)-2'-methyl-biphenyl-4-carboxylic acid (2-piperidin-1-ylmethyl-phenyl)-amide

Example 225

5'-(Cyclopropanecarbonyl-amino)-2'-methyl-biphenyl-4-carboxylic acid (3-dimethylaminomethyl-phenyl)-amide

Example 226

5'-(Cyclohexanecarbonyl-amino)-2'-methyl-biphenyl-4-carboxylic acid (4-morpholin-4-ylmethyl-phenyl)-amide

Example 227

5'-(Cyclohexanecarbonyl-amino)-2'-methyl-biphenyl-4-carboxylic acid (4-pyrrolidin-1-ylmethyl-phenyl)-amide

Example 228

5'-(Cyclopropanecarbonyl-amino)-2'-methyl-biphenyl-4-carboxylic acid (4-piperidin-1-ylmethyl-phenyl)-amide

Example 229

5'-(Cyclopropanecarbonyl-amino)-2'-methyl-biphenyl-4-carboxylic acid (4-piperidin-1-ylmethyl-phenyl)-amide

Example 230

5'-(Cyclopropanecarbonyl-amino)-2'-methyl-biphenyl-4-carboxylic acid (4-pyrrolidin-1-ylmethyl-phenyl)-amide

Example 231

5'-(Cyclohexanecarbonyl-amino)-2'-methyl-biphenyl-4-carboxylic acid (4-isoxazol-5-yl-phenyl)-amide

Example 232

5'-(Cyclohexanecarbonyl-amino)-2'-methyl-biphenyl-4-carboxylic acid (4-hydroxymethyl-phenyl)-amide

Example 233

Furan-2-carboxylic acid [4'-(1H-indol-6-ylcarbamoyl)-6-methyl-biphenyl-3-yl]-amide

Example 234

(R)-Piperidine-2-carboxylic acid (4'-{4-[4-(propane-1-sulfonyl)-piperazin-1-ylmethyl]-phenylcarbamoyl}-6-trifluoromethoxy-biphenyl-3-yl)-amide A cold (−10) stirred solution of (R)-N-Boc-2-piperidinecarboxylic acid (39.7 mg) in dry THF (4 ml) and N,N-Diisopropylethylamine (60.4 ul) was treated dropwise with isobutylchloroformate (22.5 ul) for 10 minutes. 5'-Amino-2'-trifluoromethoxy-biphenyl-4-carboxylic acid {4-[4-(propane-1-sulfonyl)-piperazin-1-ylmethyl]-phenyl}-amide (50 mg) in dry THF (1 ml) was then added and the reaction mixture allowed to warm to room temperature, stirring under nitrogen for 16 hours.

The mixture was then evaporated and the residue purified on silica gel. Gradient elution with 0%-20% 20DCM:8EtOH:1NH3 in DCM over 35 mins gave a tan solid (45 mg).

LCMS-ES+=788

The above material (45 mg) was dissolved in DCM (2 ml) and was then treated with trifluoroacetic acid (2 ml) and the mixture stirred for 2 hours. The mixture was evaporated and the residue partitioned between EtOAc and saturated potassium carbonate. The dried extracts were then evaporated and the residue purified on silica gel. Gradient elution with 0%-35% 20DCM:8EtOH:1NH3 in DCM over 30 mins. Gave the title compound as an off-white solid (35 mg).

LCMS-ES+=688

$^1$H NMR (DMSO, δ) 0.97-1.03 (t, 3H) 1.38-1.48 (m, 4H) 1.66-1.78 (m, 4H) 2.45 (m, 4H) 2.52-2.63 (m, 1H) 2.99-3.01 (m, 2H) 3.18 (m, 4H) 3.26 (m, 2H) 3.51 (m, 2H) 7.29-7.32 (d, 2H) 7.45-7.49 (d, 1H) 7.60-7.64 (d, 2H) 7.76-7.87 (m, 3H) 7.93-7.94 (m, 1H) 8.05-8.08 (d, 2H) 9.95 (s, 1H) 10.35 (s, 1H)

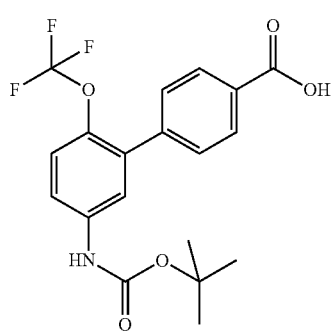
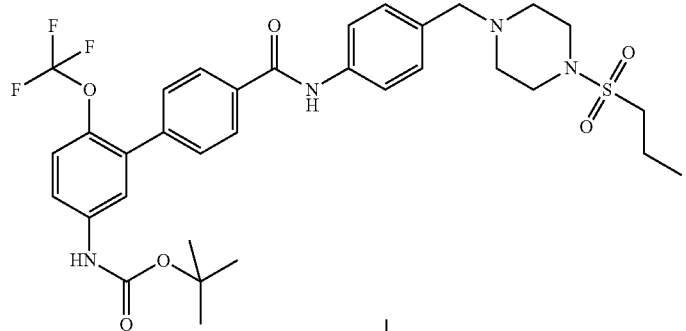
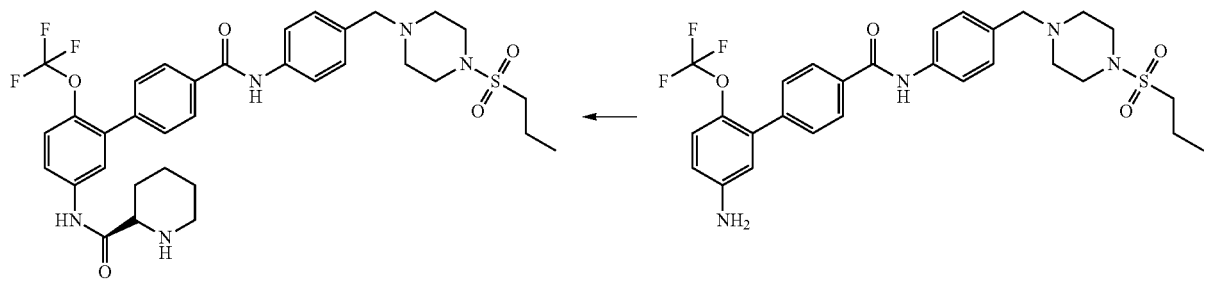

(4'-{4-[4-(propane-1-sulfonyl)-piperazin-1-ylmethyl]-phenylcarbamoyl}-6-trifluoromethoxy-biphenyl-3-yl)-carbamic acid tert-butyl ester.

A mixture of 5'-tert-butoxycarbonylamino-2'-trifluoromethoxy-biphenyl-4-carboxylic acid (300 mg), 4-[4-(propane-1-sulfonyl)-piperazin-1-ylmethyl]-phenylamine (224 mg), EDAC (144 mg), HOBT (102 mg) and N-Methylmorpholine (166 ul) in dry DMF (3 ml) was stirred for 16 hrs.

This mixture was the diluted with water (12 ml) and the tan solid produced collected and dried (459 mg).

LCMS-ES+=677

5'-Amino-2'-trifluoromethoxy-biphenyl-4-carboxylic acid {4-[4-(propane-1-sulfonyl)-piperazin-1-ylmethyl]-phenyl}-amide (4'-{4-[4-(propane-1-sulfonyl)-piperazin-1-ylmethyl]-phenylcarbamoyl}-6-trifluoromethoxy-biphenyl-3-yl)-carbamic acid tert-butyl ester (459 mg) in DCM (4 ml) and Trifluoroacetic Acid (4 ml) was stirred for 2 hrs. The mixture was evaporated and the residue partitioned between EtOAc and saturated potassium carbonate. The dried extracts were then evaporated giving the title compound as a tan foam (374 mg).

LCMS-ES+=577

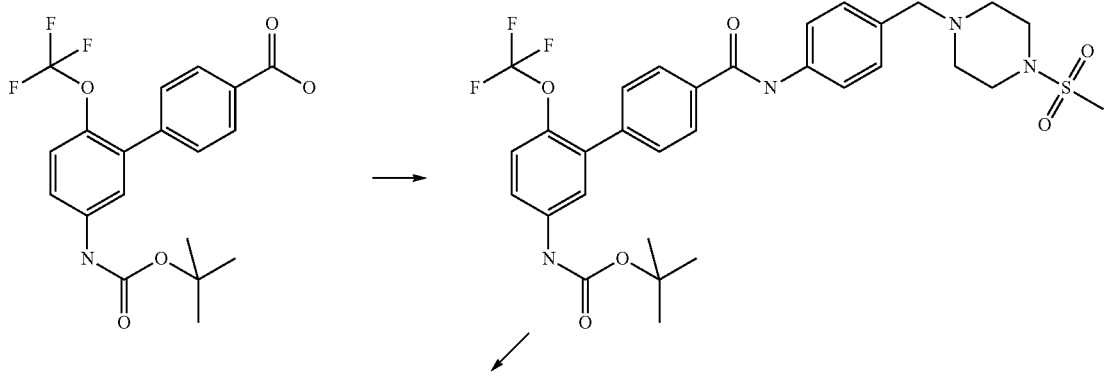

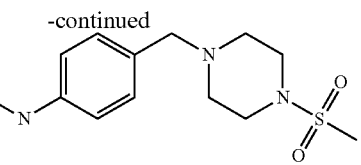
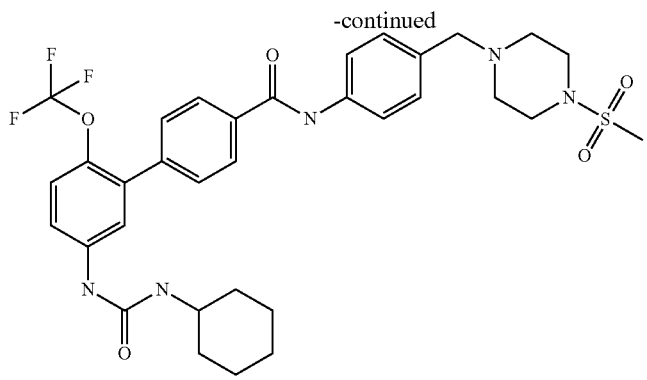

{4'-[4-(4-Methanesulfonyl-piperazin-1-ylmethyl)-phenylcarbamoyl]-6-trifluoromethoxy-biphenyl-3-yl}-carbamic acid tert-butyl ester A mixture of 5'-tert-butoxycarbonylamino-2'-trifluoromethoxy-biphenyl-4-carboxylic acid (50 mg), 4-(4-methanesulfonyl-piperazin-1-ylmethyl)-phenylamine (35.2 mg), HBTU (49.6 mg) and N-Methylmorpholine (30 ul) in dry DMF (3 ml) was stirred for 16 hrs.

The reaction mixture was then diluted with water (6 ml) and the resulting solid collected by filtration and dried to giving a tan solid (80 mg).
LCMS-ES+=649

Example 235

5'-(3-Cyclohexyl-ureido)-2'-trifluoromethoxy-biphenyl-4-carboxylic acid [4-(4-methanesulfonyl-piperazin-1-ylmethyl)-phenyl]-amide {4'-[4-(4-Methanesulfonyl-piperazin-1-ylmethyl)-phenylcarbamoyl]-6-trifluoromethoxy-biphenyl-3-yl}-carbamic acid tert-butyl ester (80 mg) in DCM (3 ml) and trifluoroacetic acid (3 ml) was stirred for 2 hrs. The reaction mixture was then evaporated giving a brown oil which was used without further purification in the next step.
LCMS-ES+=549

The crude amine (95 mg), cyclohexylisocyanate (62 mg) and N-Methylmorpholine (60 ul) in dry DMF (3 ml) was stirred at room temperature for 48 hours. The reaction mixture was then diluted with water (6 ml) and the solid formed collected by filtration. This material was then purified on silica gel. Gradient elution with 0%-30% 20DCM:8EtOH:1NH3 in DCM over 35 mins gave the title compound as an off-white solid (26 mg).
LCMS-ES+=674
$^1$H NMR (DMSO, δ) 1.16-1.34 (m, 6H) 1.55-1.83 (m, 5H) 2.47-2.51 (m, 4H) 2.89 (s, 3H) 3.13 (m, 4H) 3.51 (m, 2H) 6.21-6.24 (d, 1H) 7.29-7.75 (m, 4H) 7.59-7.66 (m, 3H) 7.76-7.79 (m, 2H) 8.03-8.66 (d, 2H) 8.66 (s, 1H) 10.37 (s, 1H)

Example 236

(S)-Pyrrolidine-2-carboxylic acid (4'-{4-[4-(propane-1-sulfonyl)-piperazin-1-ylmethyl]-phenylcarbamoyl}-6-trifluoromethoxy-biphenyl-3-yl)-amide A cold (−10) stirred solution of (S)-N-Boc-2-pyrrolidinecarboxylic acid (30 mg) in dry THF (4 ml) and N,N-diisopropylethylamine (36 µl) was treated dropwise with isobutylchloroformate (18 µl) for 10 minutes. 5'-Amino-2'-trifluoromethoxy-biphenyl-4-carboxylic acid {4-[4-(propane-1-sulfonyl)-piperazin-1-ylmethyl]-phenyl}-amide (40 mg) in dry THF (1 ml) was then added and the reaction mixture allowed to warm to room temperature, stirring under nitrogen for 16 hours.

The mixture was then evaporated and the residue partitioned between EtOAc and 0.5M HCl. The dried extracts were evaporated and the residue used without further purification.
LCMS-ES+=774

The above material was dissolved in DCM (2 ml) and treated with trifluoroacetic acid (2 ml) for 2 h. The mixture was evaporated and the residue partitioned between satd. potassium carbonate solution and EtOAc. The dried extracts were evaporated giving the title compound as a tan solid (47 mg)
$^1$H NMR (DMSO, δ) 0.87-0.93 (t, 3H) 1.56-1.63 (m, 4H) 1.65-1.68 (m, 1H) 2.36 (m, 4H) 2.84-2.96 (m, 4H) 3.09 (m, 4H) 3.41 (m, 2H) 3.69-3.73 (m, 1H) 7.19-7.22 (d, 2H) 7.37-7.40 (d, 1H) 7.52-7.55 (d, 2H) 7.66-7.74 (d, 2H) 7.76-7.78 (d, 1H) 7.83-7.84 (m, 1H) 7.96-7.99 (d, 2H) 10.25-10.27 (m, 2H)
LCMS-ES+=674

Example 237

5'-(Cyclopropanecarbonyl-amino)-2'-trifluoromethoxy-biphenyl-4-carboxylic acid {4-[4-(propane-1-sulfonyl)-piperazin-1-ylmethyl]-phenyl}-amide A stirred solution of 5'-amino-2'-trifluoromethoxy-biphenyl-4-carboxylic acid {4-[4-(propane-1-sulfonyl)-piperazin-1-ylmethyl]-phenyl}-amide (50 mg) in dry THF (1 ml) was treated with N,N-diisopropylethylamine (60 µl) followed by cyclopropane carbonyl chloride (18 mg). After 16 h the mixture was evaporated and the residue purified by chromatography. Gradient elution with 0%-30% 20DCM:8EtOH:1NH3 in DCM over 35 mins gave the title compound as an off-white solid (18 mg).
$^1$H NMR (DMSO, δ) 0.65-0.70 (d, 4H) 0.82-0.88 (t, 3H) 1.51-1.67 (m, 3H) 2.30 (m, 4H) 2.84-2.90 (m, 2H) 3.03 (m, 4H) 3.35 (m, 2H) 7.14-7.17 (d, 2H) 7.30-7.34 (m, 1H) 7.45-7.48 (d, 2H) 7.55-7.63 (m, 3H) 7.70-7.71 (m, 1H) 7.89-7.92 (d, 2H) 10.19 (s, 1H) 10.36 (s, 1H)
LCMS-ES+=645.

Example 238

(S)-Piperidine-2-carboxylic acid (4'-{4-[4-propane-1-sulfonyl)-piperazin-1-ylmethyl]-phenylcarbamoyl}-6-trifluoromethoxy-biphenyl-3-yl)-amide A cold (−10) stirred solution of (S)-N-Boc-2-piperidinecarboxylic acid (39.7 mg) in dry THF (4 ml) and N,N- diisopropylethylamine (60.4 µl) was treated dropwise with isobutylchloroformate (22.5 µl) for 10 minutes. 5'-Amino-2'-trifluoromethoxy-biphenyl-4-carboxylic acid {4-[4-(propane-1-sulfonyl)-piperazin-1-ylmethyl]-phenyl}-amide (50 mg) in dry THF (1 ml) was then added and the reaction mixture allowed to warm to room temperature, stirring under nitrogen for 16 hours.

The mixture was then evaporated and the residue purified on silica gel. Gradient elution with 0%-20% 20DCM:8EtOH:1NH3 in DCM over 35 mins gave a tan solid (83 mg).

LCMS-ES+=788

The above material (78 mg) was dissolved in DCM (2 ml) and was then treated with trifluoroacetic acid (2 ml) and the mixture stirred for 2 hours. The mixture was evaporated and the residue partitioned between EtOAc and saturated potassium carbonate. The dried extracts were then evaporated and the residue purified on silica gel. Gradient elution with 0%-35% 20DCM:8EtOH:1NH3 in DCM over 30 mins gave the title compound as a tan solid (69 mg).

$^1$H NMR (DMSO, δ) 1.01-1.07 (t, 3H) 1.49-1.60 (m, 4H) 1.70-1.96 (m, 4H) 2.49 (m, 4H) 2.73 (m, 1H) 3.04-3.07 (m, 2H) 3.13 (m, 4H) 3.55 (m, 2H) 7.33-7.37 (d, 2H) 7.52-7.56 (d, 1H) 7.65-7.68 (d, 2H) 7.80-7.95 (m, 4H) 8.09-8.13 (d, 2H) 10.15 (s, 1H) 10.40 (s, 1H)

LCMS-ES+=688

Example 239

4-Methyl-piperazine-1-carboxylic acid {4'-[4-(4-methanesulfonyl-piperazin-1-ylmethyl)-phenylcarbamoyl]-6-trifluoromethoxy-biphenyl-3-yl}-amide The product of the initial deprotection step described in Example 235 (50 mg) in DCM (4 ml) was treated with triphosgene (15 mg) and N-methyl morpholine (20 µl). The mixture was then heated to 5° C. for 30 mins. After cooling to room temperature N-methylpiperazine (11 µl) was added and stirring continued for 16 h. The mixture was then evaporated and the residue purified on silica gel. Gradient elution with 0%-35% 20DCM:8EtOH:1NH3 in DCM over 30 mins gave the title compound as an off-white solid (4 mg).

$^1$H NMR (DMSO, δ) 2.00 (s, 3H) 2.12 (m, 4H) 2.30 (m, 4H) 2.67 (s, 3H) 2.91 (m, 4H) 3.26 (m, 4H) 3.30 (m, 2H) 7.08-7.11 (d, 2H) 7.11-7.21 (d, 1H) 7.38-7.58 (m, 6H) 7.83-7.86 (d, 2H) 8.93 (s, 1H) 10.15 (s, 1H)

LCMS-ES+=676

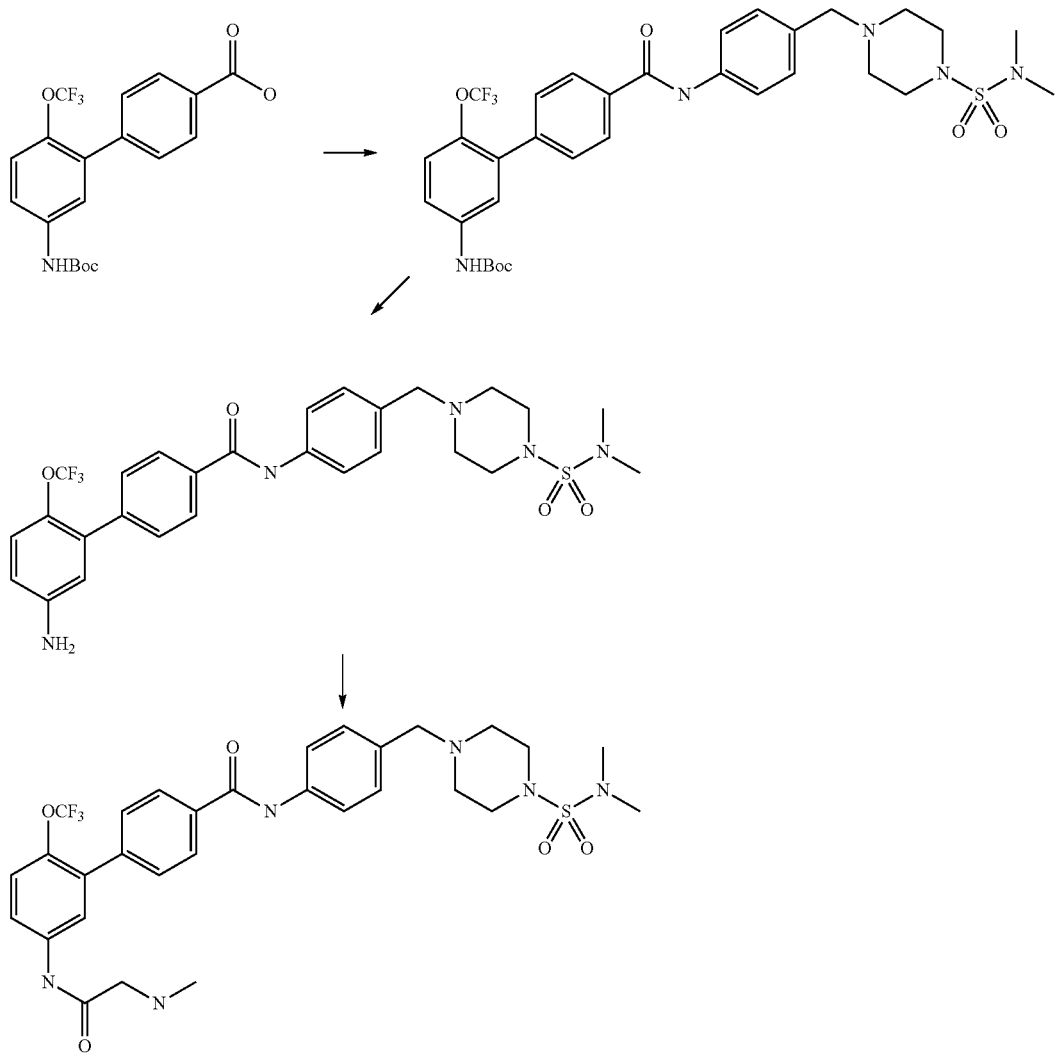

{4'-[4-(4-Dimethylsulfamoyl-piperazin-1-ylmethyl)-phenylcarbamoyl]-6-trifluoromethoxy-biphenyl-3-yl}-carboxylic acid tert-butyl ester A mixture of 5'-tert-butoxycarbonylamino-2'-trifluoromethoxy-biphenyl-4-carboxylic acid (300 mg), 4-(4-amino-benzyl)-piperazine-1-sulfonic acid dimethylamide (226 mg), EDAC (144 mg) and HOBT (103 mg) in dry DMF (3 ml) containing N-methyl morpholine (0.166 ml) was stirred for 16 h. The mixture was then added to water (12 ml) and the resulting solid collected by filtration and dried and used in the following step without purification (558 mg)
LCMS-ES+=678.

5'-Amino-2'-trifluoromethoxy-biphenyl-4-carboxylic acid [4-(4-dimethylsulfamoyl-piperazin-1-ylmethyl)-phenyl]-amide {4'-[4-(4-Dimethylsulfamoyl-piperazin-1-ylmethyl)-phenylcarbamoyl]-6-trifluoromethoxy-biphenyl-3-yl}-carboxylic acid tert-butyl ester (555 mg) was dissolved in DCM (4 ml) and was then treated with trifluoroacetic acid (4 ml) and the mixture stirred for 2 hours. The mixture was then evaporated and the residue purified by chromatography. Gradient elution with 0%-40% 20DCM:8EtOH:1NH3 in DCM over 40 mins gave an off-white solid (327 mg).
LCMS-ES+=578.

Example 240

5'-(2-Methylamino-acetylamino)-2'-trifluoromethoxy-biphenyl-4-carboxylic acid [4-(4-dimethylsulfamoyl-piperazin-1-ylmethyl)-phenyl]-amide A mixture of (tert-butoxycarbonyl-methyl-amino)-acetic acid (33 mg), 5'-amino-2'-trifluoromethoxy-biphenyl-4-carboxylic acid [4-(4-dimethylsulfamoyl-piperazin-1-ylmethyl)-phenyl]-amide (50 mg) and EEDQ (43 mg) in dry THF (1 ml) was stirred at room temp for 48 h. The mixture was then evaporated and the residue purified by chromatography. Gradient elution with 0%-30% 20DCM:8EtOH:1NH3 in DCM over 30 mins gave an off-white solid (63 mg).

This material was dissolved in DCM (2 ml) and was then treated with trifluoroacetic acid (2 ml) and the mixture stirred for 2 hours. The mixture was evaporated and the residue partitioned between satd. potassium carbonate solution and EtOAc. The dried extracts were evaporated giving the title compound as a tan solid (49 mg).

$^1$H NMR (DMSO, δ) 2.18 (s, 3H) 2.24-2.34 (m, 4H) 2.41-2.42 (s, 6H) 3.06-3.08 (m, 4H) 3.20 (m, 2H) 3.40 (m, 2H) 3.50 (t, 1H) 7.19-7.22 (d, 2H) 7.39-7.51 (d, 1H) 7.54-7.66 (d, 2H) 7.69-7.81 (m, 4H) 7.95-7.99 (d, 2H) 10.26 (s, 1H)
LCMS-ES+=649.

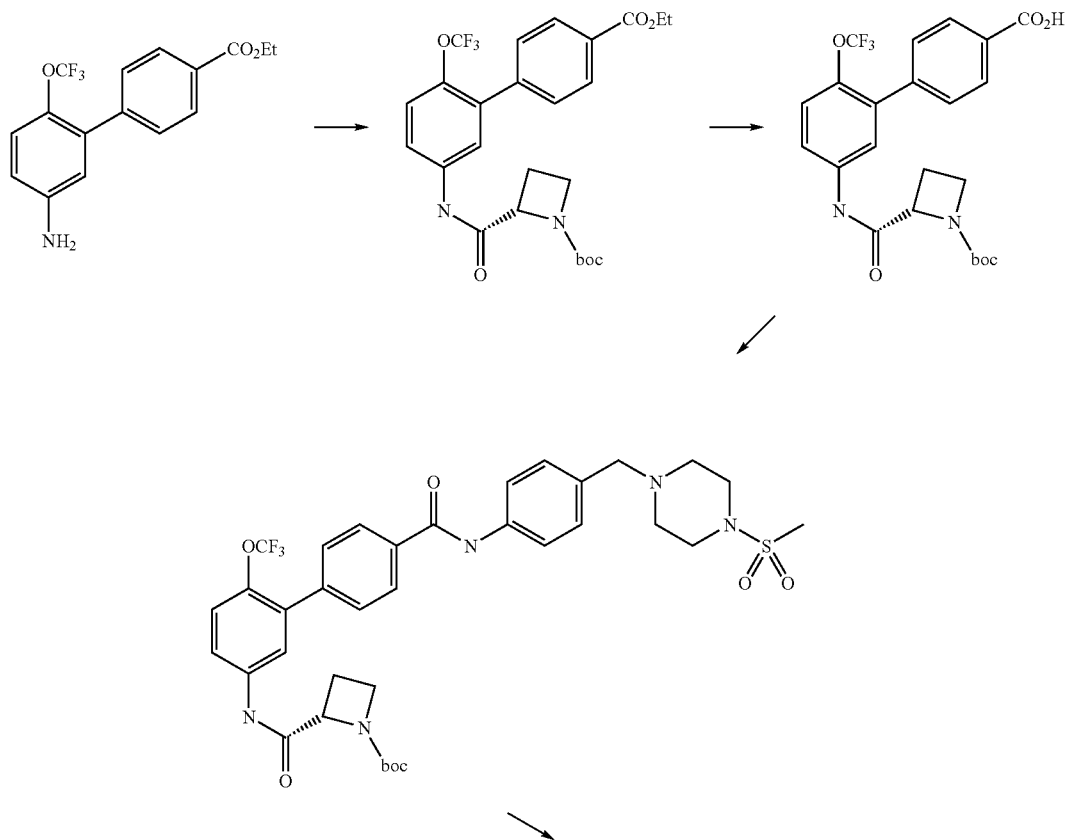

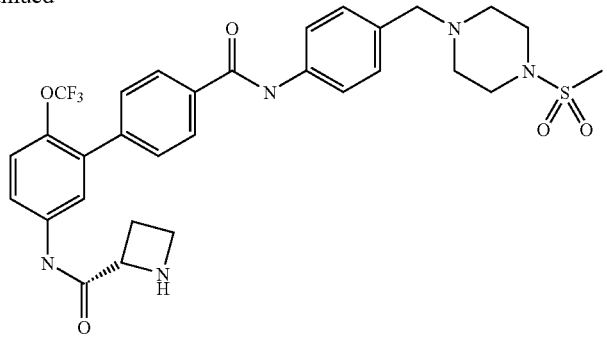

(S)-2-(4'-Ethoxycarbonyl-6-trifluoromethoxy-biphenyl-3-ylcarbamoyl)-azetidine-1-carboxylic acid tert-butyl ester A mixture of 5'-amino-2'-trifluoromethoxy-biphenyl-4-carboxylic acid (150 mg), (S)-azetidine-1,2-dicarboxylic acid 1-tert-butyl ester (93 mg), HBTU (262 mg) and N-methyl morpholine (0.14 ml) in dry DMF (3 ml) was stirred at room temp for 18 h. The mixture was then partitioned between water and DCM. The dried organic layer was evaporated and the residue purified on silica gel. Elution with ethyl acetate:petrol 1:1 gave a pale orange oil (185 mg).

(S)-2-(4'-Carboxy-6-trifluoromethoxy-biphenyl-3-ylcarbamoyl)-azetidine-1-carboxylic acid tert-butyl ester A mixture of (S)-2-(4'-Ethoxycarbonyl-6-trifluoromethoxy-biphenyl-3-ylcarbamoyl)-azetidine-1-carboxylic acid tert-butyl ester (188 mg) in ethanol (15 ml) and sodium hydroxide (2M, 5 ml) was stirred at room temp for 18 h. The mixture was acidified and the ethanol evaporated. The residue was extracted with DCM and the dried extracts evaporated giving the crude acid as a pale orange gum (154 mg).

(S)-2-{4'-[4-(4-Methanesulfonyl-piperazin-1-ylmethyl)-phenylcarbamoyl]-6-trifluoromethoxy-biphenyl-3-ylcarbamoyl}-azetidine-1-carboxylic acid tert-butyl ester A mixture of (S)-2-(4'-Carboxy-6-trifluoromethoxy-biphenyl-3-ylcarbamoyl)-azetidine-1-carboxylic acid tert-butyl ester (50 mg), 4-(4-methanesulfonyl-piperazin-1-ylmethyl)-phenylamine (29 mg), HBTU (61 mg) and N-methyl morpholine (0.033 ml) in dry DMF (3 ml) was stirred at room temp for 18 h. Water (10 ml) was then added and the cream solid collected by filtration and used without purification or characterisation.

Example 241

(S)-2-{4'-[4-(4-Methanesulfonyl-piperazin-1-ylmethyl)-phenylcarbamoyl]-6-trifluoromethoxy-biphenyl-3-ylcarbamoyl}-azetidine-1-carboxylic acid A mixture of (S)-2-{4'-[4-(4-Methanesulfonyl-piperazin-1-ylmethyl)-phenylcarbamoyl]-6-trifluoromethoxy-biphenyl-3-ylcarbamoyl}-azetidine-1-carboxylic acid tert-butyl ester in dioxan (5 ml) was treated with conc. hydrochloric acid (3 ml) and the mixture stirred at room temp for 18 h. The mixture was then carefully basified with solid potassium carbonate and the mixture then was extracted with DCM. The residue was then purified on silica gel. Elution initially with DCM:EtOH:ammonia; 200:8:1 gave a colourless foam (impure). Further purification eluting with DCM:MeOH:AcOH:water; 90:10:1:1 gave a colourless gum (nmr suggests probably acetate salt of desired product). This material was then dissolved in DCM:EtOH:ammonia;25:8:1 and then passed down an SCX cartridge giving the title compound as a colourless solid (14 mg). This material is still not entirely pure as shown by $^1$H NMR. No further purification of this material was carried out.

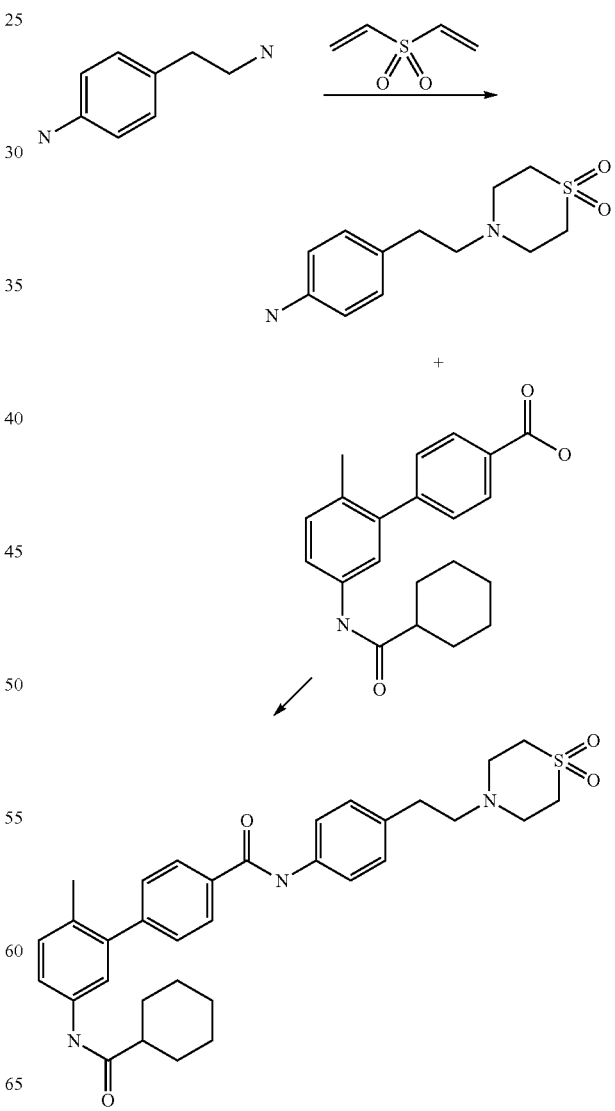

4-[2-(1,1-dioxo-1lambda*6*-thiomorpholin-4-yl)-ethyl]-phenylamine

A mixture of 4-(2-amino-ethyl)-phenylamine (1 g) and ethenesulfonyl-ethene (0.74 ml) in NMP (2.5 ml) containing triethylamine (1.02 ml) was heated to 110 C for 30 mins. The mixture was then allowed to cool and the solid produced was collected by filtration, washed with ether, and dried, giving the title compound as a pale yellow solid (1.59 g).

Example 242

5'-(Cyclohexanecarbonyl-amino)-2'-methyl-biphenyl-4-carboxylic acid {4-[2-(1,1-dioxo-1lambda*6*-thiomorpholin-4-yl)-ethyl]-phenyl}-amide A mixture of 5'-(Cyclohexanecarbonyl-amino)-2'-methyl-biphenyl-4-carboxylic acid (40 mg), 4-[2-(1,1-dioxo-1lambda*6*-thiomorpholin-4-yl)-ethyl]-phenylamine (30 mg), EDAC (23 mg), HOBT (16 mg) and N-Methylmorpholine (26 µl) in dry DMF (1 ml) was stirred for 16 hrs. This mixture was then diluted with water (8 ml) and the tan solid produced collected and dried (45 mg).

$^1$H NMR (DMSO, δ) 1.18-1.43 (m, 6H) 1.68-1.82 (m, 6H) 2.20 (s, 3H) 2.32 (m, 1H) 2.73 (m, 2H) 2.98-3.09 (m, 4H) 3.09-3.11 (m, 4H) 3.59-3.64 (m, 2H) 7.22-7.26 (d, 3H) 7.47-7.58 (m, 4H) 7.70-7.73 (d, 2H) 8.01-8.04 (d, 2H) 9.82 (s, 1H) 10.25 (s, 1H).
LCMS-ES+=574.

Example 243

5'-Cyclopropanecarbonyl-amino)-2'-methyl-biphenyl-4-carboxylic acid [4-(4-propane-1-sulfonyl-piperazin-1-ylmethyl)-phenyl]-amide A mixture of 5'-(Cyclopropanecarbonyl-amino)-2'-methyl-biphenyl-4-carboxylic acid (50 mg), 4-(4-propane-1-sulfonyl-piperazin-1-ylmethyl)-phenylamine (50 mg), HBTU (64 mg) and N-methyl morpholine (0.04 ml) in dry DMF (3 ml) was stirred at room temp for 18 h. Water (6 ml) was added and the resulting solid collected by filtration. This material was then purified on silica gel. Gradient elution with 0%-30% 20DCM:8EtOH:1NH3 in DCM over 30 mins gave the title compound as an yellow solid (43 mg).

$^1$H NMR (DMSO, δ) 0.63-0.66 (d, 4H) 0.81-0.87 (t, 3H) 1.50-1.65 (m, 4H) 2.06 (s, 3H) 2.29-2.63 (m, 4H) 3.02 (m, 4H) 3.35 (m, 2H) 7.12-7.17 (d, 2H) 7.33-7.38 (m, 3H) 7.41 (s, 1H) 7.61-7.64 (d, 2H) 7.86-7.89 (d, 2H) 10.08 (s, 1H) 10.18 (s, 1H)
LCMS-ES+=575.

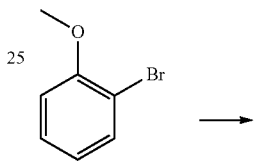

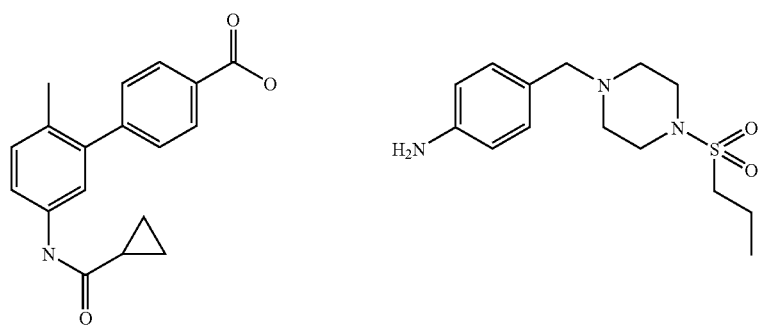

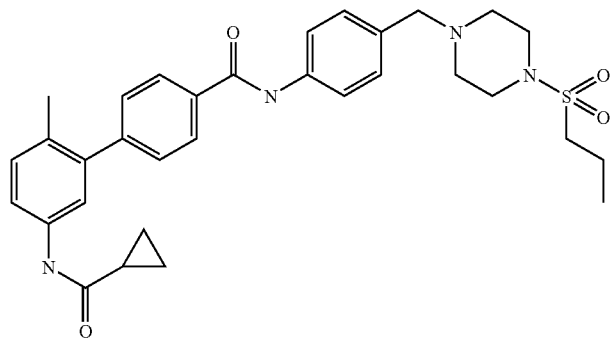

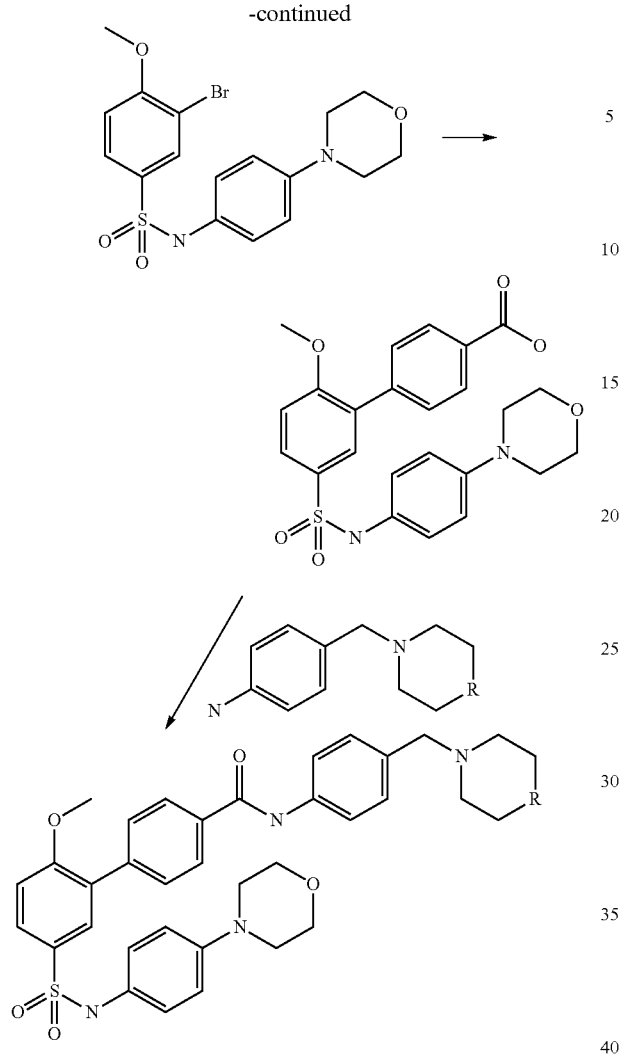

3-Bromo-4-methoxy-N-(4-morpholin-4-yl-phenyl)-benzenesulfonamide

To stirred, cold (0 C) chlorosulfonic acid was added 1-bromo-2-methoxy-benzene (1 g) dropwise. The mixture was then allowed to warm to room temp and was stirred for 1 h. The mixture was then cooled again (0 C) and ice was added carefully until no further effervescence was seen. This was further diluted with water and extracted with DCM. The dried extracts were evaporated giving a pale yellow gum. This material was then dissolved in DCM (15 ml) and was treated with 4-morpholin-4-yl-phenylamine (1.43 g) and was stirred for 18 h. The mixture was then evaporated and the residue purified by chromatography. Gradient elution with DCM then DCM:EtOH:NH3; 800:8:1 and finally 400:8:1 gave an off-white solid (1.4 g).

$^1$H NMR (DMSO, δ) 3.06 (t, 4H), 3.75 (t, 4H), 3.95 (s, 3H), 6.88 (d, 2H), 6.98 (d, 2H), 7.28 (d, 1H), 7.69 (dd, 1H), 7.88 (d, 1H), 9.84 (br. s, 1H).

2'-Methoxy-5'-(4-morpholin-4-yl-phenylsulfamoyl)-biphenyl-4-carboxylic acid

A mixture of 3-bromo-4-methoxy-N-(4-morpholin-4-yl-phenyl)-benzenesulfonamide (460 mg) and 4-carboxy-phenyl boronic acid (196 mg) in saturated sodium bicarbonate solution (4 ml) and DME (8 ml) was heated to reflux in the presence of tetrakis(triphenylphosphine)palladium$^0$ for 16 h. The mixture was allowed to cool and was evaporated. The residue was then suspended in water and 2M HCl added until the effervescence ceased. The resulting light grey solid was collected and dried (490 mg)

$^1$H NMR (DMSO, δ) 2.93 (t, 4H), 3.61 (t, 4H), 3.75 (s, 3H), 6.75 (d, 2H), 6.87 (d, 2H), 7.17 (d, 1H), 7.40 (d, 2H), 7.52 (d, 2H), 7.60 (dd, 1H), 7.90 (d, 1H), 9.62 (br. s, 1H).

Example 244

2'-Methoxy-5'-(4-morpholin-4-yl-phenylsulfamoyl)-biphenyl-4-carboxylic acid [4-(1,1-dioxo-1lambda*6*-thiomorpholin-4-ylmethyl)-phenyl]-aide 2'-Methoxy-5'-(4-morpholin-4-yl-phenylsulfamoyl)-biphenyl-4-carboxylic acid (80 mg), 4-(1,1-dioxo-1lambda*6*-thiomorpholin-4-ylmethyl)-phenylamine (41 mg), EDAC (65 mg) and HOBT (46 mg) were stirred in dry DMF (1 ml) containing N-methylmorpholine (56 µl) for 18 h. Water (10 ml) was then added and the solid collected by filtration. This material was purified by chromatography. Elution with DCM:EtOH:NH3; 400:8:1 gave the title compound as an off-white solid (31 mg).

$^1$H NMR (DMSO, δ) 2.89 (m, 4H), 3.03 (t, 4H), 3.12 (m, 4H), 3.66 (s, 2H), 3.71 (t, 4H), 3.85 (s, 3H), 6.85 (d, 2H), 6.98 (d, 2H), 7.31 (m, 3H), 7.54 (m, 3H), 7.71 (dd, 1H), 7.78 (d, 2H), 8.00 (d, 2H), 9.72 (br. s, 1H), 10.33 (br. s, 1H)
LCMS-ES+=692.

Example 245

2'-Methoxy-5'-(4-morpholin-4-yl-phenylsulfamoyl)-biphenyl-4-carboxylic acid [4-(4-methanesulfonyl-piperazin-1-ylmethyl)-phenyl]-amide This compound was prepared as described for Example 244 except that 4-(4-methanesulfonyl-piperazin-1-ylmethyl)-phenylamine (46 mg) was used. The title compound was an off-white solid (35 mg)

$^1$H NMR (DMSO, δ) 2.47 (m, 4H), 2.89 (s, 3H), 3.03 (t, 4H), 3.13 (m, 4H), 3.51 (s, 2H), 3.71 (t, 4H), 3.85 (s, 3H), 6.86 (d, 2H), 6.98 (d, 2H), 7.30 (m, 3H), 7.55 (m, 3H), 7.69 (dd, 1H), 7.77 (d, 2H), 8.01 (d, 2H), 9.82 (br. s, 1H), 10.32 (br. s, 1H)
LCMS-ES+=721

Example 246

2'-Methoxy-5'-(4-morpholin-4-yl-phenylsulfamoyl)-biphenyl-4-carboxylic acid [4-(4-propane-2-sulfonyl-piperazin-1-ylmethyl)-phenyl]-amide This compound was prepared as described for Example 244 except that 4-(4-propane-2-sulfonyl-piperazin-1-ylmethyl)-phenylamine (51 mg) was used. The title compound was an off-white solid (34 mg)

$^1$H NMR (DMSO, δ) 1.23 (d, 6H), 2.41 (m, 4H), 3.03 (t, 4H), 3.26 (m, 4H), 3.42 (m, 1H), 3.50 (s, 2H), 3.73 (t, 4H), 3.85 (s, 3H), 6.85 (d, 2H), 6.98 (d, 2H), 7.30 (m, 3H), 7.55 (m, 3H), 7.71 (dd, 1H), 7.77 (d, 2H), 8.00 (d, 2H), 9.72 (br. s, 1H), 10.32 (br. s, 1H)
LCMS-ES+=749

Example 247

2'-Methoxy-5'-(4-morpholin-4-yl-phenylsulfamoyl)-biphenyl-4-carboxylic acid [4-(4-dimethylsulfamoyl-piperazin-1-ylmethyl)-phenyl]-amide This compound was prepared as described for Example 244 except that 4-(4-amino-benzyl)-piperazine-1-sulfonic acid dimethylamide (51 mg) was used. The title compound was an off-white solid (49 mg)

$^1$H NMR (DMSO, δ) 2.43 (m, 4H), 2.77 (s, 6H), 3.03 (t, 4H), 3.17 (m, 4H), 3.50 (s, 2H), 3.71 (t, 4H), 3.85 (s, 3H), 6.85 (d, 2H), 6.98 (d, 2H), 7.29 (m, 3H), 7.55 (m, 3H), 7.71 (dd, 1H), 7.77 (d, 2H), 8.01 (d, 2H), 9.72 (br. s, 1H), 10.32 (br. s, 1H).
LCMS-ES+=750.

Example 248

2'-Methoxy-5'-(4-morpholin-4-yl-phenylsulfamoyl)-biphenyl-4-carboxylic acid [4-(4-propane-1-sulfonyl-piperazin-1-ylmethyl)-phenyl]-amide This compound was prepared as described for Example 244 except that 4-(4-propane-1-sulfonyl-piperazin-1-ylmethyl)-phenylamine (36 mg) was used. The title compound was a pale orange solid (20 mg)

$^1$H NMR (DMSO, δ) 1.00 (t, 3H), 1.71 (m, 2H), 2.45 (m, 4H), 3.02 (m, 6H), 3.18 (m, 4H), 3.51 (s, 2H), 3.70 (m, 4H), 3.86 (s, 3H), 6.85 (d, 2H), 6.98 (d, 2H), 7.29 (m, 3H), 7.55 (m, 3H), 7.71 (dd, 1H), 7.77 (d, 2H), 8.01 (d, 2H), 9.71 (br. s, 1H), 10.30 (br. s, 1H).
LCMS-ES+=749

Example 249

2'-Chloro-5'-(cyclohexanecarbonyl-amino)-biphenyl-4-carboxylic acid [4-(4-methyl-piperazin-1-ylmethyl)-phenyl]-amide A mixture of 2'-Chloro-5'-(cyclohexanecarbonyl-amino)-biphenyl-4-carboxylic acid (103 mg), 4-(4-methyl-piperazin-1-ylmethyl)-phenylamine (59 mg) and HBTU (148 mg) in dry DMF (10 ml) containing triethylamine (362 μl) was stirred at room temp for 18 h. Most of the DMF was evaporated and the residue diluted with water. The resulting solid was collected by filtration. This material was then purified by reverse phase Prep HPLC giving the title compound as a yellow solid (51 mg)

$^1$H NMR (DMSO, δ) 1.10-1.81 (10H, m), 2.17 (3H, s), 2.24-2.28 (9H, m), 3.43 (2H, s), 7.29 (2H, d), 7.41-7.61 (2H, m), 7.67 (1H, dd), 7.71-7.81 (2H, m), 8.05 (2H, d,), 8.83 (2H, m), 10.13 (1H, s), 10.36 (1H, s).
LCMS-ES+=544, 546.

(R)-2-(6-Chloro-4'-ethoxycarbonyl-biphenyl-3-ylcarbamoyl)-pyrrolidine-1-carboxylic acid tert-butyl ester A mixture of 5'-amino-2'-chloro-biphenyl-4-carboxylic acid ethyl ester (800 mg), (R) —N-Boc-2-pyrrolidinecarboxylic acid (608 mg) and HBTU (1.46 g) in dry DMF (30 ml) containing N-methylmorpholine (1.26 ml) was stirred at room temp for 18 h. Silica gel (5 g) was then added and the mixture evaporated. The residue was purified by chromatography. Elution with 12:1 petrol:ethyl acetate gave a viscous brown gum (987 mg)

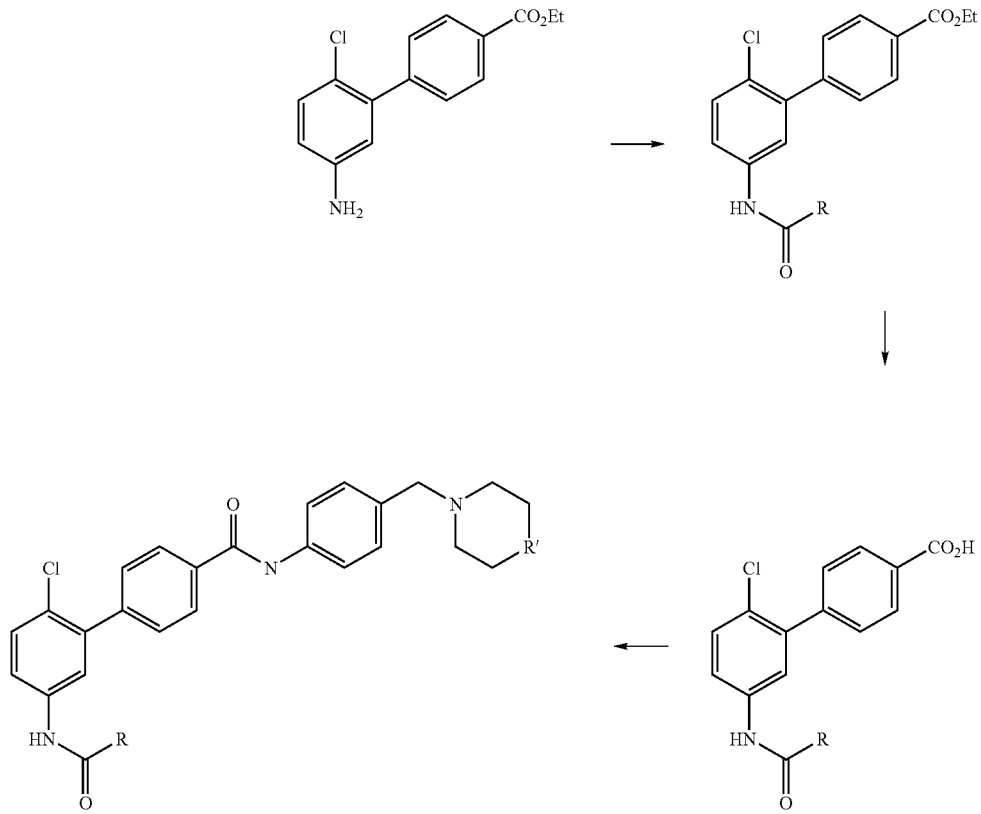

¹H NMR (DMSO, δ) 1.14-1.43 (12H, m), 1.66-1.99 (2H, m), 2.10-2.30 (1H, m), 3.32-3.57 (3H, m), 4.14-4.45 (3H, m), 7.39-7.41 (2H, m), 7.72-7.82 (2H, d), 8.02-8.11 (3H, m), 10.15 (1H, s).

(R)-2-(4'-Carboxy-6-chloro-biphenyl-3-ylcarbamoyl)-pyrrolidine-1-carboxylic acid tert-butyl ester (R)-2-(6-Chloro-4'-ethoxycarbonyl-biphenyl-3-ylcarbamoyl)-pyrrolidine-1-carboxylic acid tert-butyl ester (985 mg) in 2M NaOH (5 ml) and ethanol (7 ml) was stirred at room temp for 18 h. The ethanol was then evaporated and the residue acidified with HCl. The resulting yellow solid was collected by filtration and dried (672 mg). Material used without purification in next step.

(R)-2-{6-Chloro-4'-[4-(4-methanesulfonyl-piperazin-1-ylmethyl)-phenylcarbamoyl]-biphenyl-3-ylcarbamoyl}-pyrrolidine-1-carboxylic acid tert-butyl ester A mixture of (R)-2-(4'-Carboxy-6-chloro-biphenyl-3-ylcarbamoyl)-pyrrolidine-1-carboxylic acid tert-butyl ester (100 mg), 4-(4-methanesulfonyl-piperazin-1-ylmethyl)-phenylamine (86 mg) and HBTU (121 mg) in dry DMF (4 ml) containing N-methylmorpholine (69 µl) was stirred at room temp for 18 h.

The mixture was then evaporated and the residue purified by chromatography. Elution DCM:EtOH:NH3; 300:8:1 gave a light brown oil (118 mg).

Example 250

(R)-Pyrrolidine-2-carboxylic acid {6-chloro-4'-[4-(4-methanesulfonyl-piperazin-1-ylmethyl)-phenylcarbamoyl]-biphenyl-3-yl}-amide The above Boc-protected amine (112 mg) was stirred in THF (3 ml) and TFA (5 ml) for 18 h. The mixture was then evaporated and the residue purified by chromatography. Elution DCM:EtOH:NH3; 150:8:1 gave an off-white solid (12 mg).
¹H NMR (DMSO, δ) 1.58-1.92 (3H, m), 1.96-2.16 (1H, m), 2.47-2.52 (4H, m), 2.88 (3H, s), 3.05-3.19 (4H, m), 3.31-3.49 (2H, m), 3.51 (2H, s), 3.73 (1H, dd), 7.32 (2H, d), 7.42-7.49 (2H, m), 7.72-7.83 (4H, m), 8.01-8.12 (3H, m), 10.10 (1H, s), 10.31 (1H, s).

(R)-2-(6-Chloro-4'-ethoxycarbonyl-biphenyl-3-ylcarbamoyl)-piperidine-1-carboxylic acid tert-butyl ester A mixture of 5'-amino-2'-chloro-biphenyl-4-carboxylic acid ethyl ester (750 mg), (R)-N-Boc-2-piperidinecarboxylic acid (664 mg) and HBTU (1.37 g) in dry DMF (40 ml) containing N-methylmorpholine (1.2 ml) was stirred at room temp for 18 h. The mixture was then evaporated and the residue was purified by chromatography. Elution with 5:1 petrol:ethyl acetate gave a yellow oil (310 mg)

(R)-2-(4'-Carboxy-6-chloro-biphenyl-3-ylcarbamoyl)-piperidine-1-carboxylic acid tert-butyl ester (R)-2-(6-Chloro-4'-ethoxycarbonyl-biphenyl-3-ylcarbamoyl)-piperidine-1-carboxylic acid tert-butyl ester (306 mg) in 2M NaOH (6 ml) and ethanol (10 ml) was stirred at room temp for 18 h. The ethanol was then evaporated and the residue acidified with HCl. The resulting off-white solid was collected by filtration and dried (143 mg). Material used without purification in next step.

(R)-2-{6-Chloro-4'-[4-(4-(propane-1-sulfonyl)-piperazin-1-ylmethyl)-phenylcarbamoyl]-biphenyl-3-ylcarbamoyl}-piperidine-1-carboxylic acid tert-butyl ester A mixture of (R)-2-(4'-Carboxy-6-chloro-biphenyl-3-ylcarbamoyl)-piperidine-1-carboxylic acid tert-butyl ester (73 mg), 4-(4-(propane-1-sulfonyl)-piperazin-1-ylmethyl)-phenylamine (118 mg) and HBTU (91 mg) in dry DMF (4 ml) containing N-methylmorpholine (52 µl) was stirred at room temp for 18 h.

The mixture was then evaporated and the residue used crude in the next step (130 mg).

Example 251

(R)-Piperidine-2-carboxylic acid {6-chloro-4'-[4-(4-(propane-1-sulfonyl)-piperazin-1-ylmethyl)-phenylcarbamoyl]-biphenyl-3-yl}-amide The above Boc-protected amine (130 mg) was stirred in THF (3 ml) and TFA (5 ml) for 18 h. The mixture was then evaporated and the residue purified by chromatography.
Elution DCM:EtOH:NH3; 250:8:1 gave a brown solid (15 mg).
¹H NMR (DMSO, δ) 1.03 (3H, t), 1.22-1.88 (10H, m), 2.35-2.48 (4H, m), 2.91-3.09 (3H, m), 3.11-3.25 (4H, m), 3.50 (2H, s), 7.30 (2H, d), 7.47-7.63 (3H, m), 7.69-7.82 (3H, m), 7.82 (1H, d), 8.06 (2H, d), 9.89 (1H, brs), 10.34 (1H, s).

5'-[2-(tert-Butoxycarbonyl-methyl-amino)-acetylamino]-2'-chloro-biphenyl-4-carboxylic acid ethyl ester A mixture of 5'-amino-2'-chloro-biphenyl-4-carboxylic acid ethyl ester (750 mg), (tert-butoxycarbonyl-methyl-amino)-acetic acid (589 mg) and HBTU (1.37 g) in dry DMF (40 ml) containing N-methylmorpholine (0.79 ml) was stirred at room temp for 18 h. The mixture was then evaporated and the residue was purified by chromatography. Elution with 4:1 petrol:ethyl acetate gave a pale brown oil (494 mg)

5'-[2-(tert-Butoxycarbonyl-methyl-amino)-acetylamino]-2'-chloro-biphenyl-4-carboxylic acid 5'-[2-(tert-Butoxycarbonyl-methyl-amino)-acetylamino]-2'-chloro-biphenyl-4-carboxylic acid ethyl ester (494 mg) in 2M NaOH (10 ml) and ethanol (15 ml) was stirred at room temp for 18 h. The ethanol was then evaporated and the residue acidified with HCl. The colourless solid formed was collected by filtration and dried (420 mg).
¹H NMR (DMSO, δ) 1.25-1.47 (9H, m), 2.87 (3H, m), 3.98 (2H, m), 7.45-7.81 (5H, m), 8.05 (2H, d), 10.26 (1H, m).

({6-Chloro-4'[4-(4-methanesulfonyl-piperazin-1-ylmethyl)-phenylcarbamoyl]-biphenyl-3-ylcarbamoyl}-methyl)-methyl-carbamic acid tert-butyl ester A mixture of 5'-[2-(tert-Butoxycarbonyl-methyl-amino)-acetylamino]-2'-chloro-biphenyl-4-carboxylic acid (85 mg), 4-(4-methanesulfonyl-piperazin-1-ylmethyl)-phenylamine (81 mg) and HBTU (120 mg) in dry DMF (4 ml) containing N-methylmorpholine (65 µl) was stirred at room temp for 18 h.

The mixture was then evaporated and the residue used crude in the next step (161 mg).
LCMS-ES+=669

Example 252

2'-Chloro-5'-(2-methylamino-acetylamino)-biphenyl-4-carboxylic acid [4-(4-methanesulfonyl-piperazin-1-ylmethyl)-phenyl]-amide The above Boc-protected amine (160 mg) was stirred in THF (2 ml) and TFA (4 ml) at 45 C for 18 h. The mixture was then evaporated and the residue purified by chromatography. Gradient elution with 3%-20% 20DCM:8EtOH:1NH3 in DCM over 30 mins gave material which appeared pure by TLC but was multi-peak by HPLC. This material was then purified by reverse phase Prep HPLC giving the title compound as a yellow solid (28 mg)

$^1$H NMR (DMSO, δ) 2.36 (3H, s), 2.42-2.51 (4H, m), 2.88 (3H, s), 3.05-3.17 (4H, m), 4.14 (2H, d), 7.30 (2H, d), 7.49-7.65 (3H, m), 7.68-7.86 (4H, m), 8.05 (2H, d), 8.31 (1H, s), 10.37 (1H, s).
LCMS-ES-=569

2'-Chloro-5'-(3-cyclohexyl-ureido)-biphenyl-4-carboxylic acid ethyl ester

A mixture of 5'-amino-2'-chloro-biphenyl-4-carboxylic acid ethyl ester (350 mg) and cyclohexyl isocyanate (0.32 ml) in dry THF (15 ml) containing triethylamine (0.62 ml) was stirred at room temp for 48 h. The mixture was then evaporated and the residue partitioned between water and DCM. The dried extracts were evaporated giving the crude title compound as a white solid (616 mg, >100%, contaminated with dicyclohexyl-urea)

2'-Chloro-5'-(3-cyclohexyl-ureido)-biphenyl-4-carboxylic acid

The above ester (600 mg) in 2M NaOH (12 ml) and ethanol (20 ml) was stirred at room temp for 18 h. The ethanol was then evaporated and the residue acidified with HCl. The colourless solid formed was collected by filtration and dried (500 mg).

Example 253

2'-Chloro-5'-(3-cyclohexyl-ureido)-biphenyl-4-carboxylic acid {4-[4-(propane-1-sulfonyl)-piperazin-1-ylmethyl]-phenyl}-amide A mixture of 2'-Chloro-5'-(3-cyclohexyl-ureido)-biphenyl-4-carboxylic acid (150 mg), 4-(4-(propane-1-sulfonyl)-piperazin-1-ylmethyl)-phenylamine (236 mg) and HBTU (228 mg) in dry DMF (5 ml) containing N-methylmorpholine (0.13 ml) was stirred at room temp for 18 h. The mixture was then evaporated and the residue purified by chromatography. Gradient elution with 3%-20% 20DCM:8EtOH:1NH3 in DCM over 30 mins gave a white solid (38 mg)

$^1$H NMR (DMSO, δ) 0.91-1.89 (16H, m), 2.37-2.49 (4H, m), 2.97-3.10 (2H, m), 3.11-3.22 (4H, m), 3.50 (2H, m), 7.23-7.46 (4H, m), 7.52-7.61 (3H, m), 7.78 (2H, d), 8.04 (2H, d), 8.55 (1H, s), 10.33 (1H, s).

Example 254

2'-Chloro-5'-(3-cyclohexyl-ureido)-biphenyl-4-carboxylic acid {4-[4-(propane-2-sulfonyl)-piperazin-1-ylmethyl]-phenyl}-amide This material was prepared as described for Example 253 except that 4-(4-(propane-2-sulfonyl)-piperazin-1-ylmethyl)-phenylamine was used. The title compound was isolated as a white solid (21 mg)

$^1$H NMR (DMSO, δ) 0.91-0.96 (12H, m), 1.44-1.93 (5H, m), 2.32-2.46 (4H, m), 2.94-3.05 (1H, m), 3.19-3.29 (4H, m), 3.50 (2H, s), 7.21-7.66 (7H, m), 7.74 (2H, d), 8.05 (2H, d), 8.56 (1H, s), 10.34 (1H, s).

Example 255

2'-Chloro-5'-(3-cyclohexyl-ureido)-biphenyl-4-carboxylic acid [4-(4dimethylsulfamoyl-piperazin-1-ylmethyl]-phenyl}-amide This material was prepared as described for Example 253 except that 4-(4-amino-benzyl)-piperazine-1-sulfonic acid dimethylamide was used. The title compound was isolated as a white solid (27 mg).

$^1$H NMR (DMSO, δ) 1.06-1.43 (6H, m), 1.45-1.89 (5H, m), 2.35-2.51 (4H, m), 2.78 (6H, s), 3.08-3.25 (4H, m), 3.40-3.56 (2H, m), 6.20 (1H, d), 7.20-7.49 (4H, m), 7.51-7.64 (3H, m), 7.76 (2H, d), 8.04 (2H, d), 8.61 (1H, s), 10.34 (1H, s).

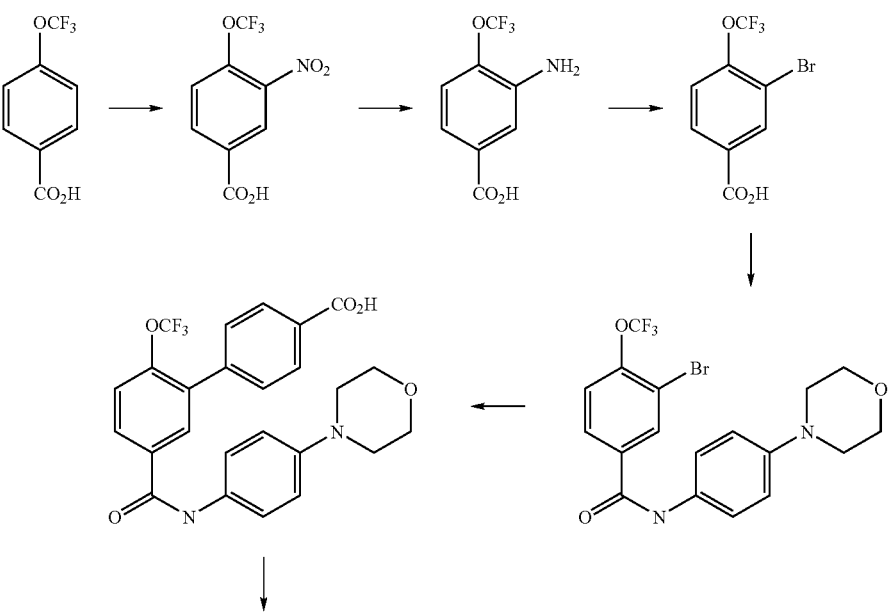

-continued

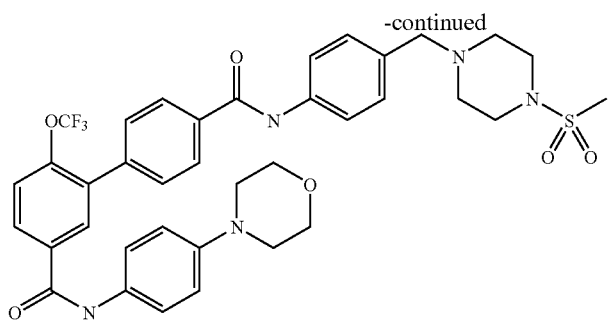

3-Nitro-4-trifluoromethoxybenzoic acid

To a stirred solution of 4-trifluoromethoxybenzoic acid (2.96 g) in concentrated sulphuric acid (19 ml) at room temperature was added a mixture of concentrated nitric acid (8.5 ml) and concentrated sulphuric acid (8.5 ml) drop-wise. After 15 min a white precipitate had formed. The reaction was slowly poured onto ice (approx. 100 ml). Once the ice had melted the resulting suspension was filtered, and the residue washed with water (3×10 ml) and then dried in vacuo to give the title compound as a white solid (3.41 g).

$^1$H NMR (DMSO, δ) 7.87 (dd, 1H), 8.36 (dd, 1H), 8.59 (d, 1H), 14.05 (br. s).
LCMS-ES-=250

3-Amino-4-trifluoromethoxybenzoic acid

A solution of 3-nitro-4-trifluoromethoxybenzoic acid (3 g) in methanol (240 ml) was hydrogenated at 50° C. and 50 bar using H-cube apparatus. The methanol solution was evaporated giving the title compound as a white solid (2.58 g).

$^1$H NMR (DMSO, δ) 5.63 (br. s, 2H), 7.13 (dd, 1H), 7.20 (dd, 1H), 7.42 (d, 1H), 12.85 (br. s).

3-Bromo-4-trifluoromethoxybenzoic acid

To a stirred solution of 3-amino-4-trifluoromethoxybenzoic acid (2 g) in a mixture of water (16 ml) and 48% HBr (12 ml) at 0° C. was added a solution of sodium nitrite (0.64 g) in water (8 ml) drop-wise. After 15 min at 0° C. the reaction mixture was diluted with water (12 ml) and carefully poured onto a stirred solution of copper (I) bromide (1.32 g) in 48% HBr (8 ml) at room temperature. The resulting suspension was filtered, and the residue washed with water (3×5 ml) and dried in vacuo to give the title compound as a beige solid (2.08 g).

$^1$H NMR (DMSO, δ) 7.87 (dd, 1H), 8.26 (dd, 1H), 8.46 (d, 1H), 13.70 (br. s, 1H).
LCMS-ES-=284.

3-Bromo-N-(4-morpholin-4-ylphenyl)-4-trifluoromethoxy-benzamide

A solution of 3-bromo-4-trifluoromethoxybenzoic acid (515 mg), N-(4-aminophenyl)morpholine (323 mg), EDAC (763 mg), HOBT (538 mg) and N-methylmorpholine (597 μl) in DMF (5 ml) was stirred at room temperature. After 1 h, water (10 ml) was added and the resulting suspension filtered. The residue was dried in vacuo and then purified by flash column chromatography, eluting with 2:1 petroleum ether: ethyl acetate. The title compound was isolated as an off-white solid (532 mg).

$^1$H NMR (DMSO, δ) 3.07 (t, 4H), 3.80 (t, 4H), 6.84 (d, 2H), 7.31 (dd, 1H), 7.42 (d, 2H), 7.68 (s, 1H), 7.76 (dd, 1H), 8.07 (s, 1H).
LCMS-ES+=446.

5'-(4-Morpholino-4-ylphenylcarbamoyl)-2'-trifluoromethoxy-biphenyl-4-carboxylic acid A mixture of 3-bromo-N-(4-morpholin-4-ylphenyl)-4-trifluoromethoxybenzamide (505 mg), 4-carboxyphenylboronic acid (207 mg) and tetrakis(triphenylphosphine)palladium (65 mg) in DME (5 ml) and a saturated aqueous solution of Na$_2$CO$_3$ (2.5 ml) was heated to reflux. After 16 h the reaction was allowed to cool to room temperature and then concentrated to dryness to yield a brown residue. The residue was taken up in water (10 ml) and treated with a 2M aqueous solution of HCl until no further effervescence occurred. The resulting suspension was filtered and the residue washed with water (3×3 ml) and dried in vacuo to give the title compound as a light brown solid (565 mg).

$^1$H NMR (DMSO, δ) 3.14 (t, 4H), 3.80 (t, 4H), 7.01 (d, 2H), 7.68 (m, 6H), 8.12 (d, 2H), 8.21 (s, 1H).
LCMS-ES+=487.

Example 256

6-Trifluoromethoxy-biphenyl-3,4'-dicarboxylic acid 4'-{[4-(4-(methanesulfonyl-piperazin-1-ylmethyl)-phenyl]-amide} 3-[(4-morpholin-4-yl-phenyl)-amide]

A mixture of 5'-(4-Morpholino-4-ylphenylcarbamoyl)-2'-trifluoromethoxy-biphenyl-4-carboxylic acid (100 mg), 4-(4-methanesulfonyl-piperazin-1-ylmethyl)-phenylamine (57 mg) EDAC (86 mg) and HOBT (61 mg) in dry DMF (1 ml) containing N-methylmorpholine (68 μl) was stirred at room temp for 18 h.

The mixture was then evaporated and the residue purified by chromatography. Elution DCM:EtOH:NH3; 200:8:1 gave a white solid (54 mg).

$^1$H NMR (DMSO, δ) 2.55 (m, 4H), 2.89 (s, 3H), 3.09 (m, 8H), 3.52 (s, 2H), 3.76 (t, 4H), 6.97 (d, 2H), 7.32 (d, 2H), 7.67 (m, 3H), 7.77 (m, 4H), 8.15 (m, 4H), 10.26 (br. s, 1H), 10.37 (br. s, 1H).

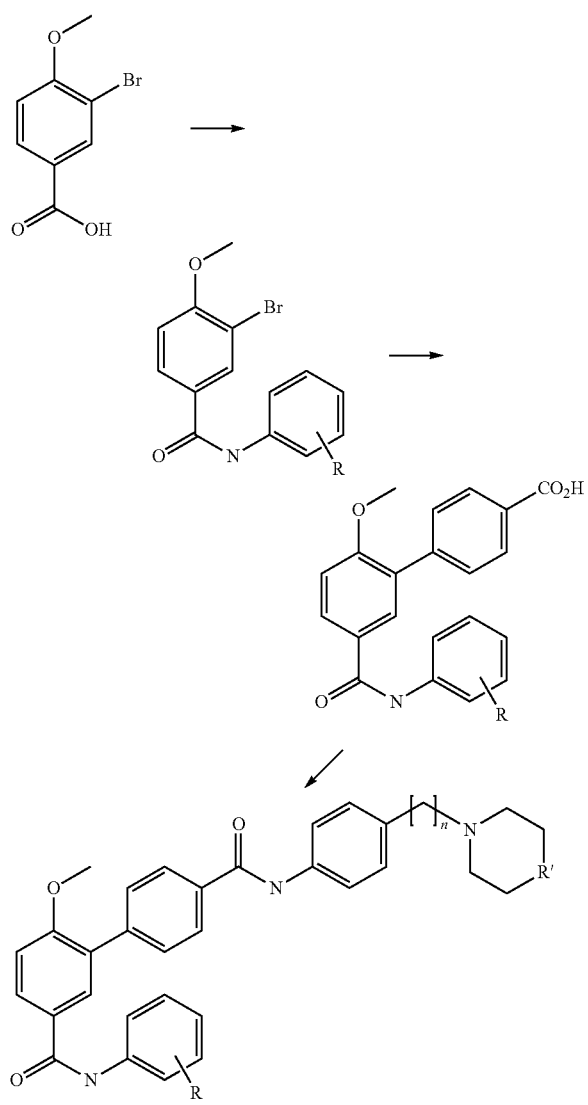

3-Bromo-4-methoxy-N-(4-morpholin-4-yl-phenyl)-benzamide

A mixture of 3-bromo-4-methoxy-benzoic acid (500 mg), N-(4-aminophenyl)morpholine (385 mg), EDAC (828 mg), HOBT (583 mg) and N-methylmorpholine (714 µl) in DMF (5 ml) was stirred at room temperature for 18 h. The mixture was then diluted with water (30 ml) and the resulting solid collected by filtration and dried (818 mg)

2'-Methoxy-5'-(4-morpholin-4-yl-phenylcarbamoyl)-biphenyl-4-carboxylic acid

A mixture of 3-Bromo-4-methoxy-N-(4-morpholin-4-yl-phenyl)-benzamide (788 mg) and 4-(ethoxycarbonyl)-phenyl boronic acid (564 mg) in 2:1 DME:water (15 ml) containing cesium carbonate (1.31 g) and tetrakis(triphenylphosphine) palladium⁰ (232 mg) was heated to reflux for 18 h.

The mixture was cooled and then evaporated. The residue was then stirred in ethanol (10 ml) and 2M NaOH (5 ml) at room temp for 16 h. The ethanol was then evaporated and the residue acidified with 2M HCl. The resulting solid was collected by filtration and dried (1.19 g)

LCMS-ES+=461.

Example 257

6-Methoxy-biphenyl-3,4'-dicarboxylic acid 3-[(4-morpholin-4-yl-phenyl)-amide] 4'-({4-[4-(propane-1-sulfonyl)-piperazin-1-ylmethyl]-phenyl}-amide)

A mixture of 2'-Methoxy-5'-(4-morpholin-4-yl-phenylcarbamoyl)-biphenyl-4-carboxylic acid (100 mg), 4-(4-(propane-1-sulfonyl)-piperazin-1-ylmethyl)-phenylamine (68 mg), EDAC (48 mg), HOBT (34 mg) and N-methylmorpholine (56 µl) in DMF (1 ml) was stirred at room temperature for 18 h. The mixture was then evaporated and the residue purified by reverse phase preparative HPLC giving the title compound as an off-white solid (42 mg).

¹H NMR (DMSO, δ) 1.00 (t, 3H), 1.71 (m, 2H), 2.46 (m, 4H), 3.01 (m, 2H), 3.06 (m, 4H), 3.18 (m, 4H), 3.51 (s, 2H), 3.75 (t, 4H), 3.89 (s, 3H), 6.95 (d, 2H), 7.30 (m, 3H), 7.64 (d, 2H), 7.73 (d, 2H), 7.79 (d, 2H), 8.04 (m, 4H), 10.02 (br. S, 1H), 10.30 (br. S, 1H).

Example 258

6-Methoxy-biphenyl-3,4'-dicarboxylic acid 3-[(4-morpholin-4-yl-phenyl)-amide] 4'-({4-[4-(propane-2-sulfonyl)-piperazin-1-ylmethyl]-phenyl}-amide)

This material was prepared as described for Example 257 except that 4-(4-(propane-2-sulfonyl)-piperazin-1-ylmethyl)-phenylamine was used. The title compound was isolated as a white solid (31 mg)

¹H NMR (DMSO, δ) 1.28 (d, 6H), 2.46 (m, 4H), 3.05 (m, 1H), 3.13 (t, 4H), 3.30 (t, 4H), 3.55 (s, 2H), 3.80 (t, 4H), 3.94 (s, 3H), 6.99 (d, 2H), 7.35 (m, 3H), 7.68 (d, 2H), 7.80 (m, 4H), 8.08 (m, 4H), 10.06 (br. s, 1H), 10.34 (br. s, 1H).

Example 259

6-Methoxy-biphenyl-3,4'-dicarboxylic acid 4'-{[4-(4-dimethylsulfamoyl-piperazin-1-ylmethyl)-phenyl]-amide} 3-[(4-morpholin-4-yl-phenyl)-amide]

This material was prepared as described for Example 257 except that 4-(4-amino-benzyl)-piperazine-1-sulfonic acid dimethylamide was used. The title compound was isolated as a white solid (28 mg)

¹H NMR (DMSO, δ) 2.44 (m, 4H), 2.77 (s, 6H), 3.08 (t, 4H), 3.18 (t, 4H), 3.50 (s, 2H), 3.75 (t, 4H), 3.89 (s, 3H), 6.95 (d, 2H), 7.30 (m, 3H), 7.63 (d, 2H), 7.75 (m, 4H), 8.04 (m, 4H), 10.01 (br. s, 1H), 10.29 (br. s, 1H).

3-Bromo-4-methoxy-N-(2-methyl-4-morpholin-4-yl-phenyl)-benzamide

A mixture of 3-bromo-4-methoxy-benzoic acid (247 mg), 2-methyl-4-morpholin-4-yl-phenylamine (205 mg), EDAC (410 mg), HOBT (289 mg) and N-methylmorpholine (353 µl) in DMF (5 ml) was stirred at room temperature for 18 h. The mixture was then diluted with water (30 ml) and the resulting solid collected by filtration and dried (464 mg)

¹H NMR (DMSO, δ) 2.22 (s, 3H), 3.07 (t, 4H), 3.79 (t, 4H), 3.90 (s, 3H), 6.72 (m, 2H), 6.89 (d, 1H), 7.19 (br. s, 1H), 7.38 (d, 1H), 7.75 (dd, 1H), 8.00 (d, 1H).

2'-Methoxy-5'-(2-methyl-4-morpholin-4-yl-phenylcarbamoyl)-biphenyl-4-carboxylic acid A mixture of 3-Bromo-4-methoxy-N-(2-methyl-4-morpholin-4-yl-phenyl)-benzamide (432 mg) and 4-(ethoxycarbonyl)-phenyl boronic acid (311 mg) in 2:1 DME:water (15 ml) containing cesium carbonate (697 mg) and tetrakis(triphenylphosphine)palladium⁰ (127 mg) was heated to reflux for 18 h.

The mixture was cooled and then evaporated. The residue was then stirred in ethanol (10 ml) and 2M NaOH (5 ml) at room temp for 16 h. The ethanol was then evaporated and the residue acidified with 2M HCl. The resulting solid was collected by filtration and dried (561 mg)

¹H NMR (DMSO, δ) ẽ₁□ş□□3.11 (t, 4H), 3.76 (t, 4H), 3.88 (s, 3H), 6.87 (m, 2H), 7.16 (d, 1H), 7.28 (d, 1H), 7.63 (m, 3H), 8.04 (m, 3H), 9.73 (br. s, 1H)

Example 260

6-Methoxy-biphenyl-3,4'-dicarboxylic acid 3-[(2-methyl-4-morpholin-4-yl-phenyl)-amide] 4'-({4-[4-(propane-1-sulfonyl)-piperazin-1-ylmethyl]-phenyl}-amide)

A mixture of 2'-Methoxy-5'-(2-methyl-4-morpholin-4-yl-phenylcarbamoyl)-biphenyl-4-carboxylic acid (60 mg), 4-(4-(propane-1-sulfonyl)-piperazin-1-ylmethyl)-phenylamine (39 mg), EDAC (50 mg), HOBT (35 mg) and N-methylmorpholine (43 µl) in DMF (1 ml) was stirred at room temperature for 18 h. The mixture was then evaporated and the residue purified by chromatography. Elution DCM:EtOH:NH3; 400:8:1 gave a white solid (53 mg).

¹H NMR (DMSO, δ)ĭt, 3H), 1.71 (m, 2H), 2.19 (s, 3H), 2.45 (m, 4H), 3.01 (m, 4H), 3.13 (t, 2H), 3.18 (m, 4H), 3.51 (s, 2H), 3.76 (t, 4H), 3.89 (s, 3H), 6.84 (m, 2H), 7.15 (d, 1H), 7.30 (m, 3H), 7.75 (m, 4H), 8.05 (m, 4H), 9.70 (br. s, 1H), 10.33 (br. s, 1H)

3-Bromo-4-methoxy-N-[4-(4-methyl-piperazin-1-yl)-phenyl]-benzamide

A mixture of 3-bromo-4-methoxy-benzoic acid (500 mg), 4-(4-methyl-piperazin-1-yl)-phenylamine (413 mg), EDAC (828 mg), HOBT (534 mg) and N-methylmorpholine (712 µl) in DMF (3 ml) was stirred at room temperature for 18 h. The mixture was then diluted with water (30 ml) and the resulting solid collected by filtration and dried (840 mg)

¹H NMR (DMSO, δ) 2.78 (s, 3H), 3.27 (m, 4H), 3.41 (m, 4H, merged with water peak), 3.94 (s, 3H), 7.00 (d, 2H), 7.25 (d, 1H), 7.67 (d, 2H), 8.03 (dd, 1H), 8.24 (d, 1H), 10.11 (br. s, 1H).

2'-Methoxy-5'-[4-(4-methyl-piperazin-1-yl)-phenyl-carbamoyl]-biphenyl-4-carboxylic acid A mixture of 3-Bromo-4-methoxy-N-[4-(4-methyl-piperazin-1-yl)-phenyl]-benzamide (748 mg) and 4-(ethoxycarbonyl)-phenyl boronic acid (538 mg) in 2:1 DME:water (15 ml) containing cesium carbonate (1.21 mg) and tetrakis(triphenylphosphine)palladium⁰ (220 mg) was heated to reflux for 18 h. The mixture was cooled and then evaporated. The residue was then stirred in ethanol (8 ml) and 2M NaOH (4 ml) at room temp for 16 h. The ethanol was then evaporated and the residue acidified with 2M HCl. The resulting solid was collected by filtration and dried (528 mg)

¹H NMR (DMSO, δ) 2.69 (s, 3H), 3.16 (m, 4H), 3.38 (m, 4H, merged with water peak), 3.88 (s, 3H), 6.99 (d, 2H), 7.28 (d, 1H), 7.69 (m, 4H), 8.03 (m, 4H).

Example 261

6-Methoxy-biphenyl-3,4'-dicarboxylic acid 3-{[4-(4-(1,1-dioxo-1lambda*6*-thiomorpholin-4-yl)-phenyl]-amide} 4'-{[4-(4-methyl-piperazin-1-yl)-phenyl]-amide}

A mixture of 2'-Methoxy-5'-[4-(4-methyl-piperazin-1-yl)-phenylcarbamoyl]-biphenyl-4-carboxylic acid (100 mg), 4-(1,1-dioxo-1lambda*6*-thiomorpholin-4-yl)-phenylamine (50 mg), EDAC (84 mg), HOBT (59 mg) and N-methylmorpholine (7311) in DMF (1 ml) was stirred at room temperature for 18 h. The mixture was then evaporated and the residue purified by chromatography. Elution DCM:EtOH:NH3; 200:8:1 gave an off-white solid (61 mg).

¹H NMR (DMSO, δ) 2.23 (s, 3H), 2.48 (t, 4H), 3.12 (m, 8H), 3.78 (m, 4H), 3.89 (s, 3H), 6.93 (d, 2H), 7.06 (d, 2H), 7.29 (d, 1H), 7.61 (d, 2H), 7.72 (m, 4H), 8.03 (m, 4H), 9.99 (br. s, 1H), 10.16 (br. s, 1H).

3-Bromo-N-[4-(1,1-dioxo-1lambda*6*-thiomorpholin-4-ylethyl)-phenyl]-4-methoxy-benzamide A mixture of 3-bromo-4-methoxy-benzoic acid (500 mg), 4-(1,1-dioxo-1lambda*6*-thiomorpholin-4-ylmethyl)-phenylamine (519 mg), EDAC (830 mg), HOBT (585 mg) and N-methylmorpholine (712 µl) in DMF (3 ml) was stirred at room temperature for 18 h. The mixture was then diluted with water (30 ml) and the resulting solid collected by filtration and dried (882 mg)

¹H NMR (DMSO, δ) 3.02 (m, 4H), 3.26 (m, 4H), 3.80 (s, 2H), 4.10 (s, 2H), 7.42 (d, 1H), 7.47 (d, 2H), 7.89 (d, 2H), 8.17 (dd, 1H), 8.39 (d, 1H), 10.35 (br. s, 1H).

5'-[4-(1,1-Dioxo-1lambda*6*-thiomorpholin-4-ylmethyl)-phenylcarbamoyl]-2'-methoxy-biphenyl-4-carboxylic acid A mixture of 3-Bromo-N-[4-(1,1-dioxo-1lambda*6*-thiomorpholin-4-ylmethyl)-phenyl]-4-methoxy-benzamide (930 mg) and 4-carboxyphenyl boronic acid (408 mg) in 2:1 DME:satd.sodium bicarbonate solution (7.5 ml) containing tetrakis(triphenylphosphine)palladium⁰ (116 mg) was heated to reflux for 18 h.

The reaction was allowed to cool to room temperature and then concentrated to dryness to yield a dark residue. The residue was taken up in water (10 ml) and treated with 2M HCl until no further effervescence occurred. The resulting suspension was filtered and the residue washed with water (3×3 ml) and dried in vacuo to give the title compound as a light grey solid (989 mg).

¹H NMR (DMSO, δ) 2.87 (m, 4H), 3.12 (m, 4H), 3.64 (s, 2H), 3.88 (s, 3H), 7.29 (m, 2H), 7.60 (m, 3H), 7.76 (m, 2H), 8.00 (m, 4H), 10.23 (br. s, 1H).

Example 262

6-Methoxy-biphenyl-3,4'-dicarboxylic acid 4'-{[4-(1,1-dioxo-1lambda*6*-thiomorpholin-4-ylmethyl)-phenyl]-amide} 4'{[4-(4-methanesulfonyl-piperazin-1-ylmethyl)-phenyl]-amide}

A mixture of 5'-[4-(1,1-Dioxo-1lambda*6*-thiomorpholin-4-ylmethyl)-phenylcarbamoyl]-2'-methoxy-biphenyl-4-carboxylic acid (100 mg), 4-(4-methanesulfonyl-piperazin-1-ylmethyl)-phenylamine (54 mg) EDAC (77 mg) and HOBT (54 mg) in dry DMF (1 ml) containing N-methylmorpholine (66 µl) was stirred at room temp for 18 h. The mixture was then evaporated and the residue purified by chromatography. Elution DCM:EtOH:NH3; 200:8:1 gave an off-white solid (59 mg).

¹H NMR (DMSO, δ) 2.53 (m, 4H), 2.94 (m, 7H), 3.18 (m, 8H), 3.57 (s, 2H), 3.71 (s, 2H), 3.96 (s, 3H), 7.37 (m, 5H), 7.82 (m, 6H), 8.11 (m, 4H), 10.25 (br. s, 1H), 10.37 (br. s, 1H).

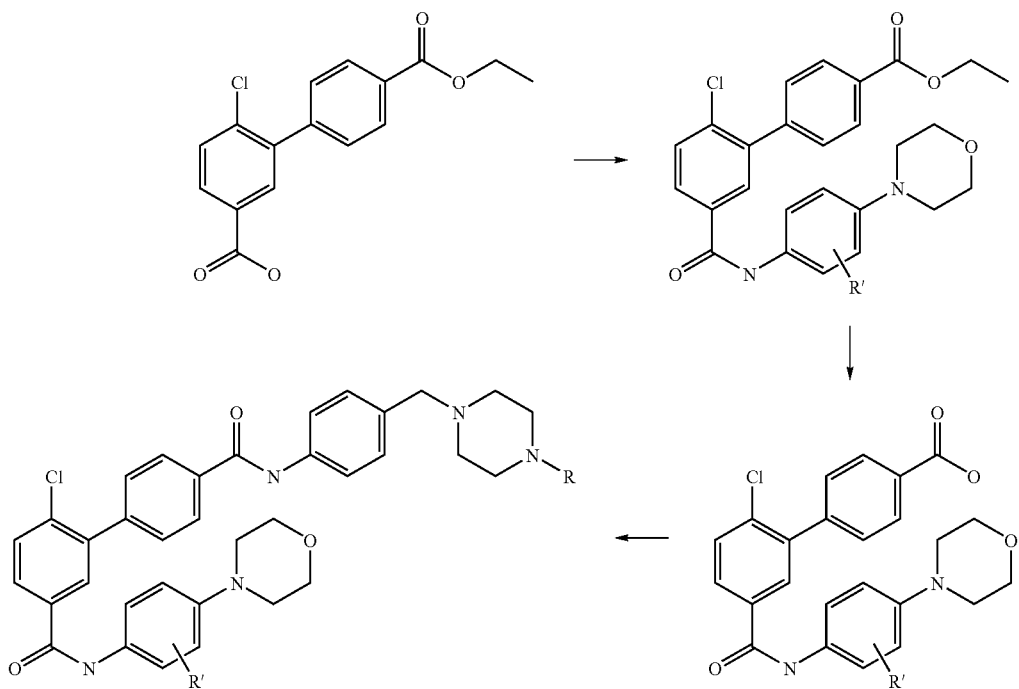

2'-Chloro-5'-(4-morpholin-4-yl-phenylcarbamoyl)-biphenyl-4-carboxylic acid ethyl ester A mixture of 6-chloro-biphenyl-3,4'-dicarboxylic acid 4'-ethyl ester (800 mg), N-(4-aminophenyl)morpholine (469 mg), EDAC (504 mg), HOBT (355 mg) and N-methylmorpholine (578 μl) in DMF (10 ml) was stirred at room temperature. After 1 h, water (80 ml) was added and the resulting suspension filtered. The residue was then purified by chromatography. Elution with 1:1 ethyl acetate:petrol gave a yellow crystalline solid (437 mg).

2'-Chloro-5'-(4-morpholin-4-yl-phenylcarbamoyl)-biphenyl-4-carboxylic acid

The above ester (778 mg) was stirred in ethanol (20 ml) and 2M NaOH (10 ml) at room temp for 18 h. The ethanol was then evaporated and the residue acidified with 2M HCl. The resulting pale pink solid was collected by filtration and dried (740 mg)

Example 263

6-Chloro-biphenyl-3,4'-dicarboxylic acid 4'-({4-[4-(butane-1 sulfonyl)piperazin-1-ylmethyl]-phenyl}-amide) 3-[(4-morpholin-4-yl-phenyl)-amide]

A mixture of 2'-chloro-5'-(4-morpholin-4-yl-phenylcarbamoyl)-biphenyl-4-carboxylic acid (57 mg), 4[-4-(butane-1-sulfonyl)-piperazin-1-ylmethyl]-phenylamine (53 mg), EDAC (33 mg), HOBT (23 mg) and N-methylmorpholine (37 μl) in DMF (1 ml) was stirred at room temperature. After 18 h, water (10 ml) was added and the resulting suspension filtered and dried giving the title compound as an off-white solid (31 mg)

$^1$H NMR (DMSO, δ) 0.91 (t, 3H), 1.39 (q, 2H), 1.65 (m, 2H), 2.47 (m, 4H), 3.07 (m, 4H), 3.19 (brs, 4H), 3.33 (s, 2H), 3.75 (m, 4H), 6.98 (d, 2H), 7.34 (d, 2H), 7.62 (d, 2H), 7.72 (d, 2H), 7.78 (m, 3H), 8.09 (m, 4H), 10.21 (s, 1H), 10.37 (s, 1H) LCMS-ES+=730, 732.

2'-Chloro-5'-(2-fluoro-4-morpholin-4-yl-phenylcarbamoyl)-biphenyl-4-carboxylic acid ethyl ester A mixture of 6-chloro-biphenyl-3,4'-dicarboxylic acid 4'-ethyl ester (213 mg), 3-fluoro-4-morpholin-4-yl-phenylamine (179 mg), EDAC (174 mg), HOBT (123 mg) and N-methylmorpholine (200 μl) in DMF (3 ml) was stirred at room temperature. After 11 h, water (30 ml) was added and the resulting suspension filtered. The residue was then purified by chromatography. Elution with 1:1 ethyl acetate:petrol gave a brown oil (235 mg).

2'-Chloro-5'-(2-fluoro-4-morpholin-4-yl-phenylcarbamoyl)-biphenyl-4-carboxylic acid The above ester (233 mg) was stirred in ethanol (4 ml) and 2M NaOH (2 ml) at room temp for 18 h. The ethanol was then evaporated and the residue acidified with 2M HCl. The resulting colourless solid was collected by filtration and dried (198 mg)

Example 264

6-Chloro-biphenyl-3,4'-dicarboxylic acid 3-[(3-fluoro-4-morpholin-4-yl-phenyl)-amide] 4'-({4-[4-(propane-1-sulfonyl)-piperazin-1-ylmethyl]-phenyl}-amide)

A mixture of 2'-chloro-5'-(2-fluoro-4-morpholin-4-yl-phenylcarbamoyl)-biphenyl-4-carboxylic acid (45 mg), 4-(4-(propane-1-sulfonyl)-piperazin-1-ylmethyl)-phenylamine (39 mg), EDAC (25 mg), HOBT (18 mg) and N-methylmorpholine (43 g) in DMF (1 ml) was stirred at room temperature for 18 h. Water (10 ml) was added and the resulting suspension filtered and dried giving the title compound as an off-white solid (57 mg)

$^1$H NMR (DMSO, δ) 1.00 (t, 3H), 1.69 (q, 2H), 2.45 (bs, 2H), 2.99 (m, 8H), 3.18 (m, 4H), 3.51 (s, 2H), 3.75 (m, 4H), 7.06 (t, 1H), 7.33 (d, 2H), 7.46 (d, 1H), 7.72 (d, 2H), 7.77 (m, 4H), 8.08 (m, 4H), 10.38 (s, 1H0, 10.42 (s, 1H)

LCMS-ES+=735, 737.

2'-Chloro-5'-[4-(4-methanesulfonyl-piperazin-1-ylmethyl)-phenylcarbamoyl]-biphenyl-4-carboxylic acid ethyl ester A mixture of 6-chloro-biphenyl-3,4'-dicarboxylic acid 4'-ethyl ester (152 mg), 4-(4-methanesulfonyl-piperazin-1-ylmethyl)-phenylamine (175 mg), EDAC (125 mg), HOBT (88 mg) and N-methylmorpholine (143 μl) in DMF (3 ml) was stirred at room temperature. After 1 h, water (30 ml) was added and the resulting suspension filtered. The residue was then purified by chromatography. Gradient elution with 30-100% ethyl acetate in petrol gave a beige solid (240 mg).

2'-Chloro-5'-[4-(4-methanesulfonyl-piperazin-1-ylmethyl)-phenylcarbamoyl]-biphenyl-4-carboxylic acid The above ester (237 mg) was stirred in ethanol (4 ml) and 2M NaOH (2 ml) at room temp for 18 h. The ethanol was then evaporated and the residue acidified with 2M HCl. The resulting colourless solid was collected by filtration and dried (229 mg)

Example 265

6-Chloro-biphenyl-3,4'-dicarboxylic acid 3-{[4-(4-methanesulfonyl-piperazin-1-ylmethyl)-phenyl]-amide} 4'-[(4-morpholin-4-yl-phenyl)-amide]

A mixture of 2'-chloro-5'-[4-(4-methanesulfonyl-piperazin-1-ylmethyl)-phenylcarbamoyl]-biphenyl-4-carboxylic acid (53 mg), N-(4-aminophenyl)morpholine (23 mg), EDAC (25 mg), HOBT (18 mg) and N-methylmorpholine (43 μl) in DMF (1 ml) was stirred at room temperature. After 18 h, water (10 ml) was added and the resulting suspension filtered. This material was then purified by reverse phase Prep HPLC giving the title compound as an off-white solid (39 mg)

$^1$H NMR (DMSO, δ) 2.47 (m, 4H), 2.88 (s, 3H), 3.10 (m, 8H), 3.51 (s, 2H), 3.76 (m, 4H), 6.99 (d, 2H), 7.32 (d, 2H), 7.71 (m, 7H), 8.07 (m, 4H), 10.21 (s, 1H), 10.40 (s, 1H)

LCMS-ES+=689, 691.

Activity Example

Cells Used:

HCV replicon cells Huh 9B (ReBlikon), containing the firefly luciferase-ubiquitin-neomycin phosphotransferase fusion protein and EMCV-IRES driven HCV polyprotein with cell culture adaptive mutations.

Cell Culture Conditions:

Cells were cultured at 37° C. in a 5% $CO_2$ environment and split twice a week on seeding at $2 \times 10^6$ cells/flask on day 1 and $1 \times 10^6$ 3 days later. G418 at 0.5 mg/ml was added to the culture medium but not the assay medium.

The culture medium consisted of DMEM with 4500 g/l glucose and glutamax (Gibco 61965-026) supplemented with 1× non-essential amino acids (Invitrogen 11140-035), penicillin (100 IU/ml)/streptomycin (100 μg/ml) (Invitrogen 15140-122), FCS (10%, 50 ml) and 1 mg/ml G418 (Invitrogen 10131-027) & 10% Australian foetal calf serum (Invitrogen 10099-141).

Assay Procedure:

A flask of cells was trypsinised and a cell count carried out. Cells were diluted to 100,000 cells/ml and 100 μl of this used to seed one opaque white 96-well plate (for the replicon assay) and one flat-bottomed clear plate (for the tox assay) for every seven compounds to be tested for $IC_{50}$. Wells G12 and H12 were left empty in the clear plate as the blank. Plates were then incubated at 37° C. in a 5% $CO_2$ environment for 24 h.

On the following day compound dilutions are made up in medium at twice their desired final concentration in a clear round bottomed plate. All dilutions have a final DMSO concentration of 1%.

Once the dilution plate had been made up, controls and compounds were transferred to the assay plate (containing the cells) at 100 μl /well in duplicate plates. Exception: no compound was added to wells $A_1$ and $A_2$ of either plate and 100 μl of 1% DMSO was added to these instead. Plates were then incubated at 37° C. with 5% $CO_2$ for 72 h.

At the end of the incubation time, the cells in the white plate were harvested by washing 23.5 mM beetle luciferin (Promega E1603), 26 mM ATP (Sigma 0-2060) in 100 nM Tris buffer pH 7.8 aliquoted and stored at −80 C was thawed and diluted 1:50 in luciferase assay buffer (20 mM Tricine (Sigma T-0377), 1.07 mM magnesium carbonate hydroxide (Sigma M-5671), 0.1 mM EDTA (Sigma E-5134), 2.67 mM $MgSO_4$ (BDH 101514Y), 33.3 mM dithiothreitol (Sigma 150460) pH 7.8).

The M injector of the microplate luminometer (Lmax, Molecular Devices) was primed with 5×300 μl injections of the diluted substrate. After 5-60 min incubation in lysis buffer at room temperature, a plate was inserted into the luminometer and 100 μl luciferase assay reagent was added by the injector on the luminometer. The signal was measured using a 1 second delay followed by a 4 second measurement programme. The $IC_{50}$, the concentration of the drug required for reducing the replicon level by 50% in relation to the untreated cell control value, can be calculated from the plot of the percentage reduction of the luciferase activity vs. drug concentration.

The clear plate was stained with 100 μl 0.5% methylene blue in 50% ethanol at room temperature for 1 h, followed by solvation of the absorbed methylene blue in 100 μl per well of 1% lauroylsarcosine. Absorbance of the plate was measured on a microplate spectrophotometer (Molecular Devices) and the absorbance for each concentration of compound expressed as a proportion of the relative DMSO control. The $TD_{50}$, the concentration of drug required to reduce the total cell area by 50% relative to the DMSO controls, can be calculated by plotting the absorbance at 620 nm minus background against drug concentration.

| Patent example No | IC50<br>\* > 5 μM,<br>\*\* = 1-5 μM,<br>\*\*\* < 1 μM | TD50<br>\* < 50 μM,<br>\*\* > 50 μM |
|---|---|---|
| 1 | ** | ** |
| 2 | ** | ** |
| 3 | ** | ** |
| 4 | ** | ** |
| 5 | ** | ** |
| 6 | ** | * |

| Patent example No | IC50 * > 5 μM, ** = 1-5 μM, *** < 1 μM | TD50 * < 50 μM, ** > 50 μM |
|---|---|---|
| 7 | ** | * |
| 8 | ** | ** |
| 9 | * | * |
| 10 | ** | * |
| 11 | ** | ** |
| 12 | ** | ** |
| 13 | * | * |
| 14 | ** | ** |
| 15 | * | * |
| 16 | ** | ** |
| 17 | ** | * |
| 18 | ** | * |
| 19 | ** | ** |
| 20 | * | ** |
| 21 | ** | ** |
| 22 | ** | ** |
| 23 | ** | * |
| 24 | * | ** |
| 25 | ** | * |
| 26 | * | ** |
| 27 | ** | ** |
| 28 | *** | ** |
| 29 | *** | ** |
| 30 | ** | ** |
| 31 | ** | ** |
| 32 | *** | ** |
| 33 | *** | ** |
| 34 | ** | ** |
| 35 | * | ** |
| 36 | ** | * |
| 37 | * | ** |
| 38 | ** | ** |
| 39 | ** | * |
| 40 | ** | ** |
| 41 | *** | ** |
| 42 | *** | ** |
| 43 | *** | ** |
| 44 | *** | * |
| 45 | ** | ** |
| 46 | * | ** |
| 47 | * | ** |
| 48 | ** | ** |
| 49 | *** | ** |
| 50 | *** | ** |
| 51 | ** | ** |
| 52 | ** | ** |
| 53 | ** | ** |
| 54 | ** | ** |
| 55 | ** | ** |
| 56 | *** | * |
| 57 | ** | ** |
| 58 | ** | ** |
| 59 | ** | ** |
| 60 | *** | * |
| 61 | ** | ** |
| 62 | *** | * |
| 63 | *** | * |
| 64 | *** | * |
| 65 | *** | * |
| 66 | ** | * |
| 67 | *** | ** |
| 68 | ** | ** |
| 69 | *** | * |
| 70 | ** | * |
| 71 | *** | * |
| 72 | ** | * |
| 73 | *** | * |
| 74 | ** | * |
| 75 | * | * |
| 76 | ** | * |
| 77 | ** | * |
| 78 | ** | * |
| 79 | * | * |
| 80 | ** | * |
| 81 | ** | * |
| 82 | ** | * |
| 83 | ** | ** |
| 84 | * | ** |
| 85 | ** | ** |
| 86 | ** | ** |
| 87 | *** | ** |
| 88 | ** | ** |
| 89 | ** | ** |
| 90 | * | ** |
| 91 | ** | ** |
| 92 | ** | ** |
| 93 | *** | ** |
| 94 | ** | ** |
| 95 | ** | * |
| 96 | ** | ** |
| 97 | ** | * |
| 98 | ** | * |
| 99 | ** | ** |
| 100 | ** | ** |
| 101 | *** | * |
| 102 | ** | * |
| 103 | ** | ** |
| 104 | ** | ** |
| 105 | ** | ** |
| 106 | ** | ** |
| 107 | *** | ** |
| 108 | ** | ** |
| 109 | ** | * |
| 110 | ** | ** |
| 111 | * | ** |
| 112 | ** | * |
| 113 | * | * |
| 114 | * | * |
| 115 | ** | * |
| 116 | ** | * |
| 117 | ** | * |
| 118 | * | * |
| 119 | ** | ** |
| 120 | ** | ** |
| 121 | ** | * |
| 122 | *** | * |
| 123 | *** | * |
| 124 | ** | * |
| 125 | ** | * |
| 126 | ** | * |
| 127 | ** | * |
| 128 | ** | * |
| 129 | *** | * |
| 130 | *** | * |
| 131 | ** | * |
| 132 | *** | * |
| 133 | ** | * |
| 134 | ** | * |
| 135 | *** | * |
| 136 | ** | * |
| 137 | ** | * |
| 138 | *** | * |
| 139 | *** | * |
| 140 | ** | * |
| 141 | ** | * |
| 142 | ** | * |
| 143 | ** | * |
| 144 | ** | * |
| 145 | ** | * |
| 146 | *** | * |
| 147 | ** | * |
| 148 | ** | * |
| 149 | *** | * |
| 150 | *** | * |
| 151 | *** | * |
| 152 | *** | ** |
| 153 | *** | * |
| 154 | *** | * |
| 155 | *** | * |
| 156 | ** | * |

| Patent example No | IC50 * > 5 μM, ** = 1-5 μM, *** < 1 μM | TD50 * < 50 μM, ** > 50 μM |
|---|---|---|
| 157 | *** | * |
| 158 | *** | * |
| 159 | *** | * |
| 160 | *** | * |
| 161 | ** | * |
| 162 | ** | * |
| 163 | *** | * |
| 164 | *** | * |
| 165 | *** | * |
| 166 | *** | * |
| 167 | *** | * |
| 168 | *** | * |
| 169 | *** | * |
| 170 | *** | * |
| 171 | *** | * |
| 172 | ** | * |
| 173 | ** | * |
| 174 | ** | * |
| 175 | *** | * |
| 176 | *** | * |
| 177 | ** | * |
| 178 | *** | * |
| 179 | *** | * |
| 180 | *** | * |
| 181 | *** | * |
| 182 | *** | * |
| 183 | *** | * |
| 184 | *** | * |
| 185 | *** | * |
| 186 | *** | * |
| 187 | *** | * |
| 188 | *** | * |
| 189 | *** | * |
| 190 | *** | * |
| 191 | * | * |
| 192 | *** | * |
| 193 | *** | * |
| 194 | *** | * |
| 195 | *** | * |
| 196 | ** | * |
| 197 | *** | ** |
| 198 | ** | * |
| 199 | ** | * |
| 200 | * | ** |
| 201 | *** | * |
| 202 | ** | ** |
| 203 | ** | * |
| 204 | ** | * |
| 205 | * | * |
| 206 | * | * |
| 207 | * | * |
| 208 | * | * |
| 209 | ** | ** |
| 210 | ** | * |
| 211 | ** | * |
| 212 | * | ** |
| 213 | ** | * |
| 214 | * | * |
| 215 | * | * |
| 216 | * | * |
| 217 | * | * |
| 218 | *** | * |
| 219 | ** | * |
| 220 | *** | * |
| 221 | *** | * |
| 222 | ** | * |
| 223 | ** | * |
| 224 | ** | * |
| 225 | * | * |
| 226 | *** | * |
| 227 | ** | * |
| 228 | ** | * |
| 229 | ** | * |
| 230 | ** | * |
| 231 | * | * |
| 232 | *** | * |
| 233 | *** | * |
| 234 | *** | * |
| 235 | *** | * |
| 236 | ** | * |
| 237 | *** | * |
| 238 | *** | * |
| 239 | *** | * |
| 240 | *** | * |
| 241 | *** | * |
| 242 | ** | * |
| 243 | *** | * |
| 244 | *** | * |
| 245 | *** | * |
| 246 | *** | * |
| 247 | *** | * |
| 248 | *** | * |
| 249 | ** | * |
| 250 | *** | * |
| 251 | *** | * |
| 252 | *** | * |
| 253 | *** | * |
| 254 | *** | * |
| 255 | *** | * |
| 256 | *** | * |
| 257 | *** | * |
| 258 | *** | * |
| 259 | *** | * |
| 260 | *** | * |
| 261 | ** | * |
| 262 | *** | * |
| 263 | *** | * |
| 264 | *** | * |
| 265 | *** | * |

The invention claimed is:

1. A compound which is a biphenyl derivative of formula (I), a pharmaceutically acceptable salt, or a mixture thereof

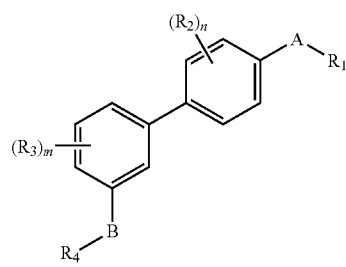

wherein:
$R_i$ is -$A_1$-$L_1$-$A_1$';
$A_1$ is a non-fused, unsubstituted phenyl group;
$L_1$ is —$CH_2$— or —$CH_2CH_2$—;
$A_1$' is a piperazinyl group which is substituted by an unsubstituted —$SO_2$—($C_1$-$C_4$ alkyl);
A is —CONH—;
B is —NH—CO—NH—, —NH—CO— or —CO—NH—;
$R_2$ and $R_3$ are the same or different and each represent $C_1$-$C_4$ alkyl, $C_1$-$C_4$ alkoxy, $C_1$-$C_4$ haloalkyl, $C_1$-$C_4$ haloalkoxy or halogen;
n and m are the same or different and each represent 0 or 1;
$R_4$ is a $C_1$-$C_6$ alkyl group or a moiety selected from the group consisting of -$A_4$, -$L_4$-$A_4$, -$A_4$-$A_4$', -$L_4$-$A_4$-$A_4$', -A₄-L₄-A₄', -A₄-Y₄-A₄', -A₄-Het₄-A₄', -L₄-A₄-Y₄-A₄', -L₄-A₄-Het₄-A₄', -L₄-Het₄-A₄, -L₄-Y₄-A₄, -L₄-Y₄-Het₄-A₄, -L₄-Het₄-Y₄-A₄, -L₄-Y₄-Het₄-L₄', -A₄-Y₄-Het₄-A₄', -A₄-Het₄-Y₄-A₄', -A₄-Het₄-L₄-A₄', -A₄-L₄-Het₄-A₄' and -L₄-Het₄-L₄', each A₄, and A₄' are the same or different and represent a phenyl, 5- to 10- membered heteroaryl, 5- to 10- membered heterocyclyl or C₃-C₈ carbocyclyl moiety;

L₄ is a C₁-C₄ alkylene or a C₁-C₄ hydroxyalkylene group;

Y₄ is —CO—, —SO— or —S(O)₂—;

L₄' is hydrogen or a C₁-C₄ alkyl group; and

Het₄ is —O—, —S— or —NR'—, wherein R' is hydrogen or a C₁-C₄ alkyl group;

the phenyl, heteroaryl, heterocyclyl and carbocyclyl moieties in R₄ are optionally fused to a phenyl, 5- to 10- membered heteroaryl or 5- to 10- membered heterocyclyl ring; and the phenyl, heteroaryl, heterocyclyl and carbocyclyl moieties in R₄ are unsubstituted or substituted by (a) a single unsubstituted substituent selected from —(C₁-C₂ alkyl)-X₁, —CO₂R''', —SO₂R''', —SO₂NR'R''', —CONR'R''', —NR'—CO—R''', —NR'—SO₂—R''' and —CO—NR'—(C₁-C₂ alkyl)—NR'R''' and/or (b) 1, 2 or 3 unsubstituted substituents selected from —(C₁-C₂ alkyl)—X₂, halogen, C₁-C₄ alkyl, C₁-C₄ alkoxy, C₁-C₄ haloalkyl, C₁-C₄ haloalkoxy, C₁-C₄ hydroxyalkyl, hydroxy, cyano and —NR'R'', wherein X₁ is —CO₂R''', —NR'-CO₂—R''', —NR'—S(O)₂—R''' or —SO₂NR'R''', each X₂ is the same or different and is cyano or —NR'R'', each R' and R'' are the same or different and represent hydrogen or C₁-C₄ alkyl and each R''' is the same or different and represents C₁-C₄ alkyl.

2. A compound according to claim 1, wherein each A₄ moiety is the same or different and is a non-fused 5- to 6-membered heterocyclyl or C₃-C₈ carbocyclyl group, or a phenyl or 5- to 6- membered heteroaryl group which is optionally fused to a phenyl ring or to a 5- to 6- membered heteroaryl or 5- to 6- membered heterocyclyl group.

3. A compound according to claim 1, wherein each A₄ moiety is unsubstituted or substituted by (a) a single unsubstituted substituent selected from —CO₂R''' and —CONR'R''' and/or (b) 1, 2 or 3 unsubstituted substituents selected from halogen, C₁-C₄ alkyl, C₁-C₄ alkoxy, —NR'R''', C₁-C₄ haloalkyl, C₁-C₄ haloalkoxy and cyano, wherein R' represents hydrogen or C₁-C₄ alkyl and R''' represents C₁-C₄ alkyl.

4. A compound according to claim 1, wherein each A₄' moiety is the same or different and represents a non-fused phenyl, 5- to 6- membered heteroaryl, 5- to 6- membered heterocyclyl or C₃-C₆ carbocyclyl group.

5. A compound according to claim 1, wherein each A₄' moiety is unsubstituted or substituted by (a) an unsubstituted —SO₂—(C₁-C₄ alkyl) substituent and/or (b) 1 or 2 unsubstituted substituents selected from halogen, C₁-C₄ alkyl, C₁-C₄ alkoxy, C₁-C₂ haloalkyl, C₁-C₂ haloalkoxy, C₁-C₄ hydroxyalkyl, hydroxy and —NR'R'', wherein each R' and R'' are the same or different and are selected from hydrogen and C₁-C₄ alkyl.

6. A compound according to claim 1, wherein L₄ is a C₁-C₃ alkylene group or a C₁-C₃ hydroxyalkylene group.

7. A compound according to claim 1, wherein Y₄ is —CO—.

8. A compound according to claim 1, wherein L₄' is a C₁-C₂ alkyl group.

9. A compound according to claim 1, wherein R₂ and R₃ are the same or different and represent C₁-C₄ alkyl, C₁-C₄ alkoxy, C₁-C₂ haloalkyl, C₁-C₂ haloalkoxy or halogen.

10. A compound according to claim 1, wherein R₄ is a C₁-C₅ alkyl group Or a moiety -A₄, -A₄-A₄', -L₄-A₄, -A₄-L₄-A₄', -A₄-Y₄-A₄' or -L₄-Het₄-L₄'.

11. A compound according to claim 1, wherein:

R₂ is C₁-C₄ alkyl;

R₃ is C₁-C₄ alkyl, C₁-C₄ alkoxy, C₁-C₂ haloalkyl, C₁-C₂ haloalkoxy or halogen;

n and m are the same or different and each represent 0 or 1;

R₄ is a C₁-C₅ alkyl group or a moiety -A₄, -A₄-A₄', -L₄-A₄,-A₄-L₄-A₄', -A₄-CO -A₄' or -L₄-Het₄-L₄';

each A₄ moiety is the same or different and is phenyl, furanyl, imidazolyl, pyrazolyl, pyrrolidinyl, azetidinyl, tetrahydrofuranyl, piperazinyl, piperidinyl, pyrrolidin-2-onyl, thiadiazolyl, isothiazolyl, C₃-C₈ cycloalkyl, morpholinyl, thienyl, pyridyl, pyrrolyl, S,S-dioxo-thiomopholinyl, tetrahydropyranyl, thiazolyl, oxadiazolyl or indazolyl group, each A₄ moiety being unsubstituted or substituted by (a) a single unsubstituted -CONR'R''' substituent and/or (b) 1 or 2 unsubstituted substituents selected from fluorine, chlorine, bromine, —NR'R''', C₁-C₄ alkyl, C₁-C₂ alkoxy, C₁-C₂ haloalkyl and cyano, wherein R' is hydrogen or C₁-C₄ alkyl and R''' represents C₁-C₄ alkyl;

each A₄' moiety is the same or different and represents a morpholinyl, piperazinyl, isoxazolyl, pyrrolidinyl, S,S-dioxothiomorpholinyl, 2,6-dioxo-piperidinyl, triazolyl, piperidinyl, cyclopropyl or cyclohexyl group which is unsubstituted or substituted by (a) a single unsubstituted —SO₂—(C₁-C₄ alkyl) substituent and/or (b) 1 or 2 unsubstituted substituents selected from chlorine, fluorine, bromine, C₁-C₂ alkyl and C₁-C₂ haloalkyl;

L₄ is a C₁-C₃ alkylene group or a C₁-C₃ hydroxyalkylene group

L₄' represents a C₁-C₂ alkyl group; and

Het₄ represents —O— or —NH—.

12. A compound according to claim 1, wherein:

R₂ is C₁-C₄ alkyl;

R₃ is C₁-C₄ alkyl, C₁-C₄ alkoxy, C₁-C₂ haloalkyl, C₁-C₂ haloalkoxy or halogen;

n and m are the same or different and each represent 0 or 1;

R₄ is a C₁-C₅ alkyl group or a moiety selected from the group consisting of -A₄, -A₄-A₄', -L₄-A₄, -A₄-L₄-A₄', -A₄-CO-A₄' and -L₄-O-L₄';

each A₄ moiety is the same or different and is phenyl, furanyl, imidazolyl, pyrazolyl, tetrahydrofuranyl, piperazinyl, piperidinyl, pyrrolidin-2-onyl, thiadiazolyl, isothiazolyl, C₃-C₈ cycloalkyl, morpholinyl, thienyl, pyridyl, pyrrolyl, S,S-dioxo-thiomopholinyl, tetrahydropyranyl, thiazolyl, oxadiazolyl or indazolyl group, each A₄ moiety being unsubstituted or substituted by (a) a single unsubstituted —CONR'R'' substituent and/or (b) 1 or 2 unsubstituted substituents selected from fluorine, chlorine, bromine, —NR'R''', C₁-C₄ alkyl, C₁-C₂ alkoxy, C₁-C₂ haloalkyl and cyano, wherein R' is hydrogen or C₁-C₄ alkyl and R'' represents C₁-C₄ alkyl;

each A₄' moiety is the same or different and represents a morpholinyl, isoxazolyl, pyrrolidinyl, S,S-dioxothiomorpholinyl, 2,6-dioxo-piperidinyl, triazolyl, piperidinyl, cyclopropyl or cyclohexyl group which is unsubstituted or substituted by 1 or 2 unsubstituted substituents selected from chlorine, fluorine, bromine, C₁-C₂ alkyl and C₁-C₂ haloalkyl;

L₄ is a C₁-C₃ alkylene group or a C₁-C₃ hydroxyalkylene group; and L₄' represents a C₁-C₂ alkyl group.

13. A compound according to claim 1, wherein:
$R_2$ is $C_1$-$C_4$ alkyl, $C_1$-$C_4$ alkoxy, $C_1$-$C_2$ haloalkyl, $C_1$-$C_2$ haloalkyl or halogen;
$R_3$ is $C_1$-$C_4$ alkyl;
n and m are the same or different and each represent 0 or 1;
$R_4$ is a $C_1$-$C_5$ alkyl group or a moiety selected from the group consisting of -$A_4$, -$A_4$-$A_4'$, -$L_4$-$A_4$-$A_4$-$L_4$-$A_4'$-$A_4$-CO-$A_4'$ and -$L_4$-O-$L_4'$;
each $A_4$ moiety is the same or different and is phenyl, furanyl, imidazolyl, pyrazolyl, tetrahydrofuranyl, piperazinyl, piperidinyl, pyrrolidin-2-onyl, thiadiazolyl, isothiazolyl, $C_3$-$C_8$ cycloalkyl, morpholinyl, thienyl, pyridyl, pyrrolyl, S,S-dioxo-thiomopholinyl, tetrahydropyranyl, thiazolyl, oxadiazolyl or indazolyl group, each $A_4$ moiety being unsubstituted or substituted by (a) a single unsubstituted —CONR'R'" substituent and/or (b) 1 or 2 unsubstituted substituents selected from fluorine, chlorine, bromine, —NR'R'", $C_1$-$C_4$ alkyl, $C_1$-$C_2$ alkoxy, $C_1$-$C_2$ haloalkyl and cyano, wherein R' is hydrogen or $C_1$-$C_4$ alkyl and R'" represents $C_1$-$C_4$ alkyl;
each $A_4'$ moiety is the same or different and represents a morpholinyl, isoxazolyl, pyrrolidinyl, S,S-dioxothiomorpholinyl, 2,6-dioxo-piperidinyl, triazolyl, piperidinyl, cyclopropyl or cyclohexyl group which is unsubstituted or substituted by 1 or 2 unsubstituted substituents selected from chlorine, fluorine, bromine, $C_1$-$C_2$ alkyl and $C_1$-$C_2$ haloalkyl;
$L_4$ is a $C_1$-$C_3$ alkylene group or a $C_1$-$C_3$ hydroxyalkylene group; and $L_4'$ represents a $C_1$-$C_2$ alkyl group.

14. A compound according to claim 1, wherein $R_4$ is -$A_4$ or -$A_4$-$L_4$-$A_4'$.

15. A compound according to claim 14, wherein when $R_4$ is $A_4$ it is $C_3$-$C_6$ cycloalkyl or when $R_4$ is -$A_4$-$L_4$-$A_4'$, $A_4$ is phenyl, $L_4$ is —$CH_2$— and $A_4'$, is a group

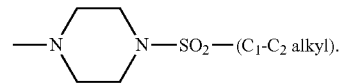

16. A pharmaceutical composition comprising a biphenyl derivative of claim 1, a pharmaceutically acceptable salt, or a mixture thereof, and a pharmaceutical acceptable diluent or carrier.

17. A pharmaceutical composition according to claim 16, which further comprises interferon and/or ribavirin.

18. A method of treating an HCV infection in a patient, which method comprises administering to said patient an effective amount of a biphenyl derivative of claim 1, a pharmaceutically acceptable salt, or a mixture thereof 19. The method of claim 18, further comprising administering interferon and/or ribavirin.

20. A compound which is 5'-(cyclopropanecarbonyl-amino)-2'-trifluoromethoxy-biphenyl-4-carboxylic acid {4-[4-(propane-1- sulfonyl)-piperazin-1 -ylmethyl]-phenyl}-amide, a pharmaceutically acceptable salt, or a mixture thereof.

* * * * *